(12) United States Patent
Malek et al.

(10) Patent No.: US 10,758,718 B2
(45) Date of Patent: *Sep. 1, 2020

(54) SYSTEMS AND METHODS FOR ENDOVASCULARLY ACCESSING A SUBARACHNOID SPACE

(71) Applicant: CereVasc, LLC, Auburndale, MA (US)

(72) Inventors: Adel M. Malek, Weston, MA (US); Carl Heilman, Wayland, MA (US); David A. Rezac, Westborough, MA (US); Jack B. Sattell, Boston, MA (US); Anthony Maiorano, Jamaica Plain, MA (US)

(73) Assignee: CereVasc, Inc., Auburndale, MA (US)

( * ) Notice: Subject to any disclaimer, the term of this patent is extended or adjusted under 35 U.S.C. 154(b) by 288 days.

This patent is subject to a terminal disclaimer.

(21) Appl. No.: 15/981,497

(22) Filed: May 16, 2018

(65) Prior Publication Data
US 2018/0256866 A1 Sep. 13, 2018

Related U.S. Application Data

(63) Continuation of application No. 15/745,961, filed as application No. PCT/US2016/059592 on Oct. 28, 2016, now Pat. No. 10,272,230.
(Continued)

(51) Int. Cl.
*A61M 27/00* (2006.01)
*A61M 25/04* (2006.01)
(Continued)

(52) U.S. Cl.
CPC ......... *A61M 27/006* (2013.01); *A61M 25/04* (2013.01); *A61B 17/3478* (2013.01);
(Continued)

(58) Field of Classification Search
CPC .............. A61M 27/006; A61M 27/002; A61M 27/008; A61M 25/04; A61M 25/0147;
(Continued)

(56) References Cited

U.S. PATENT DOCUMENTS

| 3,492,996 A | 2/1970 | Fountain |
| 3,894,541 A | 7/1975 | El-Shafei |

(Continued)

FOREIGN PATENT DOCUMENTS

| CN | 189564 | 1/2007 |
| EP | 1082070 | 5/1999 |

(Continued)

OTHER PUBLICATIONS

Amendment Response to Office Action for U.S. Appl. No. 15/862,120 dated May 1, 2018.
(Continued)

*Primary Examiner* — Philip R Wiest
(74) *Attorney, Agent, or Firm* — Vista IP Law Group, LLP

(57) ABSTRACT

Systems and methods for implanting an endovascular shunt in a patient is disclosed. The system having an expandable anchor configured for being deployed in a dural venous sinus of a patient at a location distal to a curved portion of a wall of an inferior petrosal sinus (IPS) of the patient; an elongate guide member coupled to, and extending proximally from, the anchor; a shunt delivery catheter having a first lumen configured to receive the guide member, and a second lumen extending between respective proximal and distal openings in the shunt delivery catheter, the shunt delivery catheter further having a penetrating element coupled to a distal end of the catheter; and the system further having a guard at least partially disposed over, and movable relative to, the penetrating element.

24 Claims, 79 Drawing Sheets

US 10,758,718 B2
Page 2

Related U.S. Application Data

(60) Provisional application No. 62/406,825, filed on Oct. 11, 2016, provisional application No. 62/332,444, filed on May 5, 2016, provisional application No. 62/301,523, filed on Feb. 29, 2016, provisional application No. 62/290,384, filed on Feb. 2, 2016, provisional application No. 62/249,145, filed on Oct. 30, 2015.

(51) Int. Cl.
| | |
|---|---|
| A61F 2/915 | (2013.01) |
| A61B 17/34 | (2006.01) |
| A61B 17/00 | (2006.01) |
| A61B 17/22 | (2006.01) |
| A61M 25/01 | (2006.01) |
| A61M 25/06 | (2006.01) |
| A61M 25/09 | (2006.01) |

(52) U.S. Cl.
CPC ........... *A61B 2017/00252* (2013.01); *A61B 2017/22077* (2013.01); *A61F 2/915* (2013.01); *A61M 25/0147* (2013.01); *A61M 25/065* (2013.01); *A61M 25/09* (2013.01); *A61M 2202/0464* (2013.01); *A61M 2205/32* (2013.01)

(58) Field of Classification Search
CPC ............. A61M 25/065; A61M 25/07; A61M 2002/0464; A61M 2205/32; A61B 17/3478; A61B 2017/00252; A61B 2017/22077; A61F 2/915
See application file for complete search history.

(56) References Cited

U.S. PATENT DOCUMENTS

| | | | |
|---|---|---|---|
| 4,413,985 A | 11/1983 | Wellner et al. |
| 4,474,569 A | 10/1984 | Newkirk |
| 4,475,898 A | 10/1984 | Brodner et al. |
| 4,631,051 A | 12/1986 | Harris |
| 4,737,153 A | 4/1988 | Shimamura et al. |
| 4,950,232 A | 8/1990 | Ruzicka et al. |
| 5,000,731 A | 3/1991 | Wong et al. |
| 5,137,288 A | 8/1992 | Starkey et al. |
| 5,160,325 A | 11/1992 | Nichols et al. |
| 5,193,546 A | 3/1993 | Shaknovich |
| 5,221,261 A | 6/1993 | Termin et al. |
| 5,385,541 A | 1/1995 | Kirsch et al. |
| 5,405,316 A | 4/1995 | Magram |
| 5,496,329 A | 3/1996 | Reisinger |
| 5,634,475 A | 6/1997 | Wolvek |
| 5,725,571 A | 3/1998 | Imbert et al. |
| 5,725,572 A | 3/1998 | Lam et al. |
| 5,746,725 A | 5/1998 | Shalon et al. |
| 5,800,520 A | 9/1998 | Fogarty et al. |
| 5,830,222 A | 11/1998 | Makower |
| 5,851,199 A | 12/1998 | Peerless et al. |
| 5,976,131 A | 11/1999 | Guglielmi et al. |
| 5,984,929 A | 11/1999 | Bashiri et al. |
| 6,015,405 A | 1/2000 | Schwartz et al. |
| 6,068,638 A | 5/2000 | Makower |
| 6,071,292 A | 6/2000 | Makower et al. |
| 6,093,199 A | 7/2000 | Brown et al. |
| 6,126,628 A | 10/2000 | Nissels |
| 6,126,649 A | 10/2000 | VanTassel et al. |
| 6,126,672 A | 10/2000 | Berryman et al. |
| 6,159,225 A | 12/2000 | Makower |
| 6,186,972 B1 | 2/2001 | Nelson et al. |
| 6,190,353 B1 | 2/2001 | Makower et al. |
| 6,231,587 B1 | 5/2001 | Makower |
| 6,283,934 B1 | 9/2001 | Borgeson |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,402,771 B1 | 6/2002 | Palmer et al. |
| 6,432,127 B1 | 8/2002 | Kim et al. |
| 6,491,707 B2 | 12/2002 | Makower et al. |
| 6,508,824 B1 | 1/2003 | Flaherty et al. |
| 6,527,790 B2 | 3/2003 | Chien et al. |
| 6,544,230 B1 | 4/2003 | Flaherty et al. |
| 6,561,998 B1 | 5/2003 | Roth et al. |
| 6,569,145 B1 | 5/2003 | Shmulewitz et al. |
| 6,575,997 B1 | 6/2003 | Palmer et al. |
| 6,579,302 B2 | 6/2003 | Duerig et al. |
| 6,579,311 B1 | 6/2003 | Makower |
| 6,589,164 B1 | 7/2003 | Flaherty |
| 6,602,241 B2 | 8/2003 | Makower et al. |
| 6,613,081 B2 | 9/2003 | Kim et al. |
| 6,616,675 B1 | 9/2003 | Evard et al. |
| 6,638,293 B1 | 10/2003 | Makower et al. |
| 6,655,386 B1 | 12/2003 | Makower et al. |
| 6,660,021 B1 | 12/2003 | Palmer et al. |
| 6,660,024 B1 | 12/2003 | Flaherty et al. |
| 6,685,648 B2 | 2/2004 | Flaherty et al. |
| 6,685,716 B1 | 2/2004 | Flaherty et al. |
| 6,709,444 B1 | 3/2004 | Makower |
| 6,716,238 B2 | 4/2004 | Elliott |
| 6,719,750 B2 | 4/2004 | Varner et al. |
| 6,726,677 B1 | 4/2004 | Flaherty et al. |
| 6,746,426 B1 | 6/2004 | Flaherty et al. |
| 6,746,464 B1 | 6/2004 | Makower |
| 6,863,684 B2 | 3/2005 | Kim et al. |
| 7,056,325 B1 | 6/2006 | Makower et al. |
| 7,083,588 B1 | 8/2006 | Shmulewitz et al. |
| 7,094,230 B2 | 8/2006 | Flaherty et al. |
| 7,134,438 B2 | 11/2006 | Makower et al. |
| 7,172,571 B2 | 2/2007 | Moskowitz et al. |
| 7,179,270 B2 | 2/2007 | Makower |
| 7,191,015 B2 | 3/2007 | Lamson et al. |
| 7,300,458 B2 | 11/2007 | Henkes et al. |
| 7,303,571 B2 | 12/2007 | Makower et al. |
| 7,316,655 B2 | 1/2008 | Garibotto et al. |
| 7,357,794 B2 | 4/2008 | Makower et al. |
| 7,407,506 B2 | 8/2008 | Makower |
| 7,606,615 B2 | 10/2009 | Makower et al. |
| 7,637,870 B2 | 12/2009 | Flaherty et al. |
| 7,648,517 B2 | 1/2010 | Makower et al. |
| 7,670,329 B2 | 3/2010 | Flaherty et al. |
| 7,729,738 B2 | 6/2010 | Flaherty et al. |
| 7,797,053 B2 | 9/2010 | Atkinson et al. |
| 7,846,172 B2 | 12/2010 | Makower |
| 7,955,343 B2 | 6/2011 | Makower et al. |
| 7,966,057 B2 | 6/2011 | Macaulay et al. |
| 7,989,042 B2 | 8/2011 | Obara et al. |
| 8,075,580 B2 | 12/2011 | Makower |
| 8,083,708 B2 | 12/2011 | Flaherty et al. |
| 8,088,140 B2 | 1/2012 | Ferrera et al. |
| 8,090,430 B2 | 1/2012 | Makower et al. |
| 8,214,015 B2 | 7/2012 | Macaulay et al. |
| 8,292,950 B2 | 10/2012 | Dorn et al. |
| 8,295,947 B2 | 10/2012 | Lamson et al. |
| 8,540,759 B2 | 9/2013 | Porter |
| 8,585,596 B1 | 11/2013 | Flaherty et al. |
| 8,672,871 B2 | 3/2014 | Heilman et al. |
| 8,672,920 B2 | 3/2014 | Makower et al. |
| 8,727,988 B2 | 5/2014 | Flaherty et al. |
| 8,740,833 B2 | 6/2014 | Moskowitz et al. |
| 8,753,366 B2 | 6/2014 | Makower et al. |
| 8,795,317 B2 | 8/2014 | Grandfield et al. |
| 8,876,792 B2 | 11/2014 | Holmin et al. |
| 8,926,680 B2 | 1/2015 | Ferrera et al. |
| 8,974,513 B2 | 3/2015 | Ford et al. |
| 9,039,749 B2 | 5/2015 | Shrivastava et al. |
| 9,387,311 B1 | 7/2016 | Heilman et al. |
| 9,387,331 B2 | 7/2016 | Zhao et al. |
| 9,402,982 B2 | 8/2016 | Baert et al. |
| 9,433,429 B2 | 9/2016 | Vale et al. |
| 9,545,505 B2 | 1/2017 | Heilman et al. |

(56) References Cited

U.S. PATENT DOCUMENTS

| | | |
|---|---|---|
| 9,669,195 B2 | 6/2017 | Heilman et al. |
| 9,682,216 B2 | 6/2017 | Teitelbaum |
| 9,724,501 B2 | 8/2017 | Heilman et al. |
| 1,000,462 A1 | 6/2018 | Kelly |
| 1,002,225 A1 | 7/2018 | Teitelbaum |
| 10,058,686 B2 | 8/2018 | Heilman et al. |
| 10,272,230 B2* | 4/2019 | Malek .................. A61M 25/04 |
| 10,279,154 B2 | 5/2019 | Heilman et al. |
| 10,307,576 B2 | 6/2019 | Heilman et al. |
| 10,307,577 B2* | 6/2019 | Malek .................. A61M 25/04 |
| 2002/0183786 A1 | 12/2002 | Girton |
| 2002/0188308 A1 | 12/2002 | Tu et al. |
| 2003/0135147 A1 | 7/2003 | Rosenberg et al. |
| 2003/0181938 A1 | 9/2003 | Roth et al. |
| 2003/0187495 A1 | 10/2003 | Cully et al. |
| 2003/0191520 A1 | 10/2003 | Pelton |
| 2003/0220604 A1 | 11/2003 | Al-Anazi |
| 2003/0225395 A1 | 12/2003 | Griffis et al. |
| 2003/0229366 A1 | 12/2003 | Reggie et al. |
| 2004/0059280 A1 | 3/2004 | Makower et al. |
| 2004/0087887 A1 | 5/2004 | Nilsson |
| 2004/0176743 A1 | 9/2004 | Morris et al. |
| 2004/0186368 A1 | 9/2004 | Ramzipoor et al. |
| 2004/0236309 A1 | 11/2004 | Yang |
| 2004/0236409 A1 | 11/2004 | Pelton et al. |
| 2004/0254517 A1 | 12/2004 | Quiroz-Mercado et al. |
| 2004/0260384 A1 | 12/2004 | Allen |
| 2005/0137646 A1 | 6/2005 | Wallace et al. |
| 2005/0245906 A1 | 11/2005 | Makower et al. |
| 2005/0256510 A1 | 11/2005 | Moskowitz et al. |
| 2006/0015089 A1 | 1/2006 | Meglin et al. |
| 2006/0015152 A1 | 1/2006 | Wallace |
| 2006/0079915 A1 | 4/2006 | Chin et al. |
| 2006/0089704 A1 | 4/2006 | Douglas |
| 2006/0173440 A1 | 8/2006 | Lamson et al. |
| 2006/0217755 A1 | 9/2006 | Eversull et al. |
| 2006/0224101 A1 | 10/2006 | Glenn |
| 2006/0259063 A1 | 11/2006 | Bates et al. |
| 2007/0112291 A1 | 5/2007 | Borgesen |
| 2007/0129746 A1 | 6/2007 | Mische |
| 2007/0156230 A1 | 7/2007 | Dugan et al. |
| 2007/0179426 A1 | 8/2007 | Selden |
| 2007/0179428 A1 | 8/2007 | Kralick et al. |
| 2007/0225794 A1 | 9/2007 | Thramann et al. |
| 2007/0276316 A1 | 11/2007 | Haffner et al. |
| 2008/0045863 A1 | 2/2008 | Bakos |
| 2008/0057106 A1 | 3/2008 | Erickson et al. |
| 2008/0058759 A1 | 3/2008 | Makower et al. |
| 2008/0097398 A1 | 4/2008 | Mitelberg et al. |
| 2008/0125805 A1 | 5/2008 | Mische |
| 2008/0249458 A1 | 10/2008 | Yamasaki |
| 2009/0005645 A1 | 1/2009 | Frassica et al. |
| 2009/0017098 A1 | 1/2009 | Bartolomeo |
| 2009/0076357 A1 | 3/2009 | Purdy |
| 2009/0171293 A1 | 7/2009 | Yang et al. |
| 2009/0287291 A1 | 11/2009 | Becking et al. |
| 2010/0010476 A1 | 1/2010 | Galdonik et al. |
| 2010/0016887 A1 | 1/2010 | Inderbitzi |
| 2010/0063531 A1 | 3/2010 | Rudakov et al. |
| 2010/0076404 A1 | 3/2010 | Ring |
| 2010/0121357 A1 | 5/2010 | Flaherty et al. |
| 2010/0191168 A1 | 7/2010 | Heilman |
| 2010/0222732 A1* | 9/2010 | Sevrain ............... A61M 27/002 604/8 |
| 2011/0082385 A1 | 4/2011 | Diaz et al. |
| 2011/0319917 A1 | 12/2011 | Ferrera et al. |
| 2012/0130467 A1 | 5/2012 | Selden et al. |
| 2012/0130468 A1 | 5/2012 | Khosravi et al. |
| 2012/0172844 A1 | 7/2012 | Mullen |
| 2013/0035628 A1 | 2/2013 | Garrison et al. |
| 2013/0178828 A1 | 7/2013 | Takagi et al. |
| 2014/0005586 A1 | 1/2014 | Feinstein |
| 2014/0052160 A1 | 2/2014 | Singh et al. |
| 2014/0180098 A1 | 6/2014 | Flaherty et al. |
| 2014/0180222 A1 | 6/2014 | Flaherty et al. |
| 2014/0236207 A1 | 8/2014 | Makower et al. |
| 2014/0276342 A1 | 9/2014 | Stone et al. |
| 2014/0288414 A1 | 9/2014 | Makower et al. |
| 2014/0336559 A1 | 11/2014 | Heilman et al. |
| 2015/0196741 A1 | 7/2015 | Heilman et al. |
| 2015/0201303 A1 | 7/2015 | Ji et al. |
| 2015/0209058 A1 | 7/2015 | Ferrera et al. |
| 2015/0258260 A1 | 9/2015 | Tuseth |
| 2016/0136398 A1* | 5/2016 | Heilman ............ A61B 18/1492 604/9 |
| 2017/0050000 A1 | 2/2017 | Randall |
| 2018/0015267 A1 | 1/2018 | Heilman et al. |
| 2018/0126132 A1 | 5/2018 | Heilman et al. |

FOREIGN PATENT DOCUMENTS

| | | |
|---|---|---|
| EP | 0964636 | 12/1999 |
| EP | 1047341 | 11/2000 |
| EP | 1067869 | 1/2001 |
| EP | 1067874 | 1/2001 |
| EP | 1082070 | 3/2001 |
| EP | 1171183 | 1/2002 |
| EP | 1253859 | 11/2002 |
| EP | 1359967 | 11/2003 |
| EP | 1377335 | 1/2004 |
| EP | 1496956 | 1/2005 |
| EP | 1854499 | 12/2009 |
| EP | 2589344 | 5/2013 |
| EP | 1981413 | 11/2014 |
| GB | 2089215 | 6/1982 |
| WO | WO1998016161 | 4/1998 |
| WO | WO2002/022028 | 3/2002 |
| WO | WO2006/080113 | 8/2006 |
| WO | WO2007115314 | 10/2007 |
| WO | WO2009014723 | 1/2009 |
| WO | WO2009036039 | 3/2009 |
| WO | WO2009/088783 | 7/2009 |
| WO | WO2009126935 | 10/2009 |
| WO | WO2011011787 | 1/2011 |
| WO | WO2012009518 | 1/2012 |
| WO | WO2012158152 | 11/2012 |
| WO | WO2013034602 | 3/2013 |
| WO | WO2014165754 | 10/2014 |
| WO | WO2015108917 | 7/2015 |
| WO | WO2016070147 | 5/2016 |
| WO | WO201707554 | 5/2017 |
| WO | WO2017117427 | 7/2017 |
| WO | WO2018005621 | 1/2018 |
| WO | WO2018071600 | 4/2018 |
| WO | WO2018160966 | 9/2018 |

OTHER PUBLICATIONS

Supplemental Amendment for U.S. Appl. No. 15/862,120 dated May 7, 2018.

PCT Invitation to Pay Additional Fees for International Appln. No. PCT/US2018/020667, dated May 29, 2018 (17 pages).

PCT International Search Report and Written Opinion for International Application No. PCT/2015/011317, Applicant Tufts Medical Center, Inc., Forms PCT/ISA/210, 220, and 237, dated Mar. 26, 2015 (15 pages).

Non-Final Office Action for U.S. Appl. No. 14/179,622, dated May 13, 2015 (13 pages).

PCT Notification of Transmittal of the International Search Report and Written Opinion, dated Feb. 17, 2016, for PCT/US2015/058505, Applicant CereVasc, LLC., international filing date Oct. 30, 2015 (16 pages).

Non-Final Office Action for U.S. Appl. No. 14/596,335, dated Jul. 7, 2016 (16 pages).

PCT International Search Report and Written Opinion for International Appln. No. PCTIUS2016/069280, applicant Cerevasc, LLC, dated Mar. 27, 2017 (80 pages).

Non-Final Office Action for U.S. Appl. No. 15/294,000, dated Feb. 16, 2017 (26 pages).

Final Office Action for U.S. Appl. No. 14/596,335, dated Oct. 26, 2016 (19 pages).

(56) References Cited

OTHER PUBLICATIONS

Interview Summary for U.S. Appl. No. 14/596,335, dated Oct. 11, 2016 (3 pages).
PCT Notification of Transmittal of the International Search Report and Written Opinion of the I.S.A. for PCT/US2016/0595952, dated Jan. 20, 2017, 14 pages.
PCT International Search Report and Written Opinion for International Appln. No. PCT/US2017/056227, Applicant Cerevasc, LLC, Forms PCT/ISA/210, 220, and 237, dated Mar. 29, 2018 (24 pages).
Non-Final Office Action for U.S. Appl. No. 15/862,120, dated Apr. 19, 2018.
Examination Report dated Jan. 25, 2019 for EP Appln. No. 15791220.5.
PCT International Search Report and Written Opinion for International Appln. No. PCT/US2018/020667, dated Aug. 1, 2018 (21 pages).
Non-Final Office Action dated Nov. 6, 2018 for U.S. Appl. No. 15/668,657.
Response to Non Final Office Action filed Nov. 14, 2018 for U.S. Appl. No. 15/668,657.
Notice of Allowance dated Dec. 14, 2018 for U.S. Appl. No. 15/668,657.
Notice of Allowance dated Dec. 14, 2018 for U.S. Appl. No. 15/745,961.
Non-final office action dated Mar. 21, 2019 for U.S. Appl. No. 16/212,511.
Amendment Response to Office Action for U.S. Appl. No. 16/212,547 dated Mar. 4, 2019.
Notice of Allowance dated Apr. 17, 2019 for U.S. Appl. No. 16/212,511.
Notice of Rejection for JP International Patent Appln. No. 2017-542811 dated Nov. 13, 2018.
Office Action dated Mar. 5, 2019 for Japanese Patent Appln. No. 2017-542811, with English translation provided by Foreign Associate.
Notice of Allowance dated Apr. 9, 2019 for U.S. Appl. No. 16/212,547.
PCT Invitation to Pay Additional Fees for International Appln. No. PCT/US2019/021471, dated Jun. 28, 2019 (10 pages).
PCT International Search Report and Written Opinion dated Aug. 20, 2019 for PCT Appln. No. PCT/US2019/021471, 17 pages.
Office action and search report dated Jul. 29, 2019 for Chinese Application No. 2015800588073, in Chinese with English translation provided by foreign associate.
Response to Examination Report filed Jun. 4, 2019 for EP Appln. No. 15791220.5.
Response to Foreign Office Action filed Jun. 24, 2019 for JP Patent Appln. No. 2017-542811.
PCT Invitation to Pay Additional Fees mailed Jan. 5, 2018 for PCT/US2017/056227, Applicant Cerevasc, LLC, 17 pages.
Response to Office action filed Oct. 29, 2019 for Chinese Application No. 2015800588073.
EPO communication Rule 71(3) allowance dated Nov. 7, 2019 for European patent application No. 15791220.5.

\* cited by examiner

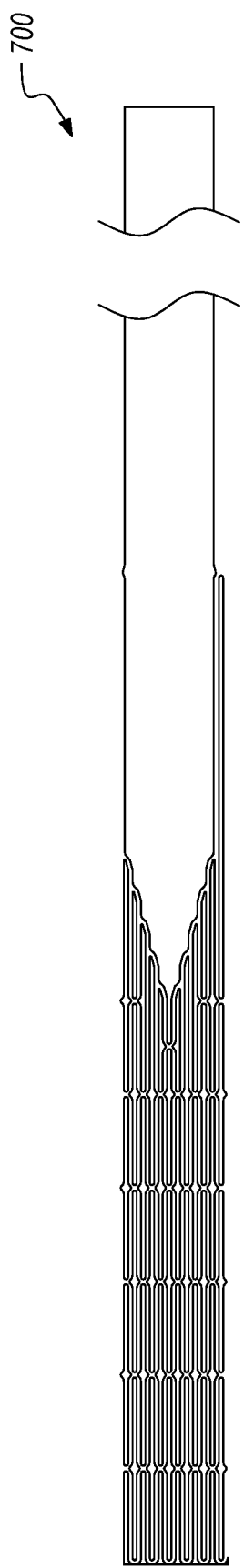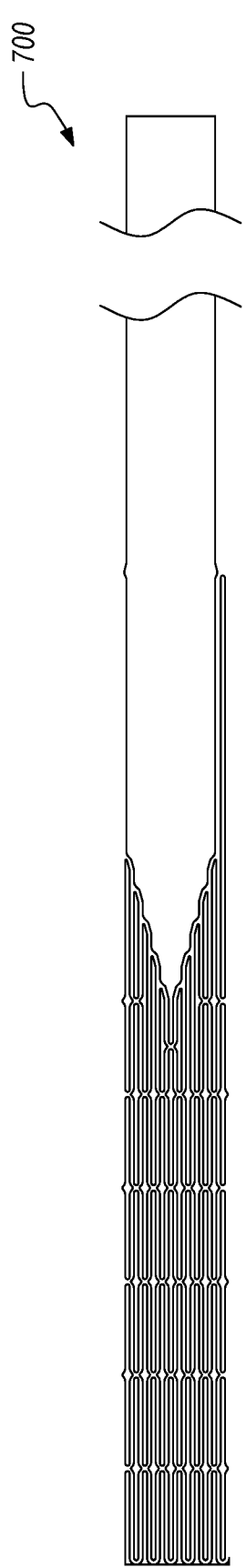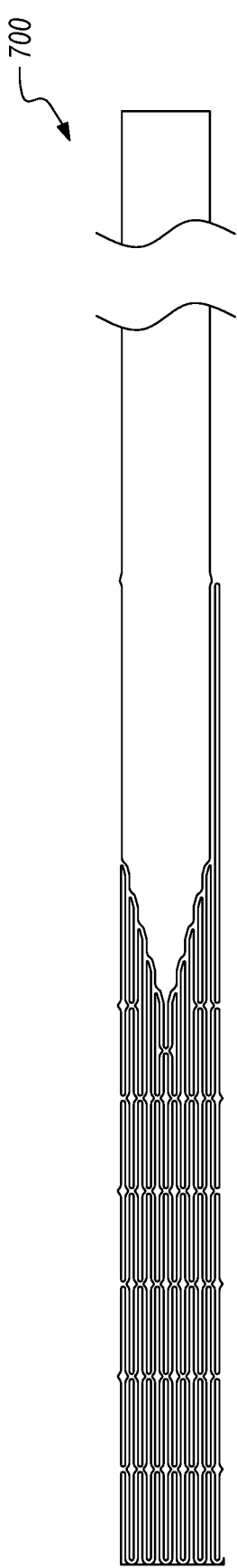

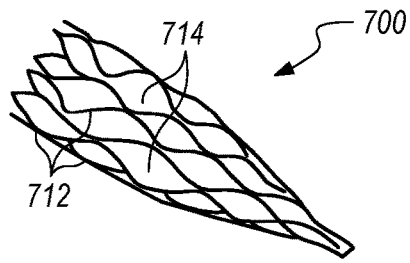
FIG. 5O
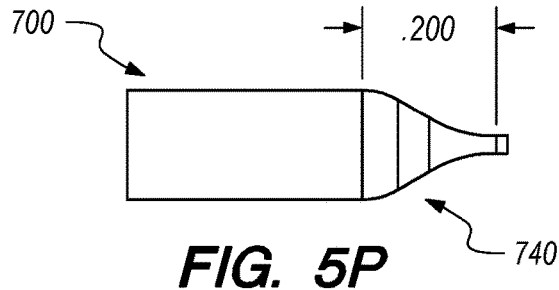
FIG. 5P
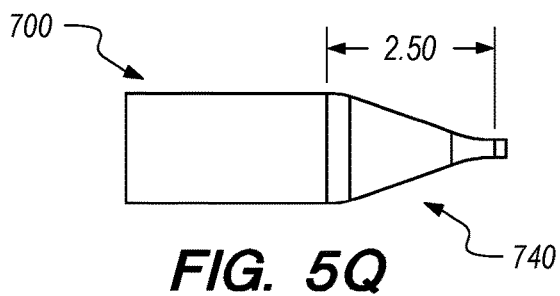
FIG. 5Q
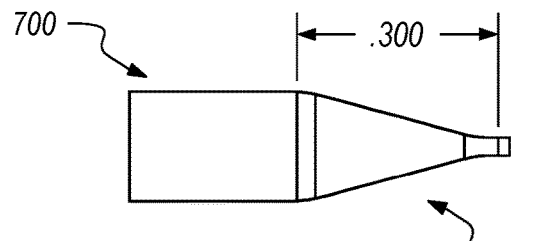
FIG. 5R
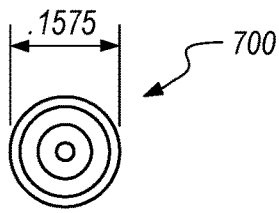
FIG. 5S
| DASH NO. | TRANSITION LENGTH |
|---|---|
| -01 | 0.200 |
| -02 | 0.250 |
| -03 | 0.300 |
FIG. 5T

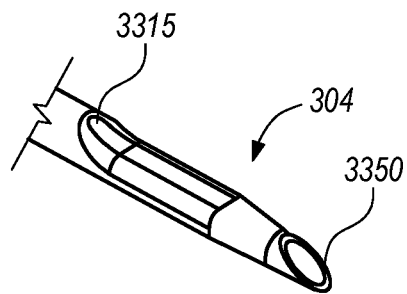
FIG. 10K
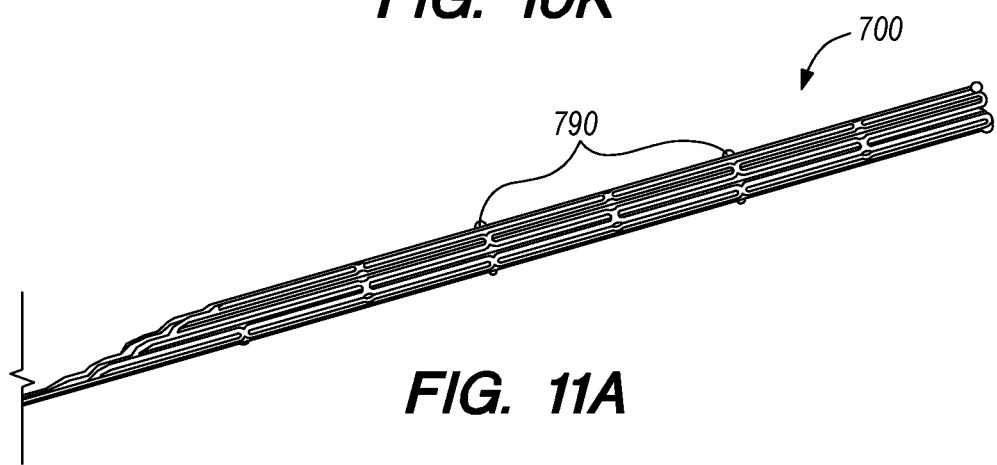
FIG. 11A
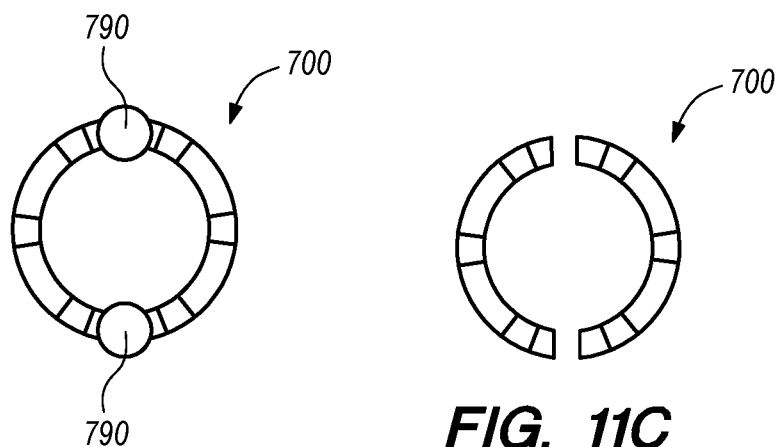
FIG. 11B
FIG. 11C
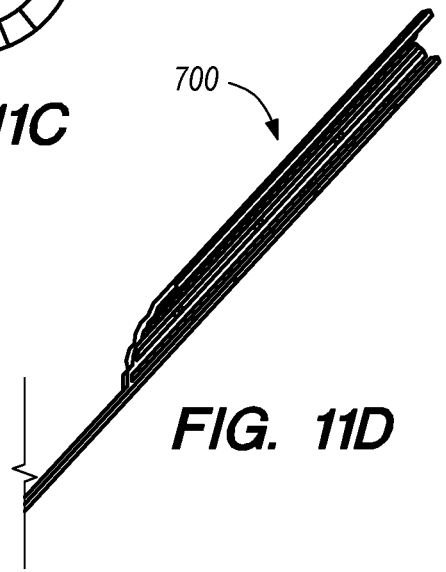
FIG. 11D

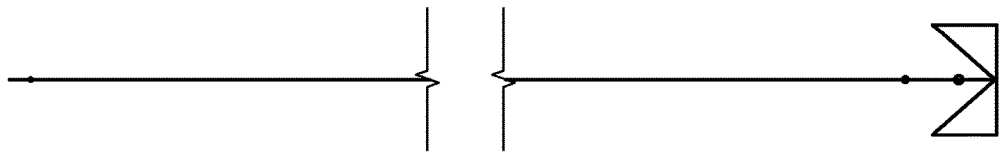
FIG. 12F
| INTEGRATED COIL AND NEEDLE TABULATED DIMENSIONS ||||
|---|---|---|---|
| DASH NO. | GAUGE | OD | ID |
| -01 | 21.5 | .03 | .024 |
| -02 | 22XX | .028 | .0235 |
| -03 | 22.5 | .026 | .0205 |
FIG. 12G
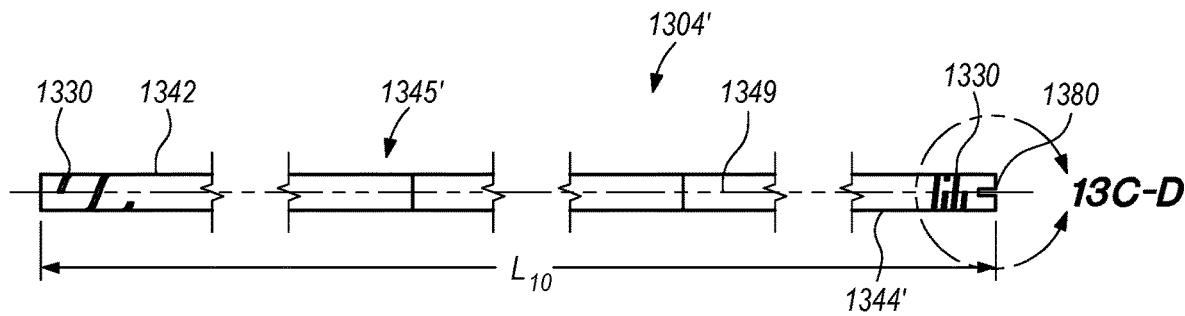
FIG. 13A
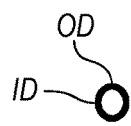
FIG. 13B

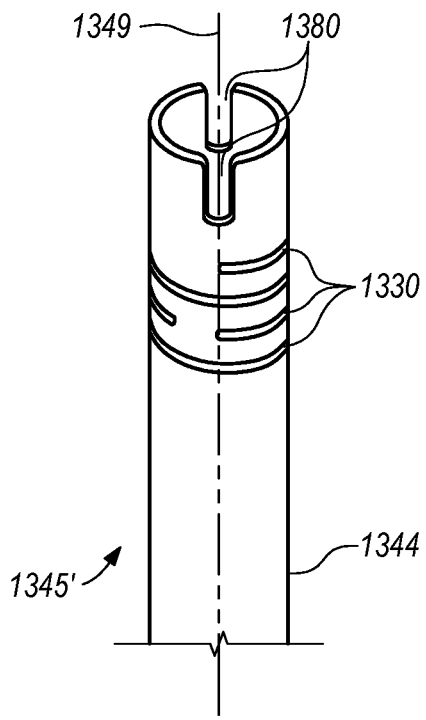
FIG. 13C
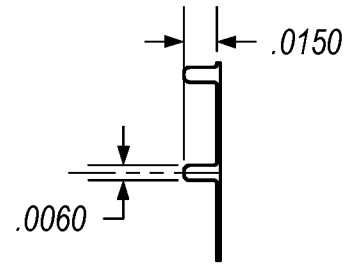
FIG. 13D
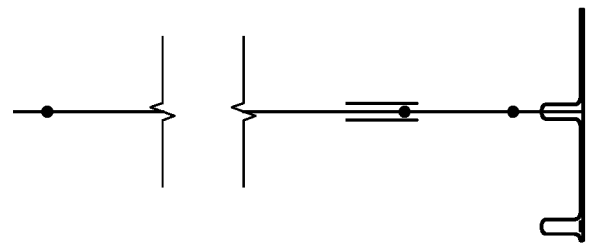
FIG. 13E
| INTEGRATED COIL AND NEEDLE TABULATED DIMENSIONS ||||
|---|---|---|---|
| DASH NO. | GAUGE | OD | ID |
| -01 | 21XX | .032 | .029 |
| -02 | 21.5 | .03 | .024 |
| -03 | 22XX | .028 | .0235 |
FIG. 13F

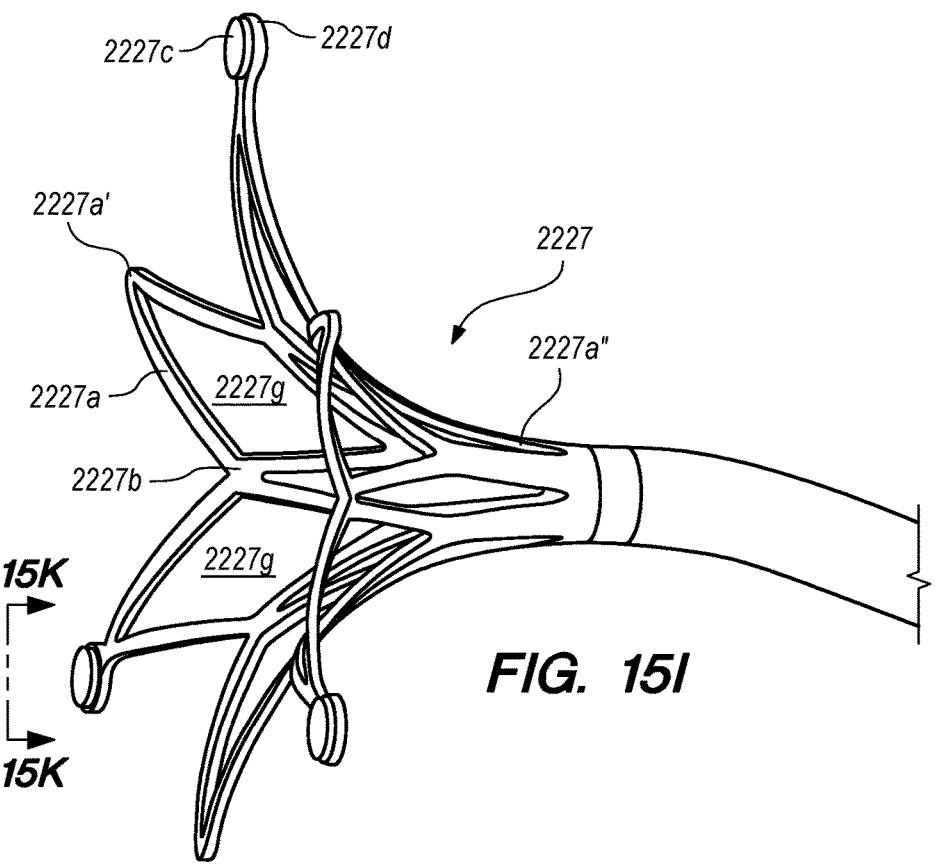
FIG. 15I
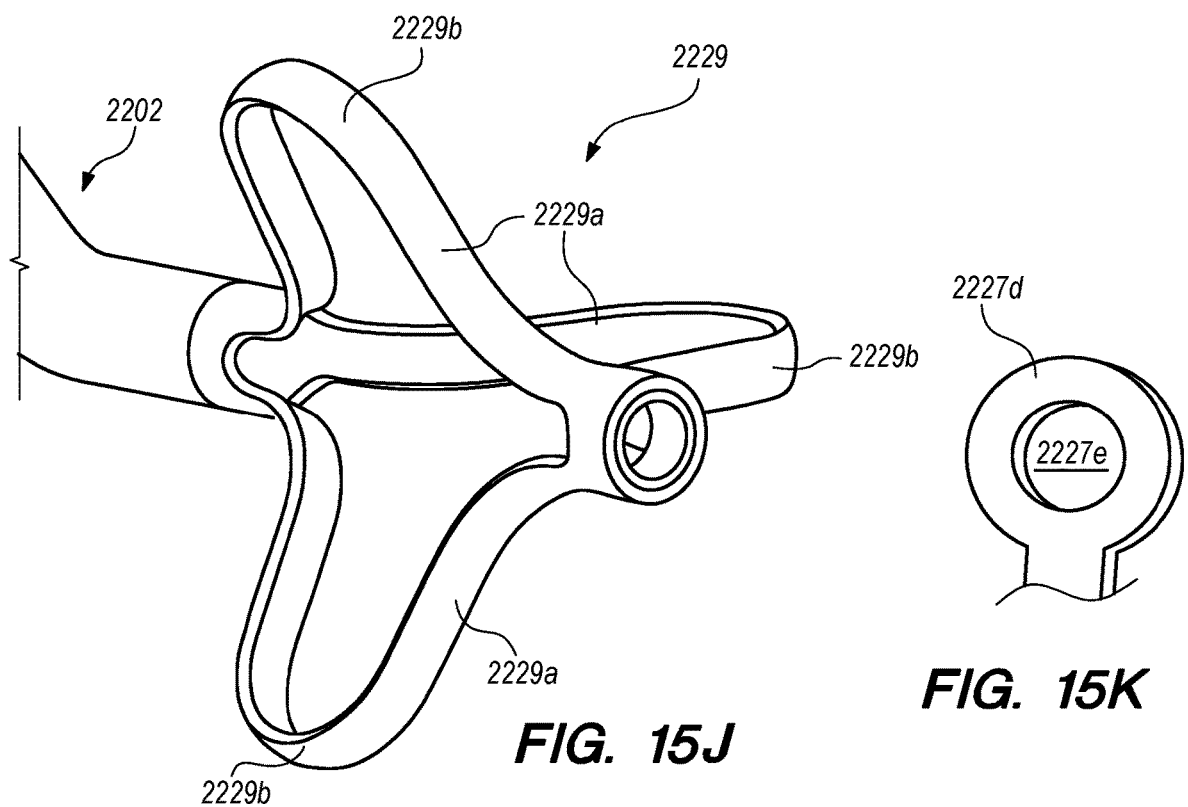
FIG. 15J
FIG. 15K

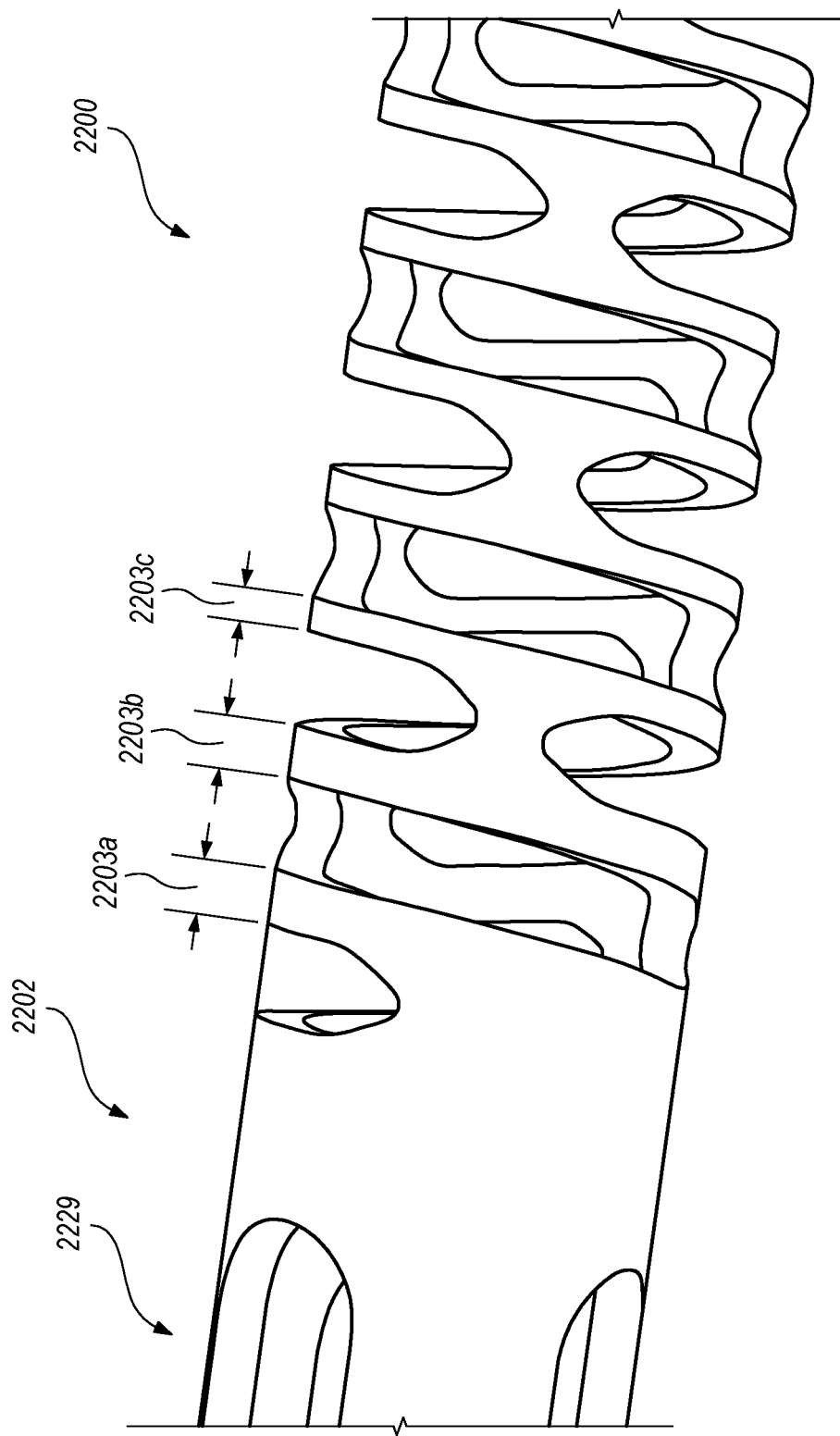

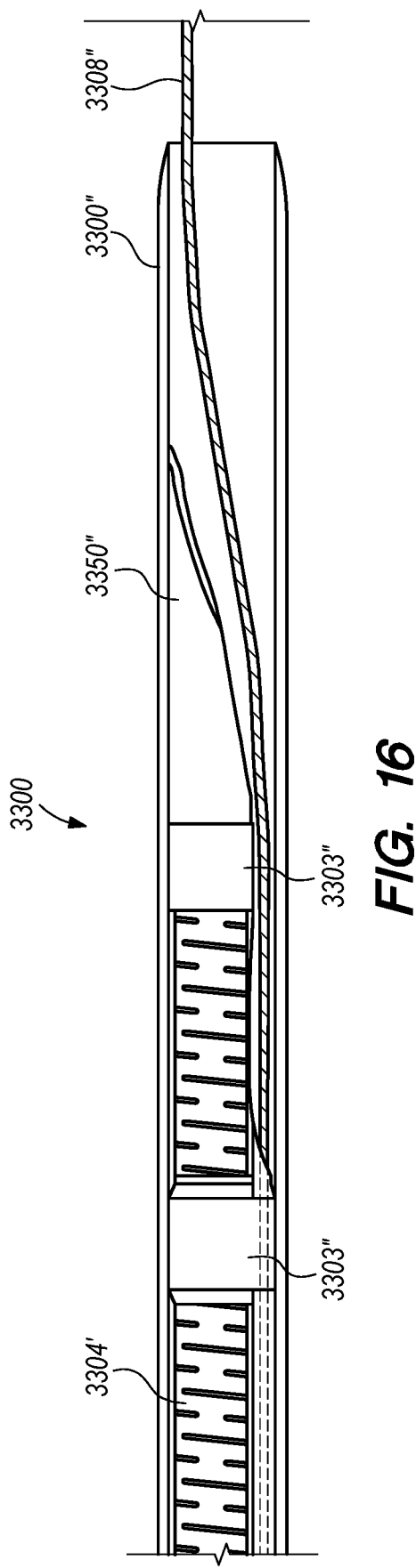
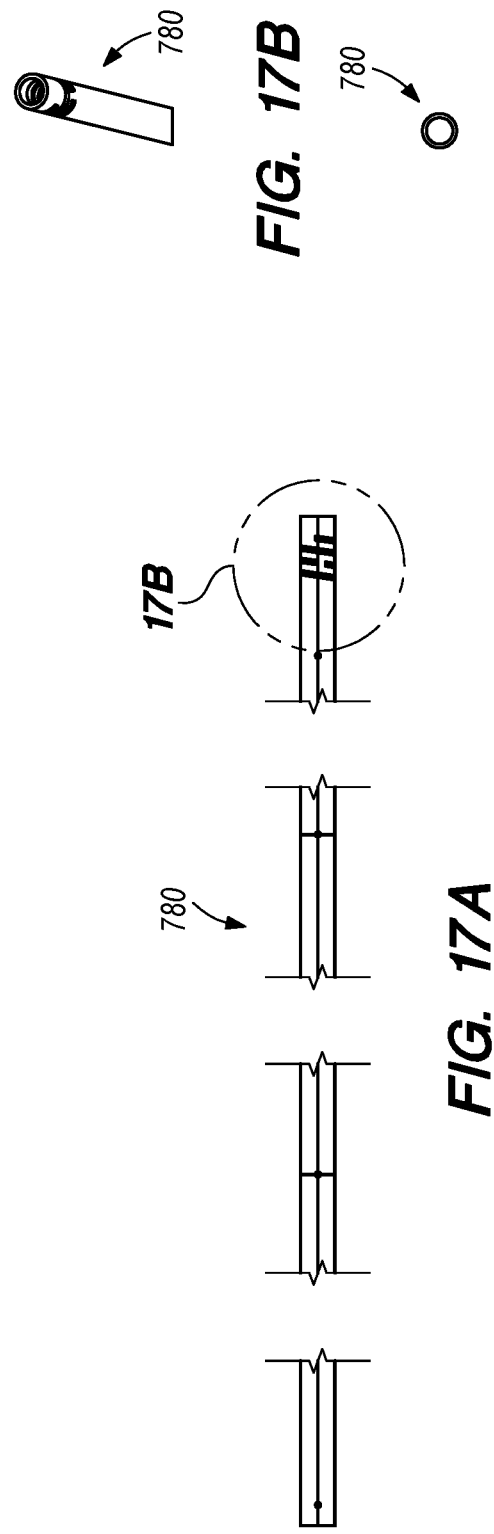
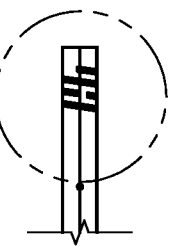
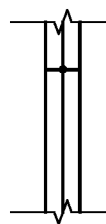
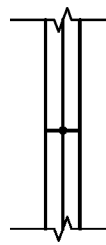
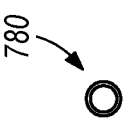
FIG. 16
FIG. 17A
FIG. 17B
FIG. 17C

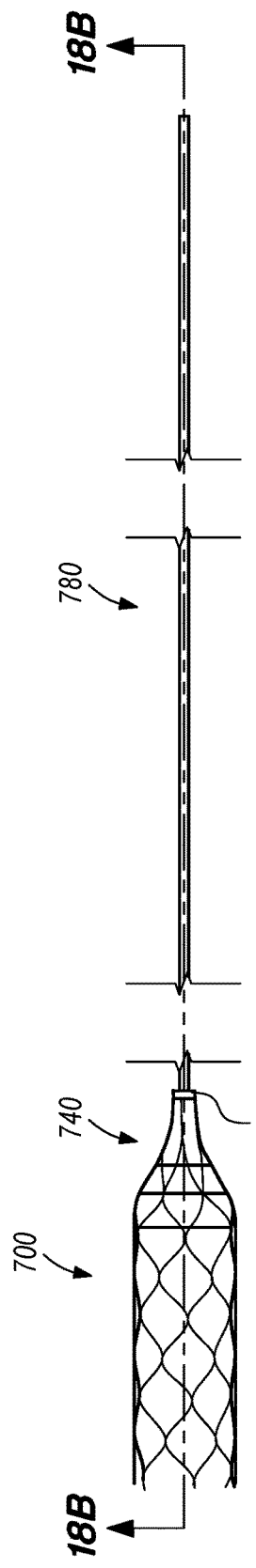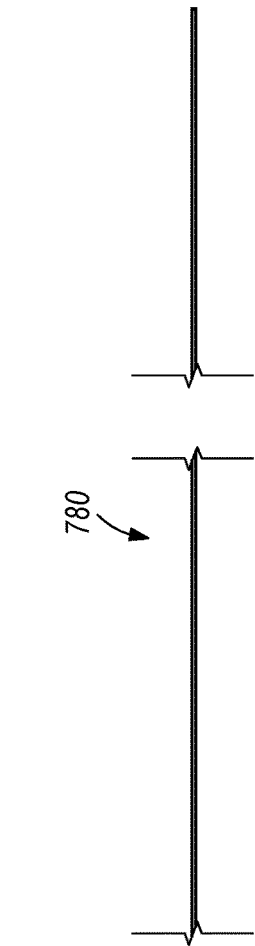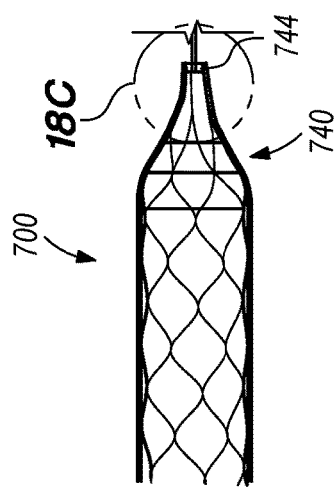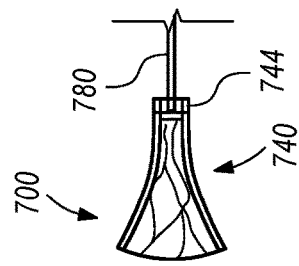
FIG. 18A
FIG. 18B
FIG. 18C

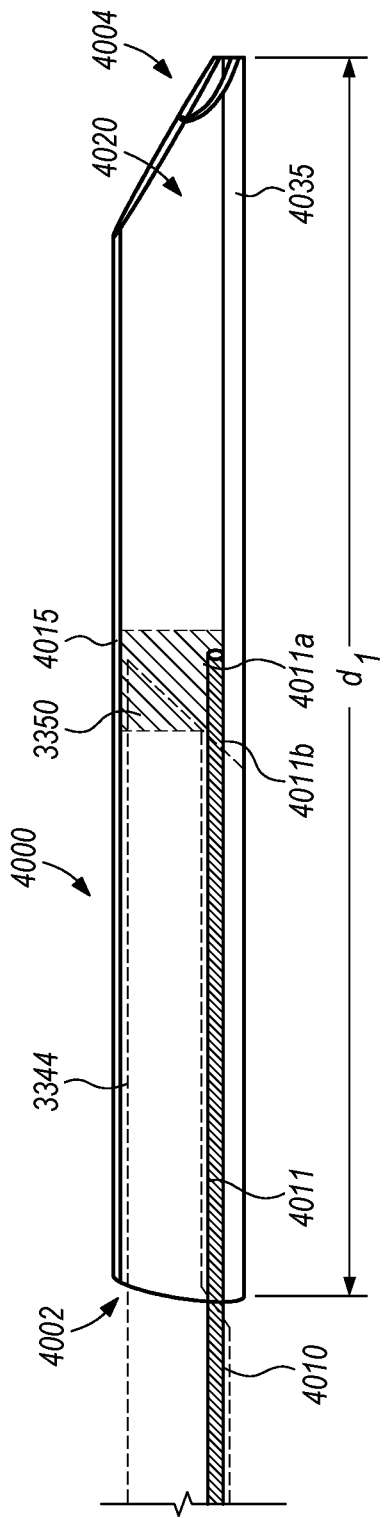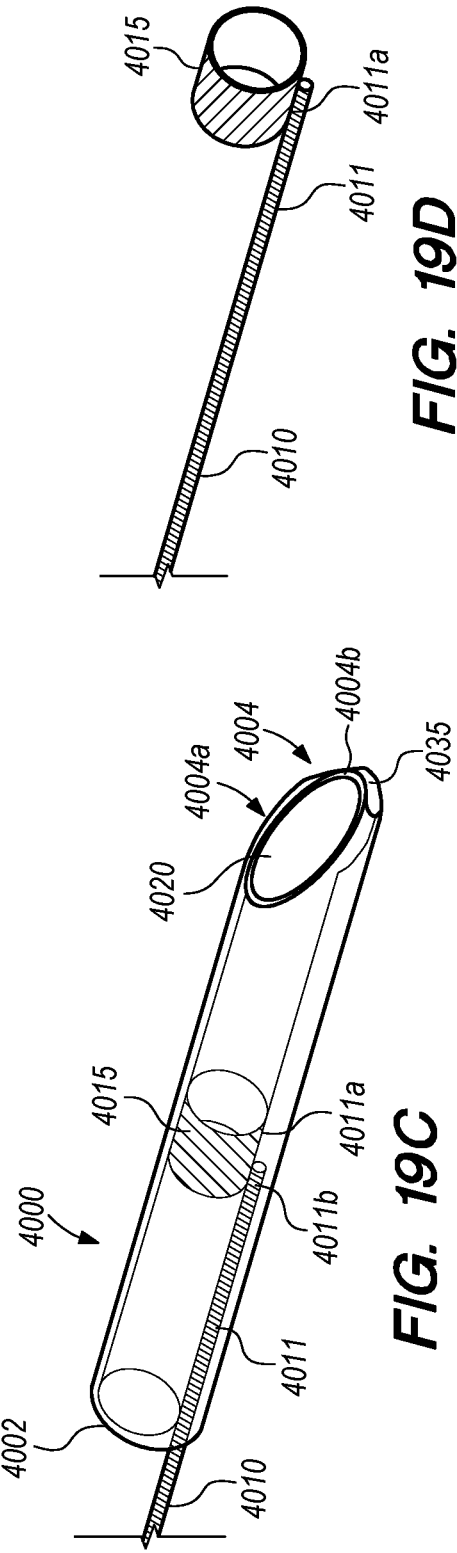

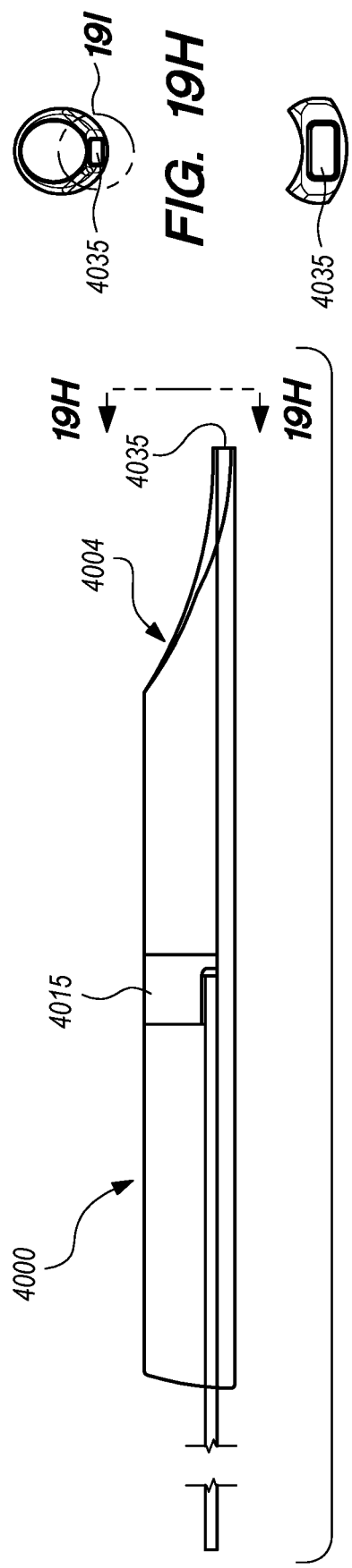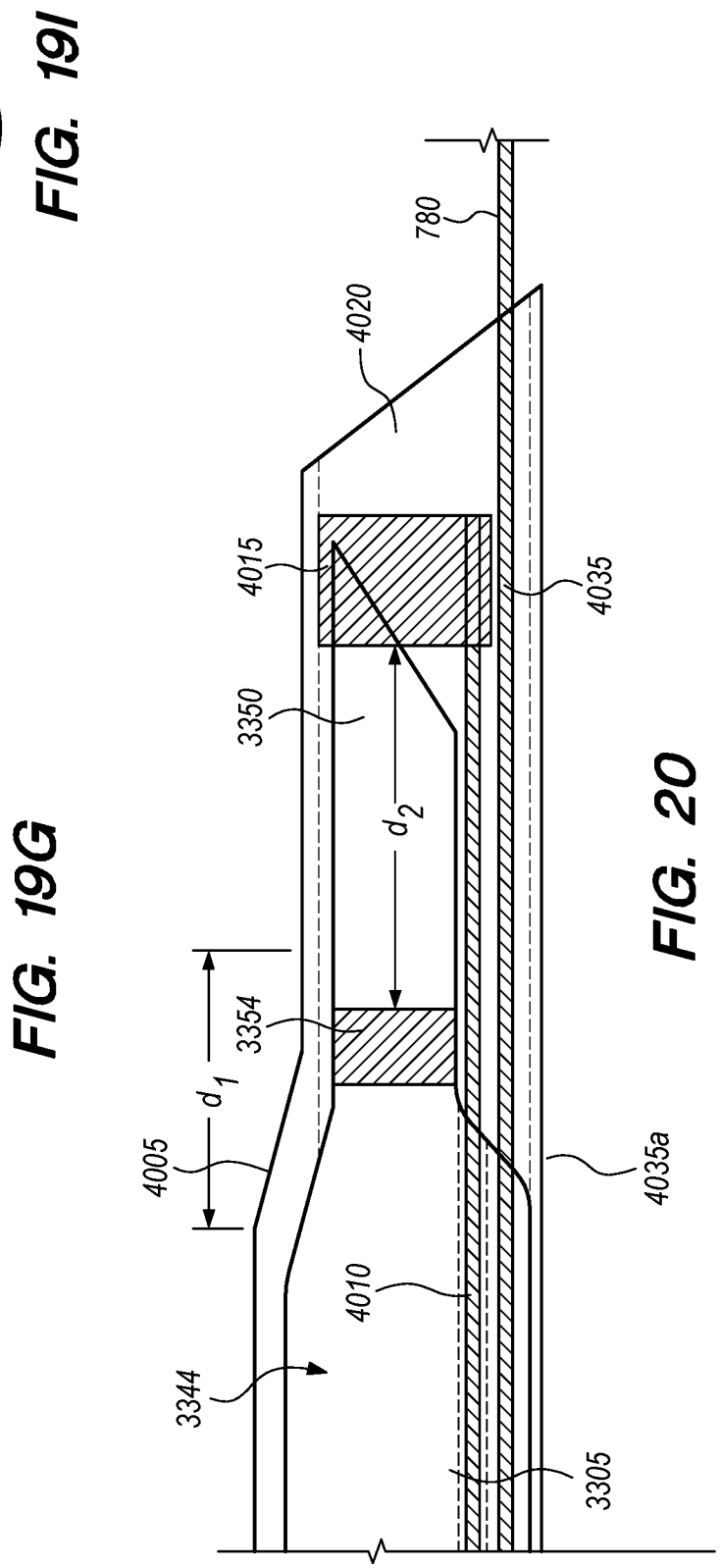

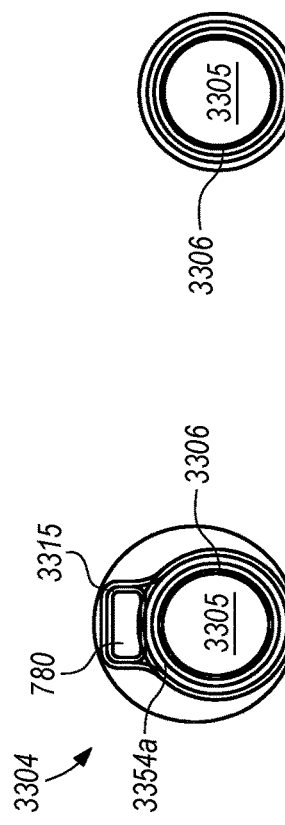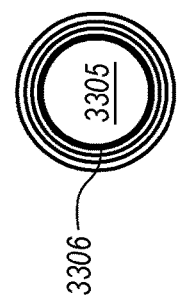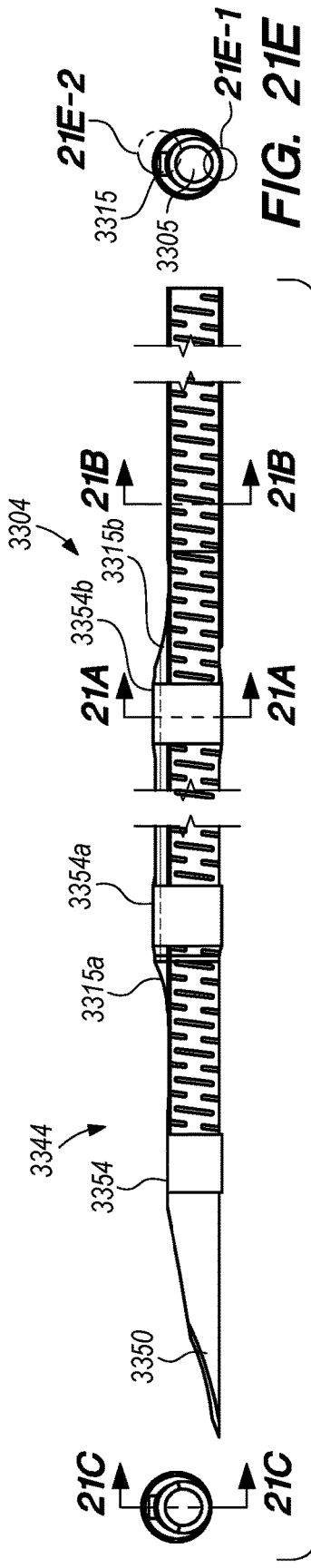

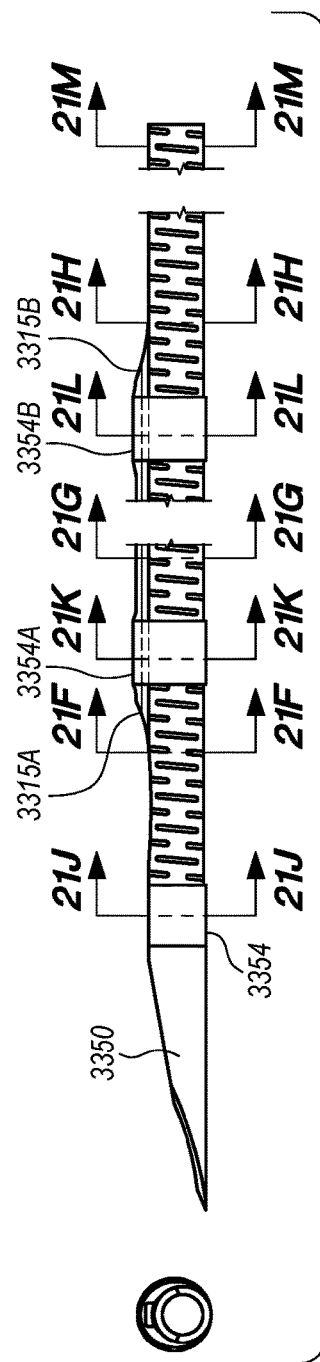

| PRODUCT NAME | GAUGE SIZE | MANUFACTURER | WALL TYPE | BEVEL LENGTH | BEVEL SHAPE | OTHER INFO |
|---|---|---|---|---|---|---|
| EXCEL HYPODERMIC NEEDLES | 22G | EXCEL INTERNATIONAL MEDICAL PRODUCTS | ULTRA-FINE | REGULAR | | |
| EXCEL HYPODERMIC NEEDLES | 20G | EXCEL INTERNATIONAL MEDICAL PRODUCTS | ULTRA-FINE | REGULAR | | |
| TERUMO HYPODERMIC NEEDLES | 22G | TERUMO MEDICAL CORPORATION | ULTRA-THIN | | UNIQUE DOUBLE BEVEL | |
| TERUMO HYPODERMIC NEEDLES | 21G | TERUMO MEDICAL CORPORATION | ULTRA-THIN | | UNIQUE DOUBLE BEVEL | |
| TERUMO HYPODERMIC NEEDLES | 20G | TERUMO MEDICAL CORPORATION | ULTRA-THIN | | UNIQUE DOUBLE BEVEL | |
| MERIT ADVANCE ANGIOGRAPHIC NEEDLES: ONE-WALL NEEDLE | 21G | MERIT MEDICAL SYSTEMS, INC. | THIN | | | |
| MERIT ADVANCE ANGIOGRAPHIC NEEDLES: ONE-WALL NEEDLE | 21G | MERIT MEDICAL SYSTEMS, INC. | THIN | | | ECHO TIP |
| MERIT ADVANCE ANGIOGRAPHIC NEEDLES: ONE-WALL NEEDLE | 20G | MERIT MEDICAL SYSTEMS, INC. | THIN | | | |
| MERIT ADVANCE ANGIOGRAPHIC NEEDLES: ONE-WALL NEEDLE | 20G | MERIT MEDICAL SYSTEMS, INC. | THIN | | | ECHO TIP |
| BD PRECISIONGLIDE NEEDLES | 21G | BECTON, DICKINSON AND COMPANY | THIN WALL IV | REGULAR | | |
| BD PRECISIONGLIDE NEEDLES | 20G | BECTON, DICKINSON AND COMPANY | | REGULAR | | |
| BD PRECISIONGLIDE NEEDLES | 20G | BECTON, DICKINSON AND COMPANY | | SHORT | | |
| BD PRECISIONGLIDE NEEDLES | 19G | BECTON, DICKINSON AND COMPANY | THIN | REGULAR | | |
| BD NOKOR FILTER NEEDLES | 19G | BECTON, DICKINSON AND COMPANY | 5 MICRON THIN | | | |

*FIG. 22A*

| | | | | | | |
|---|---|---|---|---|---|---|
| HSW FINE-JECT | 21G | HENKE-SASS, WOLF GmbH | THIN | | | |
| HSW FINE-JECT | 20G | HENKE-SASS, WOLF GmbH | THIN | | | |
| MONOJECT STANDARD HYPDOERMIC NEEDLE | 23G | COVIDIEN | REGULAR | REGULAR | QUINCKE | |
| MONOJECT STANDARD HYPDOERMIC NEEDLE | 22G | COVIDIEN | REGULAR | | QUINCKE | |
| MONOJECT STANDARD HYPDOERMIC NEEDLE | 21G | COVIDIEN | REGULAR | | QUINCKE | |
| MONOJECT STANDARD HYPDOERMIC NEEDLE | 20G | COVIDIEN | REGULAR | REGULAR | QUINCKE | |
| MONOJECT STANDARD HYPDOERMIC NEEDLE | 22G | COVIDIEN | XX | REGULAR | QUINCKE | |
| MONOJECT STANDARD HYPDOERMIC NEEDLE | 21G | COVIDIEN | XX | REGULAR | QUINCKE | |
| NIPRO HYPODERMIC NEEDLE | 22G | NIPRO MEDICAL CORPORATION | ULTRA-THIN | | | |
| NIPRO HYPODERMIC NEEDLE | 21G | NIPRO MEDICAL CORPORATION | ULTRA-THIN | | | |
| X-SHARP PERCUTANEOUS ENTRY THINWALL NEEDLES | 21G | GALT MEDICAL CORP. | THIN | | | ECHOGENIC TIP |
| X-SHARP PERCUTANEOUS ENTRY THINWALL NEEDLES | 21G | GALT MEDICAL CORP. | THIN | | | SMOOTH TIP |
| PERCUTANEOUS ENTRY THINWALL NEEDLES | 21G | GALT MEDICAL CORP. | THIN | | | ECHOGENIC TIP |
| PERCUTANEOUS ENTRY THINWALL NEEDLES | 21G | GALT MEDICAL CORP. | THIN | | | SMOOTH TIP |
| PERCUTANEOUS ENTRY THINWALL NEEDLES | 19G | GALT MEDICAL CORP. | THIN | | | ECHOGENIC TIP |

FIG. 22B

| | | | SMOOTH TIP |
|---|---|---|---|
| PERCUTANEOUS ENTRY THINWALL NEEDLES | 19G | GALT MEDICAL CORP. | THIN |
| TSK STERIJECT PREMIUM DISPOSABLE HYPODERMIC NEEDLE | 22G | TSK LABORATORY | |
| SPINAL NEEDLES | 22G | HART ENTERPRISES, INC. | THIN | SHORT | QUINCKE |

*FIG. 22C*

| *FIG. 22* |
|---|
| *FIG. 22A* |
| *FIG. 22B* |
| *FIG. 22C* |

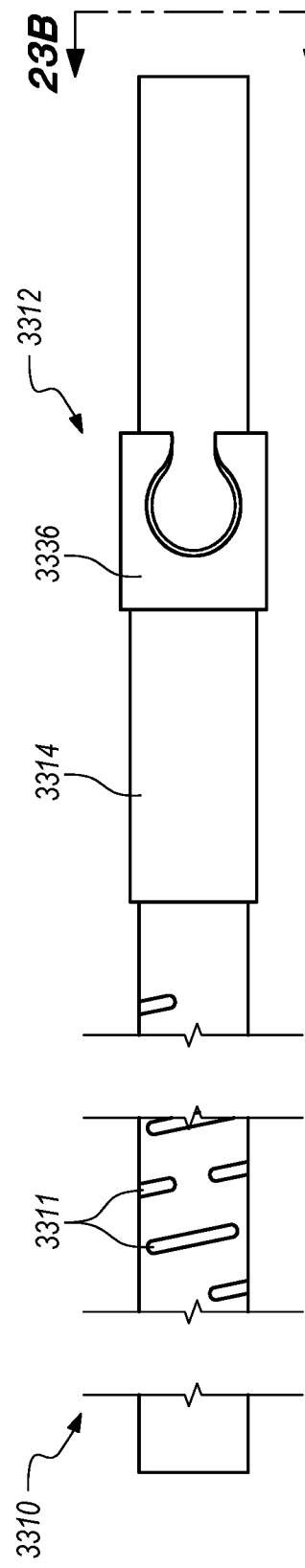
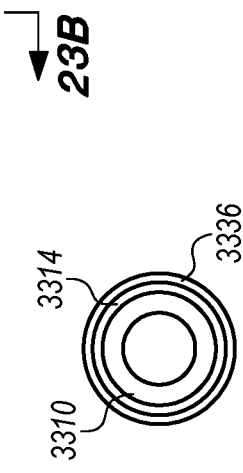
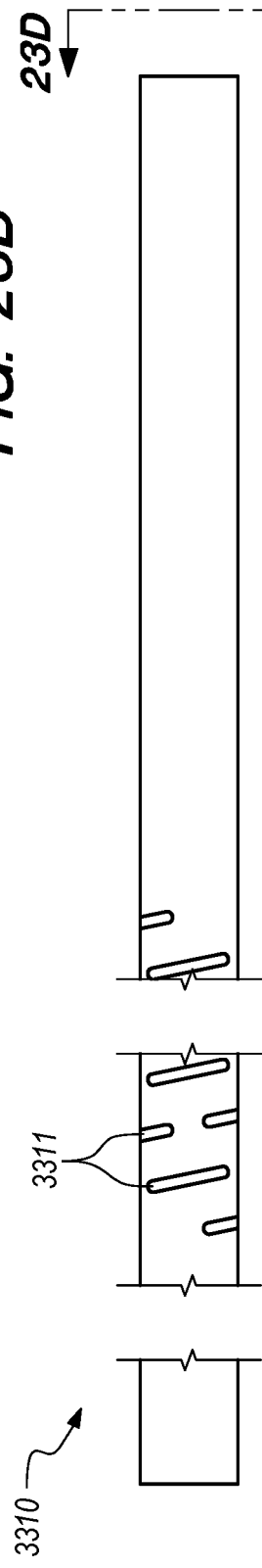
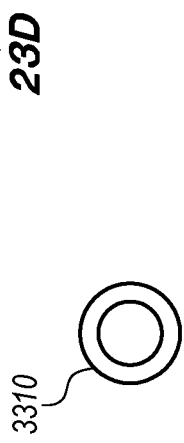

| NEEDLE TIP TABULATED DIMENSIONS |||||||
|---|---|---|---|---|---|---|
| DASH NO. | GAUGE SIZE | ID | OD | POINT | FIRST BEVEL ANGLE | SECOND BEVEL ANGLE |
| -01 | 22XX | .0235 | .028 | QUINCKE | 12° | .070 |
| -02 | 22XX | .0235 | .028 | QUINCKE | 16° | .050 |
| -03 | 22XX | .0235 | .028 | QUINCKE | 19° | .040 |
| -04 | 22XX | .0235 | .028 | QUINCKE | 22° | .040 |
| -05 | 22XX | .0235 | .028 | QUINCKE | 30° | .030 |
| -06 | 21.5 | .024 | .030 | QUINCKE | 12° | .075 |
| -07 | 21.5 | .024 | .030 | QUINCKE | 16° | .050 |
| -08 | 21.5 | .024 | .030 | QUINCKE | 19° | .040 |
| -09 | 21.5 | .024 | .030 | QUINCKE | 22° | .040 |
| -10 | 21.5 | .024 | .030 | QUINCKE | 30° | .030 |
| -11 | 21XT | .025 | .032 | QUINCKE | 12° | .075 |
| -12 | 21XT | .025 | .032 | QUINCKE | 16° | .050 |
| -13 | 21XT | .025 | .032 | QUINCKE | 19° | .040 |
| -14 | 21XT | .025 | .032 | QUINCKE | 22° | .040 |
| -15 | 21XT | .025 | .032 | QUINCKE | 30° | .030 |
| -16 | 21XX | .029 | .032 | QUINCKE | 12° | .075 |
| -17 | 21XX | .029 | .032 | QUINCKE | 16° | .050 |
| -18 | 21XX | .029 | .032 | QUINCKE | 19° | .040 |
| -19 | 21XX | .029 | .032 | QUINCKE | 22° | .040 |
| -20 | 21XX | .029 | .032 | QUINCKE | 30° | .030 |

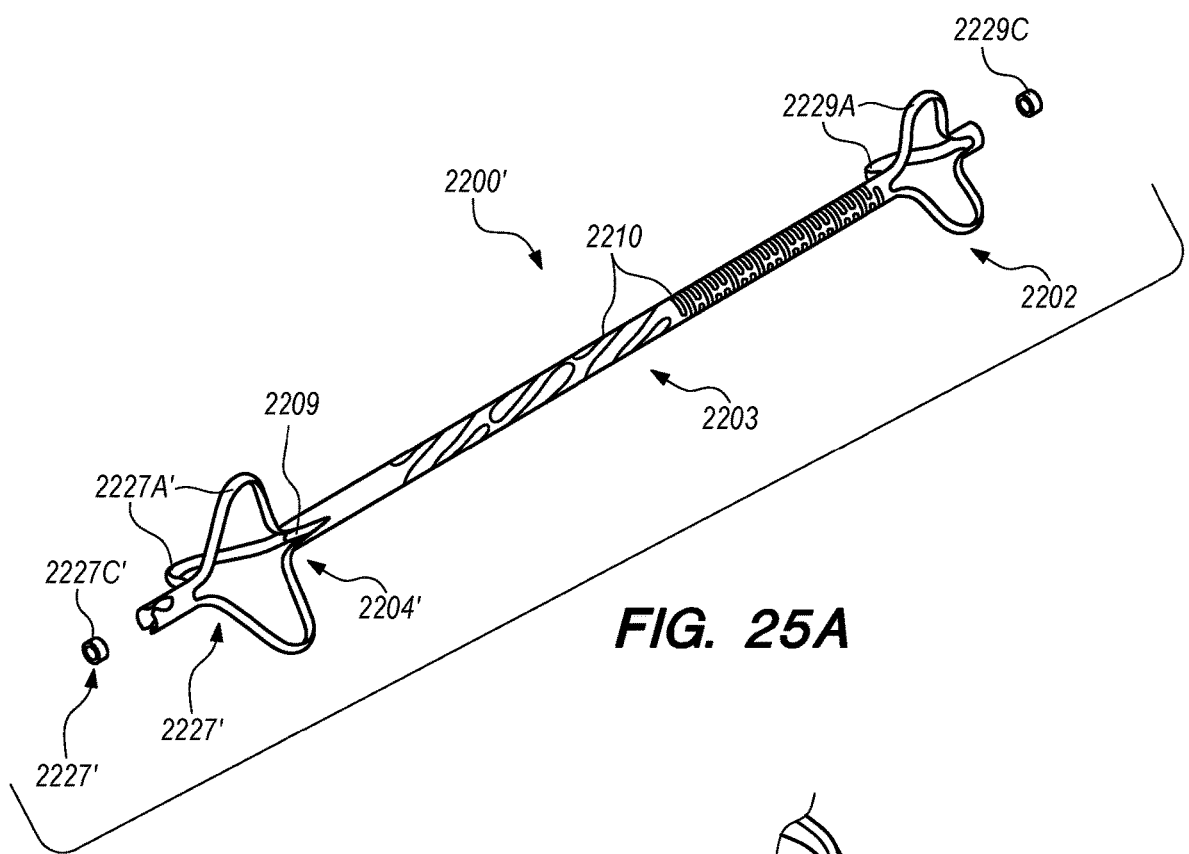
FIG. 25A
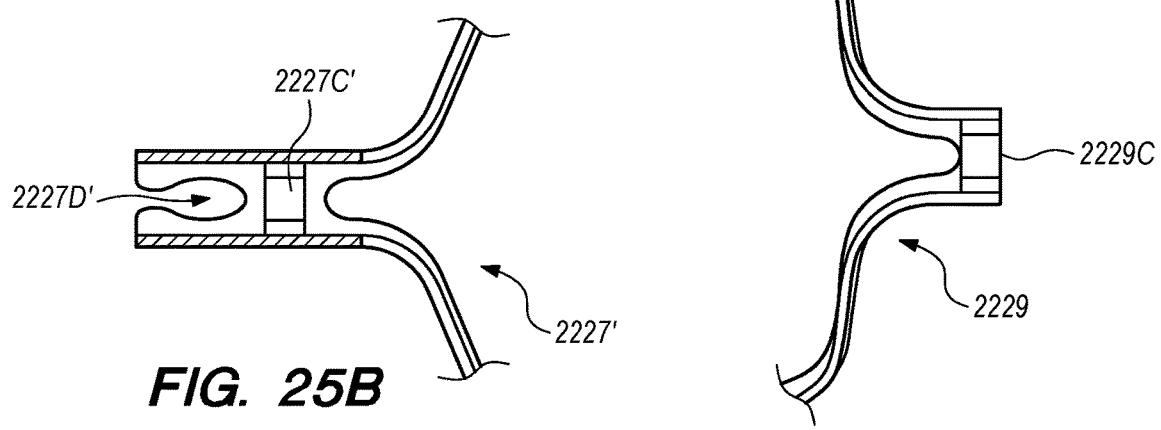
FIG. 25B
FIG. 25C

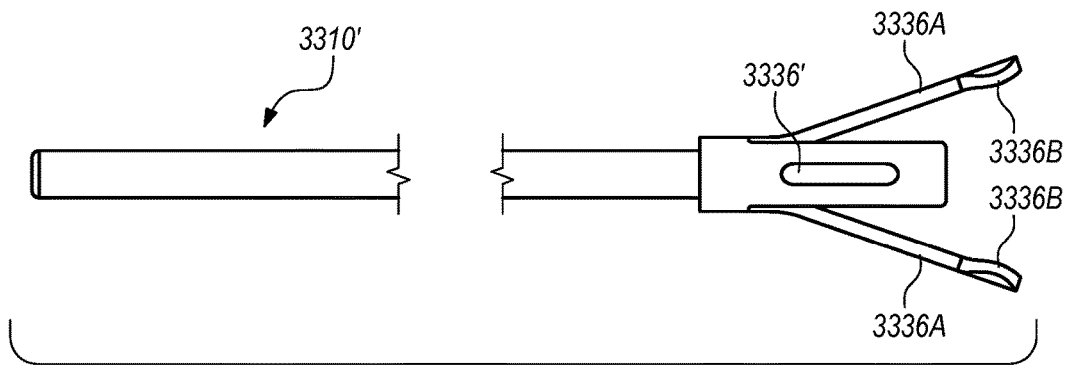
FIG. 26A
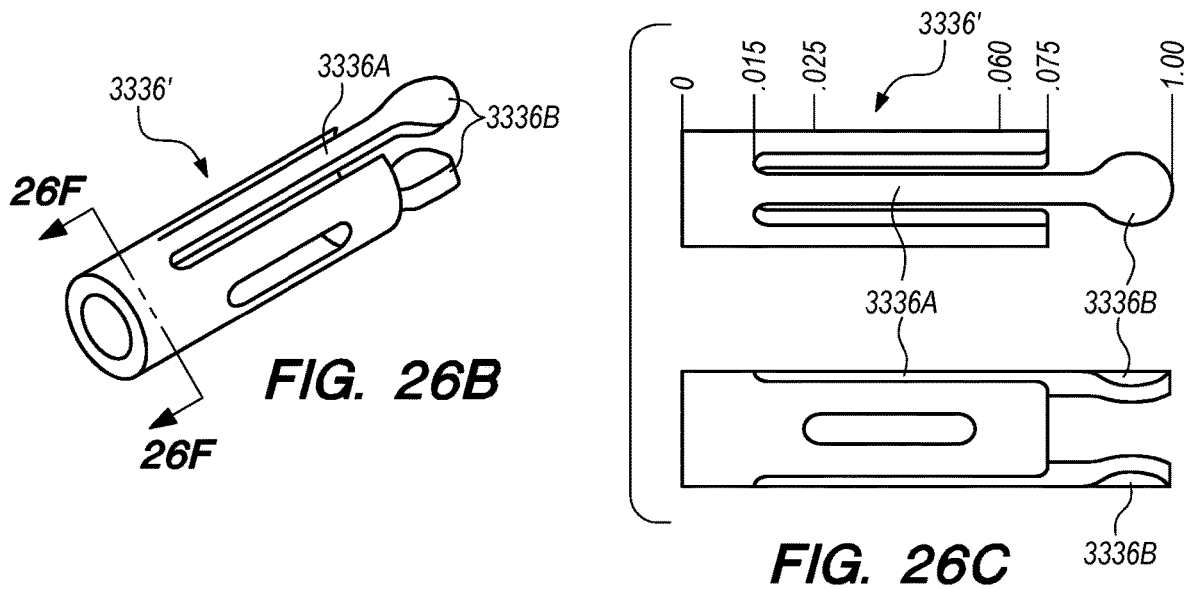
FIG. 26B
FIG. 26C
FIG. 26D
FIG. 26F

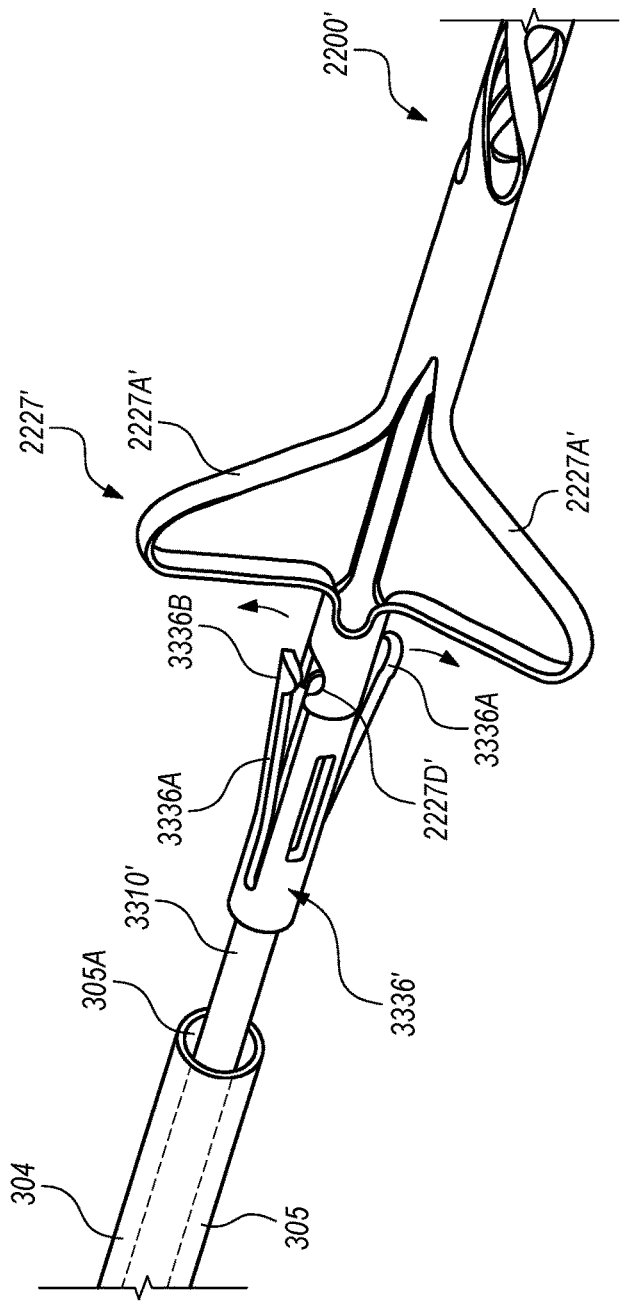
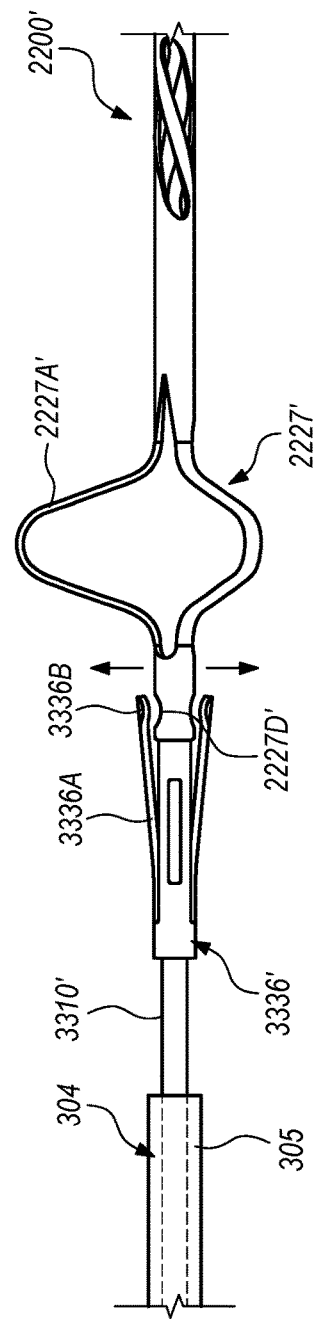
FIG. 27E
FIG. 27F

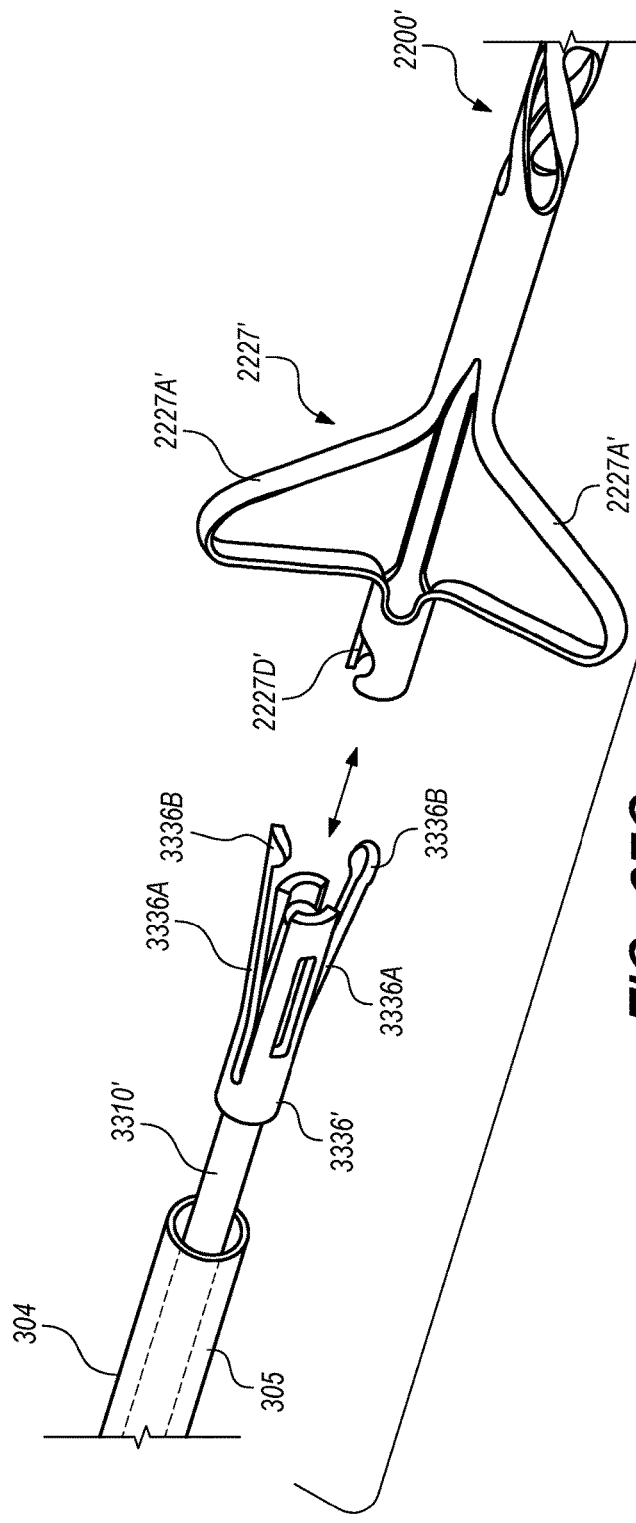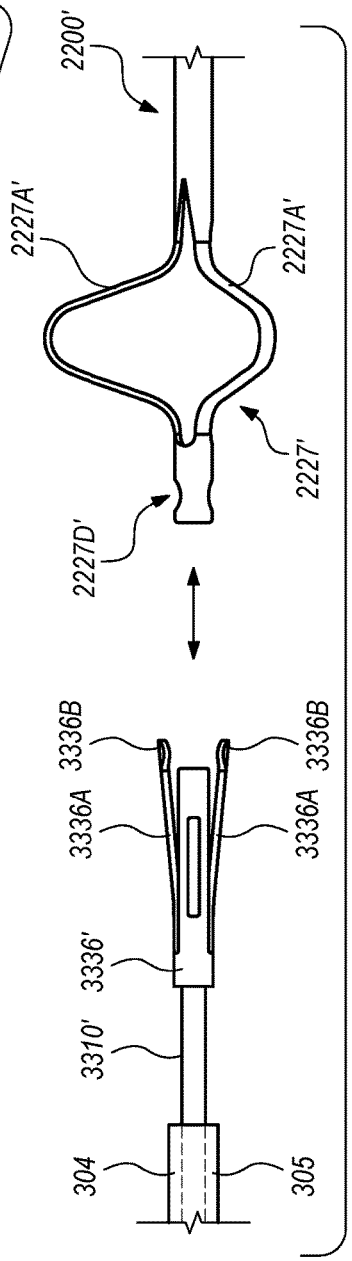

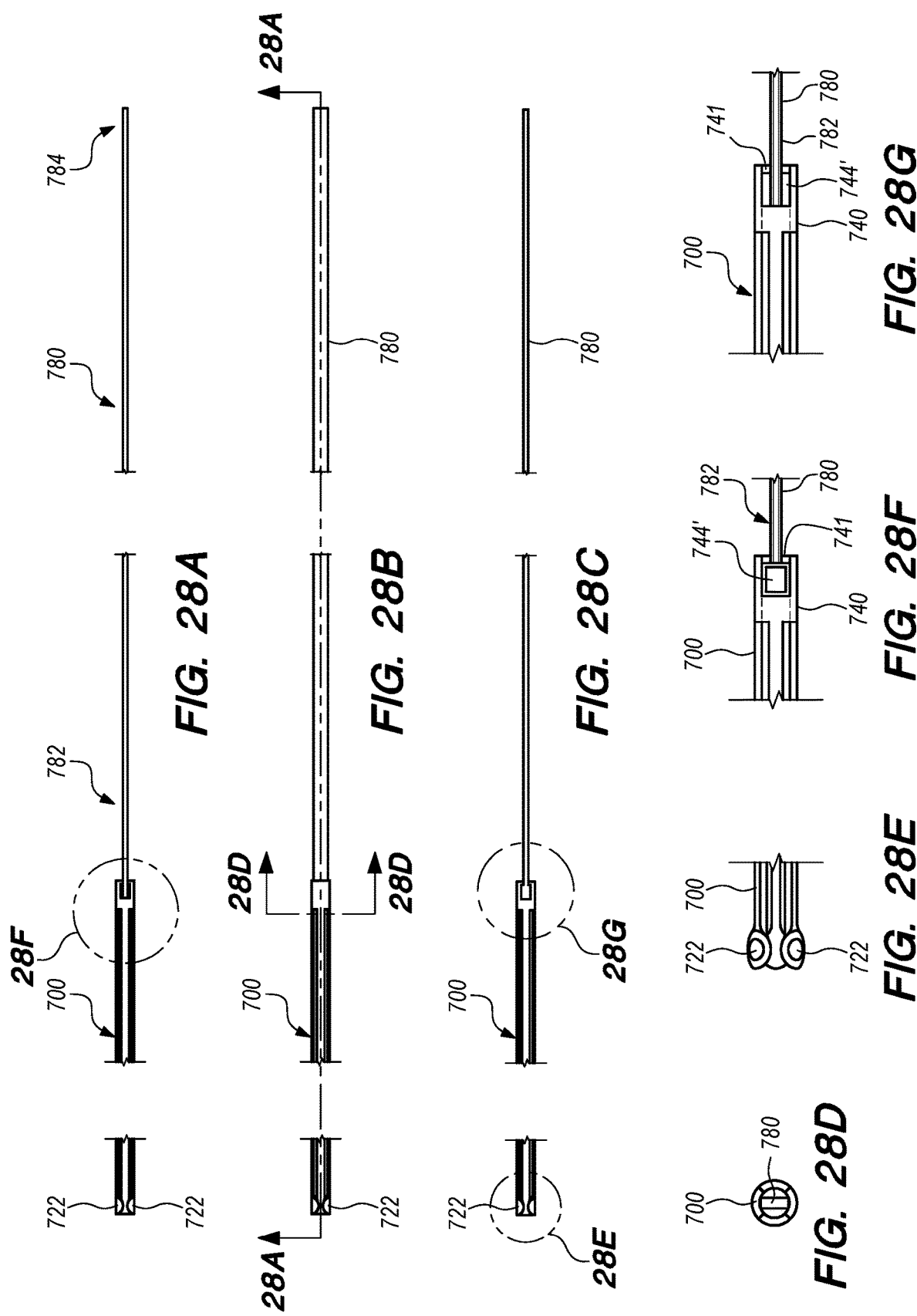

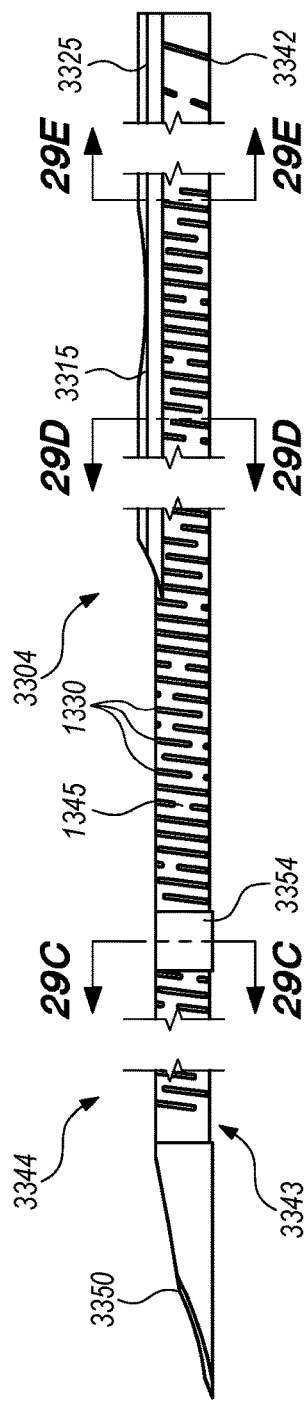
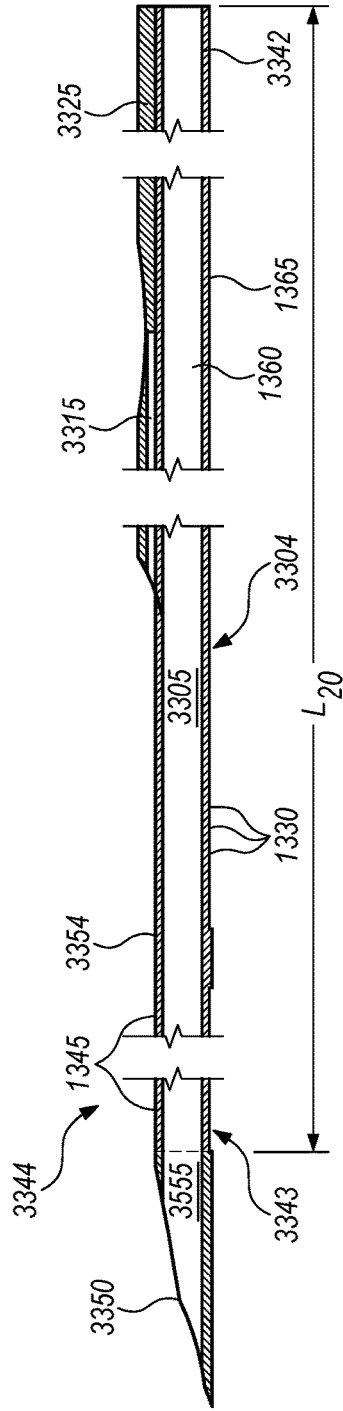
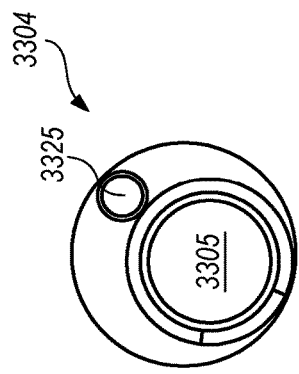
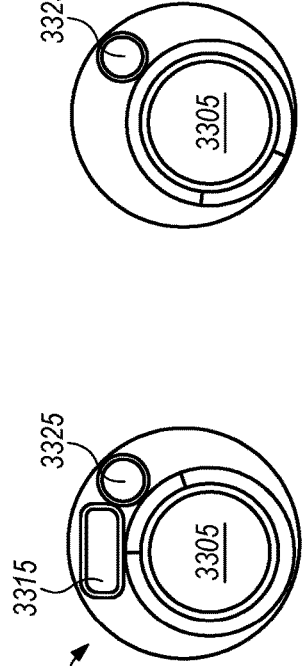
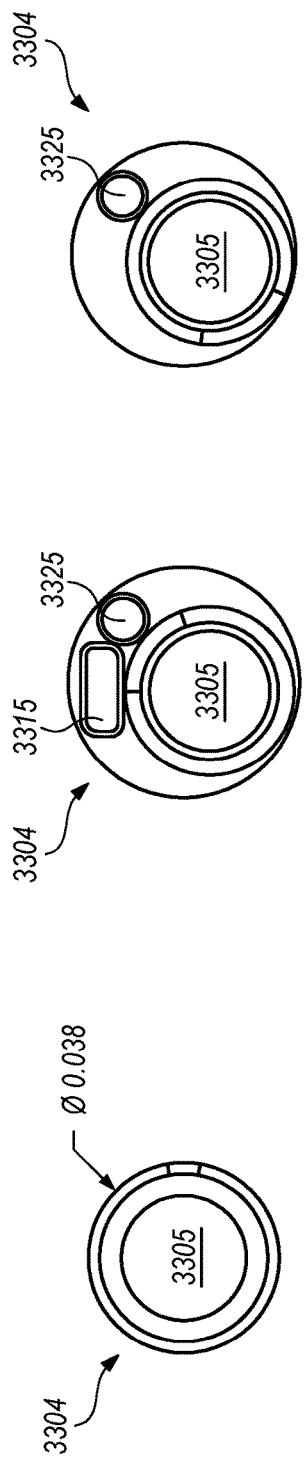

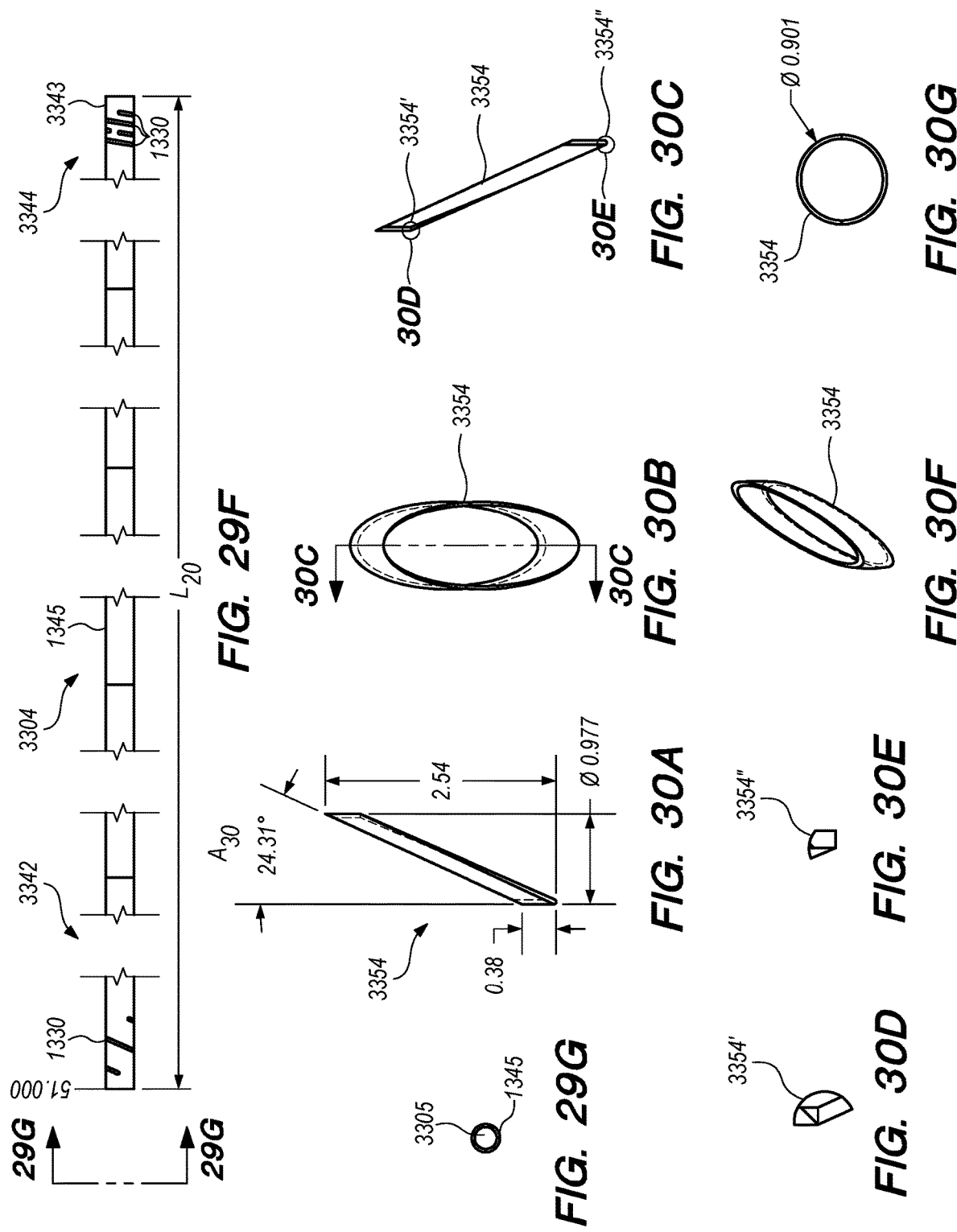

SYSTEMS AND METHODS FOR ENDOVASCULARLY ACCESSING A SUBARACHNOID SPACE

RELATED APPLICATION DATA

The present application is a continuation of pending U.S. patent application Ser. No. 15/745,961, filed on Jan. 18, 2018, which is a National Phase entry under 35 U.S.C. § 371 of International Patent Application No. PCT/US2016/059592, having an international filing date of Oct. 28, 2016, and which claims the benefit under 35 U.S.C. § 119 to U.S. provisional patent application Ser. Nos. 62/249,145, filed Oct. 30, 2015, 62/290,384, filed Feb. 2, 2016, 62/301,523, filed Feb. 29, 2016, 62/332,444, filed May 5, 2016, and 62/406,825, filed Oct. 11, 2016. The present application is related to U.S. patent application Ser. No. 14/929,066, filed on Oct. 30, 2015, which is hereby incorporated by reference into the present application in its entirety.

FIELD OF THE INVENTION

The inventions disclosed herein relate to systems and methods for accessing cerebral cisterns and draining cerebrospinal fluid (CSF), (e.g., to relieve elevated intracranial pressure), using an endovascular approach. More particularly, the present disclosure pertains to systems and methods for treatment of hydrocephalus, pseudotumor cerebri, and/or intracranial hypertension.

BACKGROUND

Hydrocephalus is one of the most common and important neurosurgical conditions affecting both children and adults. Hydrocephalus, meaning "water on the brain," refers to the abnormal CSF accumulation in the brain. The excessive intracranial pressure resulting from hydrocephalus can lead to a number of significant symptoms ranging from headache to neurological dysfunction, coma, and death.

Cerebrospinal fluid is a clear, physiologic fluid that bathes the entire nervous system, including the brain and spinal cord. Cells of the choroid plexus present inside the brain ventricles produce CSF. In normal patients, cells within arachnoid granulations reabsorb CSF produced in the choroid plexus. Arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm $H_2O$. This reabsorption pathway has been dubbed the "third circulation," because of its importance to the homeostasis of the central nervous system.

Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus.

A positive pressure gradient between the intracranial pressure of the subarachnoid space and the blood pressure of the venous system may contribute to the natural absorption of CSF through arachnoid granulations. For example in non-hydrocephalic individuals, intracranial pressures (ICPs) can range from about 6 cm H20 to about 20 cm H20. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

Normal pressure hydrocephalus (NPH) is one form of communicating hydrocephalus. NPH patients typically exhibit one or more symptoms of gait disturbance, dementia, and urinary incontinence, which can lead to misdiagnosis of the disease. Unlike other forms of communicating hydrocephalus, NPH patients may exhibit little or no increase in ICP. It is believed that in NPH the CSF-filled ventricles in the brain enlarge without a significant increase in ICP. This enlargement of the ventricles results in dysfunction of the nerve fibers passing around the walls of the cerebral ventricles. For example, while non-hydrocephalic patients typically have ICPs ranging from about 6 cm H20 to about 20 cm H20, ICPs in NPH patients can also range from about 6 cm H20 to about 20 cm H20. It has been suggested that NPH is typically associated with normal intracranial pressures during the day and intermittently increased intracranial pressure at night.

Other conditions characterized by elevated intracranial pressure include pseudotumor cerebri (e.g., benign intracranial hypertension). The elevated ICP of pseudotumor cerebri causes symptoms similar to, but that are not, a brain tumor. Such symptoms can include headache, tinnitus, dizziness, blurred vision or vision loss, and nausea. While most common in obese women 20 to 40 years old, pseudotumor cerebri can affect patients in all age groups.

Prior art techniques for treating communicating hydrocephalus (and in some cases, pseudotumor cerebri and intracranial hypertension) rely on ventriculoperitoneal shunts ("VPS" or "VP shunt" placement), a medical device design introduced more than 60 years ago. VPS placement involves an invasive surgical procedure performed under general anesthesia, typically resulting in hospitalization ranging from two to four days. The surgical procedure typically involves making two separate skin incisions, one on the scalp and one on the abdomen. A shunt catheter consisting of a pressure or flow regulated valve connected to a long length of silastic tubing is then tunneled from the scalp subcutaneously under the skin down to the abdominal incision. Often additional skin incisions are required to accomplish this tunneling, generally in the mastoid region. Once the shunt valve and tubing are in place under the skin, a burr hole is then drilled into the skull. The dura exposed through the burr hole is opened and a ventricular catheter is then passed directly through the cortex and white matter of the brain into the cerebral ventricles. Once CSF flow is confirmed the ventricular catheter is connected to the valve. The abdominal end of the shunt tubing is then placed into the peritoneal cavity through the abdominal fascia and muscular layer. CSF then flows through the ventricular catheter, valve and distal tubing into the peritoneal cavity and drips on the outside of the intestines where it is resorbed back into the vascular system from which it was created.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage. Among these complications, infection is one of the most serious, since infection rates in adults are reported between 1.6% and 16.7%. These VPS failures require "shunt revision" surgeries to repair/replace a portion or the entirety of the VP shunt system, with each of these revision surgeries carrying the same or similar risk of general anesthesia, post-operative infection, and associated cost of hospitalization as the initial VPS placement; provided, however that shunt infections can cost significantly more to treat (e.g., three to five times more) compared to initial VP shunt placement. Often these infections require additional hospital stays where the abdominal portion of the VPS is externalized and long-term antibiotic therapy is instituted. The rate of failure is a constant consideration by clinicians as they assess patients who may be candidates for VPS placement. Age, existing co-morbidities and other patient-specific factors are weighed against the likelihood of VP shunt failure that is virtually assured during the first 4-5 years following initial VP shunt placement.

Despite significant advances in biomedical technology, instrumentation, and medical devices, there has been little change in the design of basic VPS hardware since its introduction in 1952.

SUMMARY

In accordance with one aspect of the disclosed inventions, a system is provided for implanting an endovascular shunt in a patient, wherein the system includes an expandable anchor configured for being deployed in a dural venous sinus of a patient at a location distal to a curved portion of a wall of an inferior petrosal sinus (IPS) of the patient; an elongate guide member coupled to, and extending proximally from, the anchor; a shunt delivery catheter comprising a first lumen configured to receive the guide member, and a second lumen extending between respective proximal and distal openings in the shunt delivery catheter, a penetrating element coupled to a distal end of the shunt delivery catheter; and a guard at least partially disposed over, and movable relative to, the penetrating element. Without limitation, the dural venous sinus in which the anchor is configured for deployment may be the IPS itself. The anchor is preferably configured to self-expand from a compressed delivery profile to an expanded deployed profile, and wherein the deployed profile is at least twice as large as the delivery profile. In various embodiments, the penetrating element comprises a penetrating element lumen in fluid communication with the second lumen of the shunt delivery catheter.

In various embodiments, the endovascular shunt implantation system may further include an anchor pusher configured for translating the anchor through an anchor delivery catheter for deployment in the dural venous sinus. In one such embodiment, the anchor pusher comprises a handle having a lumen extending therethrough; and a hypo tube coupled to the handle, the hypo tube having a hypo tube lumen that is contiguous with or otherwise extends through the handle lumen, the respective handle and hypo tube lumens being configured to receive the guide member, wherein the handle is configured to grasp a portion of the guide member extending proximally through the handle lumen for thereby pushing the guide member, and thus the anchor, distally through the anchor delivery catheter.

In various embodiments, the first lumen of the shunt delivery catheter extends distally from a first opening in a distal portion of the shunt delivery catheter to a second opening in the distal portion of the shunt delivery catheter that is distal to the first opening and proximal to the distal end opening. The second opening in the distal portion of the shunt delivery catheter is preferably spaced proximally from the distal end opening of the shunt delivery catheter so that the penetrating element is directed to a penetration site on the curved portion of the IPS wall as the shunt delivery catheter is advanced relative to the elongate guide member into the IPS. Further, a depth of penetration into the CP angle cistern by the penetrating element corresponds to the location of the second opening in the distal portion of the shunt.

In one such embodiment, the endovascular shunt implantation system may further include a first radiopaque marker band that reinforces a circumferential portion of the shunt delivery catheter encompassing both the first and second shunt delivery catheter lumens proximate the first opening in the distal portion of the shunt delivery catheter, and a second radiopaque marker band that reinforces a circumferential portion of the shunt delivery catheter encompassing both the first and second shunt delivery catheter lumens proximate the first opening in the distal portion of the shunt delivery catheter.

In a preferred embodiment, the endovascular shunt implantation system further includes a tubular guard body having a first guard body lumen or recess configured to receive the penetrating element, and a pull wire having a distal portion attached to the guard body, wherein the pull wire is configured to translate the guard body proximally or distally relative to the shunt delivery catheter so as to at least partially expose or cover, respectively, the penetrating element. A distal portion of the guard body may be beveled or tapered. In such embodiment, the shunt delivery catheter may include a third lumen extending from the proximal opening to the distal portion of the shunt delivery catheter, wherein the third lumen is configured to receive the pull wire. Further, the guard body may be provided with a second guard body lumen configured to accommodate passage therethrough of the guide member. Such embodiments may further include a first radiopaque marker disposed in or on a wall of the guard body, wherein the guard body is movable relative to the penetrating element so that the first radiopaque marker may be positioned so as to at least partially overlie the penetrating element. For example, the pull wire may be coupled to the first radiopaque marker. Such embodiments may further include a second radiopaque marker disposed in or on the distal portion of the delivery catheter, wherein the guard body is movable relative to the delivery catheter so that the first radiopaque marker at least partially overlies the second radiopaque marker. In one such embodiment, the second radiopaque marker is disposed at an angle with respect to a longitudinal axis of the delivery catheter and indicates an orientation of the penetrating element. In another such embodiment, the second radiopaque marker comprises a marker band that reinforces a circumferential portion of the shunt delivery catheter encompassing both the first and second shunt delivery catheter lumens.

In some embodiments, the guide member is coupled to the anchor at a joint configured to allow the guide member to rotate relative to the anchor about a longitudinal axis of the guide member. In other embodiments, a distal portion of the guide member is coupled to the anchor via a marker disposed within a proximal recess of the anchor.

Embodiments of the disclosed endovascular shunt implantation system further includes an endovascular shunt device disposed in the second lumen of the delivery catheter, and an elongate pusher slidably disposed in the second lumen of the delivery catheter proximal of the endovascular shunt device, wherein the elongate pusher comprises or is otherwise coupled with a distal interlocking element configured to detachably engage corresponding proximal interlocking elements of the endovascular shunt device.

In various embodiments, the delivery catheter has an elongated reinforcing member having a plurality of partial or full fenestrations therein. In one such embodiment, the fenestrations have a first pitch in a proximal portion of the reinforcing member, and a second pitch less than the first pitch in a distal portion of the reinforcing member. In another such embodiment, the fenestrations have a first pitch in a proximal portion of the reinforcing member, a second pitch less than the first pitch in a middle portion of the reinforcing member, and a third pitch greater than the second pitch in a distal portion of the reinforcing member. The elongated reinforcing member may further comprise a strain relief element disposed in the distal portion of the delivery catheter, proximal of the penetrating element.

In accordance with another aspect of the disclosed inventions, methods are provided for implanting an endovascular shunt in a patient to treat hydrocephalus, including normal pressure hydrocephalus, and/or elevated intracranial pressure.

In one embodiment, the shunt implantation method includes deploying an anchor (which may be self-expanding) in an inferior petrosal sinus (IPS) or cavernous sinus (CS) of the patient at a location distal to a curved wall portion of the IPS that separates the IPS from a cerebellopontine (CP) angle cistern of the patient, wherein an elongate guide member extends proximally from the deployed anchor, through the curved portion of the IPS, to or through a location proximate to, or proximal of, a junction of the IPS and a jugular vein (JV) of the patient; and advancing the shunt distally along, on, and/or within the guide member through the junction with the JV, into the IPS, and through a penetration site in the curved portion of the IPS wall, respectively, so that a distal portion of the shunt is disposed within the CP angle cistern, a body of the shunt is disposed within the IPS, and a proximal portion of the shunt is disposed within or proximate to the JV.

In accordance with this method, the shunt is provided with one or more cerebrospinal fluid (CSF) intake openings in the distal portion of the shunt, a valve disposed proximally of the one or more CSF intake openings, and a lumen extending between the one or more CSF intake openings and the valve, and the implantation method further includes anchoring the distal portion of the shunt in the CP angle cistern, and anchoring a proximal portion of the shunt within or proximate to the JV, so that CSF flows from the CP angle cistern and into the JV via the shunt lumen. The method may further include, after advancing the shunt distally via the guide member so that a distal portion of the shunt is at least partially disposed within the CP angle cistern, removing the anchor, or otherwise detaching at least a proximal portion of the guide member from the anchor and/or remaining distal portion of the guide member, and removed from the patient.

In another embodiment, the shunt implantation method includes introducing a delivery system percutaneously through a venous access location in the patient, the delivery system including an expandable anchor and an elongate guide member coupled to the anchor, wherein the delivery system is introduced with the anchor in a compressed delivery configuration; navigating the delivery system through the patient's vasculature to a junction of a jugular vein (JV) and an inferior petrosal sinus (IPS) of the patient; advancing the anchor distally through the junction, and along at least one curved portion of the IPS; and deploying the anchor within the IPS or within a cavernous sinus (CS) of the patient, wherein the anchor is deployed distal to a respective curved portion of the IPS, wherein the anchor is expanded or self-expands upon deployment into an expanded deployed configuration so as to be at least temporarily secured within the respective IPS or CS of the patient, and wherein the guide member extends proximally from the deployed anchor, through the respective curved portion of the IPS, to or through a location proximate to or proximal of the junction of the JV and IPS, wherein the respective curved portion of the wall of the IPS separates the IPS from a cerebellopontine (CP) angle cistern of the patient. By way of non-limiting example, the anchor may be advanced in an anchor delivery catheter, and wherein deploying the anchor comprises expelling the anchor from a distal opening of the anchor delivery catheter. Prior to or while expelling the anchor from the anchor delivery catheter, it may be desirable to confirm (e.g., by imaging) a position and/or orientation of the anchor and/or elongate guide member relative to a targeted penetration site on the respective curved portion of the IPS wall.

The shunt implantation method may include, for example, partially expelling the anchor from the anchor delivery catheter at a first location and/or rotational orientation in the respective IPS or CS, evaluating the position and/or orientation of the anchor and/or guide member relative to the targeted penetration site, at least partially resheathing the anchor within the anchor delivery catheter, rotating and/or translating at least a distal portion of the anchor delivery catheter within the respective IPS or CS, and then fully expelling the anchor from the anchor delivery catheter at a second location and/or rotational orientation in the respective IPS or CS. For example, confirming or evaluating the position and/or orientation of the anchor and/or guide member relative to the targeted penetration site may be accomplished by locating one or more radiopaque markers on the anchor and/or guide member.

The shunt implantation method preferably further includes advancing an endovascular shunt distally along the guide member through the junction with the JV, into the IPS, and through a penetration site in the respective curved portion of the IPS wall, respectively, so that a distal portion of the shunt is disposed within the CP angle cistern, a body of the shunt is disposed within the IPS, and a proximal portion of the shunt is disposed within or proximate to the JV, wherein the shunt is advanced using a shunt delivery catheter having a first lumen configured to receive the guide member, and wherein the shunt is advanced through a second lumen of the shunt delivery catheter into the CP angle cistern. This may be accomplished by advancing a tissue penetrating element coupled to a distal end of the shunt delivery catheter distally through the junction of the JV and IPS, and to the penetration site on the IPS wall. Optionally, a trajectory of the penetrating element toward the CP angle cistern is confirmed prior to or while advancing the penetrating element. The shunt implantation method may further include (i) confirming that the distal portion of the shunt has accessed the CP angle cistern by withdrawing CSF from the CP angle cistern through the shunt or through the second lumen of the shunt delivery catheter, and/or (ii) expanding a distal anchor of the shunt in the CP angle cistern.

In yet another embodiment, the shunt implantation method includes introducing an anchor delivery catheter percutaneously through a venous access location in the patient and navigating the anchor delivery catheter through a jugular vein (JV) and into an inferior petrosal sinus (IPS); advancing an anchor and an elongate guide member coupled to the anchor through a lumen of the anchor delivery catheter; and deploying the anchor out of a distal opening of the anchor delivery catheter at a location within the IPS or other cavernous sinus (CS) that is distal to a curved portion of a wall of the IPS that separates the IPS from a cerebrospinal fluid (CSF) filled cerebellopontine (CP) angle cistern of the patient, wherein the guide member extends proximally from the deployed anchor, through the curved portion of the IPS and JV, respectively, and out of the patient at the venous access location. The implantation method may further includes exchanging the anchor delivery catheter for a shunt delivery catheter via the guide member at the venous access location, wherein the shunt delivery catheter comprises a first lumen configured to receive the guide member; navigating the shunt delivery catheter over the guide member, through the JV, and into the IPS, respectively, until a penetrating element coupled to a distal end of the shunt delivery catheter is positioned proximate the respective curved wall portion of the IPS; advancing the shunt delivery catheter toward the curved portion of the IPS wall so that the penetrating element passes through the IPS wall to access the CP angle cistern; and deploying a distal portion of a shunt into the CP angle cistern out of a second lumen of the shunt delivery catheter. By way of non-limiting example, a portion of the guide member extending through the IPS may be used to orient the respective shunt delivery catheter and penetrating element toward the curved portion of the IPS wall.

In various embodiments of this shunt implantation method, navigating the anchor delivery catheter into the IPS may be performed by navigating a guide wire through the lumen of the anchor delivery catheter and out the distal end opening thereof to access a distal portion of the IPS or other CS of the patient; advancing the anchor through the lumen of the anchor delivery catheter may be performed by advancing the guide member to thereby advance the anchor, wherein the guide member is advanced using an anchor pusher located outside of the patient's body, and wherein the anchor pusher is configured to receive and grasp the guide member; and/or the anchor may be deployed by at least partially expelling the anchor out of the anchor delivery catheter at a first location and/or rotational orientation within the IPS or CS, evaluating the position and/or orientation of the anchor and/or guide member relative to a targeted penetration site on the respective curved portion of the IPS wall, at least partially resheathing the anchor within the anchor delivery catheter, rotating and/or translating at least a distal portion of the anchor delivery catheter within the IPS or CS, and then fully expelling the anchor out of the anchor delivery catheter at a second location and/or rotational orientation within the IPS or CS.

In some embodiments, exchanging the anchor delivery catheter for the shunt delivery catheter is performed by withdrawing the anchor delivery catheter over the guide member and out of the patient at the venous access location; feeding a proximal end of the guide member through the first lumen of the shunt delivery catheter; and advancing the shunt delivery catheter over the guide member, through the venous access location, and into the patient. The method may further include pulling proximally on the guide member while advancing the delivery catheter toward the targeted penetration site.

The penetrating element may have a guard at least partially disposed on (covering) a distal end thereof, in which case the method further comprising retracting a guard proximally to expose the penetrating element after the penetration element is positioned proximate the respective curved portion of the IPS wall. The guard may comprise, without limitation, a tubular guard body and a radiopaque marker embedded within the guard body, and the method may further include observing the radiopaque marker translate proximally towards the a second radiopaque marker in/on the a distal portion of the shunt delivery catheter when retracting the guard to expose the penetration element, and retracting the guard body until the guard radiopaque marker overlaps at least a portion of the shunt delivery catheter radiopaque marker. Retracting the penetrating element guard may be performed by translating a pull wire proximally through a third lumen of the shunt delivery catheter, wherein the pull wire extends through the third lumen between a proximal portion of the pull wire located outside of the patient and a distal portion of the pull wire attached to the guard.

The foregoing shunt implantation method may further include aspirating CSF from the CP angle cistern through the second lumen of the shunt delivery catheter, wherein the CSF is preferably aspirated from the CP angle cistern through the second lumen of the shunt delivery catheter prior to deploying the distal portion of the shunt into the CP angle cistern. The distal portion of the shunt is preferably thereafter anchored within the CP angle cistern, and a proximal portion of the shunt may be anchored in the JV.

Other and further aspects and features of embodiments will become apparent from the ensuing detailed description in view of the accompanying figures.

BRIEF DESCRIPTION OF THE DRAWINGS

FIGS. 10A-K are perspective, side and cross-sectional views of a shunt delivery catheter, according to another embodiment of the disclosed inventions;

FIGS. 11A-I are perspective and cross-sectional views of an anchor and elongate guide member constructed according to yet another embodiment of the disclosed inventions;

FIGS. 12 and 12A-G are side, perspective and cross-sectional views of an elongated member of the shunt delivery catheter, constructed according to embodiments of the disclosed inventions;

FIGS. 13A-F are side, perspective and cross-sectional views of an alternative elongated member of the shunt delivery catheter, constructed according to embodiments of the disclosed inventions.

FIG. 16 is a cross-sectional and perspective view of an alternative shunt delivery catheter, constructed according to embodiments of the disclosed inventions;

FIGS. 17A-C are side, perspective and cross-sectional views of an elongated guide member, constructed according to an alternative embodiment of the disclosed inventions;

FIGS. 18A-E are side, perspective and cross-sectional views of the interface between the elongated guide member and the anchor, according to embodiments of the disclosed inventions;

FIGS. 19A-I are perspective and cross-sectional views of a delivery assembly having a penetrating element guard, according to embodiments of the disclosed inventions;

FIG. 20 is a side view of an penetrating element guard, constructed according to an alternative embodiment of the disclosed inventions;

FIGS. 21A-M are side, perspective and cross-sectional views of another shunt delivery catheter, constructed according to alternative embodiments of the disclosed inventions;

FIG. 22 is table (drawings divided in three pages, as 22A-C) of penetrating element configurations for use with the delivery assemblies constructed according to embodiments of the disclosed inventions;

FIGS. 23A-L are side, perspective and cross-sectional views of the interface between the pusher member and the shunt, according to embodiments of the disclosed inventions;

FIGS. 25A-M are side, perspective and cross-sectional views of a shunt constructed according to embodiments of the disclosed inventions;

FIGS. 26A-F are perspective and cross-sectional views of a pusher member constructed according to embodiments of the disclosed inventions;

FIGS. 27A-H are side, perspective and cross-sectional views of the pusher member and shunt interface, according to embodiments of the disclosed inventions;

FIGS. 28A-D and 28F-G are side and cross sectional views of an alternative interface between the elongated guide member and the anchor, constructed according to embodiments of the disclosed inventions; FIG. 28E is a side view of distal anchor markers, constructed according to embodiments of the disclosed inventions.

FIGS. 29A-E are side, perspective and cross-sectional views of another shunt delivery catheter, constructed according to alternative embodiments of the disclosed inventions; FIGS. 29F-G are side and cross-sectional views of a reinforcing member of the shunt delivery catheter of FIGS. 29A-E, constructed according to embodiments of the disclosed inventions.

FIGS. 30A-G are perspective and side views of a marker constructed according to embodiments of the disclosed inventions;

DETAILED DESCRIPTION OF THE ILLUSTRATED EMBODIMENTS

Figure 1:
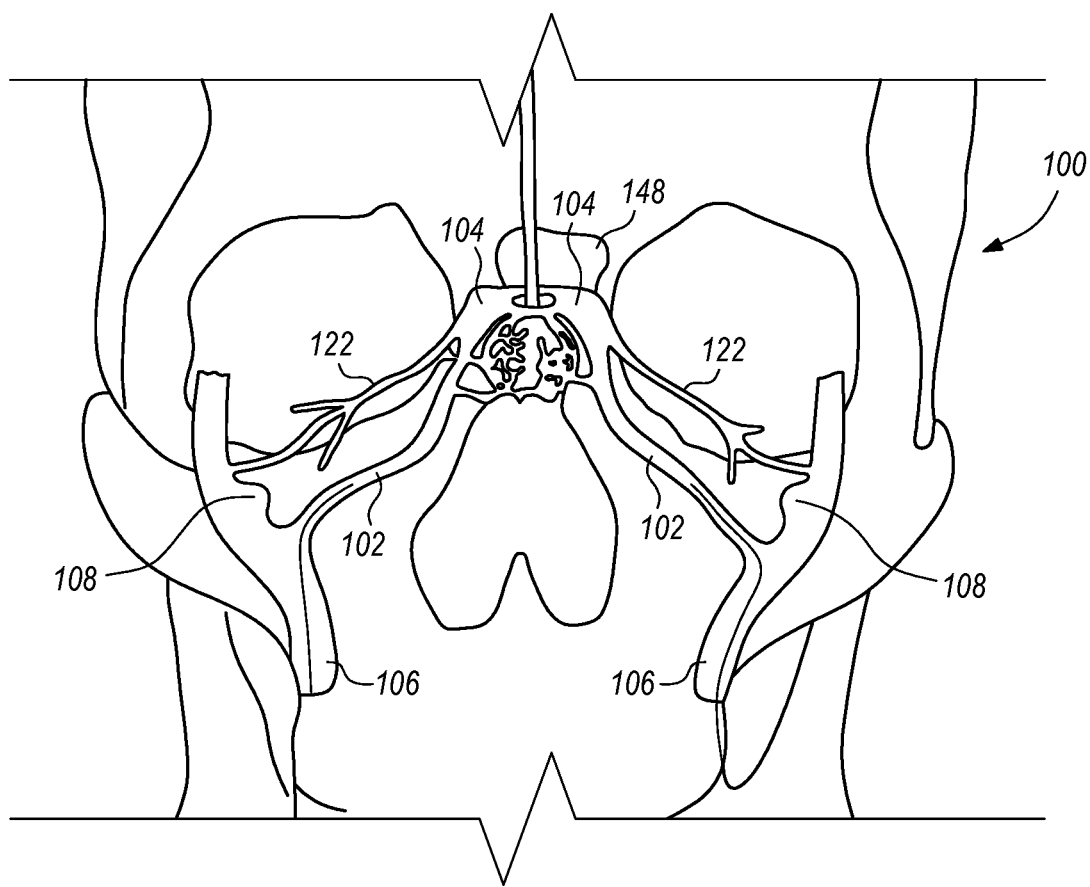
FIG. 1 is a schematic diagram of a head of a human patient.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same or similar function/result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a schematic diagram showing the head 100 of a human patient. Within each side of the patient's head, an inferior petrosal sinus (IPS) 102 connects a cavernous sinus (CS) 104 to a jugular vein 106 and/or a jugular bulb 108. For clarity, the acronym "IPS" is used herein to refer generally to the inferior petrosal sinus and more particularly to the interior space (or lumen) of the inferior petrosal sinus. The IPS 102 facilitates drainage of venous blood into the jugular veins 106. In some patients, the junction of the IPS 102 and the jugular vein 106 occurs within the jugular bulb 108. However, in other patients, this junction can occur at other locations in the jugular vein 106. Moreover, while the IPS 102 in FIG. 1 is a single sinus passageway, in some patients the IPS can be a plexus of separate channels that connect the CS to jugular vein 106 (not shown) and/or jugular bulb 108.

Embodiments of the disclosed inventions are described with respect to a target penetration site in the IPS 102 to access the CSF-filled CP angle cistern 138, which provide a conduit for CSF to flow, via an implanted shunt device, from the subarachnoid space 116 into the jugular bulb 108, jugular vein 106 (FIGS. 1, 2A-B) and/or the superior vena cava-right atrium junction (not shown). The delivery assemblies and shunts described herein can access the target penetration site in the IPS 102 through a venous access location in the patient. The delivery assemblies and shunts described herein can penetrate the dura mater IPS wall 114 and the arachnoid layer 115 to access the CP angle cistern 138 from within a superior petrosal sinus (SPS) 122 (FIG. 1) for delivery and implantation of the shunt at the target site. The dura mater IPS wall 114 is also referred to herein as the dura IPS wall 114, or simply as the IPS wall 114. The SPS is a small diameter venous sinus that connects from the sigmoid sinus (distally located to jugular bulb 108) to the cavernous sinus 104 (FIG. 1). Further, the delivery assemblies and shunts described herein can be advanced through the IPS 102 and into the cavernous sinus 104, so that an anastomosis (not shown) can be created in the upper portion or roof of the cavernous sinus 104 to access the CSP-filled suprasellar cistern 148, shown in FIG. 1, for implantation of the shunt at such target site. Whether penetration to access a target site, deployment and implantation of a shunt occurs from the lumen of the SPS or cavernous sinus to access CSF in the subarachnoid space, the embodiments of the inventions described herein provide a conduit for CSF to flow from the subarachnoid space into the jugular bulb 108, jugular vein 106, and/or the superior vena cava-right atrium junction (not shown).

Figure 2A:
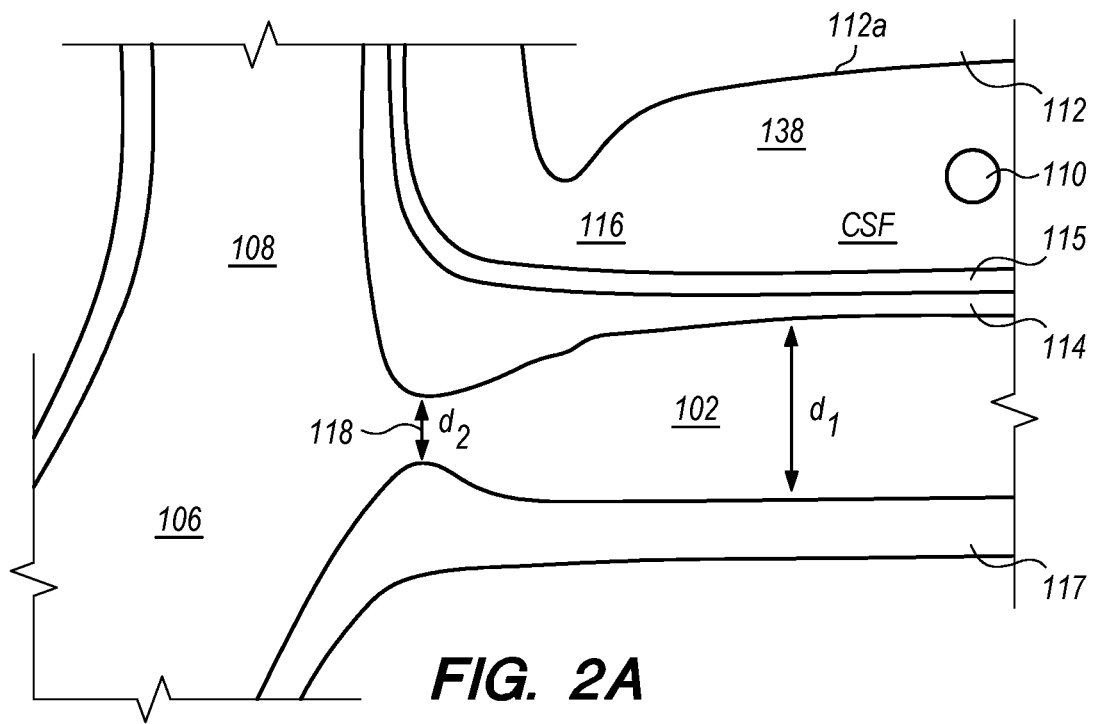
FIG. 2A-D are cross-sectional views of a portion of the head of a human patient.

FIG. 2A shows a cross-sectional view of a portion of head 100, including IPS 102, jugular vein 106, and jugular bulb 108. In addition, basilar artery 110, brain stem 112, pia 112a, and IPS wall 114 are also shown in FIG. 2A. The IPS is a relatively small diameter intracranial venous sinus that facilitates drainage of cerebral venous blood into the jugular vein; the IPS is formed by a cylindrical layer of dura mater, typically about 0.9 mm to 1.1 mm thick for the portion of IPS wall 114 shown in FIG. 2A, which creates a hollow lumen through which blood flows. In the cross-section view of FIG. 2A, the hollow lumen of the IPS resides between upper IPS wall 114 and a lower IPS wall 117, also comprised of dura mater; the IPS itself lies in a bony groove or channel in the clivus bone (not shown) beneath IPS wall 117 in FIG. 2A.

A cross-section of the IPS 102 orthogonal to the plane depicted in FIG. 2A would show that the cylindrical layer of dura mater forming IPS 102 is surrounded by bone for about 270° of its circumference with the remaining portion of the IPS circumference (i.e., IPS wall 114 in FIGS. 2A-B) covered by arachnoid matter 115 and facing CP angle cistern 138. Arachnoid mater 115 (also referred to herein as the arachnoid layer) is a delicate and avascular layer, typically about 0.05 mm to 0.15 mm thick, that lies in direct contact with the dura mater comprising the exterior of IPS wall 114; arachnoid layer 115 is separated from the pia mater surrounding brain stem 112 by the CSF-filled subarachnoid space 116 (e.g., CP angle cistern 138). The lower portion of the IPS 102, opposite to the IPS wall 114 is the IPS wall 117 formed by dura mater that sits in a channel in the clivus bone (not shown).

It should be appreciated that for the embodiments of the disclosed inventions, the methods and devices are configured to create an anastomosis via an endovascular approach by piercing or penetrating from within the hollow IPS 102 to pass through the dura of IPS wall 114, and continue penetrating through the arachnoid layer 115 until reaching the CSF-filled subarachnoid space 116 (e.g., CP angle cistern 138). For ease of illustration, it should be appreciated that the arachnoid matter 115 covering the IPS wall 114 is present, although, not shown in certain figures.

The diameter d1 of IPS 102 is approximately 3 mm but can range from approximately 0.5 mm to about 6 mm. As shown in FIG. 2A, at the junction 118 between the IPS 102 and the jugular bulb 108 and/or jugular vein 106, the diameter d2 of the IPS 102 can narrow. For example, d2 is approximately 2 mm, but can be as small as about 0.5 mm. The length of the IPS 102 from the junction 118 with the jugular vein 106 to the cavernous sinus 104 (shown in FIG. 1) is approximately in a range between 3.5 cm to 4 cm.

Figure 2B:
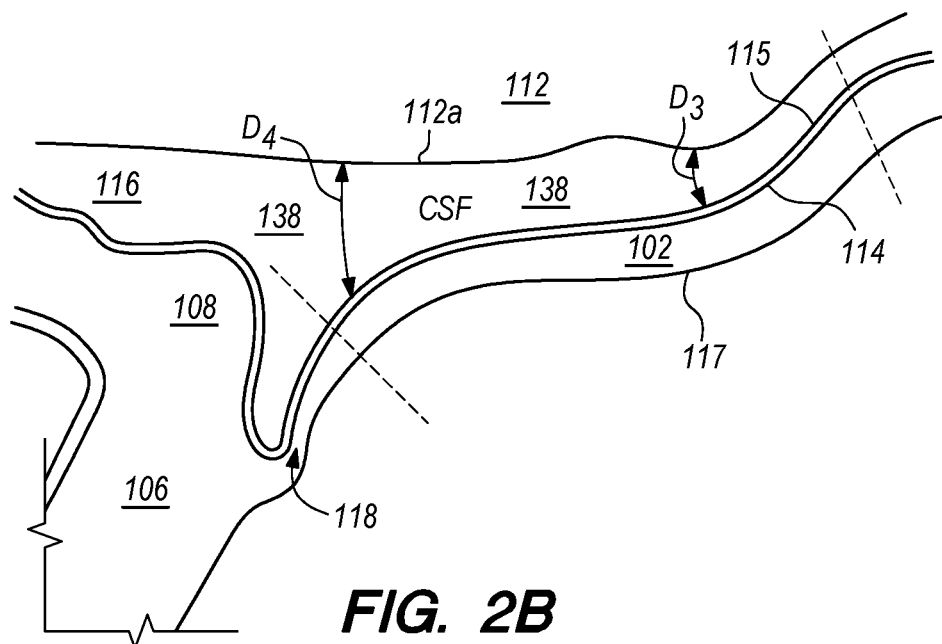

In many patients, the IPS 102 is coupled to the jugular vein 106 at a location disposed below the jugular bulb 108, depicted as junction 118, shown in FIG. 2B. The IPS 102 extends distally from the junction 118 in the medial wall of the jugular vein 106, past the 9th cranial nerve 111A and jugular tubercle (not shown) while curving rostral-medially through a first curved portion 102A shown in FIG. 2C, and then further curving medial-superiorly through a second curved portion 102B shown in FIG. 2C before connecting at the connection point 111B with the cavernous sinus (CS) 104. The IPS 102 extends distally from the junction 118 through a curvature of approximately 45° to 100° in the first and second curved portions 102A and 102B until the IPS 102 connects with the CS 104. The CSF-filled CP angle cistern 138 lies immediately posterior and slightly above the curved portion of the IPS 102.

Figure 2C:
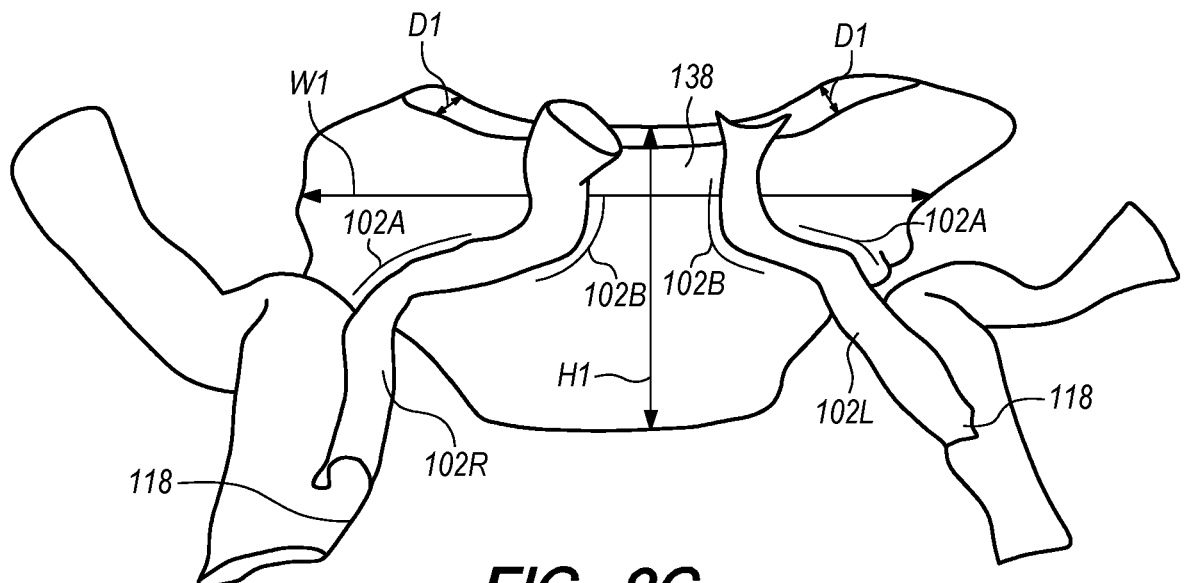
Figure 2D:
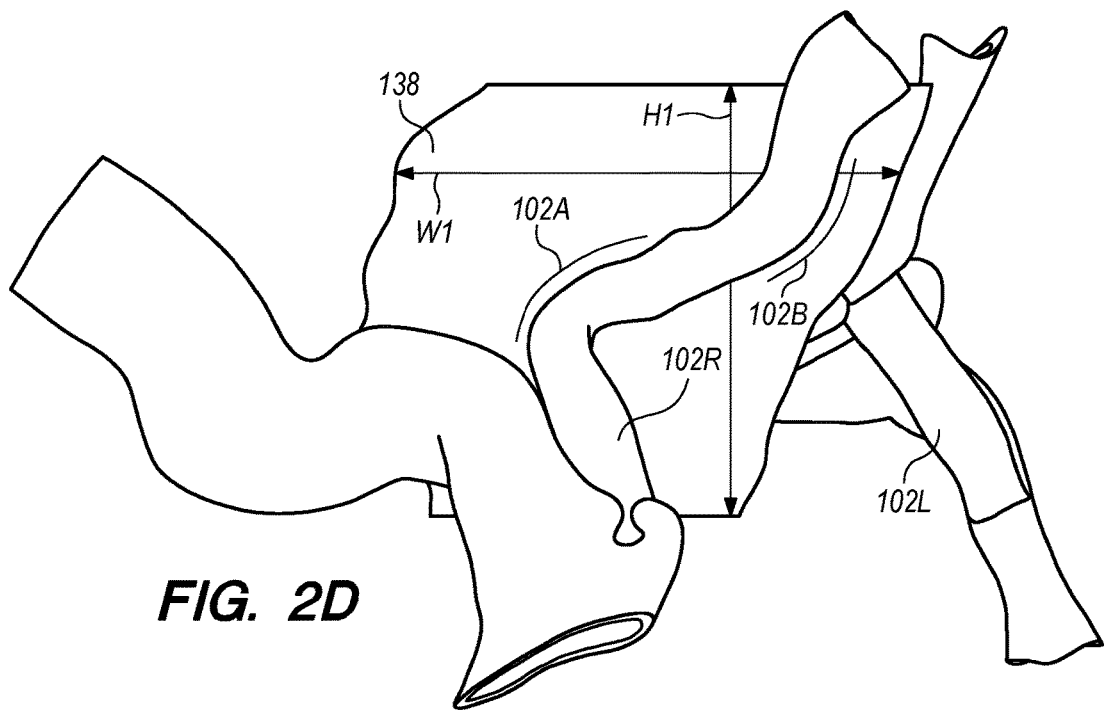

Anatomical features of CP angle cistern 138 provide a large extent of unobstructed, CSF-filled subarachnoid space to accommodate a penetrating element and shunt distal anchoring mechanism as further described herein. FIG. 2C shows a portion of CP angle cistern 138 and the relative proximity of the cistern to a patient's right IPS 102R and left IPS 102L. Beyond the lateral boundaries of the cistern depicted in the figure, the CSF filled subarachnoid space continues circumferentially around the base of the skull, albeit with a lesser extent of CSF space than in CP angle cistern 138. CP angle cistern 138 comprises a depth of free CSF space labelled D1 in FIG. 2C between the skull base and brainstem (not shown, but, e.g., between the anterior portions of the occipital and sphenoid bones and the brain stem). CP angle cistern 138 also comprises a height of free CSF space H1 in FIG. 2C that extends along the base of the skull (not shown, but extending superiorly from the jugular foramen). CP angle cistern 138 further comprises a width extent of free space W1 in FIG. 2C (e.g., extent of free CSF space extending laterally between the right and left jugular foramina, not depicted). CP angle cisterm 138 contains a relatively large volume of CSF, as defined by the exemplary depth D1, height H1, and width W1 dimensions. FIG. 2D shows an alternative view of the same patient anatomy depicted in FIG. 2C, albeit with the D1 cistern dimension portions of left IPS 102L obscured by the view.

As shown in FIGS. 1 and 2C, most patients have two IPS 102 and two jugular veins 106 (left and right). In a very small percentage of patients (e.g., less than 1%), there is no connection between one IPS and the corresponding jugular vein. It is highly unlikely, however, that any given patient will lack connections to the corresponding jugular veins on both left and right IPS.

Subarachnoid spaces are naturally occurring separations between the pia mater and the arachnoid layer where the CSF pools. Typically, the CSF is passed into a subarachnoid space over the cerebral hemispheres and then into the venous system by arachnoid granulations. The subarachnoid space 116 in FIG. 2A corresponds to a cerebellopontine (CP) angle cistern 138, which acts as a reservoir for CSF. In patients with hydrocephalus, a build-up of CSF within the CP angle cistern 138 (in addition to other cisterns and the brain ventricles) can occur, for example, if patients lack properly functioning arachnoid granulations. If the excess CSF is not removed, the resulting excess intracranial pressure can lead to symptoms such as headache, neurological dysfunction, coma, and even death.

Figure 3A:
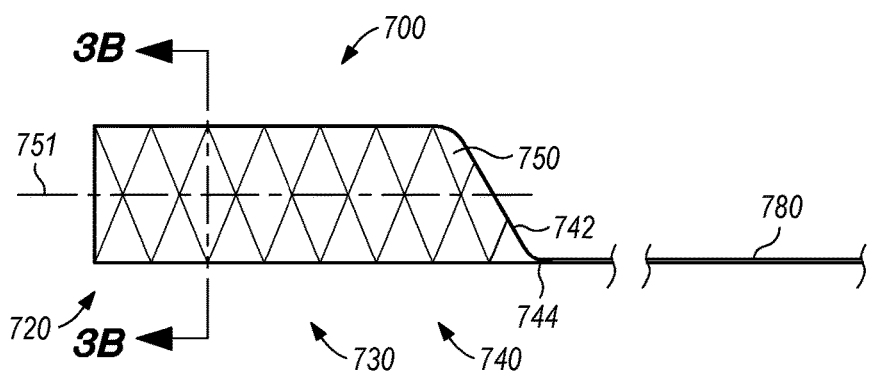
FIG. 3A-J are side, perspective and cross-sectional views of an anchor and elongate guide member, according embodiments of the disclosed inventions.
Figure 3B:
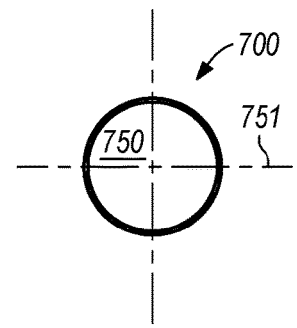
Figure 3C:
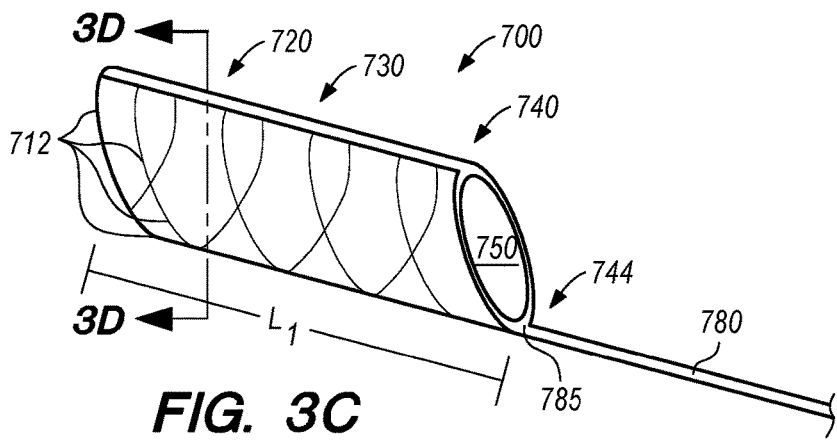
Figure 3D:
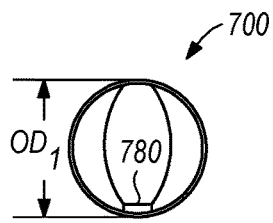
Figure 3E:
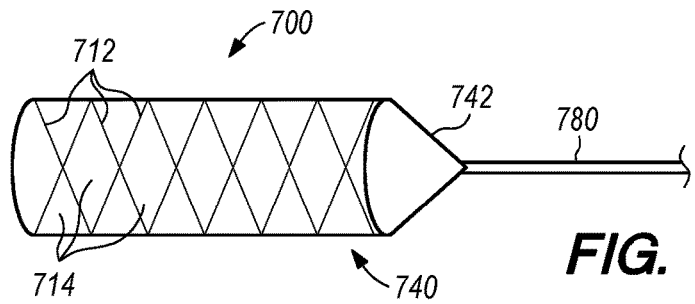
Figure 3F:
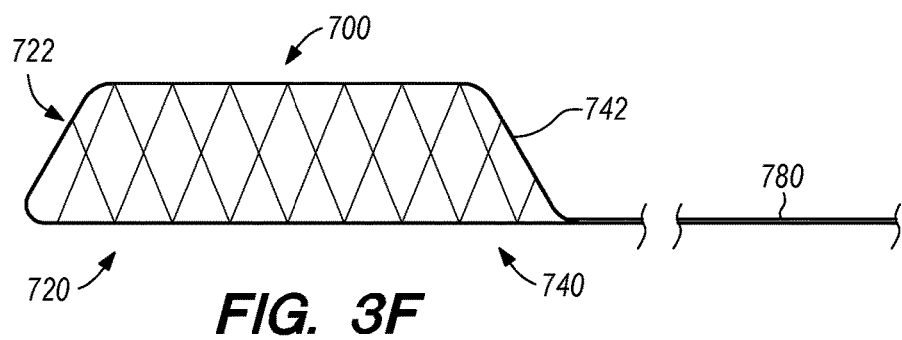
Figure 3G:
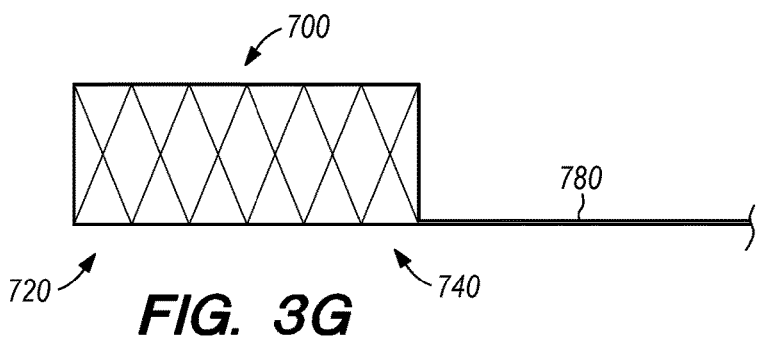
Figure 3H:
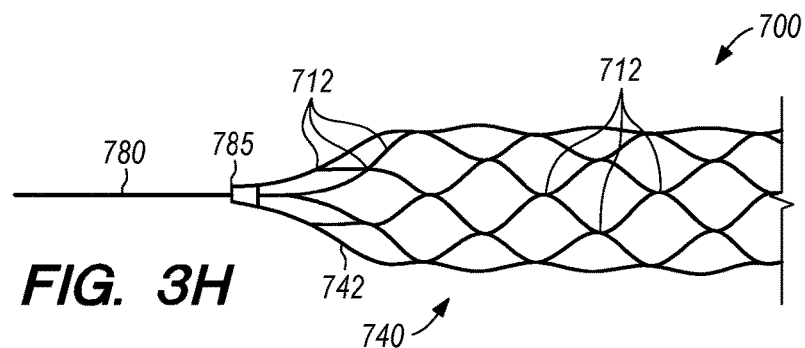

FIGS. 3A-J illustrates exemplary anchor 700, according to the embodiments of the disclosed inventions. The anchor 700 comprises a proximal portion 740, a middle or body portion 730, a distal portion 720 (FIG. 3A), and a lumen 750 extending therebetween (FIG. 3A-B). The proximal portion 740 of FIGS. 3A, 3C, 3E, 3F includes a beveled or tapered proximal section 742. The anchor 700 further comprises an elongate guide member 780 coupled to the proximal portion 740 and/or beveled/tapered proximal section 742. As shown in FIGS. 3A, 3C and 3F, the beveled/tapered proximal section 742 is offset, as the taper transitions to the bottom of proximal portion 740 and the elongate guide member 780. Alternatively, the beveled/tapered proximal section 742 may be symmetrical having the elongate guide member 780 centrally disposed, as shown in FIGS. 3E and 3H. Additionally, the distal portion 720 of the anchor 700 may include a beveled/tapered distal section 742, as shown in FIG. 3F. The proximal portion 740 and distal portion 720 of the anchor 700 may taper at a variety of suitable angles. The proximal portion 740 of the anchor 700 may comprise a strut or plurality of struts 712 directly or indirectly coupled to the elongate guide member 780 (e.g., FIG. 3E, 3H). In an alternative embodiment, the anchor 700 proximal portion 740 and distal portion 720 terminates at approximately 90° angle (i.e., without tapering), as shown in FIG. 3G.

The anchor 700 may be composed of suitable materials, such as, platinum, Nitinol®, gold or other biocompatible metal and/or polymeric materials, for example, silicon, or combinations thereof. In some embodiments, the anchor 700 may include materials that are compatible with magnetic resonance imaging and have radiopacity sufficient to allow the use of known imaging techniques. In some embodiments, the anchor 700 is composed of shape memory, self-expandable and biocompatible materials, such as Nitinol®, or other super-elastic alloys, stainless steel, or cobalt chromium, and comprises a stent-like configuration. In other embodiments, the anchor 700 may include other suitable configurations, such as tubular prosthesis, flow diverter, clot retriever, or the like. Alternatively, the anchor 700 can be composed of magnesium, zinc, or other bio-absorbable or dissolvable components.

Figure 3I:
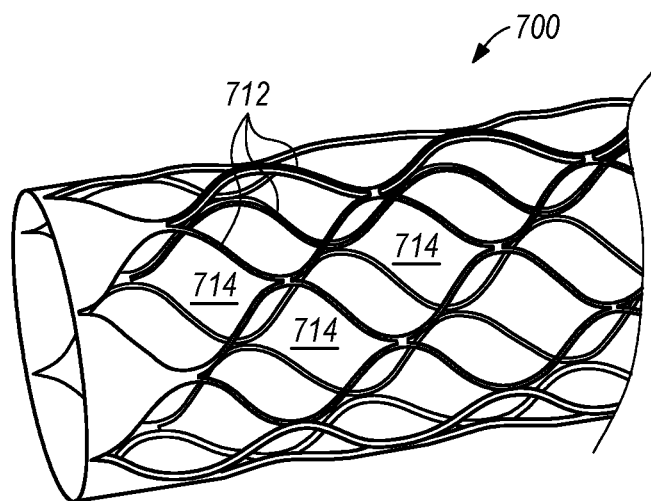
Figure 3J:
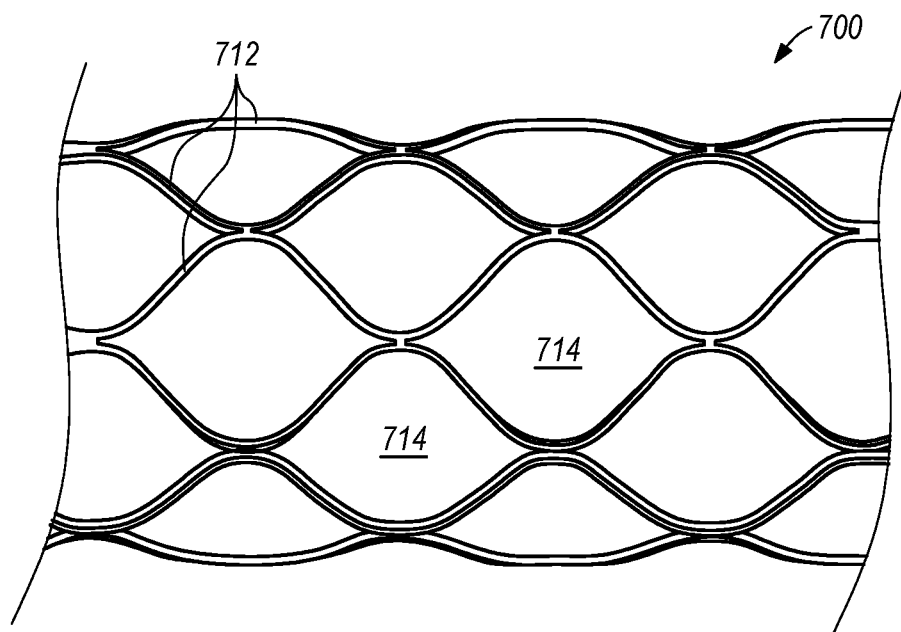

The anchor 700 may be formed by laser cutting a flat sheet, a tubular member, or other suitable configuration of the described materials into interconnected struts 712 forming an open or closed cell pattern having a plurality of cells 714, as shown by the closed cell patterns in FIGS. 3A and 3C-H. Detailed portions of exemplary closed cell patterns of the anchor 700 having the plurality of struts 712 defining the plurality of cells 714 are shown in FIGS. 3I-J. Other suitable techniques may be used to form the closed (or open) cell pattern of the anchor 700, such as etching, or having a plurality of wires braided, woven, or coupled together (not shown). The anchor 700 further comprises a radially collapsed or delivery configuration and, a radially expanded or deployed configuration. In the deployed configuration the anchor 700 is configured to radially expand and anchor itself within the IPS 102 or CS 104. The anchor 700 may include a length L1 of approximately 2 mm to approximately 20 mm, in the radially expanded configuration (FIG. 3C). The anchor 700 may include an outer diameter OD1 of approximately 2 mm to approximately 6 mm or larger, in the radially expanded configuration (FIG. 3D). The anchor 700 is radially compressible about the axis 751 of the lumen 750, and configured to collapse within a catheter (e.g., a micro catheter having an inner diameter of approximately 0.014" to approximately 0.040") such that an operator (e.g., physician, clinician, specialist, or the like) can navigate the collapsed anchor 700 through one or more catheters into the IPS 102 or CS 104.

Figure 12:
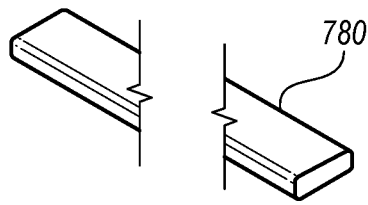

The anchor 700 and the elongate guide member 780 coupled to the proximal portion 740 of the anchor 700 can be manufactured from the same piece of material (e.g., a super-elastic alloy such as Nitinol®), or may comprise separate parts joined at a joint 744 between anchor 700 and the elongate guide member 780. As shown in FIGS. 3A, 3C, 3E-H, the elongate guide member 780 is coupled (e.g., directly or indirectly, attached, secured, joined, or their like) to the proximal portion 740 of the anchor 700. Alternatively, the elongate guide member 780 can be coupled to the distal portion 720, middle portion 730, and/or to any strut or plurality of struts 712 (FIG. 3E, 3H) of the anchor 700 (not shown). The elongate guide member 780 can have a flat, rectangular, or otherwise non-circular, cross-sectional profile, as shown for example in FIG. 3D and FIG. 12. By way of non-limiting example, the elongate guide member 780 can have a rectangular cross-sectional profile with dimensions of approximately 0.001"×0.003" to 0.008"×0.040". An elongate guide member 780 with rectangular cross-sectional profile can provide increased column strength to facilitate navigation of the anchor 700 through a catheter to a target location in IPS 102 or CS 104 and, if necessary, to assist with the re-sheathing of the anchor 700 into a catheter for re-deployment of the anchor 700 prior to penetration of the IPS wall 114/arachnoid layer 115 and deployment of the shunt, or when removing the anchor 700 from the patient's vasculature after the deployment of the shunt. When used with the shunt delivery catheter 3304 including a dedicated lumen 3315 configured to conform to the rectangular cross-sectional profile of the guide member 780 (e.g., as shown in FIG. 10), the elongate guide member 780 maintains the trajectory of the shunt delivery catheter 3304 over the guide member and at the target penetration site by limiting or preventing rotation of the shunt delivery catheter 3304 about or around the guide member 780.

Alternatively, embodiments of elongate guide member 780 can have a circular cross-sectional profile, as shown in FIGS. 17A-C. By way of non-limiting example, an elongate guide member 780 with circular cross-sectional profile can have a diameter of about 0.005" to 0.018" or more. The elongate guide member 780 having a tubular configuration may include a plurality of cuts to increase flexibility, as shown by the exemplary spiral cut pattern of kerf, pitch, cuts per rotation and cut balance depicted in sections of FIGS. 17A-C. Such configurations of the elongate guide member can improve the "trackability" of a delivery catheter over the guide member (e.g., a delivery catheter with a dedicated lumen configured to conform to the guide member profile), and provide the ability to radially orient the delivery catheter and penetrating element about the guide member in the lumen of IPS 102 or CS 104. An elongate guide member 780 with circular cross-sectional profile can provide increased column strength to facilitate navigation of the anchor 700 through a catheter to a target location in IPS 102 or CS 104 and, if necessary, to assist with the re-sheathing of the anchor 700 into a catheter for re-deployment of the anchor 700 prior to penetration of the IPS wall 114/arachnoid layer 115 and deployment of the shunt, or when removing the anchor 700 from the patient's vasculature after the deployment of the shunt. Further, the ability to radially orient the delivery catheter and penetrating element about the guide member in the lumen of IPS 102 or CS 104 can be used to correct the orientation of a mis-loaded delivery catheter over the guide member.

The profile, dimensions, and material for the elongate guide member 780 are configured to resist kinking along the length of the elongate guide member 780 and provide sufficient column strength for anchor deployment and re-sheathing, while still allowing sufficient flexibility for deployment through a delivery catheter by tracking through the curved portion of the IPS 102. Alternatively, the elongate guide member 780 can have a pre-curved distal portion, disposed closer to the joint 744 between anchor 700 and the elongate guide member 780, so as to bias the elongate guide member 780 towards IPS wall 114 or IPS wall 117 when the elongate guide member 780 is deployed through a curved portion of the IPS 102. Further, the joint 744 between the anchor 700 and the elongate guide member 780 may include a rotatable element (FIGS. 18E-F) allowing the elongate guide member 780 to assume a desirable orientation through a curved portion of the IPS 102.

Radiopaque markings or coatings can be incorporated into the anchor 700 and/or elongate guide member 780 to assist with navigation and deployment of the anchor 700 in a sinus lumen distal to a target penetration site on IPS wall 114. The radiopaque markings may be placed on one or more of the following locations along the anchor 700 and elongate guide member 780, as shown in FIG. 3C: in a plurality of struts 712 at the distal portion 720 of the anchor 700; along L1, with or without rotationally varying marker placement along the middle or body portion 730 of the anchor 700 to further aid navigation and orientation; at the joint 744 between anchor 700 and the elongate guide member 780, and/or on or around the first full-diameter portion of anchor 700 at the proximal portion 740.

Figure 4A:
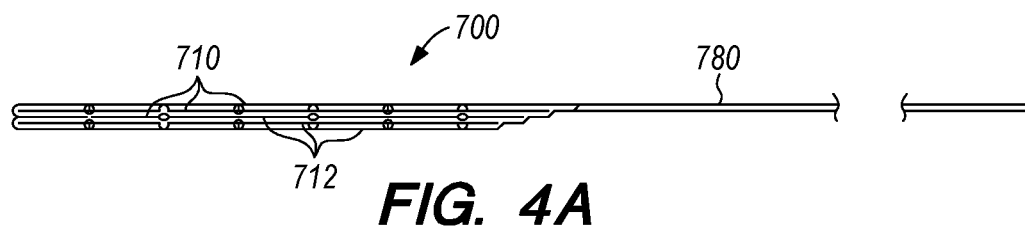
FIG. 4A-C are perspective and cross-sectional views of an anchor and elongate guide member, according another embodiment of the disclosed inventions.
Figure 4B:
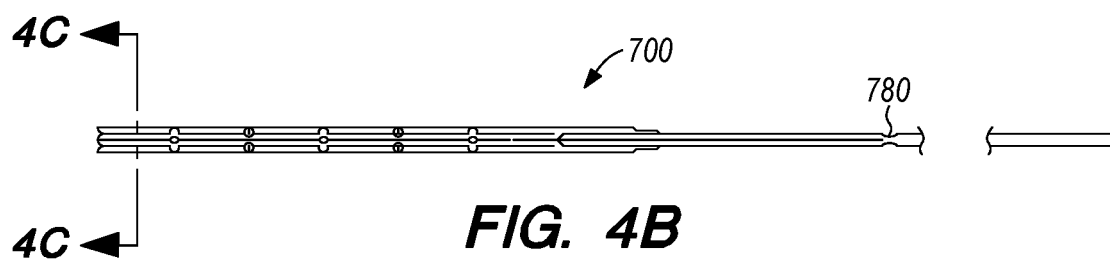
Figure 4C:
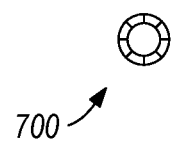
Figure 5A:
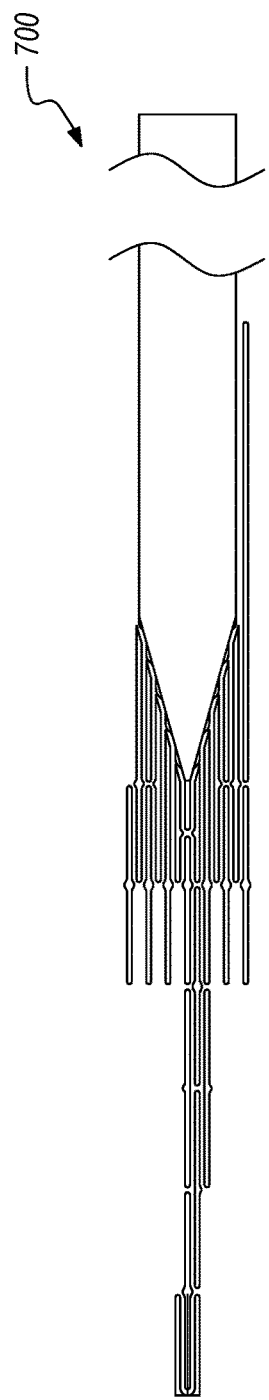
FIGS. 5A-W are perspective and cross-sectional views of an anchor, according other embodiments of the disclosed inventions.
Figure 5B:
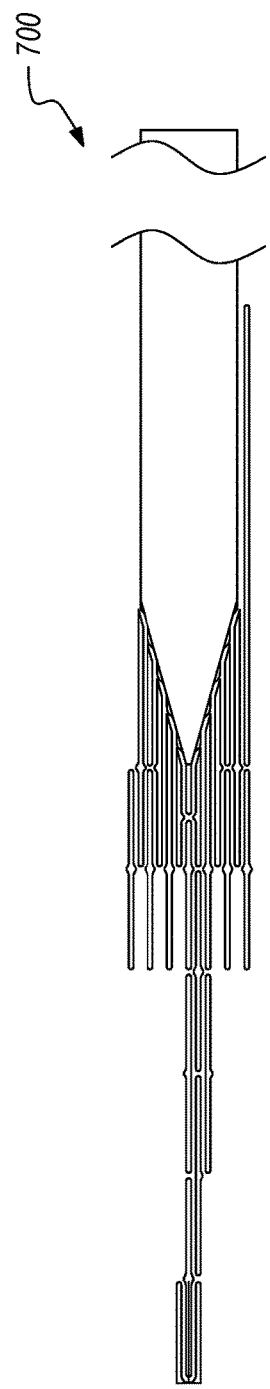
Figure 5C:
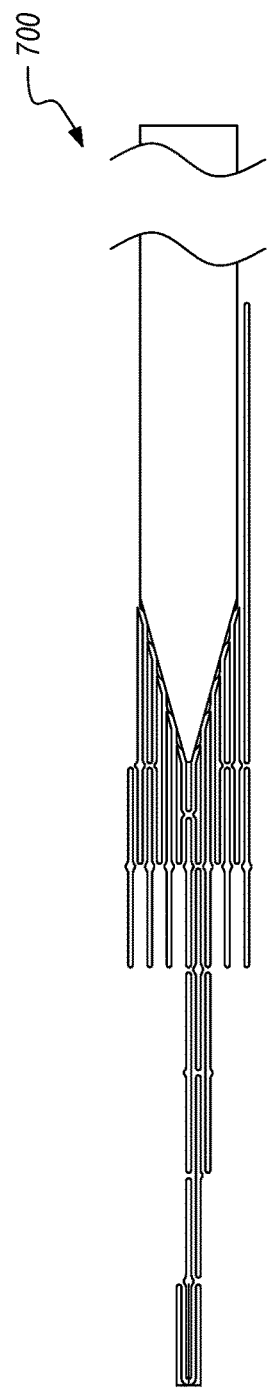
Figure 5G:
Figure 5H:
Figure 5I:
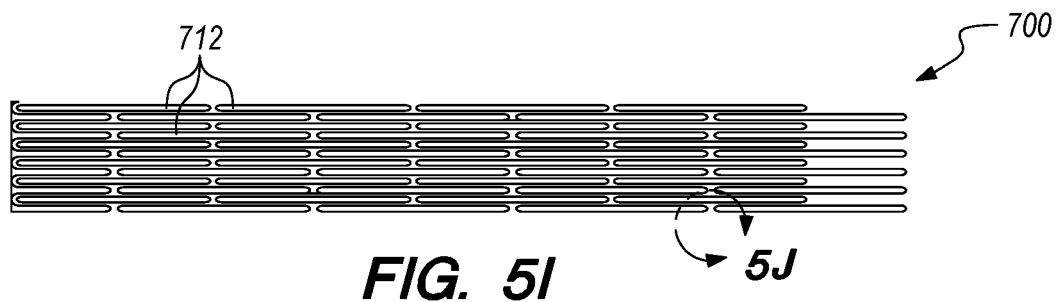
Figure 5J:
Figure 5K:
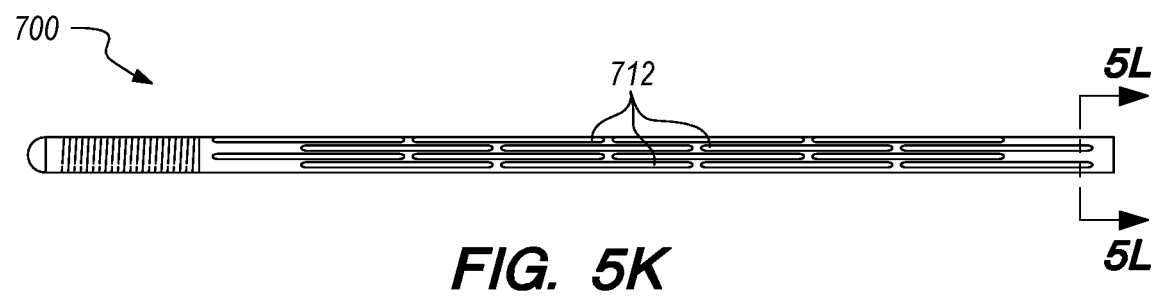
Figure 5L:
Figure 5M:
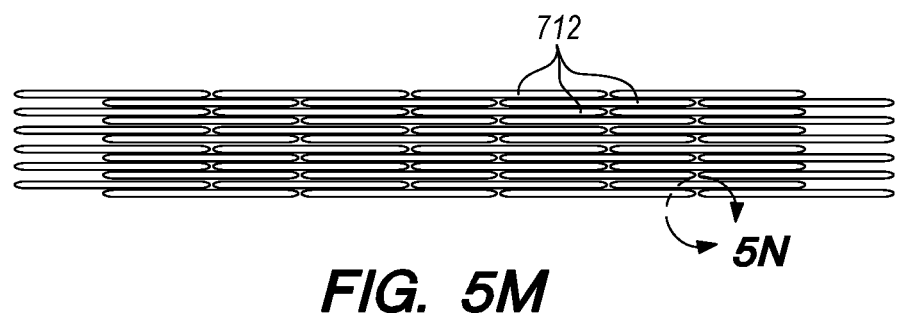
Figure 5N:
Figure 5U:
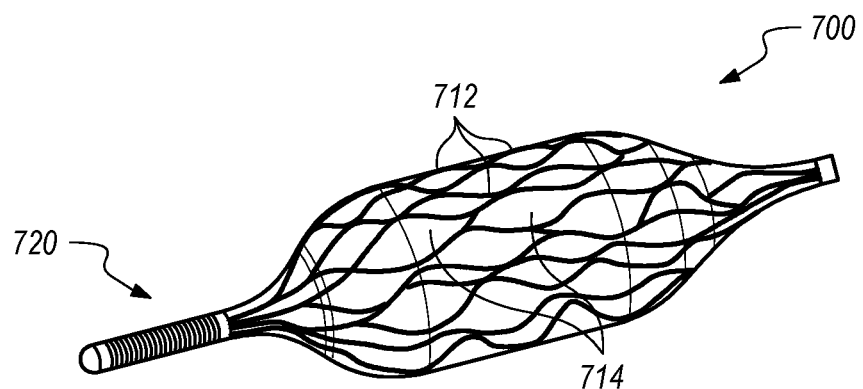
Figure 5V:
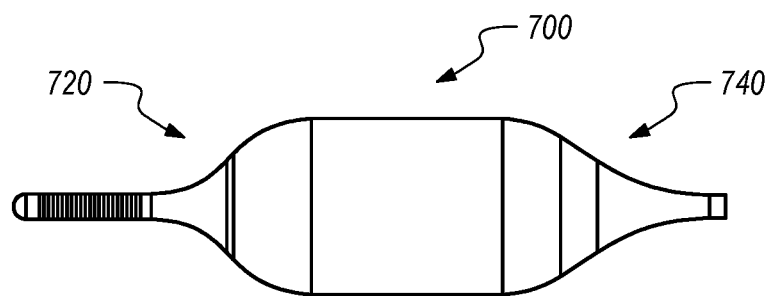
Figure 5W:
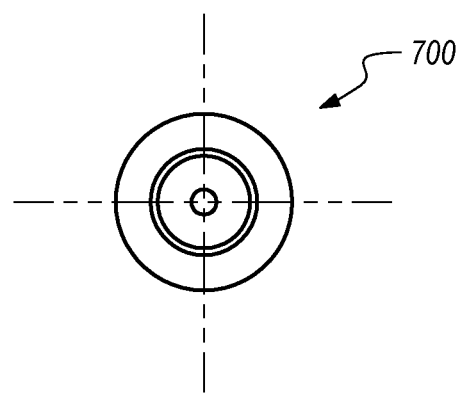

FIGS. 4A-C illustrate another exemplary anchor 700, constructed according to embodiments of the disclosed inventions. FIG. 4A-B depict respective side views, and FIG. 4C depicts a cross-sectional view of the anchor 700, comprising a plurality of cuts 710 (e.g., fenestrations or the like) forming a stent-like configuration, having a plurality of struts 712. The anchor 700, the elongate guide member 780, cuts 710 and/or the patterns of the cuts 710 may be manufactured by selectively cutting a tubular element using any suitable cutting method (e.g., laser cutting, etching or their like). FIGS. 5A-W depicts exemplary dimensions and cut patterns of the anchor 700, constructed according to embodiments of the disclosed inventions. The struts 712 of the anchor 700 form a plurality of spaces or cells 714 therebetween. The cells 714 include a closed cell pattern when the anchor 700 is in the radially expanded configuration, as for example shown in FIGS. 3E, 3H-J, 5O and 5U, and a closed cell pattern when the anchor 700 is in the radially compressed configuration, as for example shown in FIGS. 4A, 5G, and 5K. In one embodiment of the anchor 700, the cut pattern shown in the radially compressed configuration in FIG. 5G, is configured to form the radially expanded configuration of the anchor 700 shown in FIG. 5O. FIGS. 5P-T illustrate exemplary dimensions and properties of the anchor 700 of FIGS. 5G and 5O, such as the variations of the beveled/tapered proximal portions 740. Varying the taper in the proximal portion 740 (e.g., as described by the transition length measurements of FIG. 5T) can facilitate smooth anchor deployment and retrieval when paired with an appropriately sized catheter (e.g., catheter with 0.027" inner diameter). In an alternative embodiment of the anchor, the cut pattern shown in the radially compressed configuration in FIG. 5K, is configured to form the radially expanded configuration of the anchor 700 shown in FIG. 5U. FIGS. 5V-W illustrate exemplary dimensions and properties of another embodiment of anchor 700 of FIG. 5U, such as having beveled/tapered proximal portion 740 and distal portion 720. The beveled/tapered distal portion 720 of anchor 700 depicted in FIG. 5U, and corresponding flexibility provided by the spiral cut pattern of such distal portion shown in FIG. 5K, facilitates access to remote, narrowing, and/or tortuous regions of the intracranial venous anatomy such as IPS 102 and CS 104. For illustration purposes, FIGS. 5P-S and 5V-W are depicted without the struts 712 and cells 714 of the anchor 700 to better appreciate the dimensions and properties of the anchor 700 in said figures (in a radially expanded configuration). However, it should be appreciated that the anchor 700 of FIGS. 5P-S and 5V-W includes the struts 712 and cells 714 of their respective FIGS. 5O and 5U The struts 712 and cells 714 of the anchor 700 substantially extend along the length L1, as for example shown in FIG. 3C in the radially expanded configuration, and in FIG. 5G in the radially compressed configuration. However, the struts 712 and cells 714 may extend along selected portions of the anchor 700, as for example shown in FIG. 5U at the distal portion 720. Additionally, the anchor 700 can include a mesh framework between the struts 712 to increase the friction between the anchor 700 and IPS 102 (or CS 104), further securing the anchor 700 at or about the target site when deployed. The struts 712 of anchor 700 can have flat, round, elliptical, or irregularly shaped profiles or suitable cross-sections. The width of the struts 712 can vary from approximately 0.0030" to 0.0045", or larger. Additionally, the struts 712 can be configured to exhibit a negative Poisson's ratio under strain such that, after deployment in a sinus lumen (e.g., IPS 102 or CS 104), applying a retrograde force to anchor 700 (e.g., by pulling proximally on the anchor 700 via the elongate guide member 780) further expands the struts 712 radially outward to secure the anchor 700 at the target site.

Dimensions referenced in FIGS. 5A-5W in brackets (e.g., [14.67]) are provided in millimeters, while all other dimensions referenced in FIGS. 5A-5W without brackets are provided in inches. It should be appreciated that the dimensions depicted in FIGS. 4A-5W are exemplary dimensions of the anchor 700, which are not intended to limit the embodiment of the anchor 700 disclosed herein.

Figure 6:
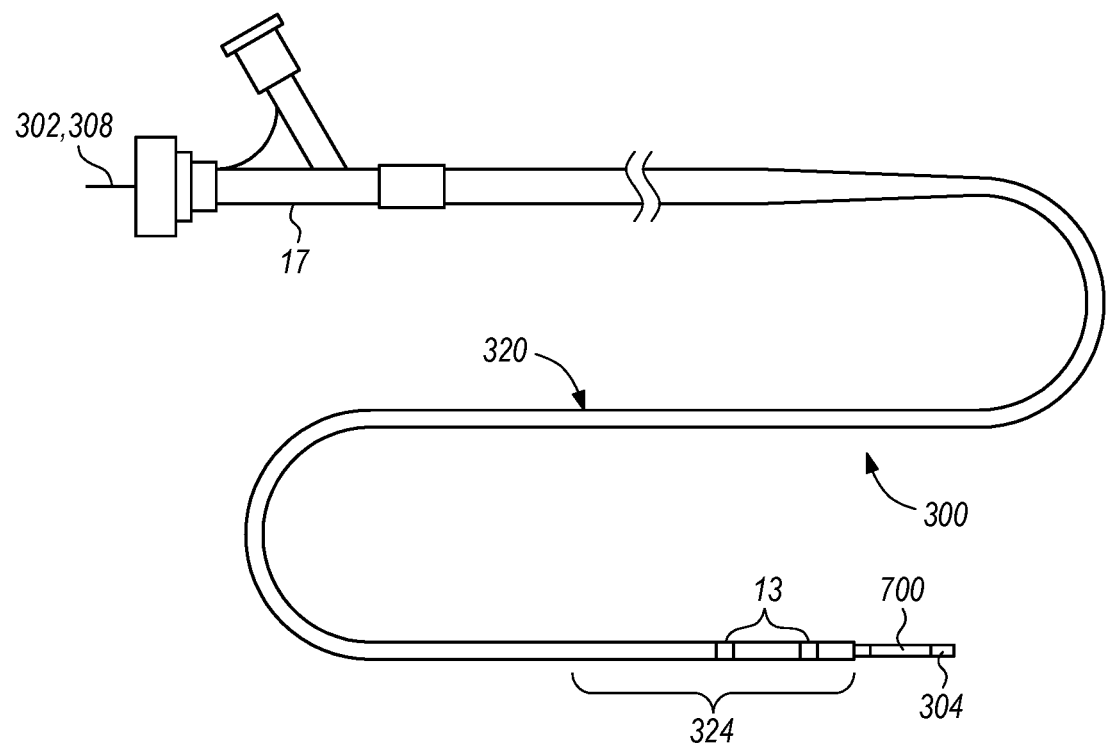
FIG. 6 is a side view of a delivery assembly according to embodiments of the disclosed inventions.

FIG. 6 is a side view of a delivery assembly 300 for delivering the anchor 700 and the shunt into a target site of a patient, constructed in accordance with embodiments of the disclosed inventions. The delivery assembly 300 includes the anchor 700 and the shunt (not shown) detachably coupled to the delivery assembly 300. The delivery assembly 300 and the shunt may be composed of suitable biocompatible materials. The delivery assembly 300 is dimensioned to reach remote locations of the vasculature and is configured to deliver the anchor 700 and the shunt percutaneously to the target location (e.g., inferior petrosal sinus). The delivery assembly 300 includes a tubular member interface having an outer tubular member 320 (i.e., guide catheter) and an inner tubular member 304 (e.g., catheter/ micro catheter/anchor delivery catheter) coaxially disposed within the outer tubular member 320 and movable relative to the outer tubular member 320. The delivery assembly 300 may include a guidewire 302 coaxially disposed within the guide catheter 320 and/or the anchor delivery catheter 304. The guidewire 302 can be, for example, 0.035 inches (0.889 mm) in diameter. Additionally to the guidewire 302, the delivery assembly 300 may include a second guidewire 308 disposed within the anchor delivery catheter 304. The second guidewire 308 has a smaller diameter (e.g., approximately 0.010 inches-0.254 mm-to 0.018 inches-0.4572 mm-or other suitable dimension to facilitate accessing intracranial venous vasculature with other components of delivery assembly 300) compared to guidewire 302.

The guide catheter 320, anchor delivery catheter 304, and guidewires 302/308 (FIG. 6) may be formed of suitable biocompatible materials, and may include markings 13 for purposes of imaging (e.g., markers composed of radio-opaque materials). Various known and often necessary accessories to the delivery assembly 300, e.g., one or more radiopaque marker bands 13 at the distal portion 324 of the guide catheter 320 to allow viewing of the position of the distal portion under fluoroscopy and a Luer assembly 17 for guidewires and/or fluids access, are shown in FIG. 6. The delivery assembly 300 and/or the shunt may include a penetrating element (not shown) configured to pierce and/or penetrate the IPS wall 114 and arachnoid layer 115 to access the CP angle cistern 138 for implantation of the shunt 200.

FIGS. 7A-F illustrate exemplary methods of delivering the anchor 700, the elongate guide member 780 and the shunt 200 at a target site, according embodiments of the disclosed inventions. The anchor 700 is configured to be deployed and disposed in a dural venus sinus (e.g., FIGS. 1-2D), such as within the IPS 102 or the CS 104 prior to penetration of the IPS wall 114 and deployment of a shunt. In some embodiments, the anchor 700 is configured to be distally disposed to a target penetration site in IPS wall 114, as to provide support (e.g., foundation) for subsequent IPS wall 114 penetration, and shunt deployment steps of the implant procedure. The anchor 700 may be deployed in the IPS 102 or CS 104 by advancing the anchor 700 out of the distal end opening of the anchor delivery catheter 304, or by withdrawing the anchor delivery catheter 304, and/or by a combination of advancing the anchor 700 and withdrawing the catheter 304 for deployment of the anchor 700 in the IPS 102 or CS 104 (not shown).

When the anchor 700 is deployed into the target site (e.g., IPS 102 or CS 104), the anchor 700 transitions from its delivery configuration (e.g., radially constrained by an inner lumen of the anchor delivery catheter 304) to its deployed configuration (e.g., expanding radially outwards, so as to engage the walls of the IPS 102 or CS lumen 131). When deployed (FIG. 7A), the struts 712 of the anchor 700 are biased to exert an outward radial force that engages and secures the anchor 700 within the IPS 102, against IPS walls 114 and 117, or against the equivalent walls of the CS 104. The ratio of the resting anchor 700 diameter (i.e., expanded, unconstrained configuration) to the reference vessel diameter (i.e., diameter of the sinus lumen where the anchor will be deployed) can range from about 1:1 up to about 2:1. In addition, the exterior surface of anchor 700 can include anchoring elements, spikes, burrs, barbs or other features to engage the dura mater of IPS walls 114 and 117 (or the walls of CS lumen 131), which further secures the anchor in IPS 102 or CS 104.

The anchor delivery catheter 304, with or without a guide wire, facilitates navigation and delivery of the anchor 700 within the patient's vasculature through the junction 118 and into the IPS 102 and/or CS 104. The compressible nature of the anchor 700 allows the operator to deploy the anchor 700 from the anchor delivery catheter 304 within the IPS 102 (or CS 104), re-sheath the anchor 700 into the anchor delivery catheter 304 (when needed), and redeploy the anchor 700 within the applicable sinus lumen (e.g. IPS 102 and/or CS 104) until the operator is satisfied with the deployment location and orientation of the anchor 700 and/or elongate guide member 780 in the patient.

Figure 7A:
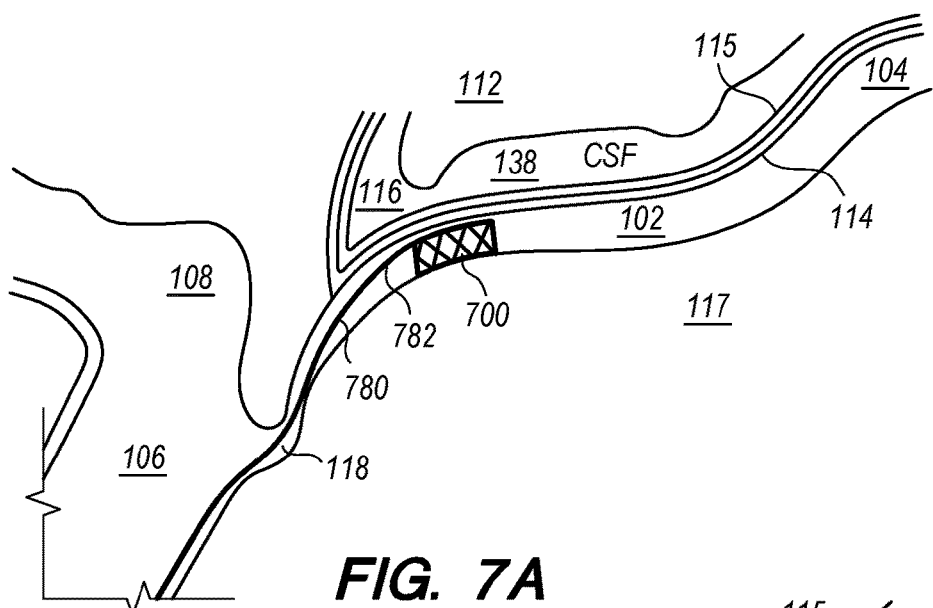
FIGS. 7A-F are cross-sectional views of exemplary methods of delivering the anchor, the elongate guide member and the shunt at a target site, according embodiments of the disclosed inventions.

As shown in FIG. 7A, the anchor 700 is deployed in the IPS 102. The anchor 700 is disposed in the IPS 102 distal to a target penetration site in IPS wall 114. The elongate guide member 780 coupled to the anchor 700 extends from the IPS 102 through the curved portion of IPS 102 into the junction 118. The elongate guide member 780 further extends into the jugular vein 106, and can extend further through venous vasculature and out of the patient's body at the peripheral access site (e.g., femoral vein). The anchor delivery catheter 304 used to deploy the anchor 700 may be withdrawn from the patient to allow for other delivery system components to access the IPS 102 after deployment of the anchor. Alternatively, the anchor delivery catheter 304 used to deploy the anchor 700 may allow further deployment of other components (e.g., piercing or penetrating elements, shunts, or their like) into the IPS 102 without needing withdrawal of the anchor delivery catheter 304 for other delivery systems. As previously disclosed, the anchor 700 can be deployed in a more distal location, such as CS 104.

The shunt 200 capitalizes on a favorable pressure gradient between the subarachnoid space 116 (e.g., CP angle cistern 138) and venous system (e.g., IPS 102, jugular vein 106, and/or a jugular bulb 108) to drive CSF through the shunt 200 (i.e., inner lumen). In patients without hydrocephalus, the normal differential pressure between the intracranial pressure of the subarachnoid space 116 and blood pressure of the venous system is about 5 to 12 cm H2O; this differential pressure between the subarachnoid space and venous system can be significantly higher in hydrocephalic patients. Once deployed and implanted, the shunt 200 facilitates one-way flow of CSF from the subarachnoid space 116 into the jugular the bulb 108 and/or jugular vein 106 where CSF is carried away by venous circulation, similar to the way that normally functioning arachnoid granulations drain CSF into the venous system. The shunt 200 prevents backflow of venous blood into subarachnoid space 116 via one or more one-way valves or any other flow regulating mechanisms. The shunt 200 allows for a more physiologic drainage of CSF by directing CSF into the cerebral venous system, a process that occurs naturally in people without hydrocephalus. In this manner, the pressure created by the excess CSF in the subarachnoid space 116 is relieved, and patient symptoms due to hydrocephalus can thereby be ameliorated or even eliminated. The shunt 200 of FIGS. 7E-F includes a valve 209 as the flow regulating mechanism configured to regulate fluid flow through the shunt 200 into the venous system.

In embodiments of the inventions, a target flow rate of CSF (e.g., in a range of about 5 ml per hour to about 15 ml per hour) through the shunt 200 occurs at a normal differential pressure between the subarachnoid space 116 and venous system (e.g., in a range between about 5 cm H2O to about 12 cm H2O between the subarachnoid space 116 and venous system (e.g., jugular vein 106 and/or a jugular bulb 108)).

In some embodiments, a target flow rate of CSF through the shunt 200 and/or valve 209 is approximately 10 ml per hour at a range of differential pressure between the subarachnoid space 116 and venous system ("ΔP") between 3 to 5 mmHg. A maximum flow rate of CSF through the shunt 200 and/or valve 209 can exceed 20 ml per hour and typically occurs immediately after shunt implantation in a patient with elevated ICP (e.g., ICP greater than 20 cm H2O). Embodiments of valve 209, as the flow regulating mechanism of the shunt 200, can have a normal operating range (CSF flow direction) of 0.5 to 8 mmHg ΔP, with a valve opening pressure (CSF flow direction) of approximately 0.5 mmHg ΔP, and a reverse opening pressure (backflow prevention) of about −40 mmHg to about −115 mmHg ΔP or greater. Additionally, embodiments of the valve 209 may comprise an allowable CSF leakage (flow direction) of less or equal to 0.5 ml per hour, and/or an allowable blood backflow (reverse direction) of less or equal to 0.25 ml per hour.

A positive pressure gradient between the intracranial pressure (ICP) of the subarachnoid space and the blood pressure of the venous system may contribute to the natural absorption of CSF through arachnoid granulations. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

The shunt 200 and/or the valve 209 are configured to handle expected acute and chronic differential pressures between the subarachnoid space 116 and venous system ("ΔP") when implanted in a patient. A maximum, acute negative ΔP occurs, for example, between a maximum venous pressure (VP) and a minimum intracranial pressure (ICP), such as, if the patient coughs while moving from a supine to upright position. Embodiments of the valve 209 is configured to seal, shut and/or close under the negative ΔP conditions (i.e., when venous pressure exceeds intracranial pressure), preventing venous blood from flowing back through the shunt 200 into the subarachnoid space 116. A maximum, acute positive ΔP occurs, for example, between a maximum ICP and a minimum VP, such as the acute positive ΔP caused by coughing when the patient transitions from an upright to supine position. Additionally, the shunt 200 and/or the valve 209 are configured to handle chronic elevated, positive ΔP conditions (e.g., approximately two or more minutes of elevated positive ΔP, such as between maximum hydrocephalus ICP and normal VP, e.g., hydrocephalus with low VP]); and to handle chronic, elevated negative ΔP conditions (e.g., approximately two or more minutes of negative ΔP, such as between minimum ICP and maximum VP, e.g., supine→upright posture change with minimal VP adjustment).

Figure 7B:
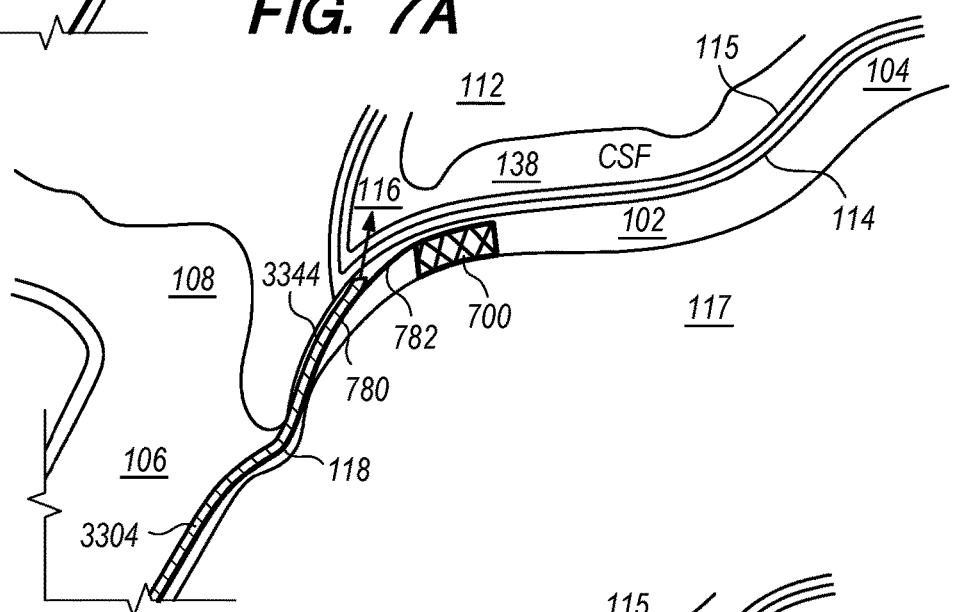
Figure 7C:
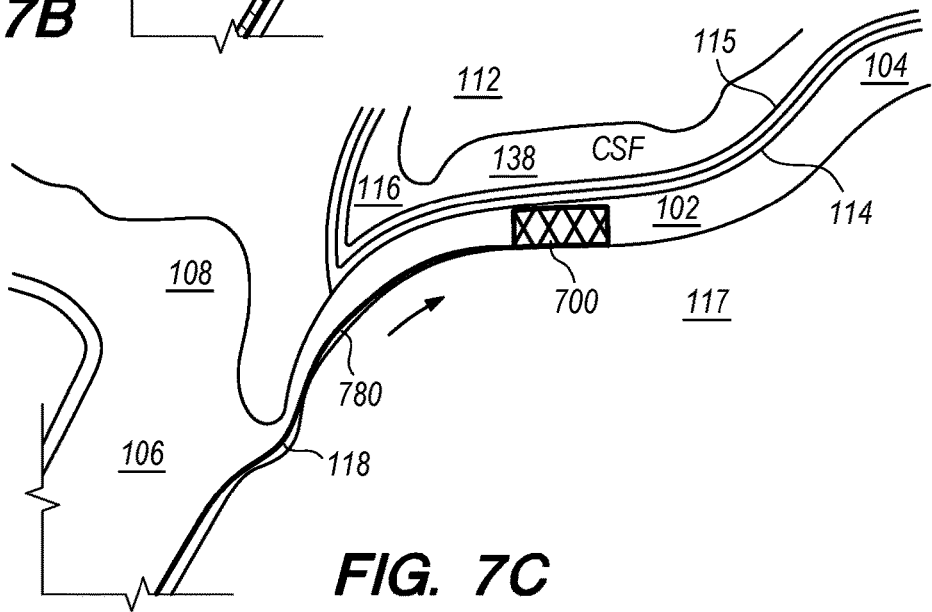
Figure 7D:
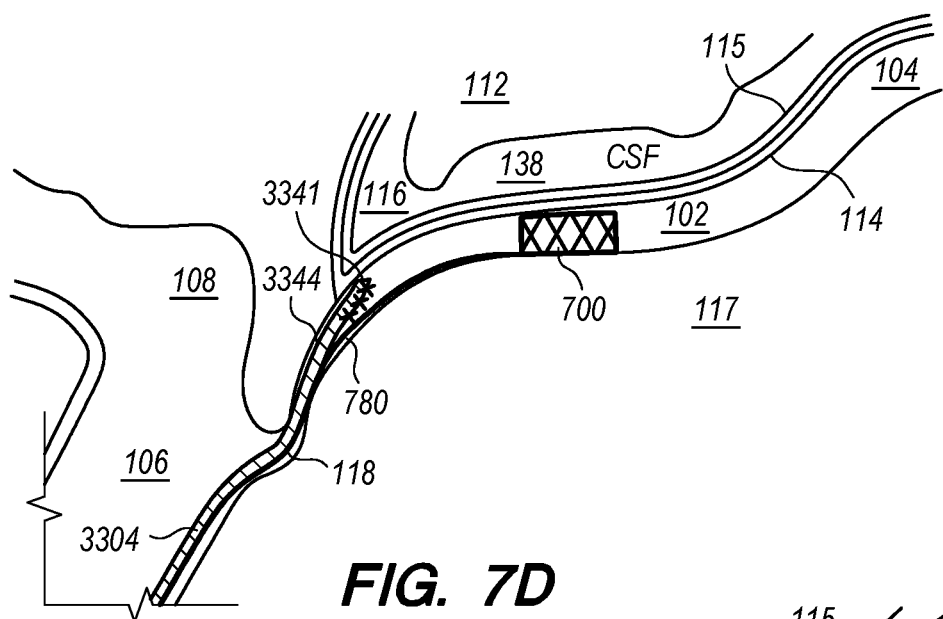
Figure 8A:
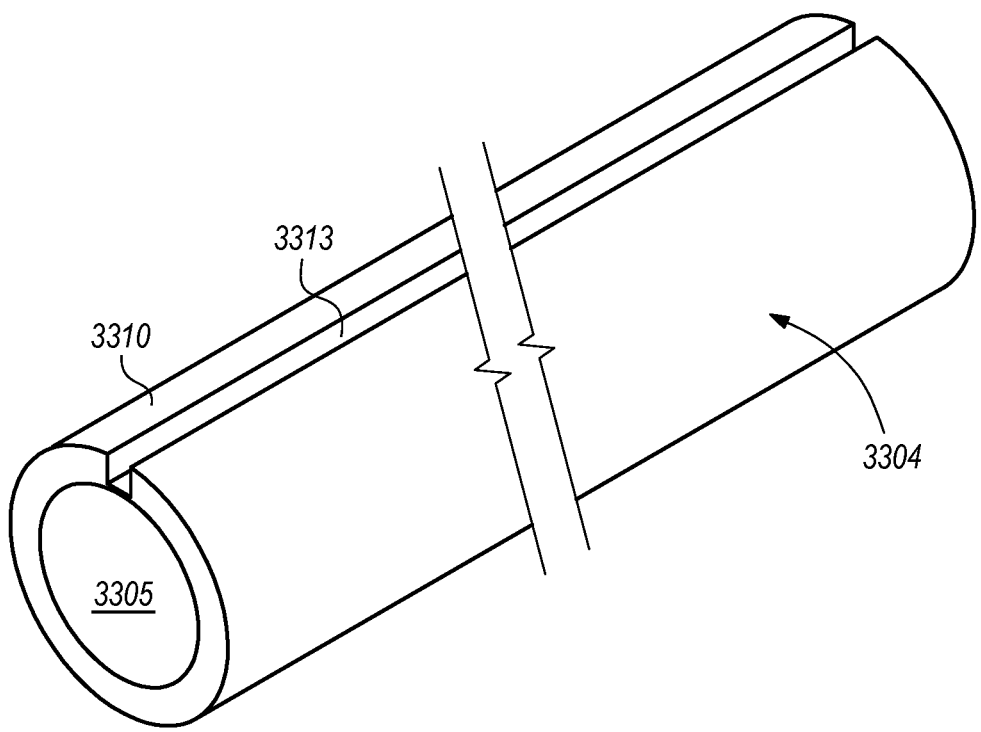
FIGS. 8A-B are perspective and cross-sectional views of a shunt delivery catheter, constructed according to embodiments of the disclosed inventions.
Figure 8B:
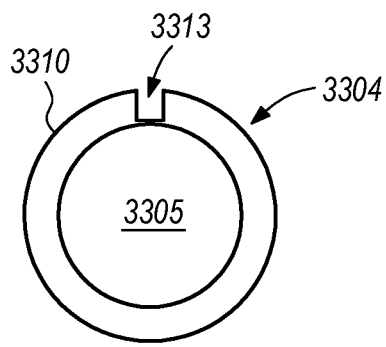

In some embodiments, a shunt delivery catheter 3304 can include one or more features that allow for accurate guidance, navigation and/or control of the deployment of the penetrating element and/or the shunt, particularly when passing through the junction 118 into the IPS 102. FIGS. 8A-B illustrate perspective and cross-sectional views of the shunt delivery catheter 3304, according to one embodiment of the disclosed inventions. The shunt delivery catheter 3304 comprises a recess 3313 formed in the outer surface 3310 of the catheter. The recess 3313 is configured to slidably engage the elongate guide member 780 of the anchor 700, so that the shunt delivery catheter 3304 rides on the elongate guide member 780 of the previously deployed anchor 700 (e.g., "side car" configuration), allowing the catheter 3304 to be guided in a desired orientation and location within the target site in the IPS 102, as shown in FIG. 7B. The elongate guide member 780 is dimensioned and configured to engage the recess 3313 in the shunt delivery catheter 3304. The elongate guide member 780 is further configured to guide the delivery catheter 3304 into the target penetration site, as shown in FIGS. 7B and 7D. The embodiment shown in FIGS. 8A-B is an exemplary control feature that can be implemented in connection with the catheter 3304. In some embodiments, the shunt delivery catheter 3304 and anchor 700 can include a plurality of such features (e.g., a plurality of elongate guide members that engage with a plurality of recesses).

Figure 9:
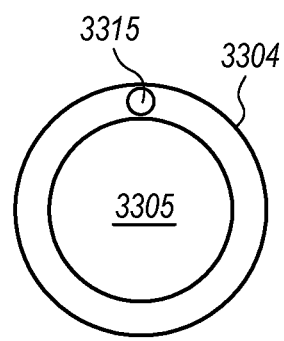
FIG. 9 is cross-sectional view of another shunt delivery catheter, constructed according to another embodiment of the disclosed inventions.
Figure 10A:
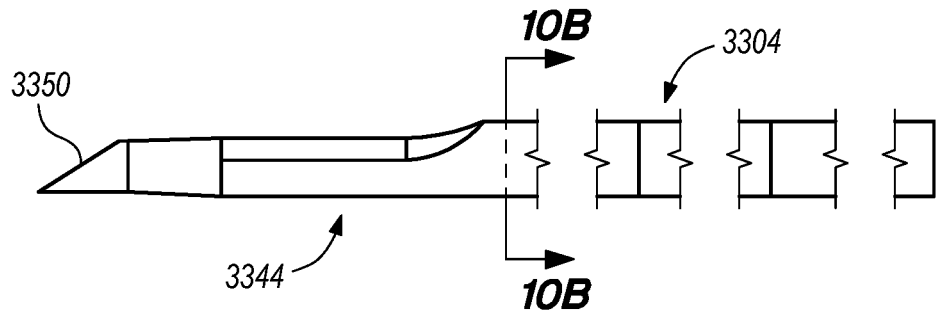
Figure 10B:
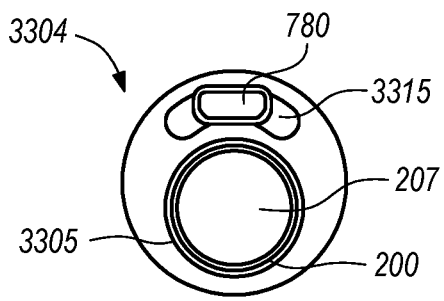
Figure 10C:
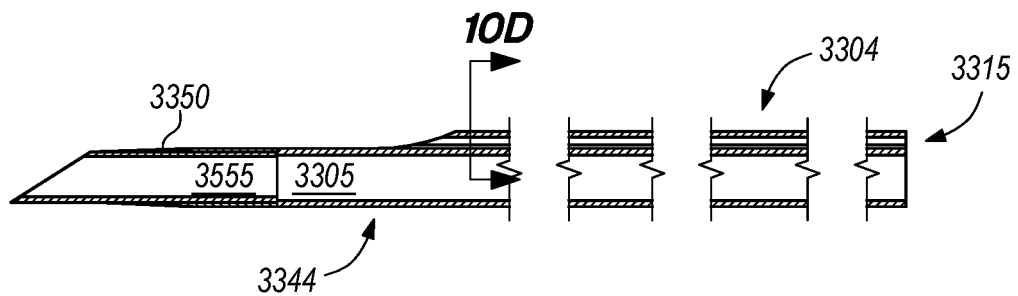
Figure 10D:
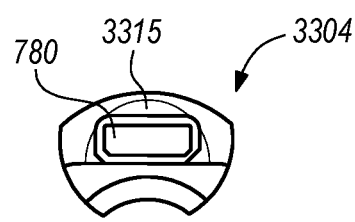
Figure 10E:
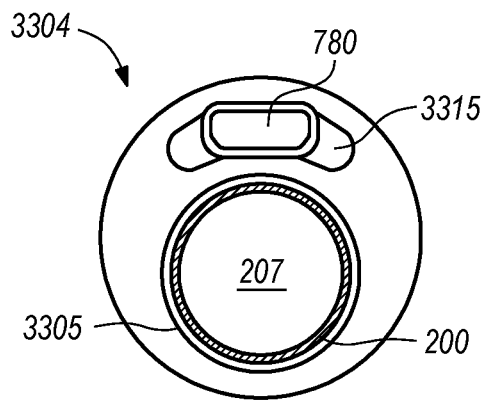
Figure 10F:
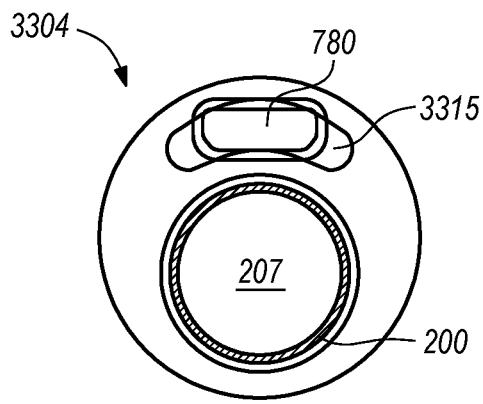
Figure 10G:
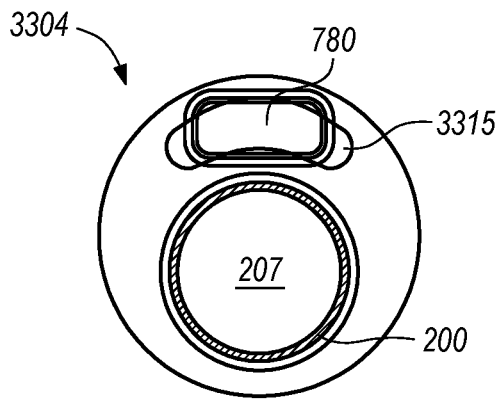
Figure 10H:
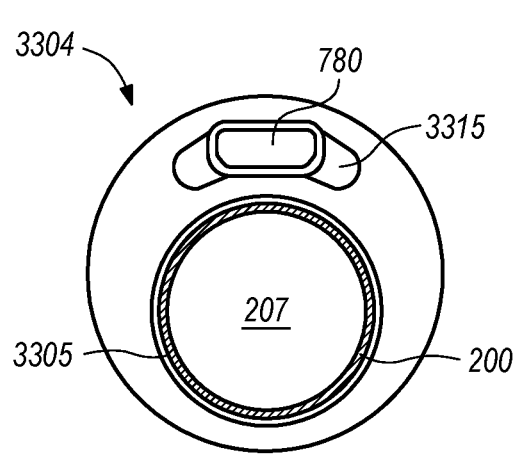
Figure 10I:
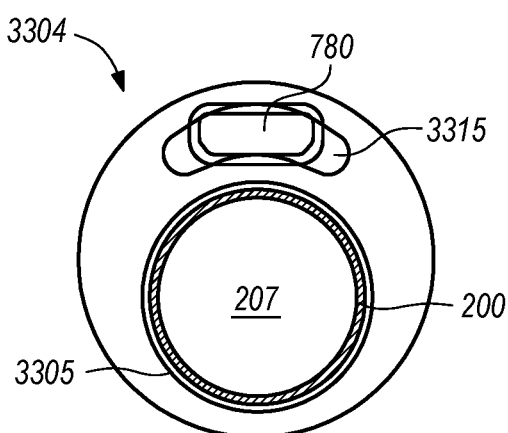
Figure 10J:
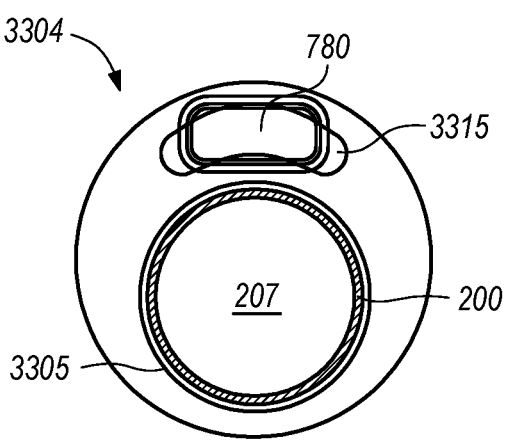

As shown in FIG. 7B, the shunt delivery catheter 3304 has been advanced over, in or on the elongate guide member 780 of the previously deployed anchor 700. Alternatively to the recess 3313 disclosed above, the shunt delivery catheter 3304 can have a dedicated lumen 3315 extending between the delivery catheter proximal and distal portions configured to accommodate the elongate guide member 780 of the anchor 700. Alternatively, the shunt delivery catheter 3304 can include a broken or incomplete lumen extending between the proximal and distal portions of the catheter, which captures the elongate guide member 780 against IPS wall 117 and allows the catheter to travel over the elongate guide member 780. At least one other lumen 3305 of shunt delivery catheter 3304 extends between the proximal and distal portions of the catheter 3304 (FIGS. 8A-B, and FIG. 9), which allows for navigation and delivery of the penetrating elements (e.g., surgical tool, needles, RF stylets, or the like) and shunt devices, with or without penetrating distal tip disclosed herein, and in the related application previously incorporated by reference herewith. The distal portion 3344 of the shunt delivery catheter 3304 intersects the IPS wall 114 at an angle of approximately 75° (or any other suitable angle) at the target penetration site, as shown in FIG. 7B.

FIGS. 10A-K depict additional embodiments of a dual lumen shunt delivery catheter 3304. As shown in FIGS. 10A-E, a distal portion 3344 of the delivery catheter includes a penetrating element 3350, having a penetration element lumen 3555 in fluid communication with lumen 3305 of the shunt delivery catheter 3304. Each catheter of FIG. 10 includes a first lumen 3315 extending between the ends of the catheter, which is configured to receive the elongate guide member 780 and, optionally, conforms to the profile of the elongate guide member. A second lumen 3305 of the foregoing catheter embodiments extends between the ends of the catheter, which allows for navigation and delivery of the penetrating elements (e.g., surgical tool, needles, RF stylets, or their like) or shunt devices with or without penetrating distal tip disclosed herein, and in the related application previously incorporated by reference herewith. Further, one or both lumens of shunt delivery catheter 3304 shown in FIGS. 10A-K can include a liner and/or can be coated with a hydrophilic agent to increase the lubricity of such lumens with respect to other delivery assembly components as described in the related application previously incorporated by reference herewith. FIGS. 10B, 10D, and 10E-J show elongate guide member 780 disposed within first lumen 3315, and FIGS. 10B, and 10E-J, show the shunt 200 with a hollow inner lumen 207 disposed within second lumen 3305 for the exemplary delivery catheter 3304 embodiments. It should be appreciated that the dimensions depicted in 10A-K are exemplary dimensions of the shunt delivery catheter 3304, first lumen 3315, second lumen 3305, penetrating element 3350, penetrating element lumen 3555, shunt 200, and shunt lumen 207, which are not intended to limit the scope of embodiments disclosed herein. For example, embodiments of delivery catheter 3304 can have a second lumen 3305 with an inner diameter in a range of about 0.012 inches (0.3048 mm) to 0.040 (1.016 mm) inches or more.

FIGS. 21A-M depict an alternate embodiment of the shunt delivery catheter 3304. FIGS. 21C and D show longitudinal side and cross section views, respectively, of shunt delivery catheter 3304. FIGS. 21A and B show cross section views of shunt delivery catheter 3304 at reference lines in FIG. 21C, respectively, as viewed from the distal portion 3344 of the catheter towards the proximal portion. FIG. 21I shows another longitudinal side view of the delivery catheter of FIGS. 21A-M. FIGS. 21F-M depict cross section views of shunt delivery catheter 3304 at various points along the longitudinal axis corresponding to the reference line designations in FIG. 21I.

With respect to FIGS. 21C, D, and I, the depicted shunt delivery catheter 3304 includes a beveled-needle penetrating element 3350 on the distal portion 3344 of the delivery catheter. The penetrating element 3350 can be fixed to the delivery catheter and, as depicted, is welded to reinforcing member 1345 (further described below). The penetrating element 3350 includes a penetrating element lumen 3555 in fluid communication with the lumen 3305 of the shunt delivery catheter 3304. Delivery catheter includes three distinct radiopaque marker bands: a distal most marker 3354 located about the proximal portion of penetrating element 3350, an intermediate marker 3354a, and proximal most marker 3345b. A first lumen 3315 in the delivery catheter accommodates elongate guide member 780 and lumen 3315 can include a polymeric liner 3306 material such as PTFE (FIG. 21B) to increase the lubricity of the lumen and facilitate smooth motion of the shunt delivery catheter 3304 over guide member 780.

As depicted, first lumen 3315 has a rapid-exchange configuration and does not span the entire longitudinal axis of shunt deliver catheter 3304, although such a configuration is possible in other embodiments. Marker bands 3354a and 3354b reinforce the distal 3315a and proximal 3315b openings of lumen 3315, as shown in FIGS. 21A and 21K-L. Embodiments of shunt delivery catheter 3304 can include longitudinal dimensions (in inches and with reference to, e.g., FIGS. 21C and 21I) along the length of delivery catheter 3304, measured from the proximal portion of penetrating element 3350 to the distal opening 3315a of first lumen 3315 (0.16 inches/0.4064 cm), to the distal edge of marker band 3354a (0.17 inches/0.4318 cm), to the distal edge of marker band 3354b (7.95 inches/20.193 cm), to the proximal opening 3315b of first lumen 3315 (8 inches/20.32 cm), and to the proximal portion of delivery catheter 3304 (39.37 inches/100 cm). Further, the shunt delivery catheter 3304 includes a second lumen 3305 to accommodate a shunt and shunt pusher delivery assembly as disclosed herein. Second lumen 3305 includes a polymeric liner material 3306 as indicated in FIGS. 21E, 21E-1, 21E-2 to FIG. 21M, such as PTFE.

The outer diameter of shunt delivery catheter 3304 of FIGS. 21A-M varies along the longitudinal axis. The cross section views of FIGS. 21F-M, working from the distal most cross-section to the proximal most cross-section along the axis of delivery catheter 3304, correspond to the reference lines shown in FIG. 21I as follows: FIG. 21J at reference line E-E in FIG. 21I; FIG. 21F at reference line F-F in FIG. 21I; FIG. 21K at reference line G-G in FIG. 21I; FIG. 21G at reference line H-H in FIG. 21I; FIG. 21L at reference line 1-1 in FIG. 21I; FIG. 21H at reference line J-J in FIG. 21I; and FIG. 21M at reference line K-K in FIG. 21I. Each of FIGS. 21A-B and F-M depict an outer diameter along the longitudinal axis of the shunt delivery catheter 3304 at the location of the particular cross section depicted, which varies depending on the longitudinal location of the cross section along the axis of the catheter (e.g., ranging from 0.036 to 0.046 inches/0.09144 to 0.11684 cm). FIGS. 21K, 21F, and 21J depict a gradually tapering outer diameter in the distal portion of the delivery catheter 3304, moving in the distal direction along the axis of the catheter (i.e., from 0.046 to 0.036 inches/0.11684 to 0.09144 cm), which facilitates access to tortuous anatomy and narrowings in the vasculature (e.g., junction 118 of jugular vein 106 and IPS 102).

While FIGS. 21A-M and the foregoing description reference a two-lumen shunt delivery catheter 3304, additional embodiments of the shunt delivery catheter can include a third lumen (e.g., lumen 3325 of FIG. 19A, FIGS. 29A-D to accommodate, for example, a pull wire of a penetrating element guard 4000, as further described below).

Figure 24A:
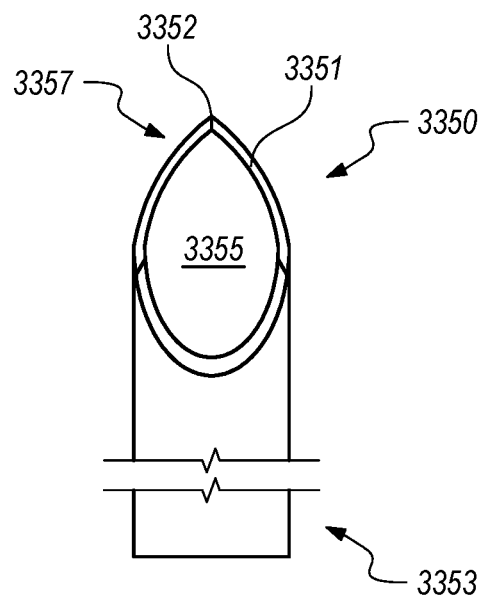
FIGS. 24A-K are side, perspective and cross-sectional views of penetrating element configurations and table for use with the delivery assemblies, constructed according to embodiments of the disclosed inventions.
Figure 24B:
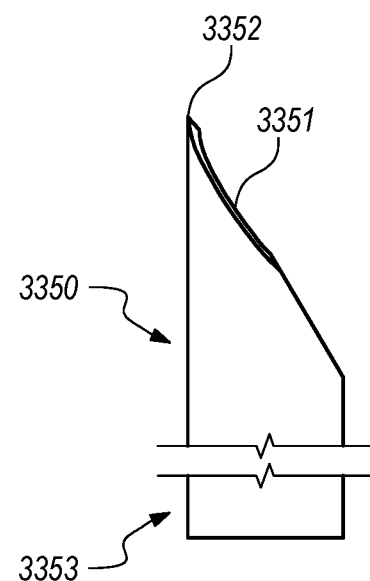
Figure 24C:
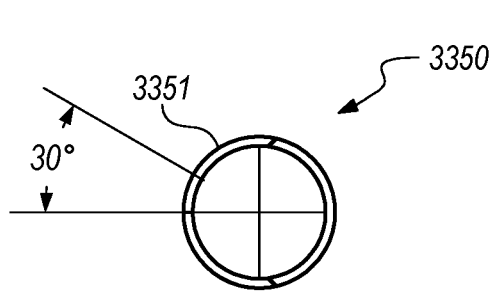
Figure 24D:
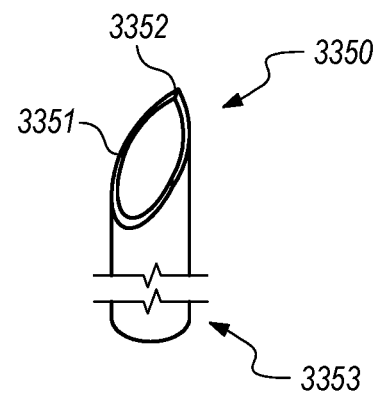
Figure 24E:
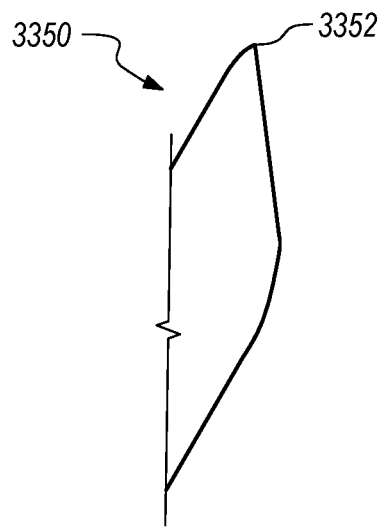
Figure 24F:
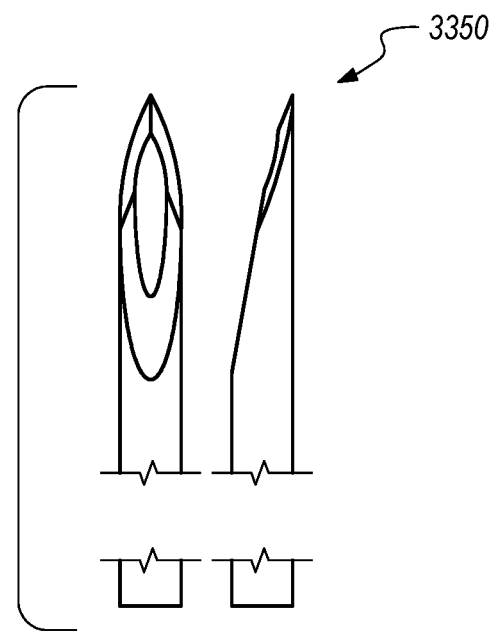
Figure 24G:
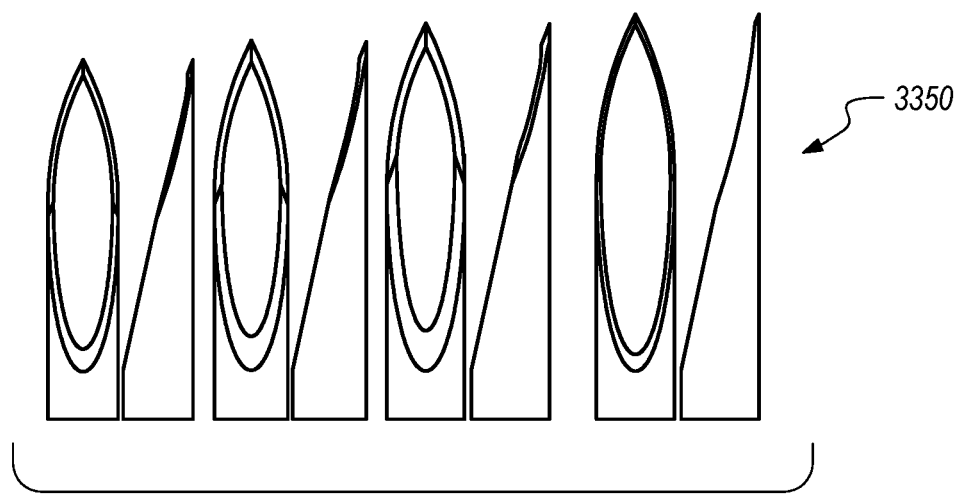
Figure 24H:
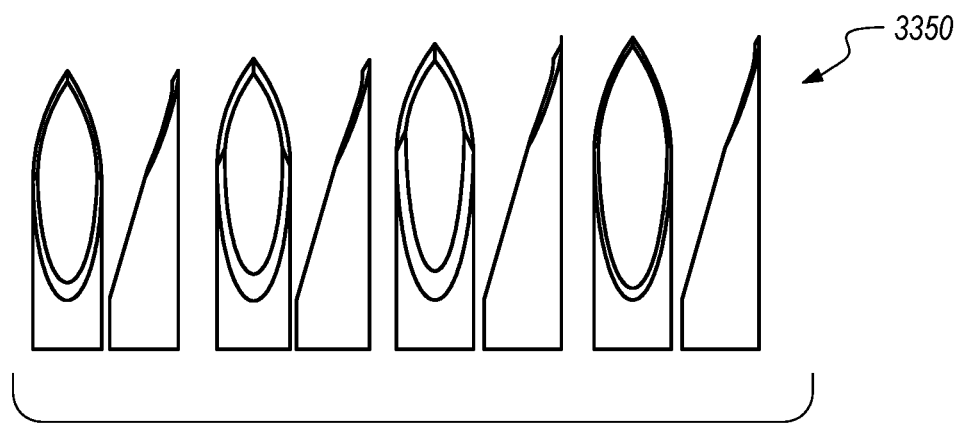
Figure 24I:
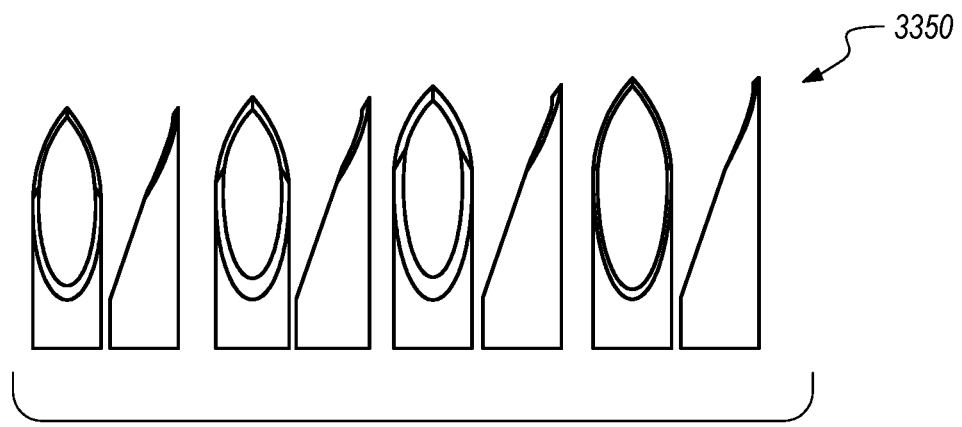
Figures 24J, 24K:
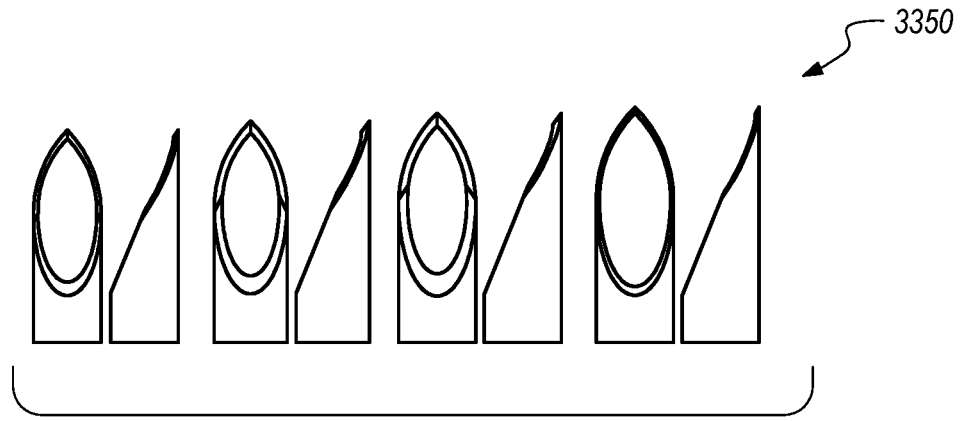

Embodiments of penetrating element 3350 can comprise a commercially available hypodermic needle. FIG. 22 includes a table describing various details of needles that can be used as a penetrating element 3350 of the delivery assembly, e.g., mounted or fixed on the distal portion 3344 of shunt delivery catheter 3304. For each needle option, FIG. 22 specifies a product name, manufacturer, and gauge size (standardized to an outer diameter of the needle), and in certain instances, wall thickness, bevel length, bevel type, and/or other information. Further embodiments of the penetrating element 3350 constructed according to embodiments of the disclosed inventions are depicted in FIGS. 24A-K. The tissue penetrating element 3350 comprises a tubular configuration having a proximal end portion 3353 and a distal end portion 3357, and lumen 3355 extending therebetween (FIGS. 24A-B). The distal end portion 3357 of the tissue penetrating member 3350 comprises a tapered/beveled piercing edge 3351 that terminates in the piercing tip 3352 (FIGS. 24A-E). FIG. 24K includes a table describing various details of needles that can be used as the penetrating element 3350 of the delivery assembly. FIGS. 24F-J depicts further embodiments of the penetrating element 3350, such as having variations in the bevel angle. FIGS. 24A-K illustrate exemplary dimensions (in inches), angles and properties of the tissue penetrating member 3350, which are not intended to limit the embodiment of FIGS. 24A-K.

Criteria for selecting a particular needle as the penetrating element 3350 of a delivery assembly 300 include bevel length, force required to penetrate IPS wall 114, and needle wall thickness. Bevel length is inversely related to the puncture force required to penetrate IPS wall, though longer bevels can make navigation of delivery assembly 300 more difficult as compared to shorter bevels, particularly in tortuous anatomy, given that needles do not flex as the distal portion 3344 of the shunt delivery catheter 3304 navigates through the vasculature. Lower puncture forces facilitate a smooth penetration step of the shunt implant procedure, as the penetrating element passes through IPS wall 114 into the subarachnoid space. Puncture force for candidate penetrating element embodiments can be assessed in vitro using a dura surrogate, e.g., DuraGuard® Dural Repair Patch available from Synovis Surgical Innovations, and force gauge as further described in U.S. patent application Ser. No. 14/929,066 filed on Oct. 30, 2015. Penetrating element embodiments comprising a needle configuration can have a puncture force of about 0.1 pounds-force or less. A thinner needle wall minimizes the gap between the anastomosis through IPS wall 114 and the outer surface of deployed shunt 2200. Reducing this gap is clinically significant to minimize or eliminate venous blood from leaking from the IPS 102 or CS 104 through the anastomosis (e.g., between the penetration tract through IPS wall 114 and the outer surface of implanted shunt 2200) into the subarachnoid space and, conversely, CSF leaking from the subarachnoid space into the IPS lumen.

The anchor 700 and the elongate guide member 780 can be optimized to orient the penetrating element or shunt advancing via the shunt delivery catheter 3304 over the elongate guide member 780 towards a target penetration site on the IPS wall 114 along a curved portion of IPS 102. For example, the elongate guide member 780 coupled to the anchor 700 at a location along the top edge of anchor 700, is configured to orient a distal portion 782 of the elongate guide member 780 proximate or adjacent to the IPS wall 114, as shown in FIGS. 7A-B. Alternatively, the anchor 700 and the elongate guide member 780 can be configured such that the elongate guide member 780 orients (e.g., "hugs") nearest the IPS wall 117 through the curved portion of IPS 102, as shown in FIGS. 7C-D, when the anchor 700 is deployed distally to a target penetration site along the IPS wall 114.

Additionally, the deployment location of the anchor 700 in the sinus lumen can vary the path of the elongate guide member 780 through the curved portion of IPS 102, regardless of how the elongate guide member 780 is oriented with respect to the top, midline, or bottom portions of the anchor 700. For example, deploying the anchor 700 more distally than the deployment location shown in FIGS. 7A-B will orient the elongate guide member 780 more proximate to the IPS wall 117 than IPS wall 114.

Additionally, embodiments of the shunt delivery catheter 3304 (or a shunt if delivered over the elongate guide member 780 without a delivery catheter) can be optimized to orient a penetrating element and/or shunt advancing through or over the elongate guide member 780 towards a target penetration site in the IPS wall 114 along a curved portion of IPS 102 (e.g., first curved portion of IPS 102). The distal portion 3344 of the shunt delivery catheter 3304 can have multiple interface points to accommodate the elongate guide member 780, as denoted by the "x" markings in FIG. 7D. The interface point on the distal portion 3344 of the shunt delivery catheter 3304 for the elongate guide member 780 provides a penetration stop to limit the distance the penetrating element 3350 can travel through IPS wall 114 and into CP angle cistern 138 (e.g., the maximum penetration depth corresponds to the distance between the distal tip of penetrating element 3350 and the interface point on delivery catheter 3304 for receiving elongate guide member 780). Introducing the elongate guide member 780 into or along the shunt delivery catheter 3304 at a more proximal location on the catheter 3304 allows for more separation between the penetrating element 3350 and/or a distal open end 3341 of the delivery catheter 3304 and the elongate guide member 780. The greater extent of separation between the penetrating element 3350 and elongate guide member 780 provides a relatively longer depth of penetration through IPS wall 114 and arachnoid layer 115 along the curved portion of IPS 102. Conversely, a more distal entrance point or connection along the shunt delivery catheter 3304 and the elongate guide member 780 decreases the separation between the elongate guide member 780 and the penetrating element 3350 and/or distal open end 3341 of delivery catheter 3304. The lesser extent of separation between the penetrating element 3350 and elongate guide member 780 provides a relatively shorter depth of penetration through IPS wall 114 and arachnoid layer 115 along the curved portion of IPS 102. The operator can adjust the interface point between the elongate guide member 780 and delivery catheter 3304 to optimize the trajectory of a penetrating element from the delivery catheter 3304 and penetration depth at a target penetration site along the IPS 114. The interface point between the elongate guide member 780 and the shunt delivery catheter 3304 can range from the distal end 3341 of delivery catheter 3304 (e.g., where the distal end of the delivery catheter includes a distal opening to a dedicated rail lumen) to an interface point about 10 cm proximal from the distal end of delivery catheter 3304.

Once deployed, the anchor 700 and the elongate guide member 780 provide a stable, intra-sinus platform that creates an off-axis trajectory for the penetrating element during shunt implantation. The deployed anchor 700 and elongate guide member 780, along with other aspects of the delivery system, afford operators controlled access to the greatest extent of CSF-filled space in the CP angle cistern 138 during shunt deployment. The elongate guide member 780 extending through the curved portion of IPS 102 advantageously orients the penetrating element 3350 (i.e., advancing via the guide member) toward IPS wall 114 into CP angle cistern 138. As shown in FIG. 7D, the portion of the shunt delivery catheter 3304 distal to the interface point separates from the axis of the elongate guide member 780 as the delivery catheter advances over the guide member through the curved portion of the IPS; that is, the distal most portion of delivery catheter 3304 including penetrating element 3350 travel off-axis from elongate guide member 780 to puncture IPS wall 114 and access the CSF-filled CP angle cistern 138. This orienting feature of the elongate guide member with respect to the shunt delivery catheter 3304 ensures that advancement of the penetrating element will: (a) intersect the IPS wall 114 at a target penetration site along the curved portion of IPS 102 at an angle of approximately 90° (i.e., oriented orthogonal to IPS wall 114) to approximately 30° (although, other suitable angles may be provided), and (b) continue on a trajectory through the dura mater of the IPS wall 114 and through the arachnoid layer 115 to access at least 2-3 mm of unobstructed, CSF-filled space of CP angle cistern 138 as measured distally from the penetration point on the IPS wall 114. Features of anchor 700 and the elongate guide member 780 disclosed herein allow operators to access and deploy a shunt in a relatively larger extent of free CSF-filled space in the cistern, often more than 3 mm to 5 mm of unobstructed CSF-filled space, compared to other endovascular shunt delivery techniques.

After the anchor 700 and the elongate guide member 780 have been deployed at a desired location in the sinus lumen and the penetrating element has been advanced over the elongate guide member 780 to a target penetration site along the IPS wall 114, the operator can proceed by creating anastomosis between the IPS 102 and the CP angle cistern 138, followed by the shunt delivery and implantation steps of procedure. The operator can penetrate the IPS wall 114 to access the CP angle cistern 138 with the penetrating element (e.g., penetrating element advanced via the catheter, on the shunt, or carried by the catheter distal end) by pulling the elongate guide member 780 in the proximal direction (or locking the elongate guide member 780 in place relative to other delivery system components) while advancing the penetrating element over the elongate guide member 780, toward the IPS wall 114. The retrograde force on the elongate guide member 780 during the penetration step further secures the guide member and anchor 700 in the sinus lumen, thereby stabilizing the elongate guide member 780 in the curved portion of the IPS 102 while it orients a penetrating element towards IPS wall 114 and off-axis from the trajectory of elongate guide member 780 in the curved portion of the IPS lumen. And by simultaneously advancing the penetrating element and/or shunt 200 (as previously disclosed) through the IPS wall 114 and arachnoid layer 115 until a distal anchoring mechanism 229 of the shunt 200 is deployed in the CP angle cistern 138 (i.e., without an exchange of delivery system components between the penetration and shunt deployment steps) eliminates the risk of bleeding from the sinus lumen into the subarachnoid space.

Radiopaque markings or coatings can be incorporated on the penetrating element 3350 (e.g., penetrating element advanced via the catheter, on the shunt, or carried by the distal end of the delivery catheter) and/or the delivery catheter to assist the operator visualize the orientation of delivery system elements in the sinus lumen and the trajectory of such elements prior to or during the penetration step of the shunt implant procedure. For example, a semi-circle piece or half-band of radiopaque material can be coupled to or incorporated within the penetrating element 3350 and/or in the distal portion 3344 of the delivery catheter 3304. Depending on the location of the marker in the penetrating element 3350 and/or distal portion 3344 of the shunt delivery catheter 3304 (e.g., distal section or proximal section of the penetrating element to assist with the visualization of the respective section of the inner diameter or lumen), the operator can confirm whether the penetrating element 3350 is properly oriented toward the IPS wall 114 and/or improperly oriented toward the IPS wall 117.

After the distal anchoring mechanism 229 of the shunt 200 has been deployed in the CP angle cistern 138, the shunt delivery catheter 3304 can be withdrawn (i.e., pull in the proximal direction) from the curved portion of IPS 102. The distally anchored shunt 200 emerges from the distal end opening 3341 of the delivery catheter 3304 as the catheter is withdrawn through the IPS 102 into the junction 118; the distal anchoring mechanism of the shunt disposed within the CP angle cistern 138 retains, secures and/or anchors the shunt in its deployed location within the subarachnoid space 116 as the delivery catheter 3304 is withdrawn from the IPS 102. Thereafter, the delivery catheter 3304 can be further withdrawn through the junction 118 to allow the proximal anchoring mechanism 227 of shunt 200 to be deployed in the jugular vein 106, as shown in FIG. 7E.

After the shunt 200 has been fully deployed and/or secured at the target site by the shunt 200 respective anchoring mechanisms 227, 229, the operator can advance the shunt delivery catheter 3304 and/or a anchor delivery catheter (e.g., catheter having an inner diameter of 0.027" or 0.021") over the elongate guide member 780 to re-sheath the anchor 700, and then withdraw the catheter 3304 containing anchor 700 and elongate guide member 780 from the patient (e.g., via a femoral access point). Alternatively, the elongate guide member 780 can include an electrolytic detachment element 785 in or around the joint 744 with anchor 700 (FIGS. 3C, 3H) or at any other suitable portion of the elongate guide member 780 (e.g., FIG. 7F), so as to detach the elongate guide member 780 from the anchor 700. After detachment of the elongate guide member 780 from the anchor 700, the elongate guide member 780 can be withdrawn from the patient while anchor 700 remains deployed in the IPS 102 or CS 104. This configuration can be advantageous to avoid accidental pullout of an implanted shunt from CP angle cistern 138 while retrieving the anchor 700 from its distal deployment location by snagging the anchor 700 on a portion of the deployed shunt, as the anchor 700 is withdrawn through the IPS 102 and the junction 118.

Figure 11E:
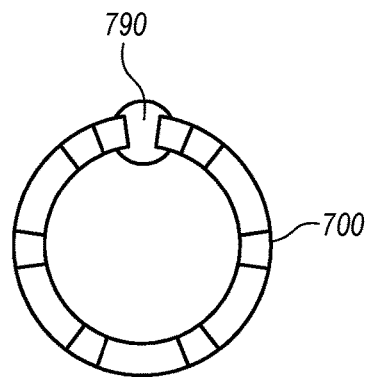
Figure 11F:
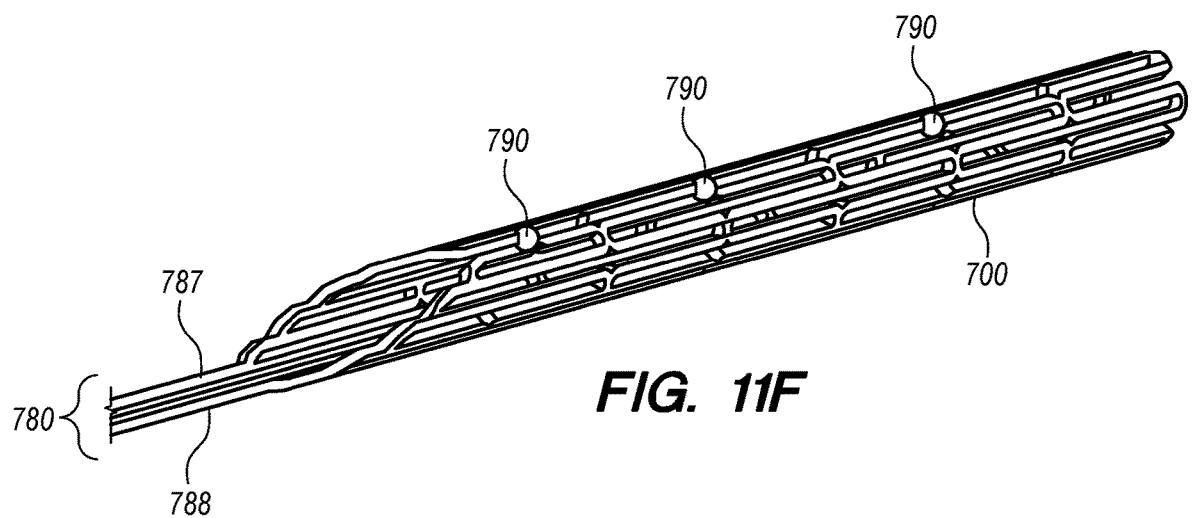
Figure 11G:
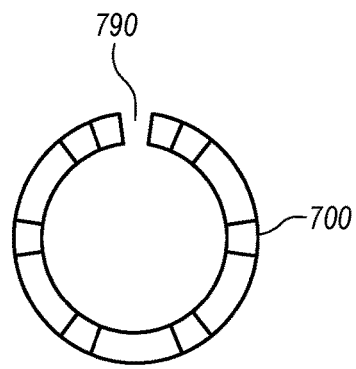
Figure 11H:
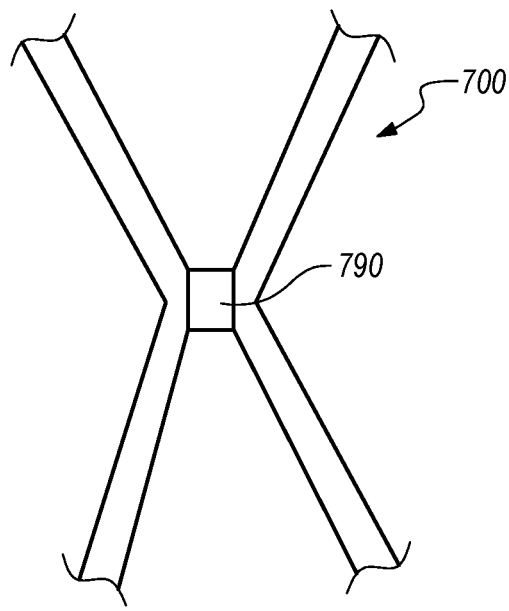
Figure 11I:
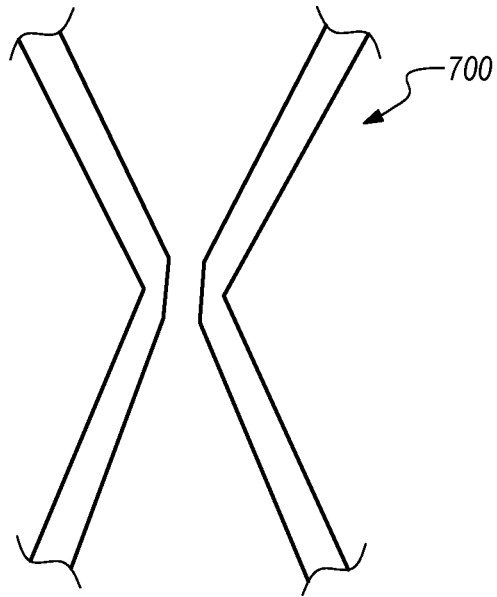

FIG. 11A-I illustrate an alternative configuration of anchor 700 and method steps to facilitate removal of the anchor 700 from the patient's vasculature after shunt deployment. The anchor 700 can include one or more electrolytic detachment elements 790 in one or more of the proximal portion 740, middle or body portion 730, and distal portion 720 of the anchor 700 (FIGS. 11A, B, E, F). The electrolytic detachment elements 790 are configured to break, disintegrate or the like, as shown in FIGS. 11H-I, thereby separating the anchor 700 into two or more sections, as illustrated in FIG. 11A-D, to facilitate withdrawal of the sections of the anchor 700 past the deployed shunt, and along the curved portion of IPS 102. Additionally, each of the sections of the anchor 700 may be coupled to respective elongated elements 787, 788 (e.g., tether, or the like) configured to facilitate withdrawal of the sections of the anchor 700, as shown in FIGS. 11A and 11D. It should be appreciated that the one or more elongated elements 788 (e.g., adjacently disposed) may jointly comprise the elongate guide member 780, or one or more elongated elements 788 may be included to the anchor 700 in addition to the elongate guide member 780.

Figure 7E:
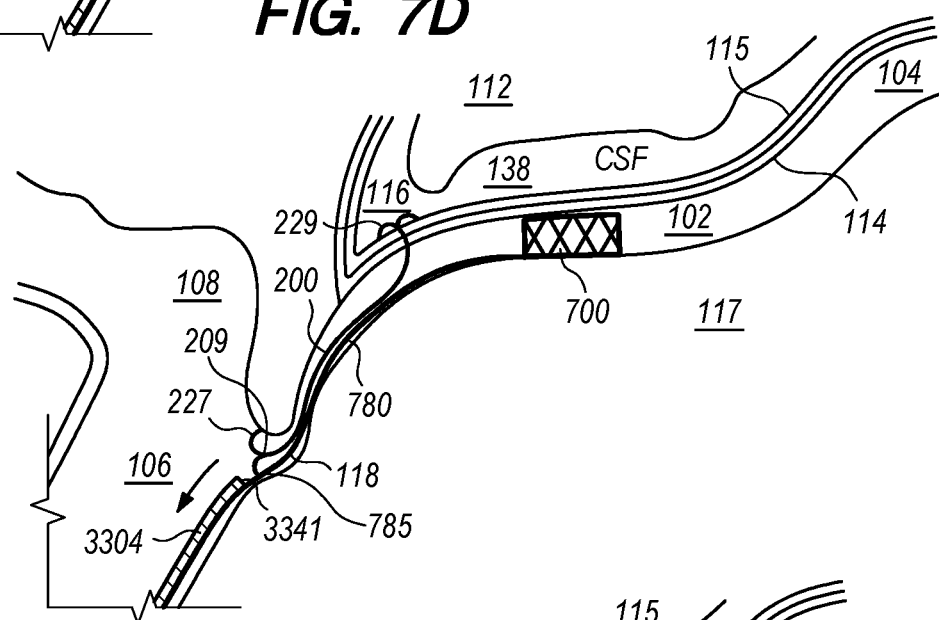
Figure 7F:
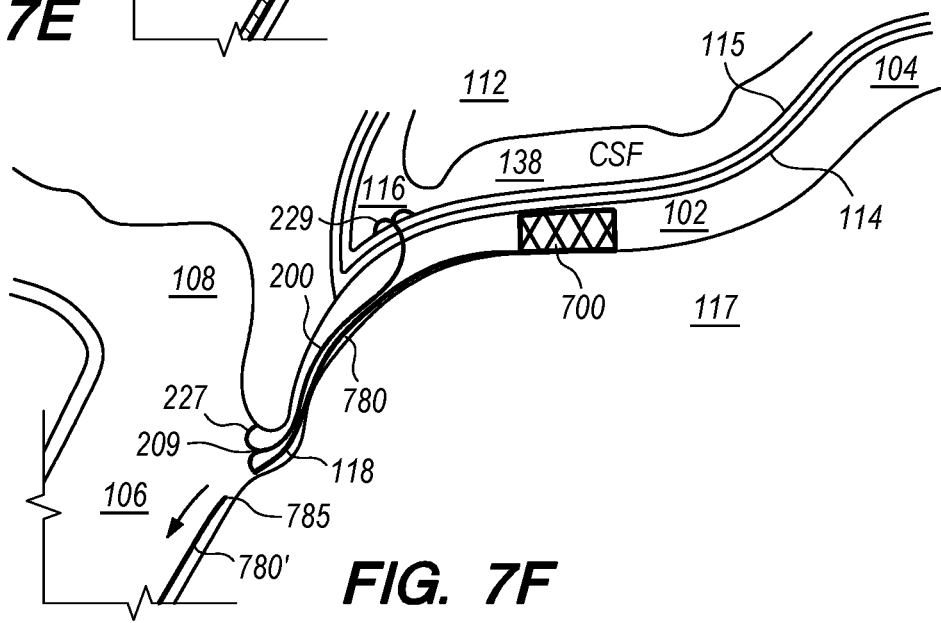

In further alternative embodiments, the electrolytic detachment element 785 can be proximately disposed from the joint 744 (e.g., at the elongate guide member 780 portion configured to be disposed around the junction 118), as shown in FIGS. 7E and 7F. The anchor 700 and a portion of the elongate guide member 780 can be part of the implanted shunting system where a deployed shunt includes one or more connection points or interfaces with the elongate guide member 780, allowing the deployed anchor 700 and portion of the elongate guide member 780 to further anchor the shunt at its deployed location. In such embodiments, the elongate guide member 780 can include the electrolytic detachment element 785 at a portion of the elongate guide member 780 configured to be disposed around the junction 118. So that, a proximal portion 780' (i.e., proximately to the electrolytic detachment element 785) of the elongate guide member 780 is withdrawn from the patient after deployment of the shunt, while the distal portion of the elongate guide member 780 remains coupled to the anchor 700. In this embodiment, the anchor 700 may further provide a scaffold support for the deployed shunt 200, as shown in FIG. 7F.

The anchor 700 and the elongate guide member 780 system can have the following advantages over other endovascular shunt delivery systems and techniques:

Separate anchor 700 and shunt 200 deployment steps preserve critical working and deployment space in the IPS 102 and/or CS 104 around the target penetration site to accommodate delivery system components such as the shunt delivery catheter 3304 and shunt 200 compared to a delivery system configured for a single anchor and shunt 200 deployment step comprising multiple, concentric elements (e.g., a delivery catheter, delivery system anchor and/or guide wire, a shunt, and a penetrating element).

The anchor 700 and the elongate guide member 780 system provides a stable platform to secure delivery system components during (a) penetration through the dura mater IPS wall 114 and arachnoid layer 115 into CP angle cistern 138, and (b) deployment of the shunt distal anchoring mechanism 229 in the cistern compared to a conventional delivery catheter and guide wire system.

The anchor 700 and the elongate guide member 780 system resists "kickout" of delivery system components (e.g., shunt delivery catheter 3304) from the IPS 102 and/or CS 104 into the jugular vein 106 resulting from tortuous anatomy during critical procedure steps such as penetrating dura mater IPS wall 114 and arachnoid layer 115 and deploying the shunt and its distal anchoring mechanism 229.

In some embodiments of anchor 700, for example when the anchor is left behind in the sinus lumen (IPS 102 or CS 104) to secure that the implanted shunt 200, the anchor can be configured for hydraulic expansion using stainless steel or cobalt chromium materials, thereby simplifying system design and reducing product manufacturing costs.

The elongate guide member 780 extending proximally from a deployed anchor 700 along the IPS wall 117 eliminates or decreases the risk that an uncovered or unprotected penetrating element inadvertently snags a portion of the IPS wall 114 as the penetrating element is delivery to the target penetration site.

FIGS. 12A-F illustrate an alternative shunt delivery catheter 1304 for delivering a shunt into a target site of a patient, constructed in accordance with embodiments of the disclosed inventions. For ease in illustration, the features, functions, and configurations of the delivery catheter 1304 that are the same or similar as in the shunt delivery catheter 3304 of the present disclosure and the delivery catheters 304, 304' in the related application previously incorporated by reference herewith, are given the same or similar reference numerals. The delivery catheter 1304 comprises an elongated configuration having a proximal portion 1342, a distal portion 1344 and a lumen 1341 extending therebetween. The delivery catheter 1304 is dimensioned to reach remote locations of the vasculature and is configured to deliver the shunt percutaneously to the target site (e.g., IPS, CS, CP angle cistern, or the like). The delivery catheter 1304 comprises variable stiffness sections (e.g., varying ratio of material, including selective reinforcement, varying the properties or distribution of the materials used and/or varying the durometer or thickness of the materials during the process of manufacturing) suitable to provide sufficient "pushability" (e.g., exhibits sufficient column strength to enable delivery to target locations such as IPS 102 or CS 104; in embodiments comprising a tissue penetrating element 1350, provides sufficient column strength to transmit about 0.1 N to 2.0 N force or more for the penetrating or piercing element to penetrate dura of IPS wall 114 and arachnoid layer 115) and "torqueability" (e.g., in the vasculature exhibits a torque response of about 1:1 such that a single clockwise turn of the catheter at the patient's groin or proximal portion results in approximately single clockwise turn of the distal portion of the catheter at a target location such as IPS 102 or CS 104) to allow the catheter 1304 to be inserted, advanced and/or rotated in the vasculature to position the distal portion 1344 of the catheter at the target site within the IPS 102 or CS 104. Further, the distal portion 1344 has sufficient flexibility so that it can track and maneuver into the target site, particularly in tortuous anatomy.

Known components, such as embedded coils or braids, are often used to provide selective reinforcement to delivery catheters. Delivery catheters including embedded coils can provide suitable flexibility, however, the embedded coils usually fail to provide the necessary column strength for the catheter, particularly at the distal portion of micro-catheters. Delivery catheters including embedded braids can provide suitable column strength, while sacrificing flexibility, particularly if the embedded braids are disposed at the distal portion of the catheter.

Figure 12A:
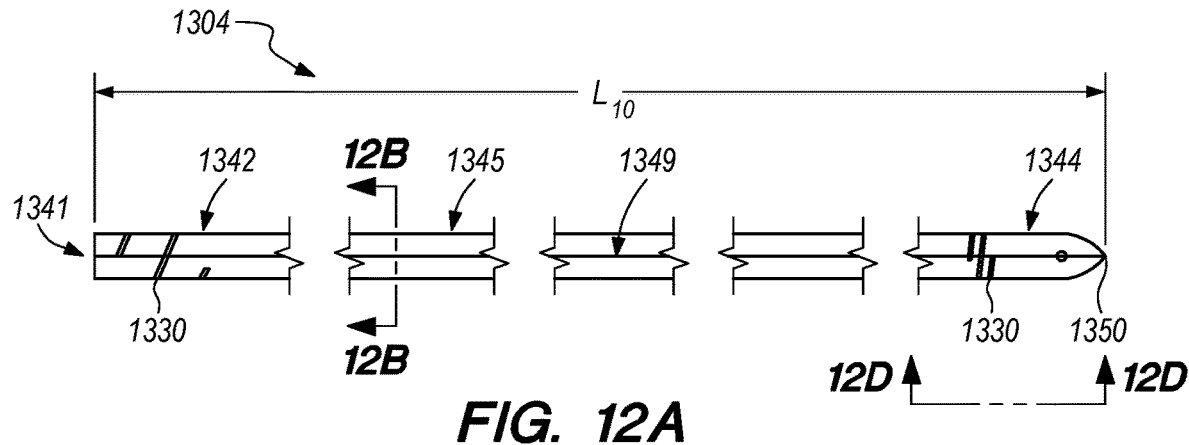
Figure 12B:
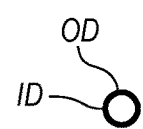
Figure 12C:
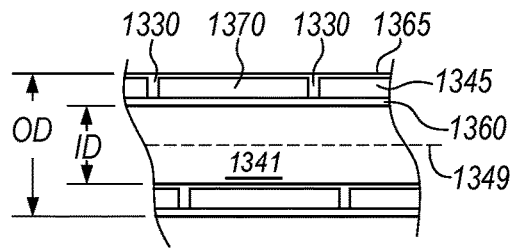

In the embodiments of FIGS. 12A-C, the delivery catheter 1304 comprises an reinforcing member 1345 configured to reinforce the catheter 1304 while providing a suitable balance between column strength and flexibility (e.g., "pushability" and "torqueability"). The reinforcing member 1345 is composed of suitable biocompatible and elastomeric materials such as, stainless steel, Nitinol® or the like. In some embodiments, the reinforcing member 1345 comprises a stainless steel or Nitinol hypotube providing suitable column strength, the hypotube further comprises selective cuts 1330 (e.g., fenestrations or the like), which provides suitable flexibility.

The reinforcing member 1345 may extend along a substantial length of the catheter 1304 (e.g., the reinforcing member 1345 extends from the proximal portion 1342 to the distal portion 1344 of the catheter 1304). In the embodiment of FIG. 12A, length L10, measured along a central axis 1349 of the reinforcing member 1345 is approximately 59 inches (150 cm). Alternatively, the reinforcing member 1345 can extend along a section of the catheter 1304 (e.g., the reinforcing member 1345 extends along the distal portion 1344 without extending to the proximal portion 1342 of the catheter 1304). For example, L10 can range between 1.9 inches (5 cm) to 6 inches (15.2 cm), or any other suitable length.

Further, in the embodiment of FIGS. 12A-C, the inner diameter (ID) of the reinforcing member 1345 (e.g., lumen 1341) measured in a direction orthogonal to axis 1349 can range between 0.0205 inches (0.5207 mm) to 0.024 inches (0.6096 mm), and the outer diameter (OD) of the reinforcing member 1345 measured in the same or similar direction (i.e., orthogonal to axis 1349) can range between 0.026 inches (0.6604 mm) to 0.03 inches (0.762 mm). It should be appreciated that the ID, OD and/or the L10 and any other length, width, or thickness of the reinforcing member 1345 of the delivery catheter 1304 may have any suitable dimension for delivering the shunt in the target site (e.g., IPS, CP angle cistern, or the like). Exemplary dimensions (in inches) and properties of the reinforcing member 1345 are shown in FIG. 12G, which are not intended to limit the embodiment of FIGS. 12A-C.

In the embodiments of FIGS. 12A and 12C, the reinforcing member 1345 comprises one or more cuts 1330 (e.g., fenestrations, kerfs, slots, key-ways, recesses, or the like) selectively disposed at the proximal portion 1342 and the distal portion 1344 of the reinforcing member 1345. Additionally, the one or more cuts 1330 can be disposed in sections of the reinforcing member 1345 along L10, as shown by the exemplary spiral cut pattern of kerf, pitch, cuts per rotation and cut balance depicted in sections of FIG. 12A. Alternatively, the cuts 1330 can be continuously disposed substantially along L10 (not shown), and the continuously disposed cuts 1330 can have variable spiral cut patterns of kerf, pitch, cuts per rotation and cut balance along L10 or combinations thereof.

The cuts 1330 of the reinforcing member 1345 can have a variety of suitable patterns, and can be manufactured by laser cutting the reinforcing member 1345 of the delivery catheter 1304. Alternatively, the cuts 1330 and their patterns can be manufactured by etching or other suitable techniques. FIGS. 12E-F depict an exemplary cut pattern of the reinforcing member 1345 of FIGS. 12A-C. In these embodiments, the laser cutting of the reinforcing member 1345 creates between 1.5 to 2.5 cuts 1330 per rotation of the reinforcing member 1345, having a cut balance of between 100° to 202° of rotation with laser on, and then 34° to 38° of rotation with laser off.

As shown in FIG. 12A, the cuts 1330 of the reinforcing member 1345 that are disposed at the proximal portion 1342 comprise a larger pitch (e.g., 0.015) than the pitch (e.g., 0.006) of the cuts 1330 disposed at the distal portion 1344 of the reinforcing member 1345. The smaller the pitch of the cuts 1330 (i.e., smaller separation between cuts) provides for an increase in flexibility of the reinforcing member 1345, such as at the distal portion 1344 of the delivery catheter 1304. The transition between the larger pitch to the smaller pitch cuts 1330 can be subtle, providing for a progressively more flexible delivery catheter towards the distal portion. By way of non-limiting examples, the spiral cut pattern to create the cuts 1330 disposed at the proximal portion 1342 of the reinforcing member 1345 comprise a kerf of 0.001, a pitch of 0.015, creating 2.5 cuts per rotation, having a cut balance of 100° of rotation with laser on, and then 34° rotation with laser off. The spiral cut pattern applied to create the cuts 1330 disposed between the proximal portion 1342 and the distal portion 1344 of the reinforcing member 1345 comprises a kerf of 0.001, a pitch transition from 0.006 to 0.015, creating 1.5 cuts per rotation, having a cut balance of 202° of rotation with laser on, and then 38° rotation with laser off. The spiral cut pattern applied to create the cuts 1330 disposed at the distal portion 1344 of the reinforcing member 1345 comprises a kerf of 0.001, a pitch of 0.004, creating 1.5 cuts per rotation, having a cut balance of 202° of rotation with laser on, and then 38° rotation with laser off. The cuts 1330 may have a width that ranges between 0.0005 inches (0.0127 mm) to 0.002 inches (0.0508 mm), or any other suitable width. It should be appreciated that the width, length and depth of the cuts 1330 and patterns of the cuts 1330 in the reinforcing member 1345 of the delivery catheter 1304, can comprise any suitable dimensions. By way of non-limiting example, the pattern of cuts 1330 can transition to a larger pitch (e.g., greater than 0.004) in the distal portion 1344 of reinforcing member 1345 to increase column strength and provide support to a delivery catheter during the penetration step of the shunt implant procedure.

Additionally, the reinforcing member 1345 comprises an inner liner 1360 and an outer jacket 1365, as better seen in FIG. 12C. The inner liner 1360 and outer jacket 1365 are composed of suitable implantable polymeric materials, such as polytetrafluoroethylene "PTFE", polyethyleneterephthalate "PET", High Density Polyethylene "HDPE", expanded polytetrafluoroethylene "ePTFE", urethane, silicone, or the like. The inner liner 1360 and outer jacket 1365 are configured to cover—substantially completely or partially—the cuts 1330 of the reinforcing member 1345, from within lumen 1341 and over the elongated member outer surface 1370, respectively. In such configuration, the reinforcing member 1345 becomes an impermeable tubular element having the cuts 1330 covered by the respective inner liner 1360 and outer jacket 1365, while maintaining the flexibility provided by the selective cuts 1330 and column strength afforded, in part, by the reinforcing member 1345.

The inner liner 1360 provides a smooth inner surface in the lumen 1341 of the reinforcing member 1345 that facilities translation and delivery of the shunt (or other delivery systems or devices delivered through the lumen). Further, the inner liner 1360 can be configured to line the interior reinforcing member 1345 using an extrusion process. Alternatively, the liner material can be deposited (e.g., using a dispersion technique) on a mandrel (e.g., nickel coated copper); thereafter, the liner-coated mandrel can be placed within the reinforcing member 1345 for application of outer jacket 1365 and adhering the inner liner 1360 to the reinforcing member 1345, after which the mandrel can be withdrawn from the reinforcing member 1345 leaving inner liner 1360 in place within the lumen 1341 of the reinforcing member 1345.

The outer jacket 1365 provides a smooth outer surface to the reinforcing member 1345, which facilitates the navigation of the delivery catheter 1304 through tortuous vasculature. As noted above, the outer jacket 1365 can comprise one or more implant-grade polymers including, but not limited to, polyurethane or silicone-polyurethane blends. In some embodiments, a gas or liquid dispersion of polymer is applied to the reinforcing member 1345 and inner liner 1360, which forms the outer jacket 1365 and bonds the inner liner 1360, the reinforcing member 1345, and outer jacket 1365 together in an integrated configuration of the delivery catheter 1304.

The outer jacket 214 can substantially cover the entire outer surface of the reinforcing member 1345; however, in some embodiments, the outer jacket can be placed selectively along sections of reinforcing member 1345 to adhere the inner liner 1360 to the reinforcing member 1345. By way of non-limiting example, a liquid dispersion of polymer or an epoxy-based adhesive can be placed at discrete locations along L10. Alternatively, the outer surface of inner liner 1360 can be coated with polymer or adhesive, and then placed within reinforcing member 1345; the polymer or adhesive can seep into the cuts 1330, substantially completely or partially filling some or all of the cuts 1330 along L10.

In the embodiment of FIG. 12C, the inner liner 1360 can have a thickness of 0.0005 inches (0.0127 mm); though the thickness of inner liner 1360 can range from 0.0005 inches (0.0127 mm) to 0.0015 inches (0.0381 mm) in other embodiments. In the embodiment of FIG. 12C, the outer jacket 1365 can have a thickness of 0.001 inches (0.0254 mm); though the thickness of outer jacket 1365 can range from 0.0001 inches (0.00254 mm) to 0.001 inches (0.0254 mm) in other embodiments. It should be appreciated that the inner liner 1360, and the outer jacket 1365 of the reinforcing member 1345 may comprise any suitable dimensions.

Figure 12D:
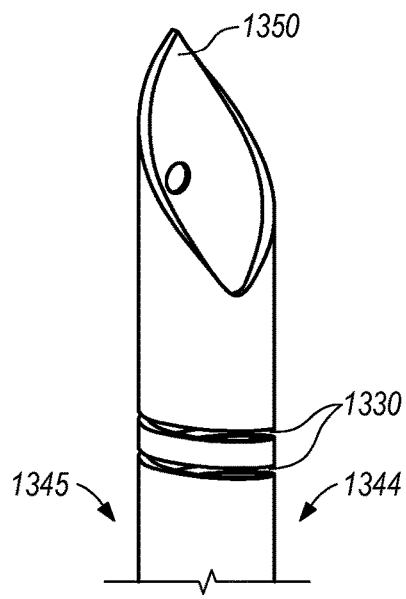
Figure 12E:
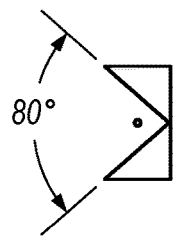

Referring back to FIG. 12A, the reinforcing member 1345 further comprises an integrated penetrating element 1350 (e.g., sharp, tapered, cannula-like end, bevel, pencil, or Quincke tip needle, or the like) extending or disposed at the distal portion 1344 of the elongated member, as also depicted in FIG. 12D. The penetrating element 1350 is configured to penetrate the dura mater of the IPS wall 114 and the arachnoid layer 115 creating an anastomosis between the IPS 102 and the CSF-filled CP angle cistern 138 for deployment of the shunt, as previously disclosed herein, and in the related application previously incorporated by reference herewith. The cuts 1330 proximately disposed to the penetrating element 1350 are configured to provide suitable flexibility to the distal portion 1344 of the delivery catheter 1304, allowing the distal portion 1344 to bend, curve and/or orient the penetrating element 1350 towards the IPS wall 114, while maintaining suitable column strength to support the penetrating element 1350 at the distal portion 1344 as it penetrates through the IPS wall 114 and arachnoid layer 115. The penetrating element 1350 extending from, integrated with and/or incorporated to the distal portion 1344 of the reinforcing member 1345 allows for a secure withdrawal of the penetrating element 1350 when the delivery catheter 1304 is withdrawn from the patient.

FIGS. 13A-F illustrate another alternative delivery catheter 1304' for delivering a shunt into a target site of a patient, constructed in accordance with embodiments of the disclosed inventions. For ease in illustration, the features, functions, dimensions and configurations of the delivery catheter 1304' of FIGS. 13A-F that are the same or similar as in the delivery catheter 1304 of FIGS. 12A-G, are given the same reference numerals and are incorporated herein. The delivery catheter 1304' comprises an elongated configuration having a proximal portion 1342, a distal portion 1344' and a lumen 1341 extending therebetween. The delivery catheter 1304' comprises an reinforcing member 1345' configured to reinforce the catheter 1304' while providing a suitable balance between column strength and flexibility (e.g., "pushability" and "torqueability"). The reinforcing member 1345' is composed of suitable biocompatible and elastomeric materials such as, stainless steel, Nitinol or the like, further comprises selective cuts 1330.

Similarly to the reinforcing member 1345 of FIG. 12A, the reinforcing member 1345' of FIG. 13A can extend along a substantial length of the catheter 1304' (e.g., length L10, measured along a central axis 1349 of the reinforcing member 1345'). Alternatively, the reinforcing member 1345' can extend along a section of the catheter 1304'. The inner diameter (ID) and outer diameter (OD) of the reinforcing member 1345' measured in a direction orthogonal to axis 1349 can comprise the same or similar dimensions and ranges of the reinforcing member 1345 described above. It should be appreciated that the ID, OD and/or the L10 and any other length, width, or thickness of the reinforcing member 1345' of the delivery catheter 1304' can have any suitable dimension for delivering the shunt in the target site (e.g., IPS, CP angle cistern, or the like). Exemplary dimensions (in inches) and properties of the reinforcing member 1345' are shown in FIG. 13F, which are not intended to limit the embodiment of FIGS. 13A-C.

In the embodiments of FIGS. 13A and 13C, the reinforcing member 1345' comprises one or more cuts 1330 (e.g., kerfs, slots, key-ways, recesses, or the like) selectively disposed at the proximal portion 1342 and the distal portion 1344' of the reinforcing member 1345'. Additionally, the one or more cuts 1330 may be disposed in sections of the reinforcing member 1345' along L10, as shown by the exemplary spiral cut pattern of kerf, pitch, cuts per rotation and cut balance depicted in sections of FIG. 13A. Alternatively, the cuts 1330 can be continuously disposed substantially along L10 (not shown), and the continuously disposed cuts 1330 can have variable spiral cut pattern of kerf, pitch, cuts per rotation and cut balance along L10 or combinations thereof.

The cuts 1330 of the reinforcing member 1345' can have a variety of suitable patterns, and can be manufactured by laser cutting the elongated member 1345' of the delivery catheter 1304'. Alternatively, the cuts 1330 and their patterns can be manufactured by etching or other suitable techniques. FIGS. 13D-E depict an exemplary cut pattern of the reinforcing member 1345' of FIGS. 13A-C. In these embodiments, the laser cutting of the reinforcing member 1345' creates between 1.5 to 2.5 cuts 1330 per rotation of the reinforcing member 1345', having a cut balance of between 100° to 202° of rotation with laser on, and then 34° to 38° of rotation with laser off.

As shown in FIG. 13A, the cuts 1330 of the reinforcing member 1345' that are disposed at the proximal portion 1342 comprise a larger pitch (e.g., 0.013) than the pitch (e.g., 0.004-0.012) of the cuts 1330 disposed at the distal portion 1344' of the reinforcing member 1345'. By way of non-limiting examples, the spiral cut pattern applied to create the cuts 1330 disposed at the proximal portion 1342 of the reinforcing member 1345' comprises a kerf of 0.001, a pitch of 0.013, creating 2.5 cuts per rotation, having a cut balance of 100° of rotation with laser on, and then 34° rotation with laser off. The spiral cut pattern applied to create the cuts 1330 disposed between the proximal portion 1342 and the distal portion 1344' of the reinforcing member 1345' comprises a kerf of 0.001, a pitch transition from 0.009 to 0.013, creating 2.5 cuts per rotation, having a cut balance of 100° of rotation with laser on, and then 34° rotation with laser off. The spiral cut pattern applied to create the cuts 1330 disposed at the distal portion 1344' of the reinforcing member 1345' comprises a kerf of 0.001, a pitch transition from 0.004 to 0.012, creating 1.5 cuts per rotation, having a cut balance of 202° of rotation with laser on, and then 38° rotation with laser off. It should be appreciated that the width, length and depth of the cuts 1330 and patterns of the cuts 1330 in the reinforcing member 1345' of the delivery catheter 1304', may comprise any suitable dimensions.

Additionally, the reinforcing member 1345' may comprise the inner liner 1360 and the outer jacket 1365 of the reinforcing member 1345, as previously described in FIG. 12C.

Referring back to FIG. 13A, the reinforcing member 1345' further comprises one or more slots 1380 disposed at the distal portion 1344 of the reinforcing member 1345'. The slots 1380 may be longitudinally disposed in the direction of the axis 1349 of the reinforcing member 1345'. The slots 1380 are configured to engage respective proximally disposed protrusions of a penetrating element (not shown) and secure the piercing element to the distal portion 1344' of the reinforcing member 1345'. Additionally, the interface between the slots 1380 of the reinforcing member 1345' and the protrusions of the piercing element can be further secured by welding, adhesive and other suitable techniques.

FIGS. 14A-D illustrate an endovascular shunt delivery assembly 2300 in accordance with another embodiment of the disclosed inventions. The delivery assembly 2300 includes a delivery catheter 2304, an inner tubular member or dilator 2361, and a delivery guidewire 2308. The delivery catheter 2304 comprises a proximal portion (not shown), a distal portion 2344 and an inner lumen 2305 extending therebetween. The dilator 2361 is coaxially disposed within the lumen 2305 of the delivery catheter 2304, and the delivery guidewire 2308 is coaxially disposed within dilator 2361. The distal portion 2344 of the catheter 2304 comprises a distal end opening 2346 and a side aperture 2377. The distal end opening 2346 of the delivery catheter 2304 may be tapered or include any suitable configuration that allows passage of the dilator 2361 and the delivery guidewire 2308. The side aperture 2377 of the delivery catheter 2304 is sized and dimensioned to allow passage of a shunt and/or a penetrating element towards the IPS wall 114, and may further include radio-opaque materials or include markings for purposes of imaging, according to the disclosed inventions.

The delivery catheter 2304 may further comprise a hypotube providing suitable column strength, the hypotube including selective cuts to provide the catheter 2304 with suitable flexibility, as previously described in FIGS. 12A-13E. The delivery catheter 2304 may comprise one or more inner liners to increase lubricity and facilitate passage of further delivery system components through the delivery catheter lumen 2305, and may further comprise one or more outer jackets (e.g., Pebax or other suitable polymeric material), as described in FIGS. 12A-13E.

Figure 14A:
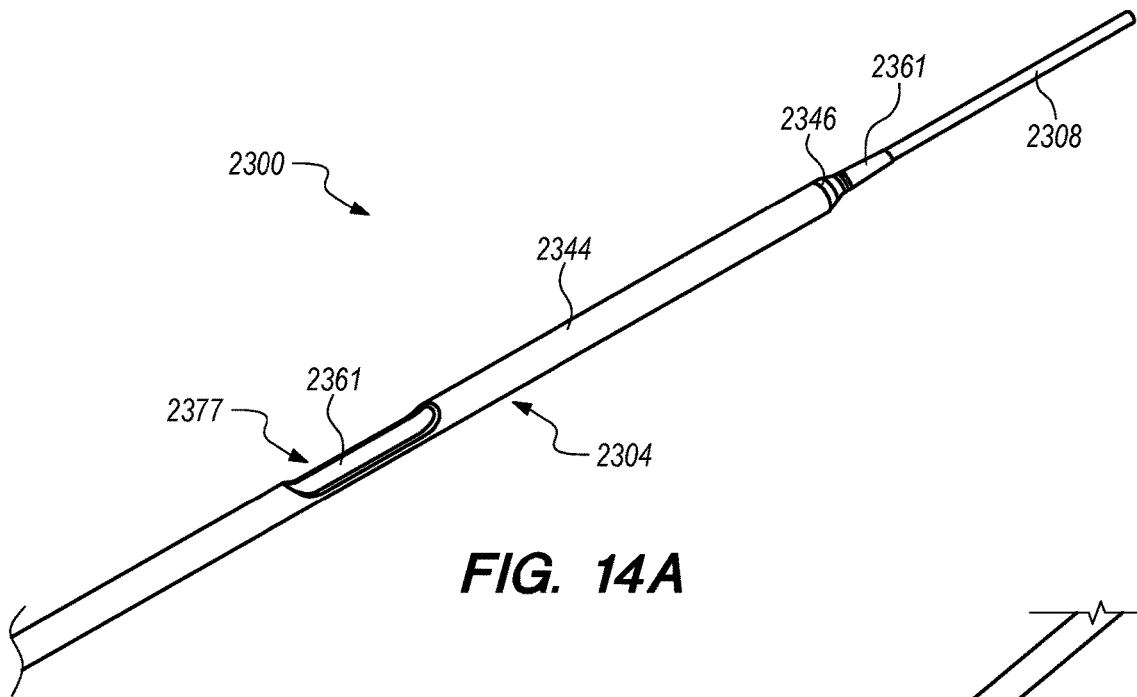
FIGS. 14A-E are perspective and cross-sectional views of shunt delivery catheter, constructed according to yet another embodiment of the disclosed inventions.
Figure 14B:
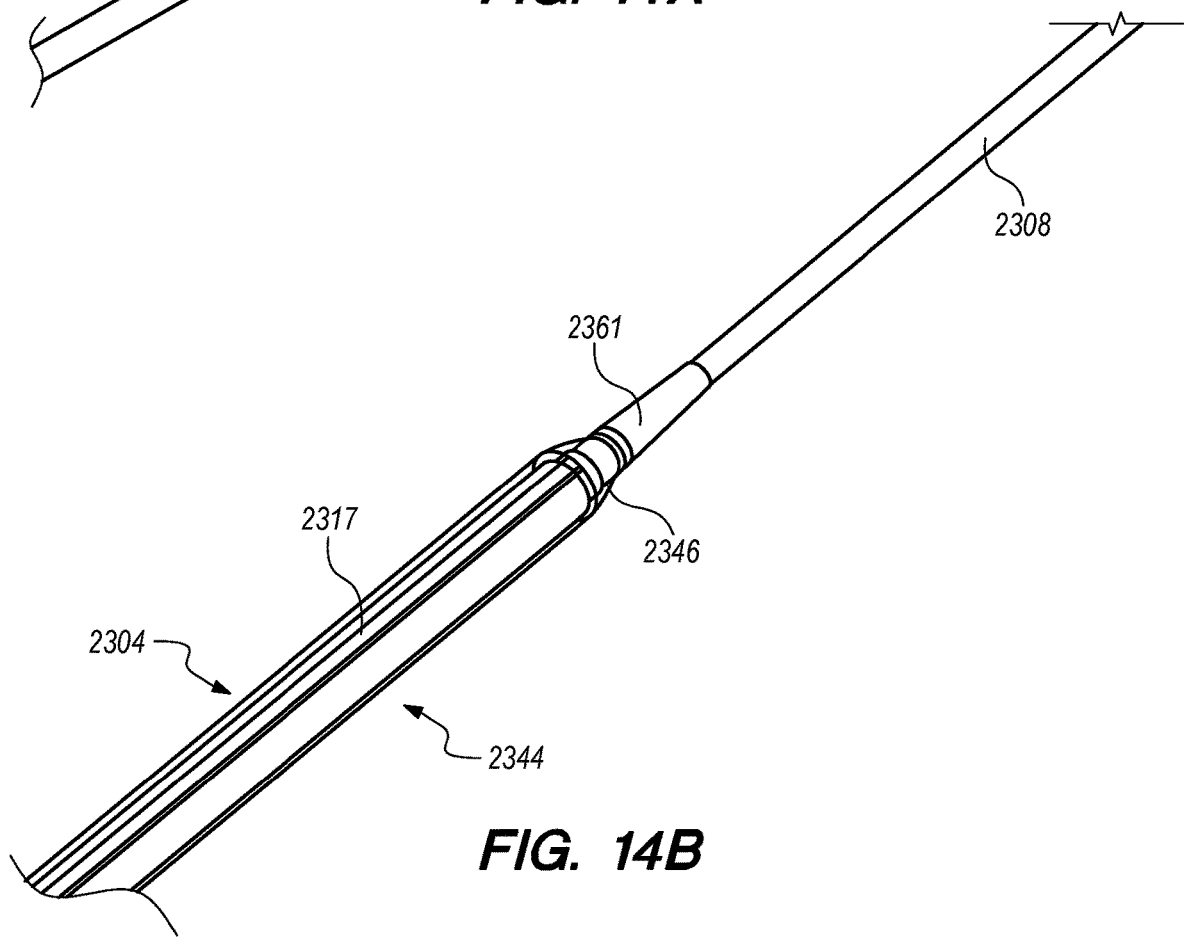
Figure 14C:
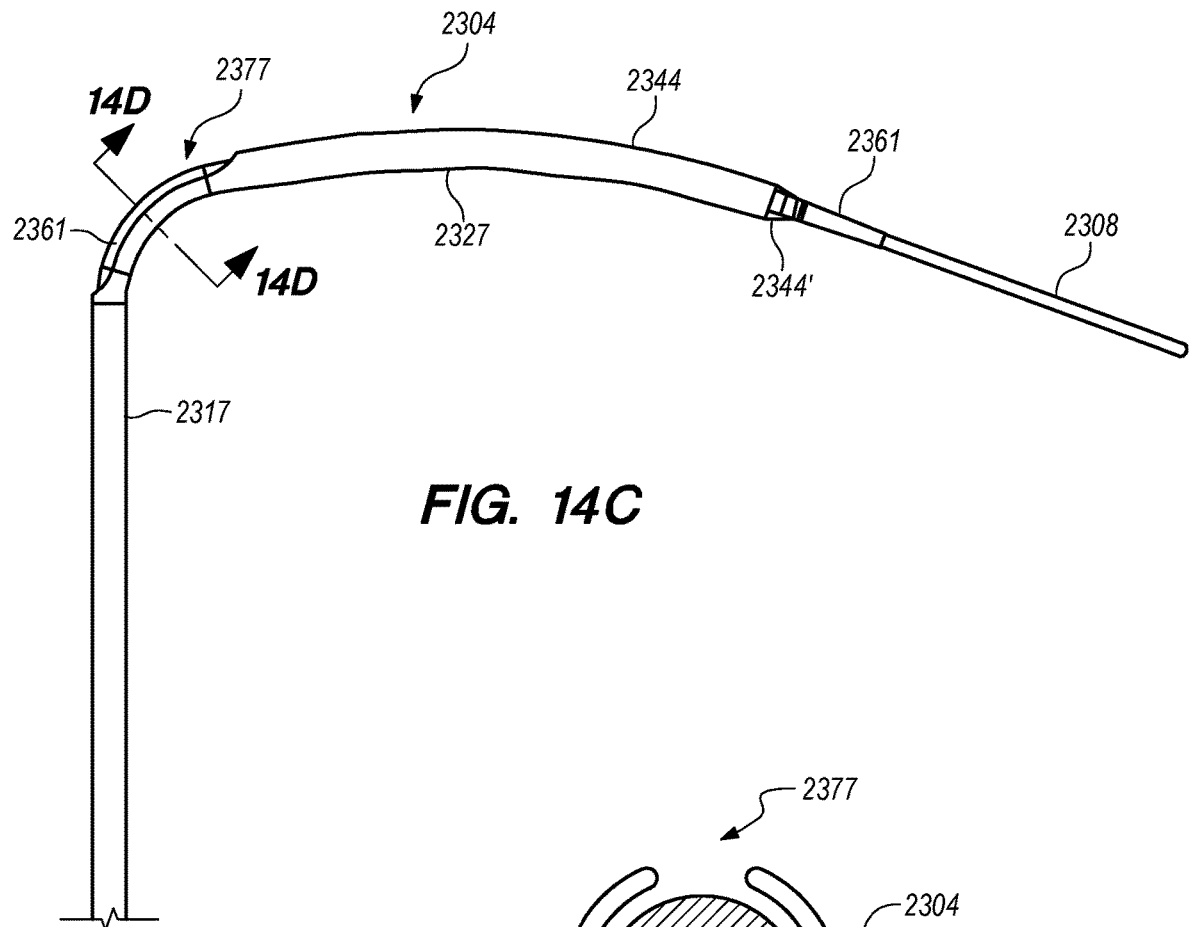
Figure 14D:
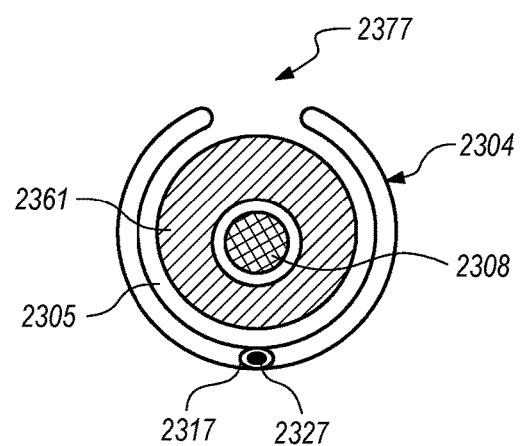
Figure 14E:
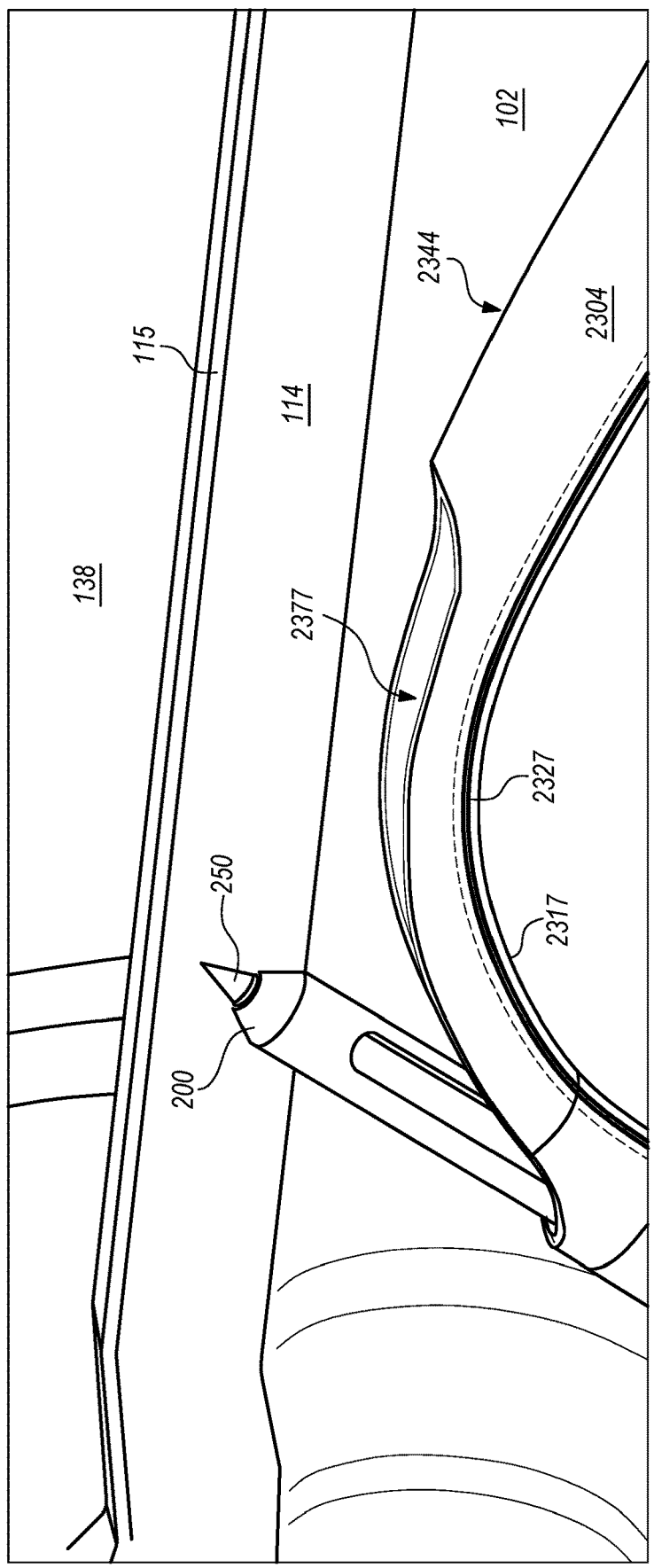

The delivery catheter 2304 further comprises an additional lumen 2317 that extends from the proximal portion (not shown) to the distal portion 2344 of the catheter 2304, as shown in FIGS. 14B-E. The lumen 2317 of the delivery catheter 2304 is disposed opposite to the side aperture 2377 of the catheter 2304, as better appreciated in FIGS. 14C-D. A pull-wire 2327 is disposed within the lumen 2317 of the catheter 2304 and extends from or beyond the proximal portion of the catheter (not shown) to the distal portion 2344 of the catheter 2304. The pull-wire 2327 is fixedly coupled to at least the distal portion 2344 of the catheter, at least a portion distally disposed from the aperture 2377 of the catheter. As shown in FIG. 14C, the pull-wire 2327 may be coupled to the tapered distal end portion 2344' of the catheter. The pull-wire 2327 is configured to be pulled so as to bend the distal portion 2344 of delivery catheter 2304 orienting the side aperture 2377 towards the IPS wall 114, allowing the delivery of the shunt 200 and/or penetrating element 250 (FIGS. 14C and 14E).

The delivery catheter 2304 having the pull-wire 2327 can be introduced into the patient from a venous access location. The guidewire 2308 can be passed through the junction 118 between the IPS 102 and the jugular bulb 108 and/or jugular vein 106 (FIG. 2A), and beyond the junction to a more distal location in the IPS 102 or cavernous sinus (CS) 104. The tapered distal portion 2344 of the delivery catheter 2304 and dilator 2361 facilitate access into tortuous, small diameter intracranial venous channels, e.g., the JV-IPS junction 118. Alternatively, the delivery catheter 2304, without the dilator 2361, can be advanced over the guidewire 2308. In the alternative embodiment without the dilator 2361, the distal portion 2344 of the delivery catheter 2304 further tapers towards the guidewire 2308, and the catheter may have a smaller diameter than the catheter over the dilator. Then, the delivery catheter 2304 is navigated along the curved portion of the IPS 102 until the aperture 2377 is properly oriented, faces or is adjacent the target penetration site along IPS wall 114.

Prior to the piercing of the IPS wall 114 to create anastomosis and access the CP angle cistern 138, the proper orientation of the distal portion 2344 of the delivery catheter 2304, particularly, the proper orientation of the aperture 2377, may be verified according to the imaging methods previously disclosed. When needed, the positioning and orientation of the aperture 2377 at the distal portion 2344 of the delivery catheter 2304 may be adjusted, for example, by applying a rotational force directly to the body of the delivery catheter 2304. The guidewire 2308 and dilator 2361 may be removed from the delivery catheter 2304, prior, during or after the proper orientation of the aperture 2377 is achieved.

When the proper orientation of the aperture 2377 is obtained, the physician pulls on the proximal portion of the pull-wire 2327 retracting the pull-wire 2327 in the proximal direction inducing a bend in the distal portion 2344 of the delivery catheter, which positions the aperture 2377 towards and/or against a target penetration site along IPS wall 114 for a subsequent penetration step of the shunt implant procedure (FIG. 14E). The pull-wire 2327 can be actuated before and during the delivery of the shunt to assist with the steering of the system through the vasculature. That is, actuating the pull-wire 2327 can articulate the distal portion 2344 of the delivery catheter to access particular locations within the patient's vasculature. In addition, the pull-wire 2327 actuation allows the operator to control placement of the aperture 2377 relative to a target penetration along IPS wall 114, thereby directing the trajectory of a penetrating member from the IPS into the CP angle cistern 138. A shunt and/or penetrating element (e.g., a shunt with a stylet disposed within the shunt lumen, or any other suitable disclosed shunt and/or penetrating element) can be advanced through the delivery catheter lumen 2305, and further advanced through IPS wall 114 into CP angle cistern 138 (FIG. 14E). The shunt 200 with distal radiopaque marker (e.g., gold tapered distal portion of the shunt) and stylet 250 disposed within the shunt lumen are advancing from the aperture 2377 of the delivery catheter 2304 through IPS wall 114. The shunt 200 and stylet 250 are further advanced through IPS wall 114 until the distal anchoring mechanism 229 of shunt (e.g., malecot) deploys within CP angle cistern 138 (as shown, for example in FIGS. 7E-F). Thereafter, the stylet 250 can be removed from the shunt 205, and the pull-wire 2327 can be released before withdrawing the delivery catheter 2034 from the patient's vasculature.

Figure 15A:
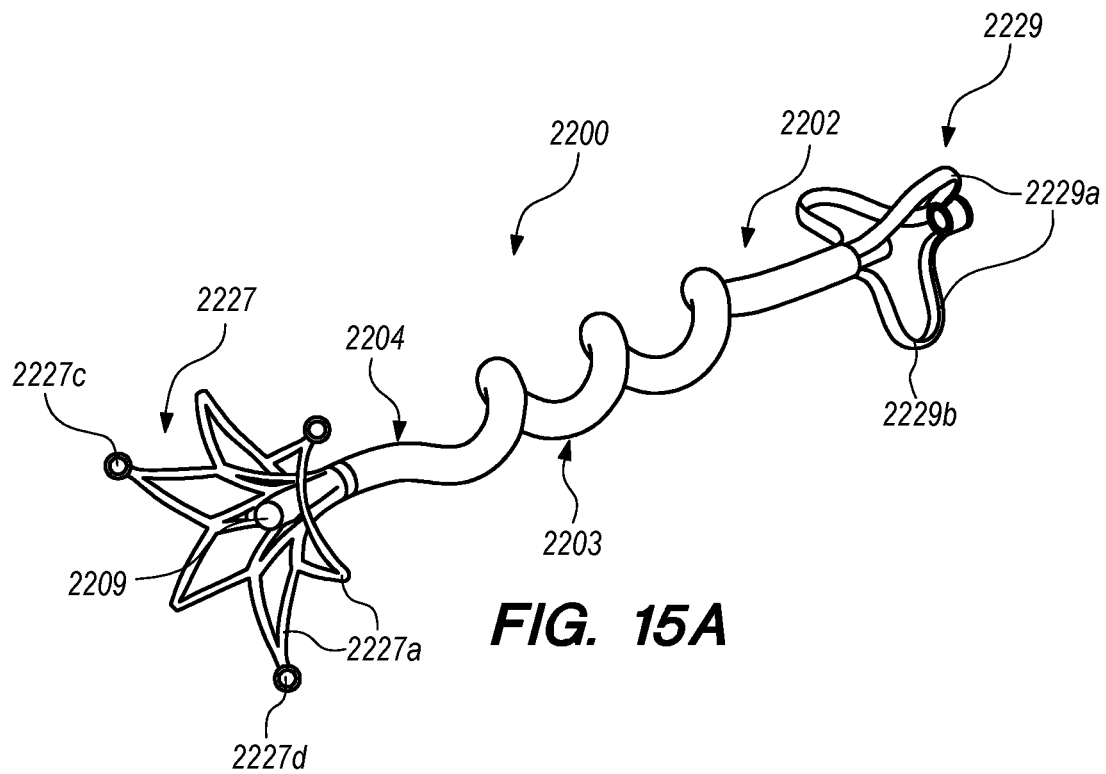
FIGS. 15A-Z are side, perspective and cross-sectional views of a shunt, constructed according to another embodiment of the disclosed inventions.
Figure 15B:
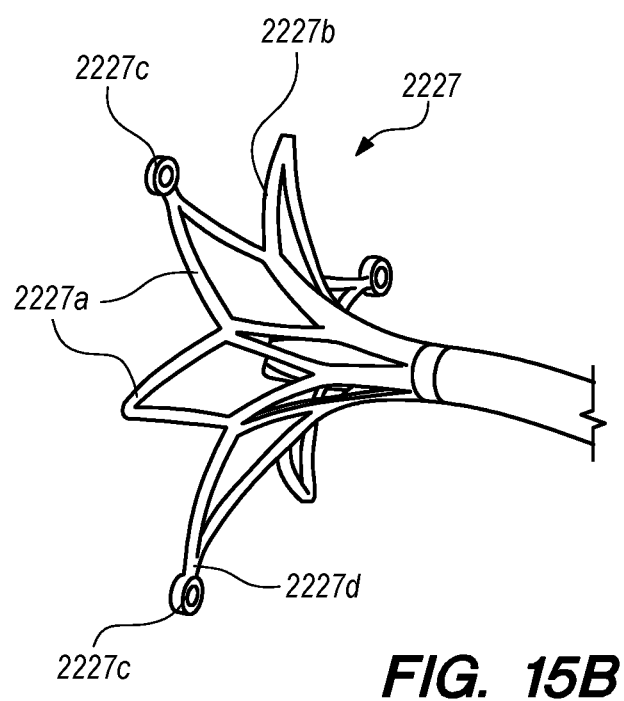
Figures 1, 15C:
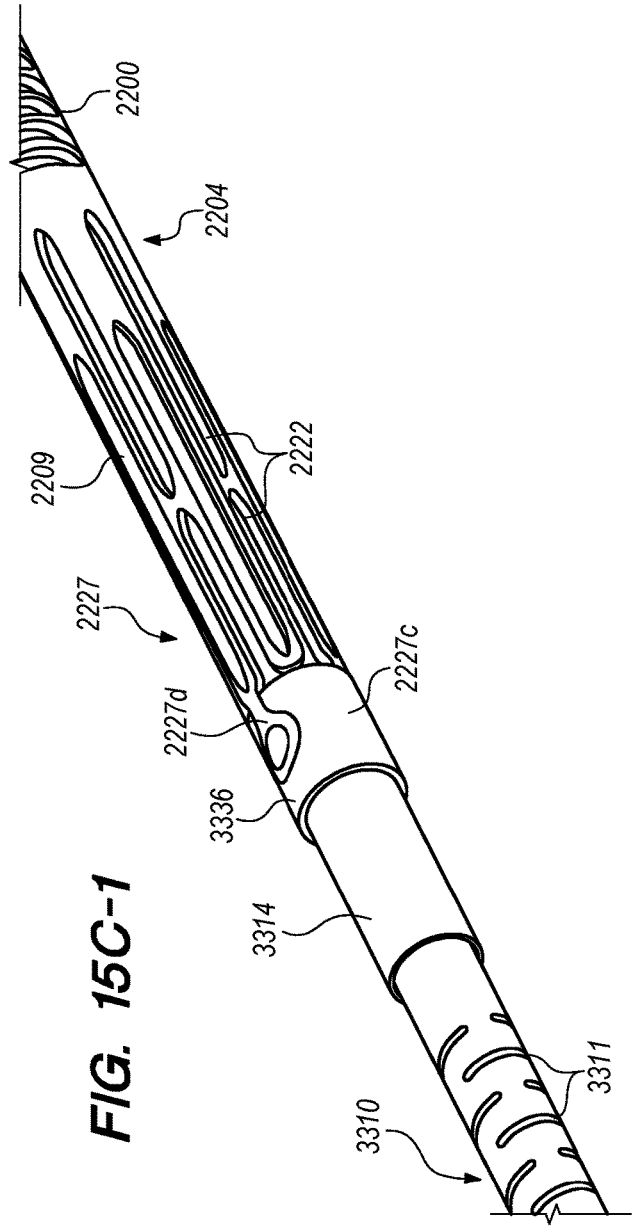
Figures 2, 15C:
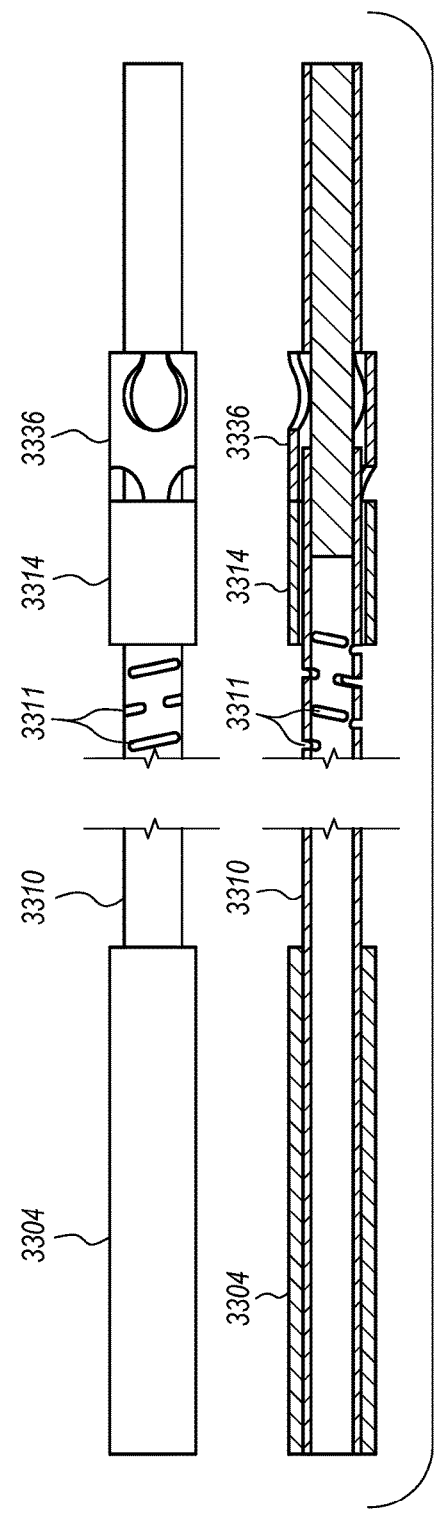
Figure 15D:
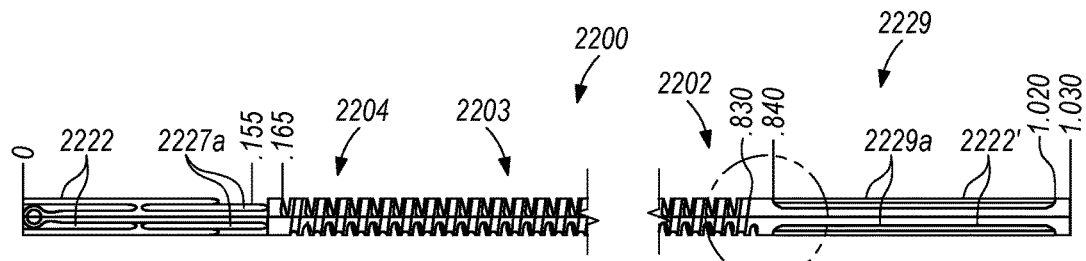
Figure 15E:
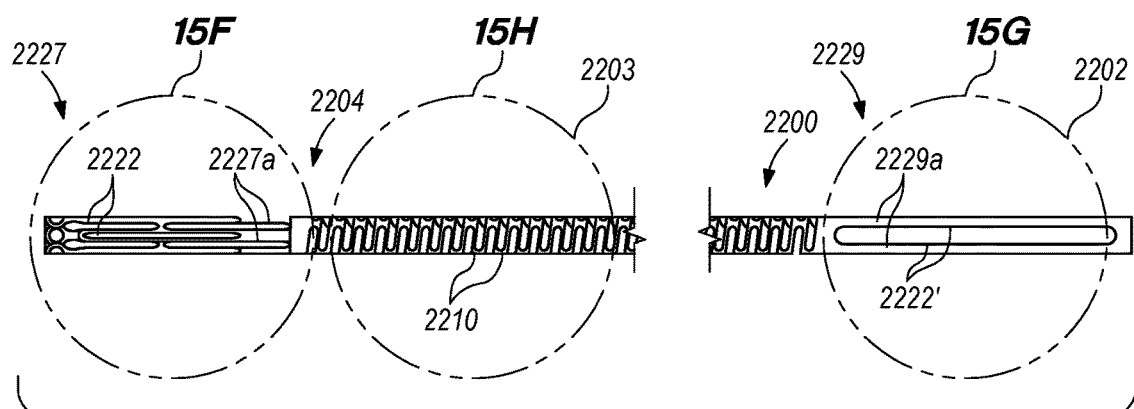
Figure 15F:
Figure 15G:
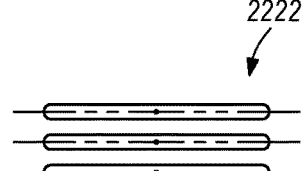
Figure 15H:
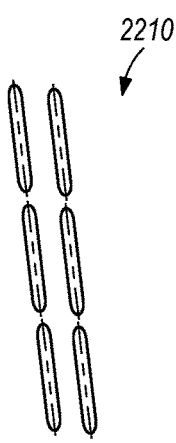
Figure 15L:
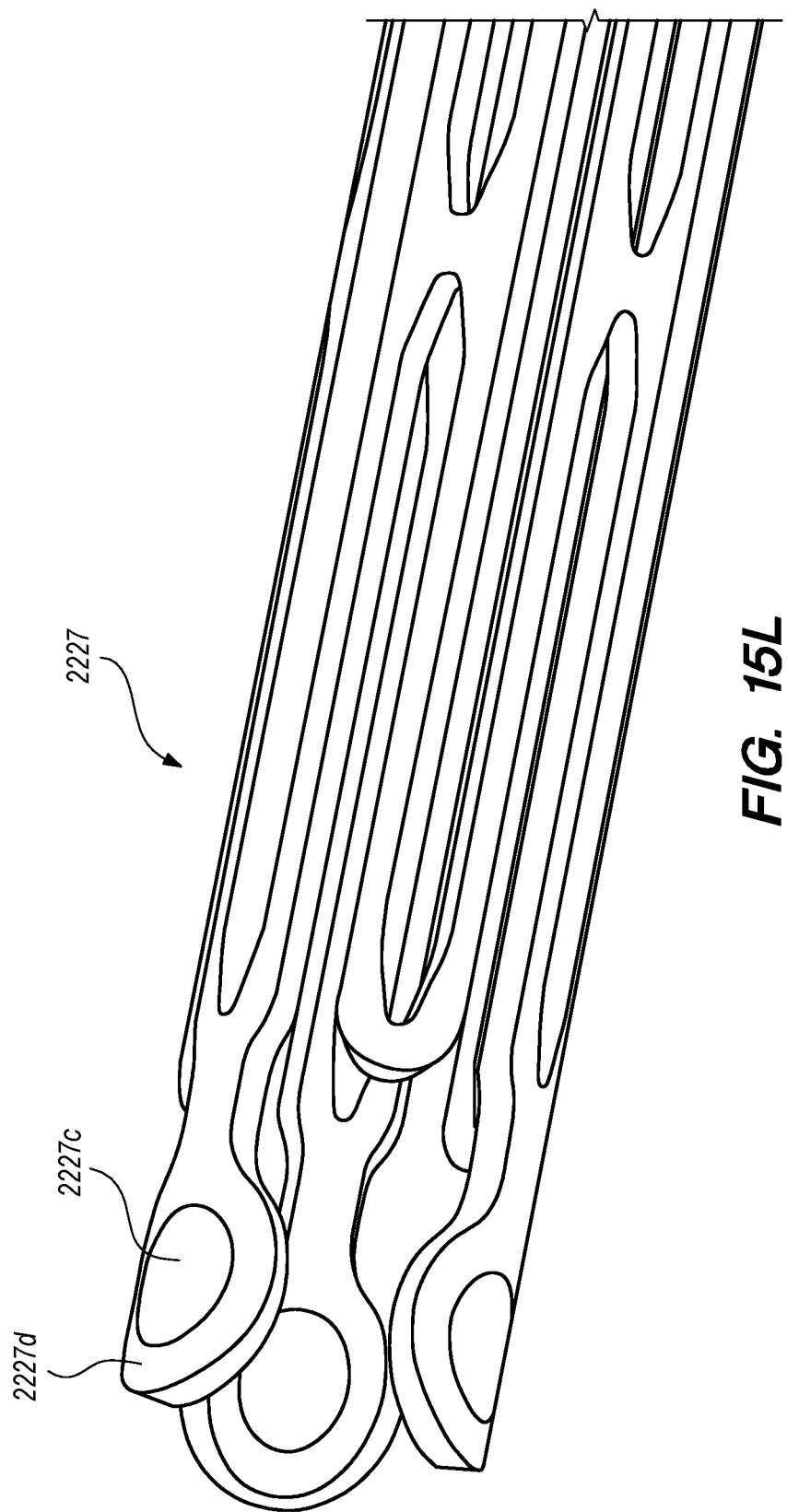
Figure 15M:
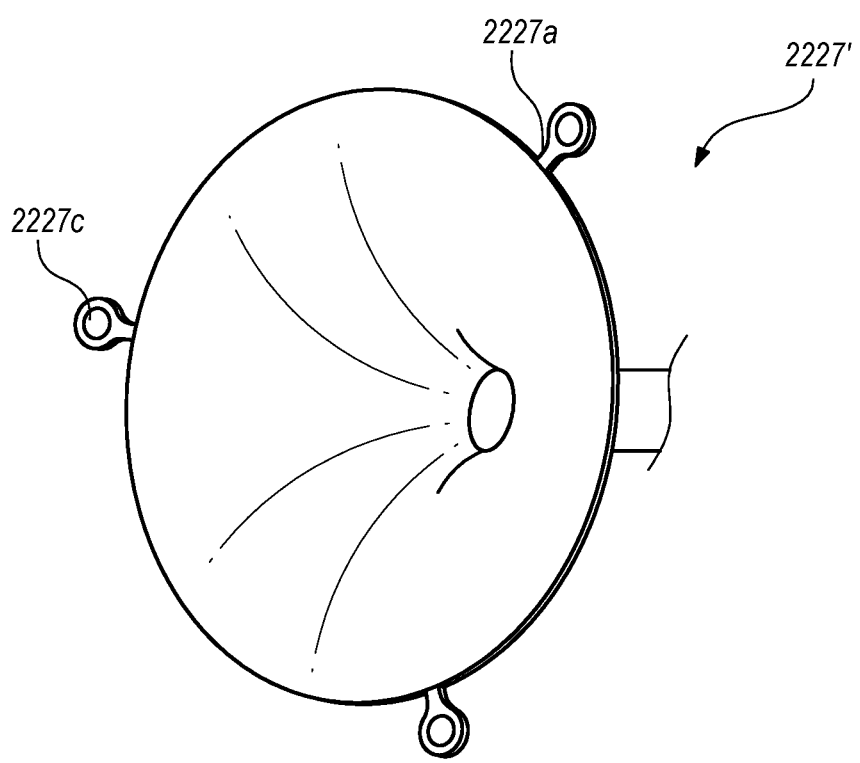
Figure 15O:
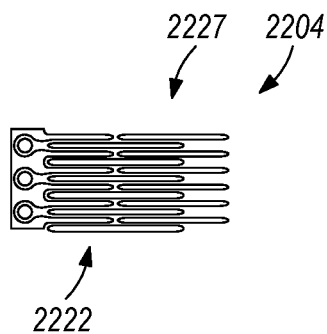
Figure 15P:
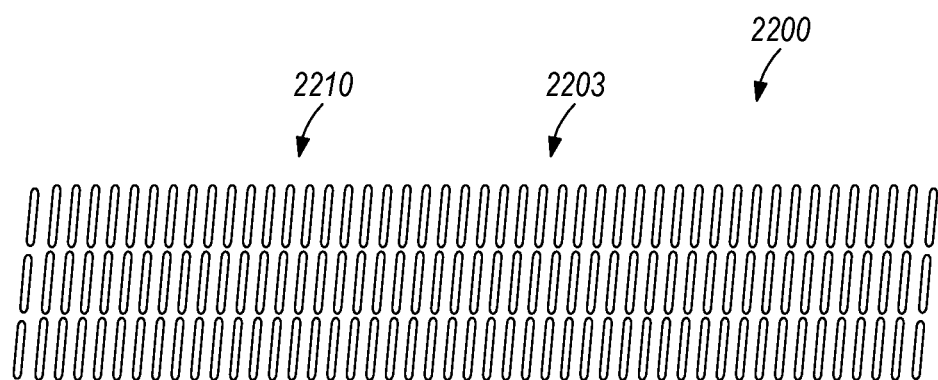
Figure 15Q:
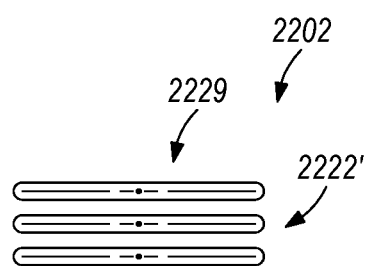
Figure 15R:
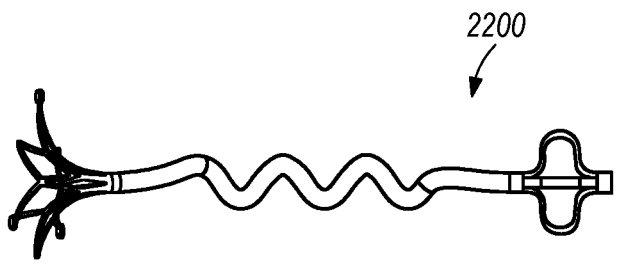
Figure 15S:
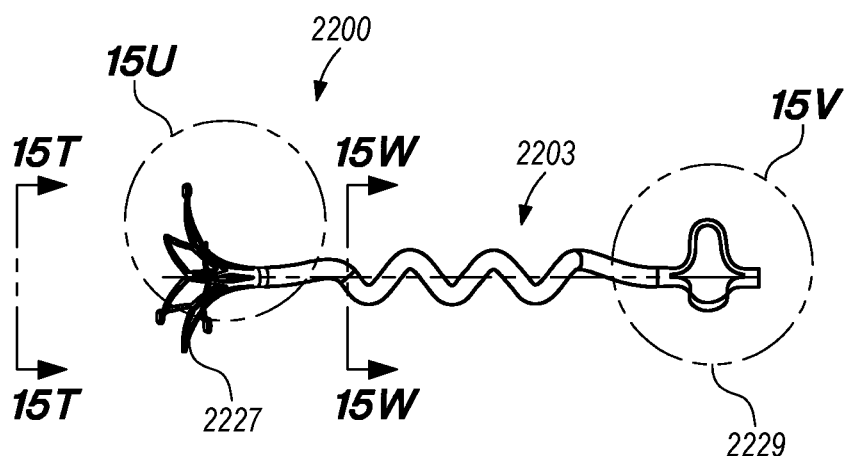
Figure 15T:
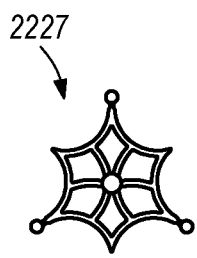
Figure 15U:
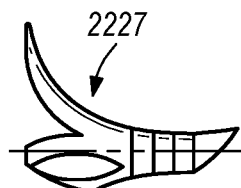
Figure 15V:
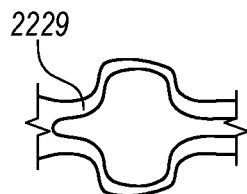
Figure 15W:
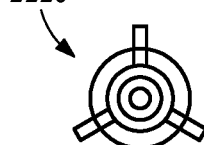
Figure 15X:
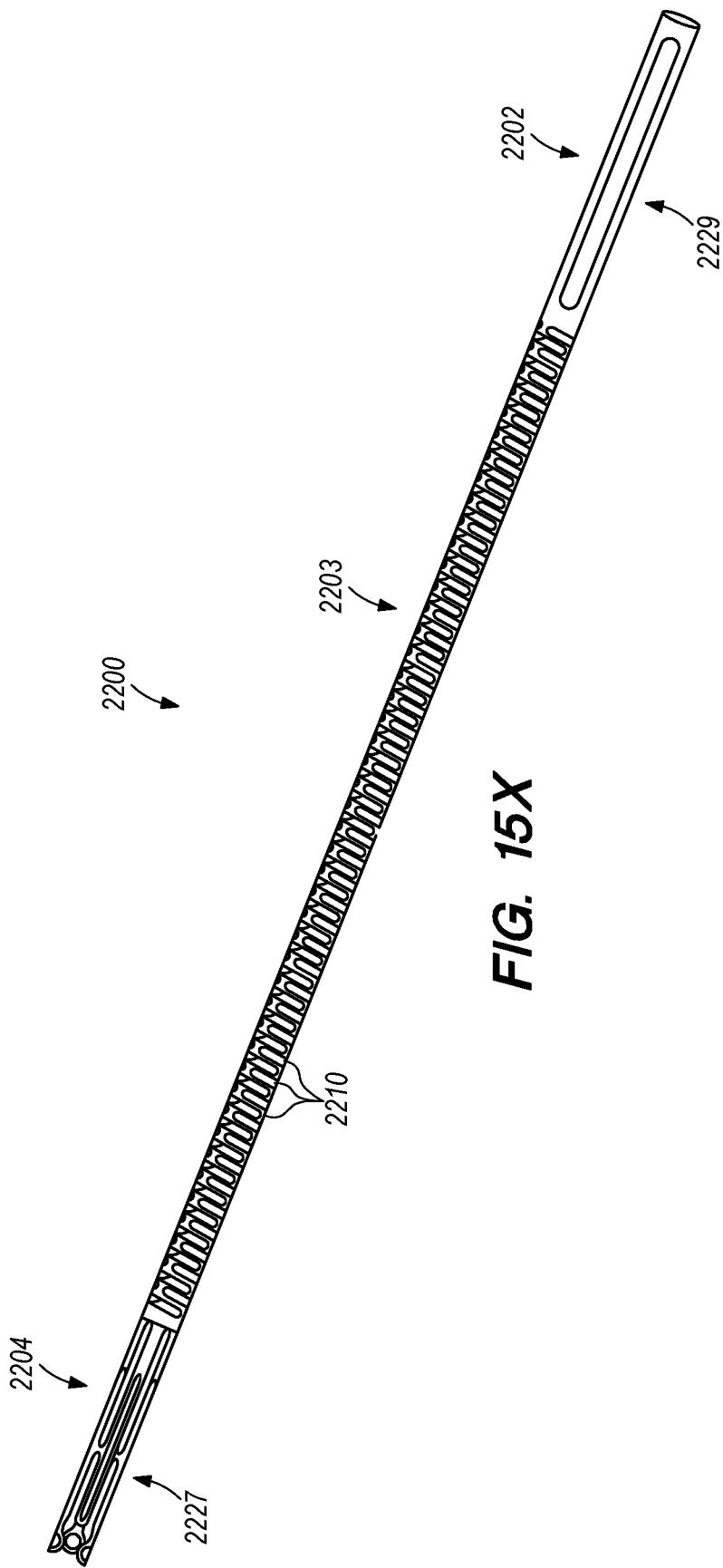
Figure 15Y:
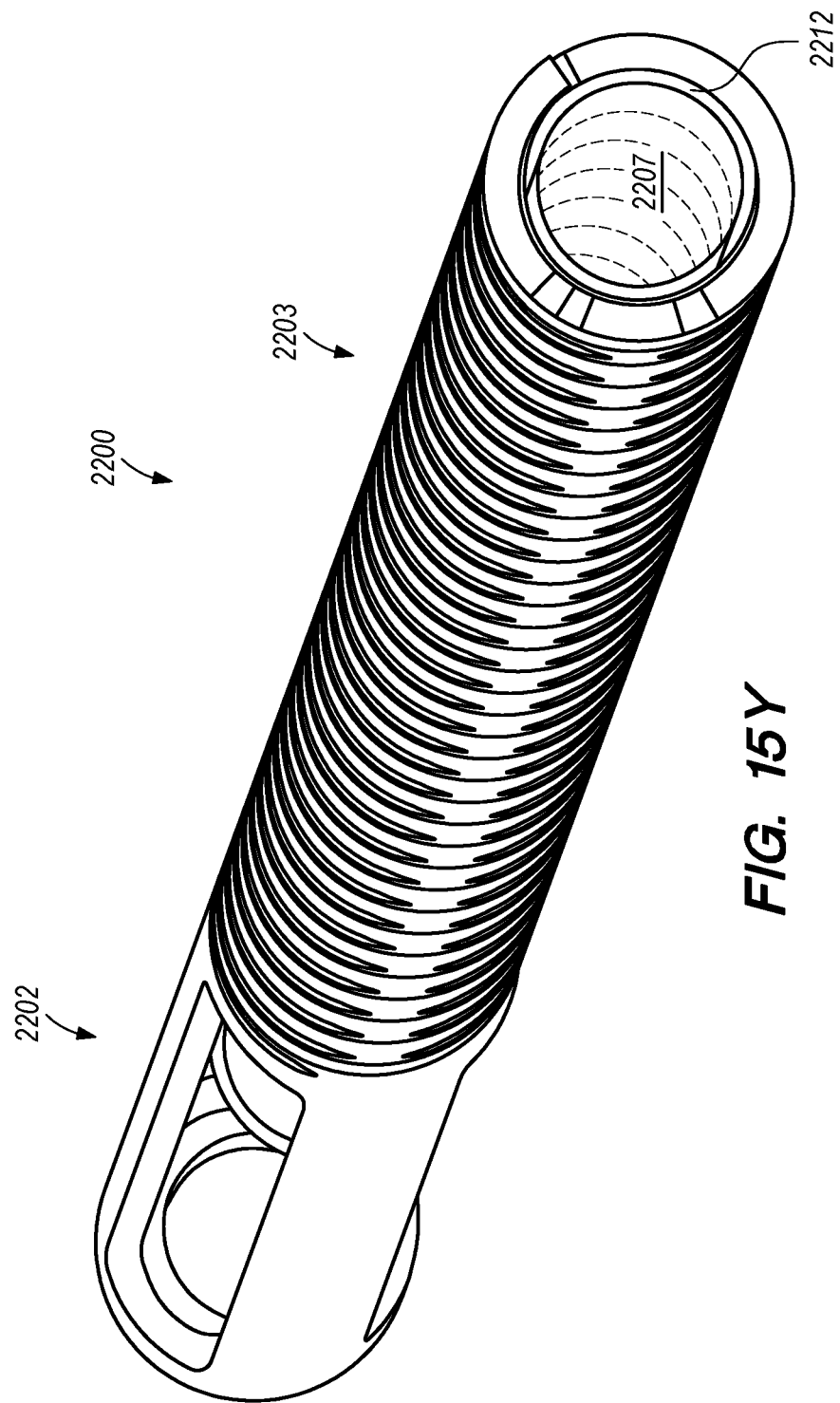
Figure 15Z:
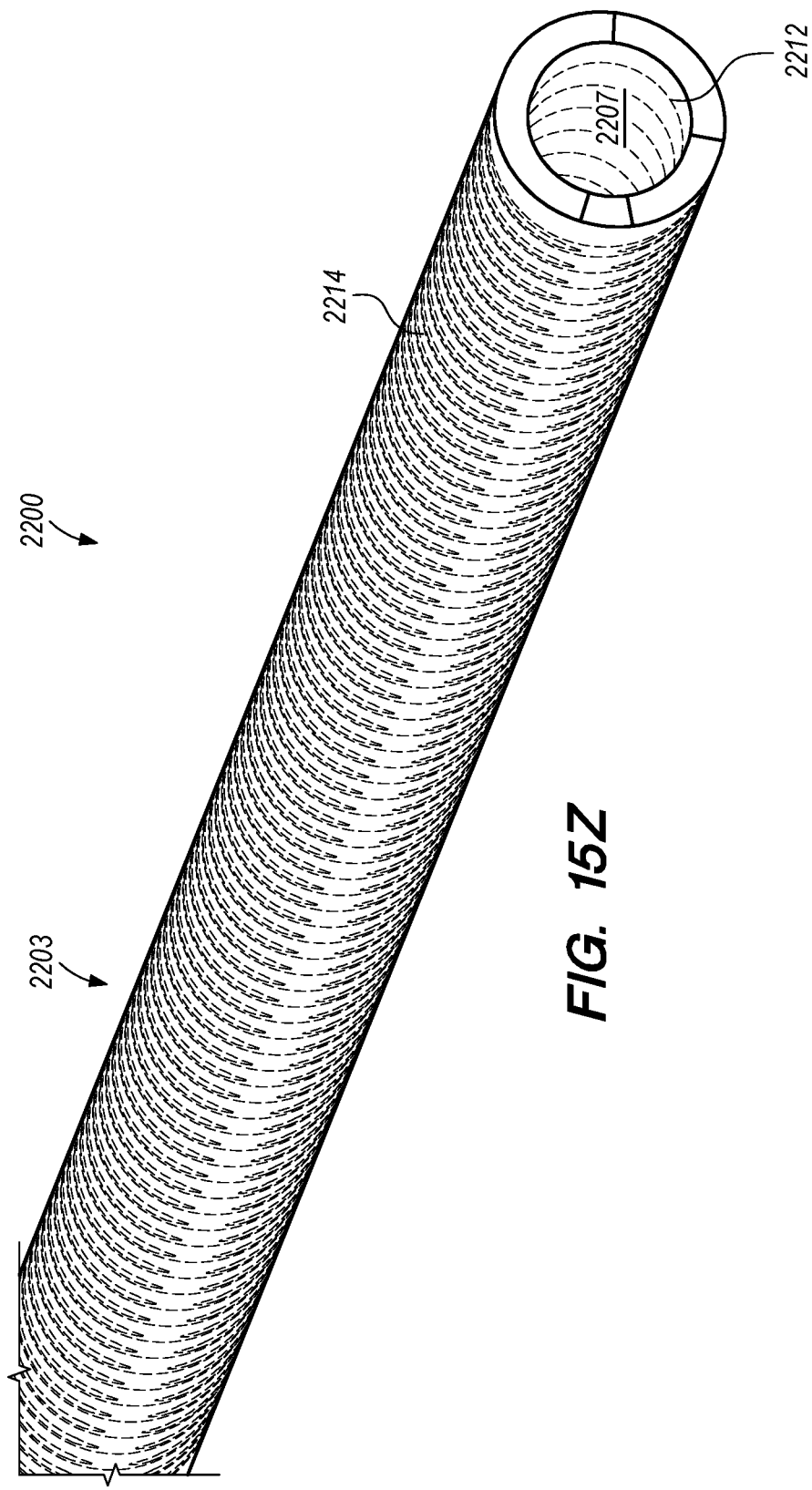

FIGS. 15A-Z illustrate another exemplary shunt 2200 constructed and implanted according to embodiments of the disclosed inventions. A proximal portion 2204 of the shunt 2200 includes an anchoring mechanism 2227 (i.e., proximal anchor), and a valve 2209 (e.g., duck-bill, cross cut, elastic vales, molded silicone valves as disclosed herein, or other suitable one-way valves). A distal portion 2202 of the shunt 2200 includes an anchoring mechanism 2229. The shunt 2200 further comprises an elongate body 2203 extending between the proximal 2204 and distal 2202 portions. The anchoring mechanisms 2227 and 2229 include a plurality of respective deformable elements 2227a and 2229a (e.g., arms) that are disposed radially outward in the deployed configuration of the shunt 2200 (FIG. 15A). Anchoring mechanisms 2227 and 2229 may have a preformed expanded or deployed configuration, for example, when constructed from super-elastic materials such as Nitinol®. The deployed anchoring mechanism 2227 engages the jugular bulb 108, the jugular vein 106, the IPS wall 117, and/or another portion of the IPS 102, anchoring the proximal portion 2204 of the shunt 2200 within the jugular vein 106, so that the valve 2209 is disposed within the jugular vein 106 or at least facing the blood flowing through the jugular vein (e.g., transversally disposed towards the vein), as shown, for example in FIGS. 7E-F. Alternatively, the anchoring mechanism 2227 may engage the IPS walls 114 and 117 at the junction 118 (not-shown). The deployed anchoring mechanism 2229 secures the distal portion 2202 of the shunt 2200 within the CP angle cistern 138, so that CSF flows through the implanted shunt 2200 into the jugular vein 106 (e.g., FIGS. 7E-F).

The anchoring mechanism 2227 and 2229 are formed by series of cuts 2222 and 2222' (e.g., kerfs, slots, key-ways, recesses, or the like) along the length of the respective proximal 2204 and distal 2202 portions of the shunt 2200 (FIGS. 15C1-G), forming the deformable elements 2227a (FIGS. 15A-E) and 2229a (FIGS. 15A, 15D-E, 15G, 15J). The cuts 2222 and 2222' and their patterns are preferably manufactured by laser cutting, etching or other suitable techniques. FIGS. 15D-F illustrate exemplary patterns and relative dimensions of the cuts 2222 in the proximal portion 2204 of the shunt 2200, the cuts 2222 forming the deformable elements 2227a configured to a flared open (e.g., funnel, flower-petal, or the like) deployed configuration (FIGS. 15A-B and 15I). The deformable elements 2227a in the flared-open deployed configuration of the anchoring mechanism 2227, as shown in detail in the perspective view of FIG. 15B, combined with a malecot distal anchor 2229 configuration, provides a "flarecot" shunt configuration as shown in FIG. 15A. Further, FIG. 15I illustrates another perspective view of the flared anchoring mechanism 2227. The deformable element 2227a may comprise hinge-like points 2227b (e.g., living hinge, joint, or the like) to assist with the deployment of the anchor 2227 into the flared configuration. Each of the deformable elements 2227a is coupled to one or more adjacent deformable element 2227a defining a plurality of closed cells 2227g, as shown in FIG. 15I. The anchoring mechanism 2227 having the plurality of closed cells 2227g is configured to minimize disruption and allow passage of fluids (e.g., blood, CSF) through the anchor 2227 when anchoring the proximal portion 2204 of the shunt 2200 within the jugular vein 106. FIG. 15M illustrates the circumferential area of an exemplary, flared open anchoring mechanism 2227. Alternatively, the anchoring mechanism 2227 may include a liner, mesh, braid or other suitable permeable material or combinations thereof, coupled to the deformable element 2227a. In other embodiments, the anchoring mechanism 2227 may be composed of a liner, mesh, braid or other suitable permeable material or combinations thereof configured to flare open into the flarecot configuration when the anchor is deployed (not shown).

Referring back to the anchoring mechanism or proximal anchor 2227 of FIGS. 15A-B and 15I, the deformable elements 2227a may include one or more radiopaque markers 2227c (e.g., gold, or other suitable radiopaque materials) for imaging purposes during the delivery of the shunt 2200. The markers 2227c assist with the deployment and/or placement of the anchoring mechanism 2227 at the target site within the patient. Further, suitable markers 2227c can be included (e.g., embedded, attached, coupled) or applied (e.g., coatings) in/on the deformable elements 2227a. The radiopaque marking scheme on the proximal anchoring mechanism 2227 depicted in FIGS. 15A-B and 15I allows the operator to visualize deployment of the proximal anchoring mechanism about the jugular vein 106, as the anchor transitions from a radially compressed to a flared, deployed configuration. In the embodiments of FIGS. 15A-B and 15I, each of deformable elements 2227a include a first end portion 2227a' and a second end portion 2227a", wherein at least two deformable elements 2227a are coupled at their respective first end portions 2227a' having an interlocking element 2227d therein. The anchoring mechanism 2227 includes one or more interlocking elements 2227d having a respective marker 2227c. The interlocking elements 2227d of the anchoring mechanism 2227 are sized and dimensioned to detachably engage the shunt 2200 to the delivery system (e.g., pusher member or the like), described in FIG. 15C-1 in further detail. Each interlocking element 2227d includes a substantially round shape, as shown in FIGS. 15A-B, 15I, and 15K, configured to arcuate in the delivery configuration to conform to the delivery system, as shown in FIGS. 15C-1, 15C-2 and 15L. The interlocking elements 2227d may include any other suitable shape, such as spherical, rectangular, or the like. Further, each interlocking element 2227d have a recess 2227e (e.g., hole, eyelet, cavity, or the like) (FIG. 15K) configured for receiving a respective marker 2227c. As shown in FIGS. 15A-B and 15I, the markers 2227c are formed as rivets by pressing a respective marker 2227c into the corresponding recess 2227e. The markers 2227c may extend or protrude out of the interlocking elements 2227d (e.g., riveted), as shown in FIGS. 15A-B and 15I, or may be flushed with the interlocking elements 2227d (e.g., welded), as shown in FIG. 15L, or may be coupled to the interlocking elements 2227d with any other suitable techniques or combinations thereof.

The interlocking elements 2227d of the proximal anchor 2227 are shaped and dimensioned to detachably engage (i.e., engage and disengage) an interlocking element 3336 coupled to the distal portion 3314 of a pusher member 3310, as shown in FIGS. 15C-1 and 15C-2. The pusher member 3310 (e.g., hypotube, such as a stainless steel hypotube (FIGS. 15C-1 and 15C-2) comprises a plurality cuts 3311 to increase flexibility, a radiopaque marker 3314 (FIGS. 15C-1 and 15C-2) for imaging purposes, and a distal interlocking element 3336 (FIGS. 15C-1 and 15C-2) configured to interlock with corresponding interlocking elements 2227d of the anchoring mechanism 2227, as further shown in FIGS. 23A-L. FIGS. 15C-1 and 15C-2 illustrate the interface between the pusher member 3310 and anchoring mechanism 2227 of the shunt 2200, having the interlocking elements 2227d of the proximal anchor 2227 engaged with the interlocking element 3336 of the pusher member 3310. FIG. 15C-1 further depicts the valve 2209 disposed on the proximal portion 2204 of the shunt 2200 within the compressed anchoring mechanism 2227. The pusher member 3310 is configured to deliver the shunt 2200 through a delivery catheter while avoiding contact, bumping or interfering with the valve 2209. While the interlocked anchoring mechanism remains compressed within lumen 3305 of the delivery catheter 3304, the operator can advance and retract the shunt 2200 within the delivery catheter prior to shunt deployment via pusher member 3310 (e.g., advancing shunt slightly proximal of the penetrating element 3350 to provide additional column strength to the delivery catheter 3304 during the penetration step of the shunt implant procedure, or alternatingly advancing the delivery catheter 3304 and then shunt 2200 through lumen 3305 to maintain the flexibility of the delivery assembly while accessing and navigating through tortuous anatomy).

In the embodiment of FIGS. 15A-I, the proximal anchor 2227 is composed of super-elastic materials (e.g., Nitinol®) having a preformed, flared configuration. When the proximal portion 2204 of the shunt 2200 is advanced out of the delivery catheter by translating the pusher member 3310 and/or withdrawing the delivery catheter, with or without holding pusher member 3310 member in place, the anchor interlocking elements 2227d disengage from the interlocking element 3336 of the pusher member 3310 by the anchor 2227 assuming the flared configuration, shown in FIGS. 15A-B and 15I. In some embodiments, the flared configuration of the proximal anchor 2227 and/or disengaging of the anchor interlocking elements 2227d from the interlocking element 3336 of the pusher member 3310 may be actuated and controlled by the operator.

Referring back to the anchoring mechanism or distal anchor 2229 of the shunt 2200, FIG. 15G illustrates exemplary patterns and relative dimensions of the cuts 2222' in the distal portion 2202 of the shunt 2200 (FIGS. 15A, 15D-E, and 15G). The cuts 2222' are parallel and radially spaced to form the deformable elements 2227a configured to extend radially outward when deployed assuming a malecot configuration (FIGS. 15A and 15J). Each of the deformable elements 2229a has a respective hinge-like point 2229b (e.g., living hinge, joint, or the like) configured to move radially outward from the axis of the shunt 2200 in a hinge-like fashion, allowing the deformable elements 2229*a* to be outwardly disposed when deployed. The cuts 2222' forming the deformable elements 2227*a* of the distal anchor 2229 are substantially longitudinal along the axis of the shunt 2200 allowing the distal anchor 2229 and/or distal portion 2202 of the shunt 2200 to maintain a suitable column strength and pushability through tissue during deployment at a target site.

FIG. 15H illustrates exemplary patterns and relative dimensions of the cuts 2210 along the elongated body 2203 of the shunt 2200. The cuts 2210 of the elongated body 2203 may have a variety of suitable patterns. The cuts 2210 and their patterns are preferably manufactured by laser cutting the elongated body 2203 of the shunt 2200. Alternatively, the cuts 2210 and their patterns may be manufactured by etching or other suitable techniques. For example, with a laser oriented orthogonal to the longitudinal axis of the body 2203 and with a laser capable of holding body 2203 while rotating and advancing the body relative to the fixture, the laser can be activated and deactivated to form specific cut patterns in shunt body 2203. The laser cutting of the elongated body 2203 creates 1.5 cuts 2210 per rotation of the body, having a cut balance of about 210° of rotation with laser on, and then 30° of rotation with laser off. Further, while the pitch of the cut pattern is approximately 0.0070 inches (0.1778 mm) in the embodiments of FIG. 15H, each cut 2210 may have a variety of widths; for example 0.005 inches (0.12446 mm). Additionally, the pitch of the cut pattern may be varied. For example, the pitch of the cut pattern of the body 2203 proximately disposed to the proximal portion 2204 and/or to the distal portion 2202 of the shunt 2200 may be larger/wider than the pitch of the cut pattern along the middle section of the body 2203, as shown in FIGS. 15D-E. As depicted in the exemplary embodiment of FIG. 15N, the pitch of the cut pattern proximately disposed to the distal portion 2202 of the shunt 2200 is larger than the adjacent pitch, making the section 2203*a* and 2203*b* of the body 2203 proximately disposed to the distal portion 2202 of the shunt 2200 wider than the adjacent section 2203. The wider cuts and/or sections of the body 2203 proximately disposed to the proximal 2204 and distal 2202 portions of the shunt 2200 are configured to provide strain relief to the shunt 2200, allowing movement of the respective proximal 2204 and distal 2202 portions of the shunt 2200 with respect to the elongated body 2203 or longitudinal axis of the shunt 2200 while protecting from strain, fracture, break or separation of the portions of the shunt 2200. FIGS. 15O-15Q depict exemplary cut patterns in a two dimensional view of their respective cuts 2222 of the proximal portion 2204 anchoring mechanism 2227, the cuts 2210 of the elongated body 2203, and the cuts 2222' of the distal portion 2202 anchoring mechanism 2229 of the shunt 2200.

Additionally, FIGS. 15R-W illustrate additional views and exemplary relative dimensions of the features of the shunt 2200, according to the embodiments of the disclosed inventions. The length of the shunt 2200 in the deployed, unconstrained configuration can range from approximately 0.693 inches (17.602 mm) to 0.040 inches (1.016 mm), as shown in FIG. 15R. As shown in the perspective side view of the shunt 2200 in the deployed, unconstrained configuration of FIG. 15S, the length of the body 2203 can be approximately around 0.271 inches (6.883 mm), the length of the proximal anchor 2227 in the flared configuration can be approximately around 0.091 inches (2.312 mm), and the length of the distal anchor 2229 in the malecot configuration can range from approximately 0.101 inches (2.565 mm) to 0.010 inches (0.254 mm). FIG. 15T illustrates a frontal view of the proximal anchor 2227 in the flared configuration having a diameter that can range from approximately 0.180 inches (4.572 mm) to 0.020 inches (0.508 mm). FIG. 15U illustrates a detailed view of the proximal anchor 2227 in the flared configuration. FIG. 15V illustrates a side view of the distal anchor 2229 in the malecot configuration, and FIG. 15W illustrate a frontal view of the distal anchor having a diameter that can range from approximately 0.143 inches (3.632 mm) to 0.020 inches (0.508 mm).

FIGS. 15X-Z illustrates the endovascular shunt 2200 in accordance with the embodiment of the disclosed inventions. Similarly to the embodiment of FIG. 15E, FIG. 15X illustrates the structural frame of the shunt 2200 including the proximal portion 2204 having the anchoring mechanism 2227, the body 2203 having the plurality of cuts 2210, and distal portion 2202 having the anchoring mechanism 2229, in a delivery, constrained configuration. The body 2203 of the shunt 2200 comprises an inner liner 2212 that provides a sealed, fluid conduit for CSF to flow through the shunt and, optionally, an outer jacket 2214, as better seen in FIGS. 15Y-Z. The inner liner 2212 and outer jacket 2214 are composed of suitable implantable polymeric materials, such as polytetrafluoroethylene "PTFE", polyethyleneterephthalate "PET", High Density Polyethylene "HDPE", expanded polytetrafluoroethylene "ePTFE", urethane, silicone, or the like. Preferably, inner liner 2212 is composed of materials that resist aggregation of CSF proteins and cells flowing through shunt lumen 2207 to maintain long-term shunt lumen patency such as HDPE, PET, PTFE, silicone, or urethane. The inner liner 2212 and outer jacket 2214 are configured to cover—substantially completely or partially— the cuts 2210 of the elongated body 2203, from within shunt lumen 2207 and over shunt body 2203, respectively; in such configuration, the elongated body 2203 becomes a frame that supports the inner liner 2212 and, optionally, an outer jacket 2214 (FIGS. 15Y-Z). Shunt 2200 with its inner liner 2212, shunt body frame 2203, and outer jacket 2214 is impermeable to venous and sinus blood flow, and the integrated liner-frame-jacket configuration maintains the flexibility and pre-determined configuration that the cuts 2210 provide to the shunt 2200.

Inner liner 2212 provides a smooth surface within shunt lumen 2207 and maintains a laminar flow profile for CSF flowing through the shunt under normal differential pressure (5-12 cm H2O) between the subarachnoid space 116 and cistern 138. In addition to material selection criteria for liner 2212 previously described, maintaining laminar flow within shunt lumen 2207 further eliminates or reduces the risk of occlusion from protein accumulation and cell aggregation. Liner 2212 can be configured to line the interior of shunt body 2203 using an extrusion process. Alternatively, the liner material can be deposited (e.g., using a dispersion technique) on a mandrel (e.g., nickel coated copper); thereafter, the liner-coated mandrel can be placed within shunt body 2203 for application of outer jacket 2214 and adhering inner liner 2212 to shunt body 2203, after which the mandrel can be withdrawn from shunt 2200 leaving inner liner 2212 in place within shunt lumen 2207. Without an inner liner 2212, cuts 2210 inside the lumen 2207 can provide surfaces for proteins and cells to accumulate, which could occlude lumen 2207 and prevent CSF from flowing from the subarachnoid space into the venous system.

The outer jacket 2214 provides a smooth exterior surface to shunt 2200, which reduces the risk of thrombus formation in the IPS 102 compared to shunt 2200 with cuts 210 on the exterior surface of shunt body 2203. As noted above, the outer jacket 2214 can comprise one or more implant-grade polymers including, but not limited to, polyurethane or silicone-polyurethane blends. In some embodiments, a gas or liquid dispersion of polymer is applied to shunt body 2203 and inner liner 2212, which forms the outer jacket 2214 and bonds the inner liner 2212, the shunt body 2203, and outer jacket 2214 together in an integrated configuration of shunt 2200, for example, as shown in FIG. 15Z.

Outer jacket 2214 can completely or substantially completely cover the exterior surface of shunt body 2203; however, in other embodiments, the outer jacket can be placed selectively along portions of shunt body 2203 to adhere inner liner 2212 to shunt body 2203. By way of non-limiting example, a liquid dispersion of polymer or an epoxy-based adhesive can be placed at discrete locations along the length of shunt body 2203 (e.g., proximal portion, middle portion, and/or distal portion of shunt body 2203). Alternatively, the exterior surface of inner liner 2212 can be coated with polymer or adhesive, and then placed within shunt body 2203; the polymer or adhesive can seep into cuts 2210, substantially completely or partially filling some or all of the cuts 2210 along shunt body 203. In these embodiments, exterior portions of the shunt body 2203 material are exposed to the implant site within the patient. In the embodiment of FIGS. 15Y-Z, the inner liner 2212 may have a thinness of 0.0007 inches (0.01778 mm), the elongated body 2203 wall may have a thinness of 0.0018 inches (0.04572 mm) and, the outer jacket 2214 may have a thickness of 0.0005 inches (0.0127 mm).

It should be appreciated that the above disclosed units are exemplary dimensions, angles and properties of the shunt 2200, which are not intended to limit the embodiment of FIGS. 15A-Z.

As previously disclosed, embodiments of the disclosed shunts can include an anti-thrombotic coating on all or a portion of the exterior of the device, to minimize clotting in the IPS after shunt deployment. Such anti-thrombotic coatings may comprise phosphorylcholine (e.g., Lipidure® products available from NOF Corporation) or Heparin-based compositions (e.g., CBAS® Heparin Surface available from Carmdea AB). Anti-thrombotic coatings can also be applied to anchor 700 and/or elongate guide member 780 to further minimize the risk of clotting in the IPS during the shunt implant procedure.

FIG. 16 illustrates a delivery catheter 3300, constructed according to embodiments of the invention. The delivery catheter 3300 (or distal most portion of the delivery catheter) can include an oversheath member 3300" (e.g., a larger, concentric sheath that covers the outer diameter of the delivery catheter and/or the penetrating element). The oversheath 3300" can translate longitudinally about the delivery catheter, and can be retracted proximally to expose the needle tip 3350" for the penetration step of the procedure. The oversheath 3300" disposed over a delivery catheter 3304 and penetrating element advanced over a guide member 3308"; the bands 3303" located proximal of the penetrating element comprise radiopaque markings to confirm orientation of the penetrating element and assess penetration trajectory during a shunt deployment procedure. The oversheath member covers the penetrating element as the delivery system navigates through the patient's vasculature, thereby preventing inadvertent vessel punctures. The operator can position the distal portion of the oversheath adjacent or abutting the target site penetration along IPS wall 114 until the operator is ready to expose the penetrating element or advance the penetrating element through the tissue into the CP angle cistern 138.

Figure 18D:
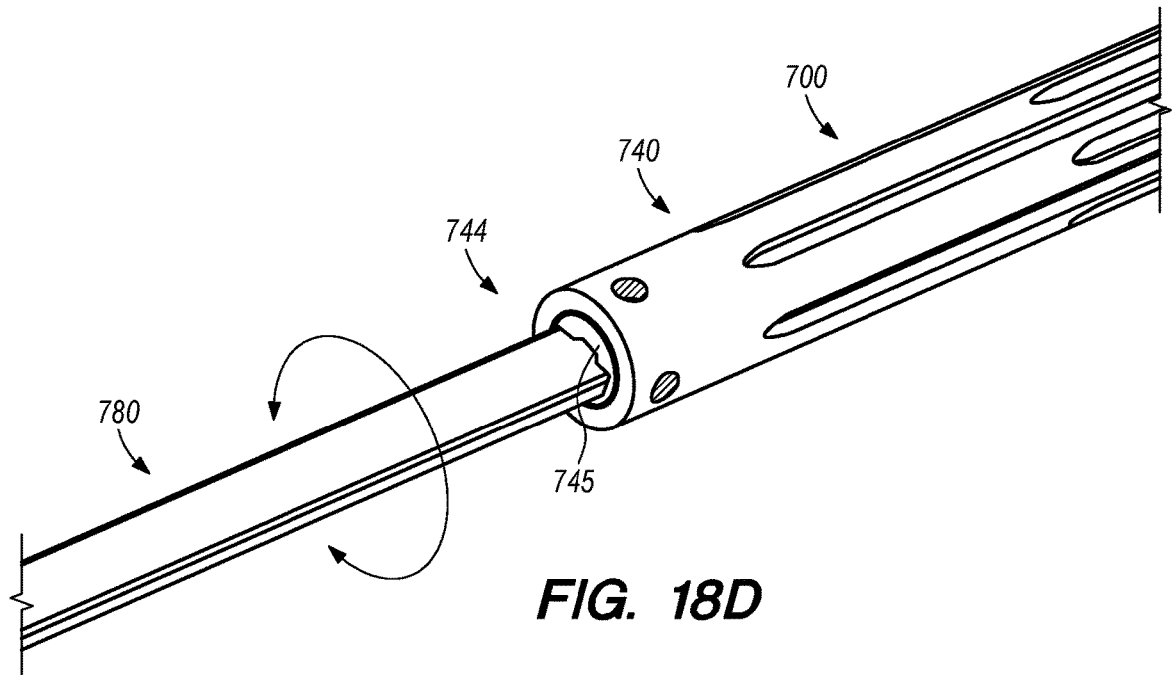
Figure 18E:
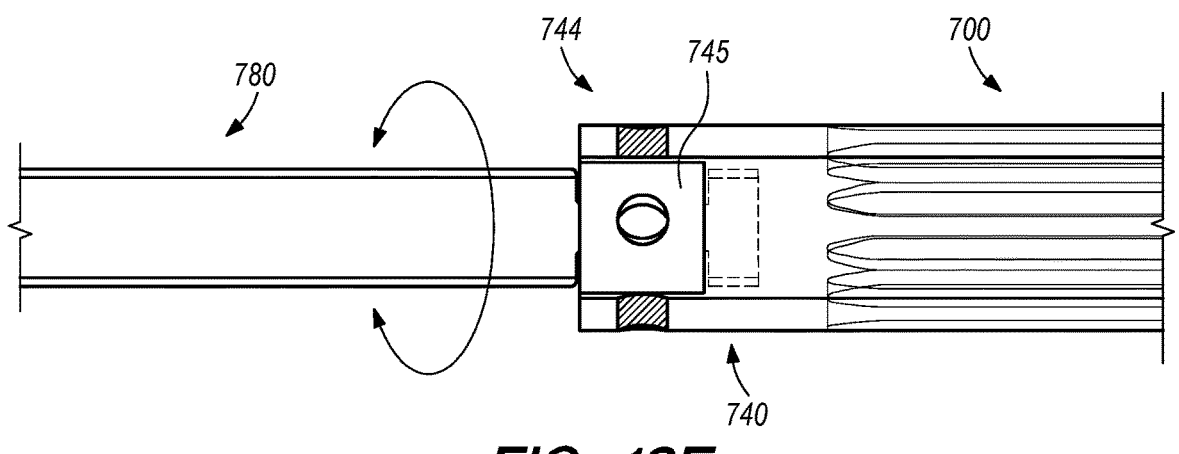

As described above, FIGS. 17A-B illustrate an exemplary elongate guide member 780 for delivering of the anchor 700 at a target site, constructed according to the disclosed inventions. FIGS. 18A-E illustrate another exemplary elongate guide member 780 for delivering of the anchor at a target site, constructed according to the disclosed inventions. The elongate guide member 780 of FIGS. 18A-E includes a flat, rectangular cross-sectional profile, as described in FIG. 3D and FIG. 12. As shown in FIGS. 18A-E, the elongate guide member 780 is coupled to the proximal portion 740 of anchor 700 via joint 744, as previously described (e.g., directly or indirectly, fixedly or detachably coupled or the like). FIGS. 18A-E illustrate exemplary, relative dimensions and properties of the interface of the elongate guide member 780 with the anchor 700, which are not intended to limit the embodiment of the interface disclosed herein. In the embodiments of FIGS. 18D-E, the joint 744 between the anchor 700 and the elongate guide member 780 includes a rotatable element 745 configured to allow the elongate guide member 780 to rotate clockwise and/or counter-clockwise with respect to the anchor 700. The independent rotation of the elongate guide member 780 relative to the anchor 700 via the rotatable element 745 at the joint 744 allows for the elongate guide member 780 to assume a desirable orientation through the curved portion of the IPS 102 during delivery of the anchor 700. For example, the anchor 700 may be delivered at a random orientation at the IPS 102, yet the elongate guide member 780 would assume a desirable orientation by rotating (if needed).

FIGS. 19A-I depict an embodiment of a delivery assembly 300 comprising a penetrating element guard 4000. The guard 4000 covers the penetrating element 3350 during navigation of the shunt delivery catheter 3304 (FIG. 19A) through the patient's vasculature to the target penetration site on IPS wall 114 and during withdrawal of delivery catheter 3304 after shunt deployment, thereby preventing inadvertent puncture or damage to other components of delivery assembly (e.g., guide catheter) and the patient's vasculature. As will be further described below, the operator can actuate a pull wire 4010 to retract guard 4000 proximally and expose the penetrating element 3350 to the dura of IPS wall 114 prior to the penetration step of the shunt implant procedure and then re-cover the penetrating element 3350 after the penetration step (e.g., after distal anchoring mechanism 229 of the shunt has been deployed). Radiopaque markers located on the guard 4000 and delivery catheter 3304 provide an indication of whether the guard has been retracted and penetrating element 3350 is exposed or the guard remains in a delivery configuration, covering the penetrating element 3350 for navigation through the patient's vasculature, as will be further described below.

Figure 19A:
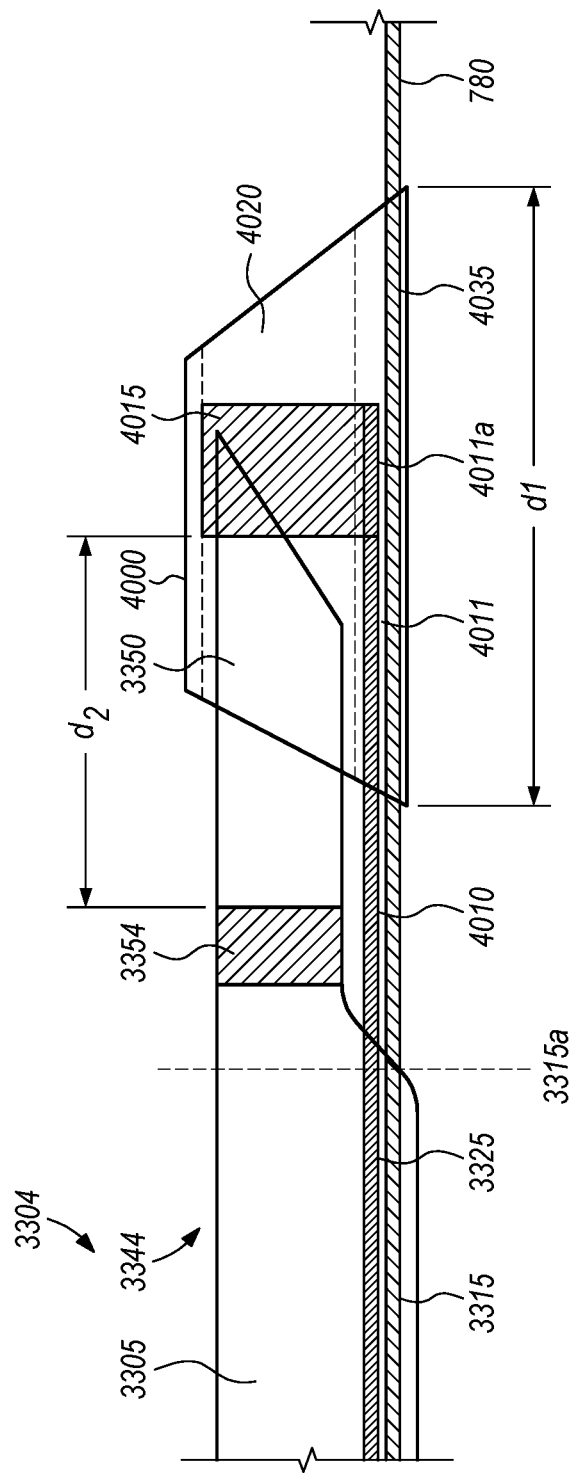

With reference to FIG. 19A, the distal portion 3344 of the shunt delivery catheter 3304 comprises penetrating element 3350 and a radiopaque marker 3354. As previously described, delivery catheter 3304 includes a first lumen 3315 to accommodate elongate guide member 780 and a second lumen 3305 to accommodate a shunt 2200 (not shown). The guard 4000 comprises a pull wire 4010, the pull wire 4010 having a distal portion 4011 attached to a guard body 4000, where the pull wire 4010 is configured to translate the guard body 4000 proximally or distally relative to the shunt delivery catheter 3304 so as to at least partially expose or cover, respectively, the penetrating element 3350. The distal portion 4011 of pull wire 4010 is embedded or encased within guard 4000 (as will be further described below) and includes an attachment point 4011a (e.g., a weld) to radiopaque marker 4015 also embedded within guard 4000

(as will be further described below). The guard 4000 further comprises a tubular body having a first lumen or recess 4020 configured to receive the penetrating element 3350 and allows the guard 4000 to retract proximally (direction of arrow d2 in FIG. 19A) over the penetrating element 3350 and distal portion 3344 of delivery catheter and distally (e.g., to re-cover penetrating element 3350) via pull wire 4010. The enlarged circumference in the distal portion 3344 of the shunt delivery catheter 3304 at interface point 3315a where the elongate guide member 780 enters the first lumen 3315 of the delivery catheter prevents guard 4000 from retracting further proximally over the delivery catheter. Guard 4000 can advance distally, via pull wire 4010 and as will be further described below, to re-cover penetrating element 3350. As shown in FIG. 19A, the shunt delivery catheter 3304 includes a third lumen 3325 that extends throughout the length of the delivery catheter, from the distal portion 3344 to the proximal portion 3342; third lumen 3325 accommodates pull wire 4010 of guard 4000.

FIGS. 19B and 19C show cross section and perspective views, respectively, of penetrating element guard 4000. FIG. 19B depicts a guard 4000 in a delivery configuration with respect to the distal portion 3344 of the shunt delivery catheter 3304 (represented by dashed lines in the figure), covering penetrating element 3350. Penetrating element 3350 is positioned within lumen 4020 of the guard 400 and inside of radiopaque marker 4015 embedded or encapsulated within the walls of guard 4000 (as will be further described below). Guard 4000 can be approximately 0.5 inches (1.27 cm) long or other suitable dimensions sufficient to cover penetrating element 3350 on the distal portion 3344 of the delivery catheter. The guard lumen 4020 is sized to allow guard 4000 to retract proximally over the penetrating element 3350 and distal portion 3344 of the delivery catheter, indicated by the direction of arrow d2 shown in FIG. 19A. For example, the inner diameter of guard lumen 4020 can be approximately 0.0385 inches (0.09779 cm). Marker 4015 comprises a cylindrical profile (as can be seen in FIGS. 19B-D and 19G) such that penetrating element 3350 can reside inside of marker 4015 and the guard first lumen 4020, as depicted in FIG. 19A. The marker 4015 may include any suitable configuration (e.g., band, ring, angular band, arrowhead shape or the like). The radiopaque marker 4015 disposed in or on a wall of the guard body 4000 is movable relative to the penetrating element 3350 so that the radiopaque marker 4015 may be positioned so as to at least partially overlie the penetrating element 3350. For example, the radiopaque and/or alloy material of marker 4015 shields the concentrically disposed penetrating element 3350 and can prevent the penetrating element from inadvertently puncturing through the guard 4000 when the distal portion of 3344 of delivery catheter 3304 bends as the operator navigates the delivery assembly 300 through tortuous anatomy to the target penetration site along IPS wall 114.

The distal portion 4004 of the guard 4000 has a beveled edge, as shown in FIGS. 19B and 19C. The bevel facilitates access to narrow and/or tortuous vasculature as the operator navigates the delivery assembly distally beyond the inferior vena cava (e.g., to access and navigate through junction 118 of jugular vein 106 and IPS 102). Alternatively, the distal portion 4004 of the guard 4000 may have an arcuate beveled edge, as shown in FIG. 19G, or any suitable edge that facilitates access and navigation through narrow and/or tortuous vasculature. FIGS. 19H-I are cross-sectional views of the guard 4000 of FIG. 19G.

The guard 4000 further comprises a second lumen 4035 configured to accommodate passage therethrough of the elongate guide member 780. The delivery assembly 300 comprising delivery catheter 3304 and guard 4000 can advance along the elongate guide member 780 distally, toward the penetration site; that is, the guide member 780 passes through second lumen 4035 of the guard 4000 and lumen 3315 of delivery catheter 3304. Embodiments of guard 4000 can be optimized to facilitate trackability of the delivery catheter to the IPS or CS (e.g., varying dimensions of lumen 3315, stiffness of material of guard 4000, or the like).

FIG. 19D depicts the pull wire 4010 and radiopaque marker 4015 subassembly of guard 4000. Pull wire 4010 can comprise PFTE-coated stainless steel or other suitable materials. The diameter of pull wire 4010 can range from about 0.003 to 0.012 inches (0.0762 to 0.3048 mm). While pull wire 4010 depicted in FIG. 19B-D has a circular cross-sectional profile, other pull wire embodiments can include non-circular cross-sectional profiles (e.g., rectangular). The PTFE coating on pull wire 4010 increases the lubricity of the wire within the third lumen 3325 of delivery catheter 3304, thereby facilitating smooth proximal and distal actuation of guard 4000 to expose and re-cover penetrating element 3350 (not shown in FIG. 19D). Radiopaque marker 4015 can comprise platinum-iridium 90/10 alloy or other suitable materials that provide sufficient radiopacity and allow for a connection point 4011a between the marker and distal portion 4011 of pull wire 4010. The inner diameter of marker 4015 can be 0.0385' or other suitable dimensions compatible with a guard lumen 4020 sufficient to accommodate the distal portion of delivery catheter 3344 and penetrating element 3350. As shown in FIG. 19D, the distal portion 4011 of pull wire 4010 may not include the PTFE coating depicted on the body portion of pull wire 4010; the uncoated stainless steel distal portion 4011 of pull wire allows for a weld or other connection point 4011a to radiopaque marker.

Figure 19E:
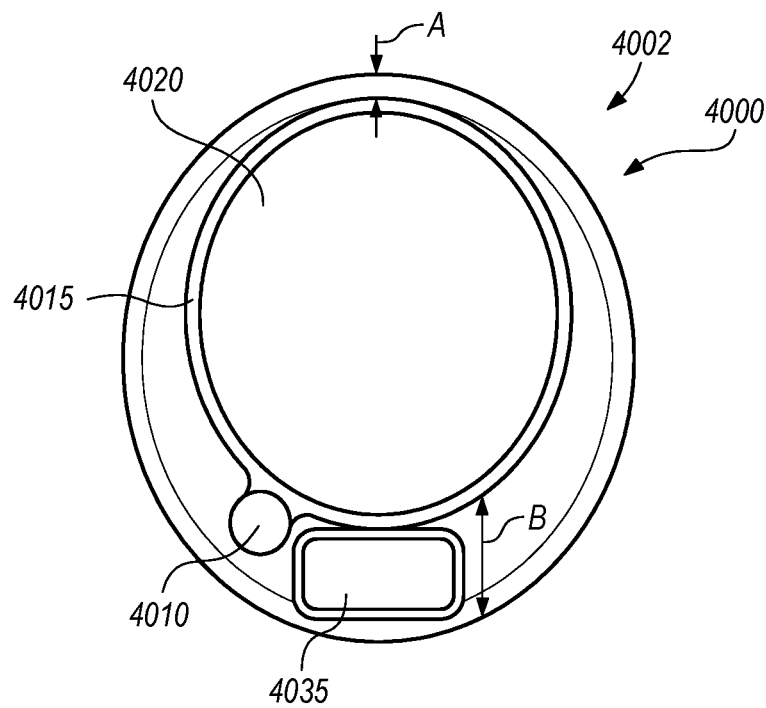
Figure 19F:
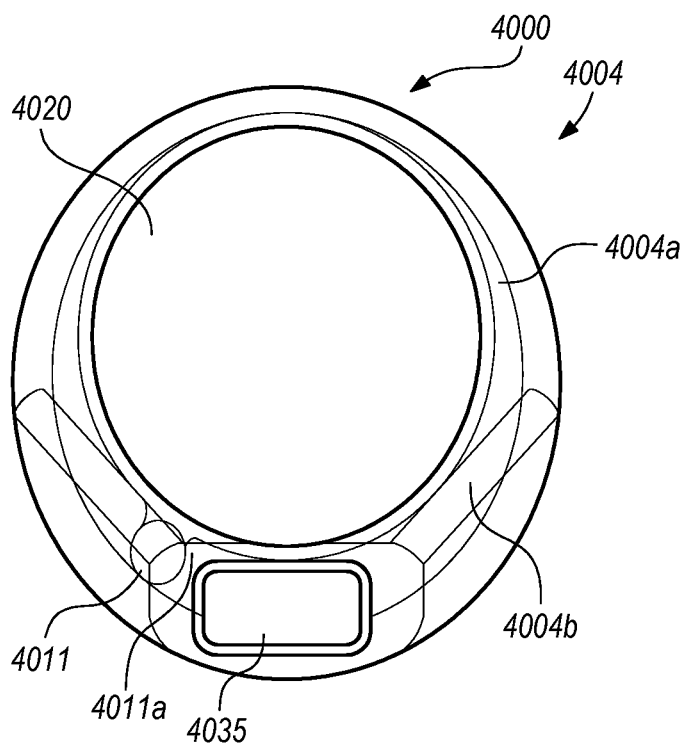
Figure 23E:
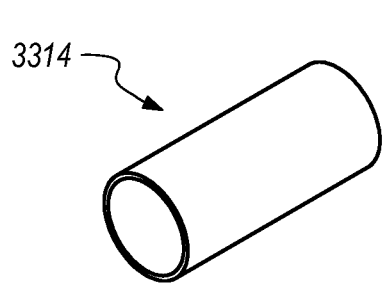
Figure 23F:
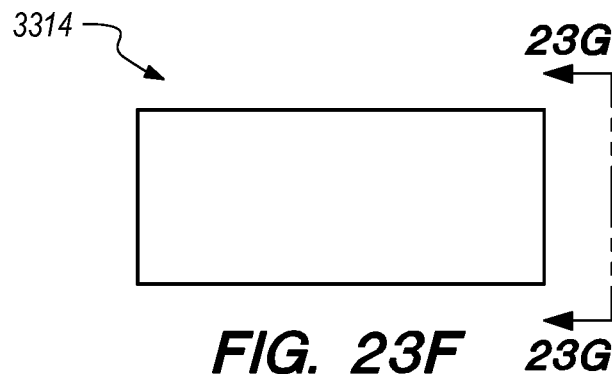
Figure 23G:
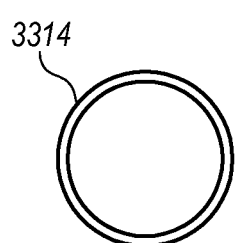
Figure 23H:
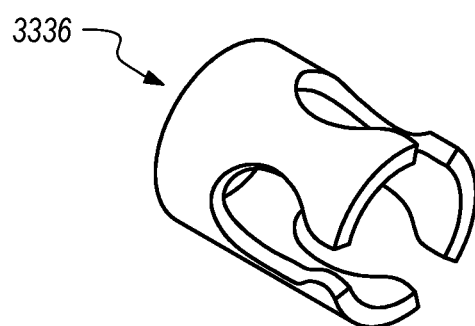
Figure 23I:
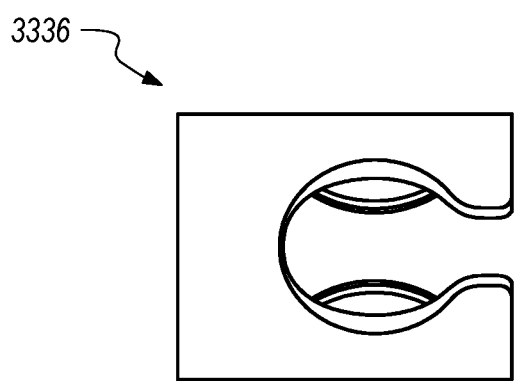
Figure 23J:
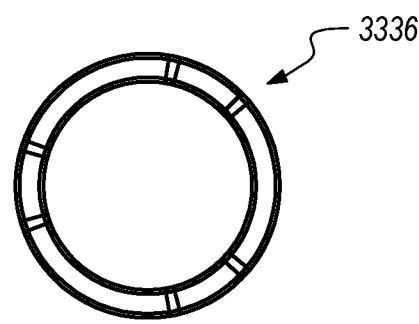
Figure 23K:
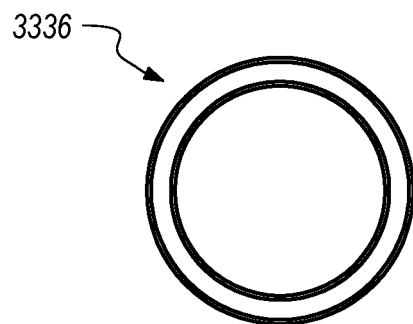
Figure 23L:
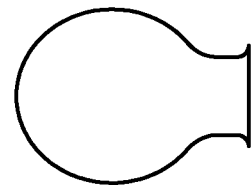

FIGS. 19E and 19F show cross section views of the proximal portion 4002 and distal portion 4004, respectively, of the guard 4000. As depicted in FIG. 19E, marker 4015 and pull wire 4010 are embedded or encapsulated within the wall of guard 4000. Guard 4000 can comprise polymeric materials such as polyether block amide (Pebax® available from Arkema Group), HDPE, PTFE, urethanes or the like. Pebax embodiments of guard 4000 can range from 25 D to 72 D hardness (e.g., Pebax 63D). The wall thickness of guard 4000 can vary depending on top-to-bottom orientation of the guard. The top portion of guard 4000 (represented by line A in FIG. 19E) can range from about 0.001 to 0.006 inches (0.0254 to 0.1524 mm) or larger. The bottom portion of guard 4000 (represented by line B in FIG. 19E) can range from about 0.006 to 0.014 inches (0.1524 to 0.3556 mm) or larger.

As previously disclosed and during the shunt implant procedure, an operator can deploy an anchor 700 distal to a target penetration site along IPS wall 114. Thereafter, the operator advances a delivery assembly 300 comprising the shunt delivery catheter 3304 and penetrating element guard 4000 via elongate member 780 to the target penetration site. The radiopaque marking 3354 on the distal portion 3344 of the delivery catheter 3304 and radiopaque marking 4015 within guard 4000 provide reference points for the operator to visualize the location of the delivery assembly and penetrating element 3350 at the target penetration site. When the operator is prepared to penetrate IPS wall 114, the operator can pull the proximal end of pull wire 4010 proximally, which retracts guard 4000 proximally over the distal portion 3344 of delivery catheter (indicated by the direction of the arrow d2 shown in FIG. 19A) and exposes penetrating element 3350 from the delivery assembly 300. Observing the transition of marker 4015 in guard 4000 proximally towards and/or until it abuts marker 3354 on the distal portion 3344 of the delivery catheter (e.g., in the direction of arrow d2 shown in FIG. 19A) confirms that guard 4000 actuated properly and penetrating element 3350 is exposed from the delivery assembly in the patient's vasculature. Conversely, after shunt implantation, the operator can advance pull wire 4010 distally to re-cover penetrating element 3350 and confirm that the guard 4000 is in a delivery or withdrawal configuration (e.g., penetrating element not exposed in IPS 102 or jugular vein 106 lumens).

FIG. 20 depicts an alternate embodiment of penetrating element guard 4000. For ease in illustration, like features of the penetrating element guard 4000 and the shunt delivery catheter 3304 shown in FIG. 20 have been given the same reference numerals from FIGS. 19A-F. Guard 4000 comprises a guard 4000 having a full-length, "oversheath" configuration; that is, guard 4000 is a sheath that extends along the length of and over the delivery catheter 3304 disposed concentrically within shuttle lumen 4020. Guard 4000 can be retracted proximally (direction of arrow d2 in FIG. 20), e.g., by an operator pulling on the proximal portion of guard 4000 to uncover and expose a protected penetrating element 3350. Optionally, guard 4000 can include a scored or weakened portion (e.g., indicated by dotted line d1 in FIG. 20) that splits or tears (e.g., along the longitudinal axis of the guard) to facilitate guard retraction.

Guard 4000 includes a second lumen 4035 that accommodates elongate guide member 780. Lumen 4035 can extend from the distal portion or end of guard 4000 and include an exit port 4035a located in the distal portion of guard 4000, as shown in FIG. 20. As compared to the guard configuration described in connection with FIGS. 19A-F, the guard configuration shown in FIG. 20 simplifies the design of the delivery assembly 300 by eliminating pull wire 4010 and a corresponding pull wire lumen 3325 in the shunt delivery catheter 3304.

FIGS. 23A-L illustrate the pusher member 3310, constructed according to embodiments of the disclosed inventions. As described in FIGS. 15C-1 and 15C-2, the pusher member 3310 comprises a plurality of cuts 3311 (FIGS. 23A and 23C), a radiopaque marker 3314 (FIGS. 23A and 23E-G), and a distal interlocking element 3336 (FIGS. 23A and 23H-L). The plurality of cuts 3311 is configured to increase flexibility of the pusher member 3310 during delivery of the shunt 2200 of FIGS. 15A-Z. The radiopaque marker 3314 is disposed at the distal portion 3312 of the pusher member 3310 for imaging purposes, and the distal interlocking element 3336 is configured to interlock with corresponding interlocking elements 2227d of the anchoring mechanism 2227 of the shunt 2200, as previously disclosed. FIGS. 23A-L discloses exemplary, relative dimensions, cut patterns, angles, configurations and/or properties of the pusher member 3310, the radiopaque marker 3314, and the distal interlocking element 3336. It should be appreciated that the disclosed dimensions, cut patterns, angles, configurations and/or properties are exemplary and not intended to limit the embodiments of FIGS. 23A-L.

Figure 25D:
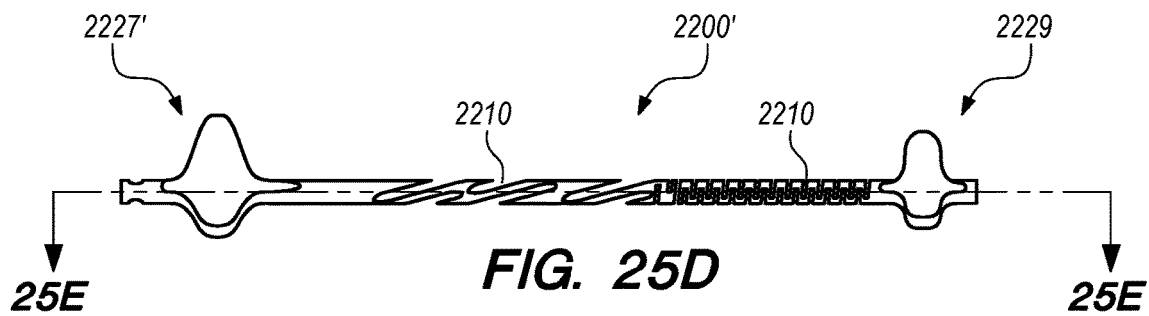
Figure 25E:
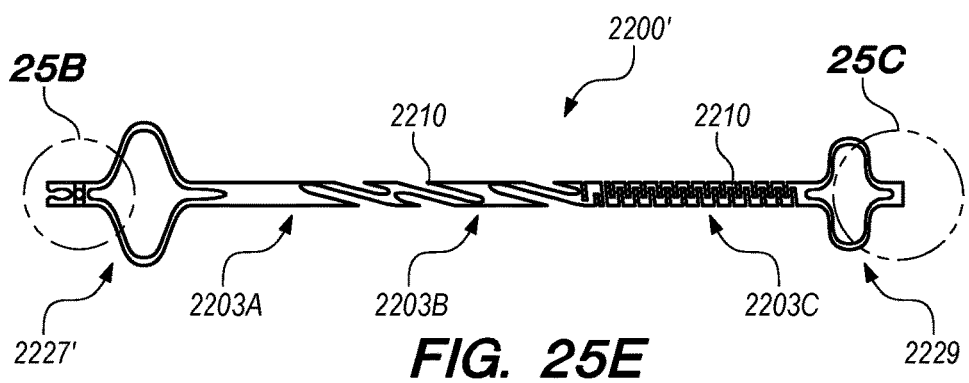
Figure 25F:
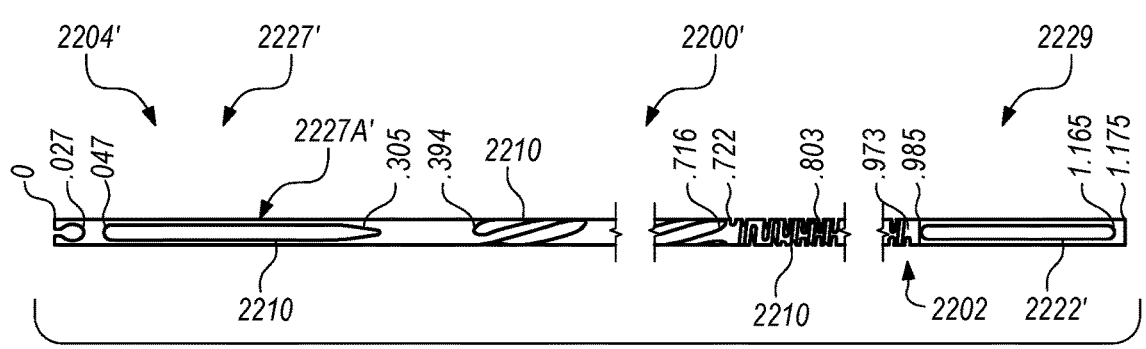
Figure 25G:
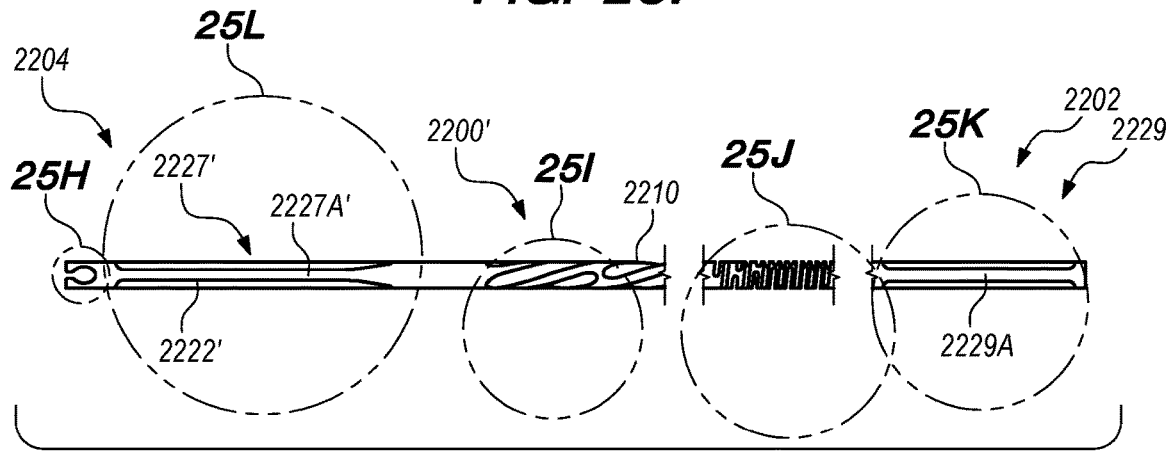
Figure 25H:
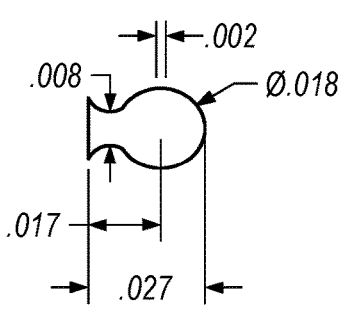
Figure 25I:
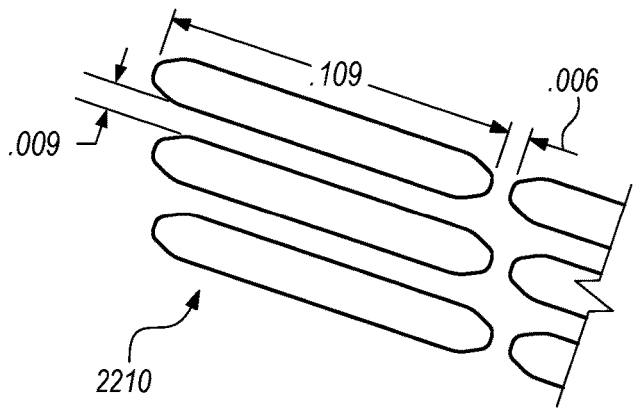
Figure 25J:
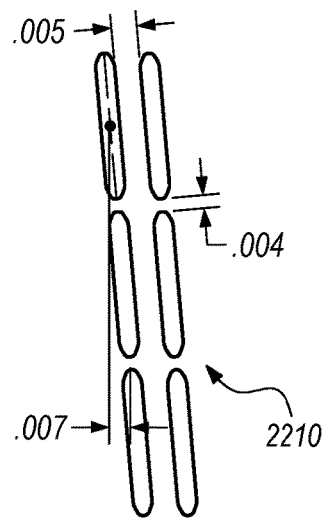
Figure 25K:
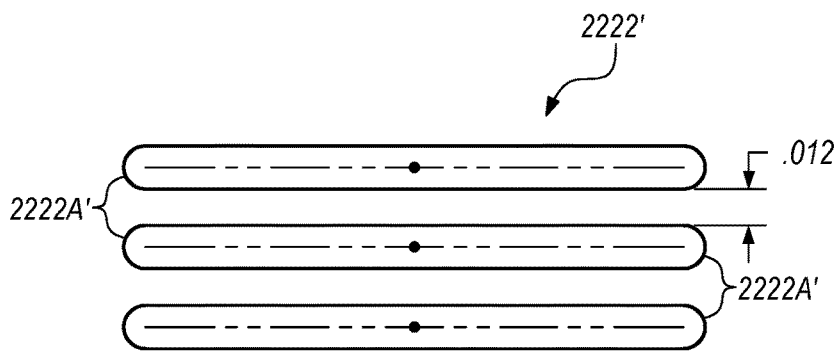

FIGS. 25A-M illustrate yet another exemplary shunt 2200' constructed and implanted according to embodiments of the disclosed inventions. For ease in illustration, the features, functions, dimensions and configurations of the shunt 2200' that are the same or similar as in the shunt of FIGS. 15A-Z are given the same reference numerals and are incorporated herein. The shunt 2200' includes an elongate body 2203 extending between the proximal 2204' and distal 2202 portions and having a lumen therebetween (not shown). The body 2203 of the shunt includes selective cuts 2210 (e.g., kerfs, slots, key-ways, recesses, or the like) forming transition areas configured to vary the flexibility of the shunt 2200', such as, from the body proximal portion 2203a (less flexible) to the body distal portion 2203c (more flexible), as shown in FIGS. 25A and 25D-E. As better appreciated in the embodiment of FIG. 25E, the body proximal portion 2203a has no cuts 2210, instead the cuts 2210 are disposed in a body middle portion 2203b and the body distal portion 2203c, such that the body distal portion 2203c includes more cuts 2210 than the body middle portion 2203b. In the embodiments of FIGS. 25A, 25D-G, the patterns of the cuts 2210 are achieved by laser cutting the elongated body 2203 while rotating the body at a selected angle as the laser and body move relative to each other. In some embodiments, the cuts 210 may be manufactured by etching or other suitable techniques. The body 2203 of the shunt 2200' further comprises an expandable elastomeric/polymeric cover/liner (not shown); the cover/liner may be an outer jacket and/or inner liner, as previously disclosed. The cover/liner is composed of suitable biocompatible polymeric materials, such as polytetrafluoroethylene "PTFE", polyethyleneterephthalate "PET", High Density Polyethylene "HDPE", expanded polytetrafluoroethylene "ePTFE", urethane, silicone, or the like. The cover/liner is configured to cover—substantially completely or partially—the cuts 2210 of the body 2203 of the shunt 2200'.

The proximal portion 2204' of the shunt 2200' further includes an anchoring mechanism 2227' (i.e., proximal anchor), similar to the distal anchoring mechanism 2229 of the shunt 2200' and the previously described distal anchoring mechanism 2229 of FIG. 15A (e.g., malecot). The anchoring mechanisms 2227' and 2229 include a plurality of respective deformable elements 2227a' and 2229a (e.g., arms) that are disposed radially outward in the deployed configuration of the shunt 2200'. The anchoring mechanisms 2227' and 2229 are biased to their respective deployed, expanded configuration (e.g., constructed from super-elastic materials such as Nitinol®) and constrained to a delivery configuration to pass through a delivery catheter into the deployment site. As shown in FIGS. 25A-B and 25D-E, the proximal anchoring mechanism 2227' further includes a proximal interlocking element 2227d' configured to interlock with corresponding interlocking elements 3336'/3336b of the pusher member 3310 of FIGS. 26A-F. The proximal interlocking element 2227d' and their patterns (FIGS. 25H, 25M) are preferably manufactured by laser cutting, etching or other suitable techniques. Some differences between the shunt 2200' of FIGS. 25A-M and the shunt 2200 of FIGS. 15A-B is that the proximal anchoring mechanism 2227' of the shunt 2200' includes a malecot configuration, further comprising the interlocking element 2227d' such as, eyelet, slot, recess, groove, or the like. The proximal interlocking element 2227d' is better appreciated in FIGS. 25B, and 25F-H. The anchoring mechanisms 2227' and 2229 further include respective radiopaque markers 2227c' and 2229c (e.g. annular, ring, angled-arrow marker or the like). The marker 2227c' and 2229c are coupled to their respective anchoring mechanism 2227' and 2229 by any suitable technique (e.g., mechanical, chemical bonding or their like). For example, the markers 2227c' and 2229c are shown uncoupled in the exploded view of FIG. 25A having annular configurations, and coupled to their respective anchoring mechanism in FIGS. 25B-C. In the embodiment of FIG. 25C, the marker 2229c is pressed flush to the anchoring mechanism 2229.

Figure 25L:
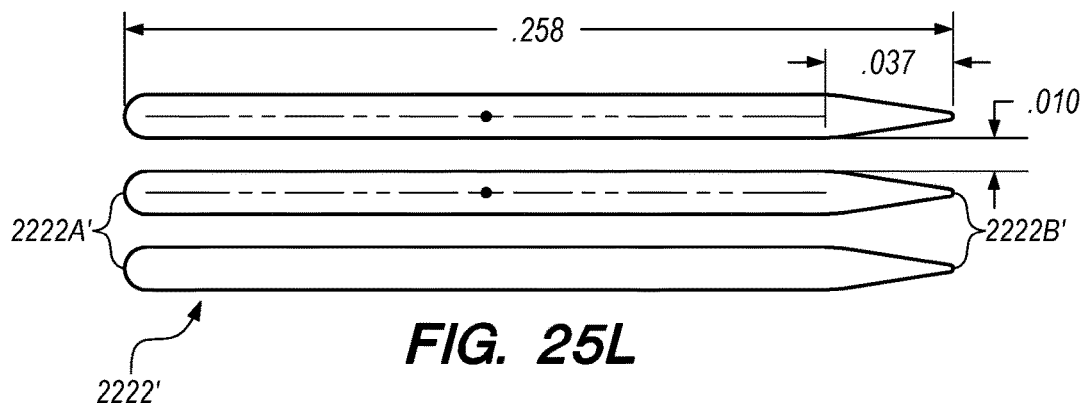
Figure 25M:
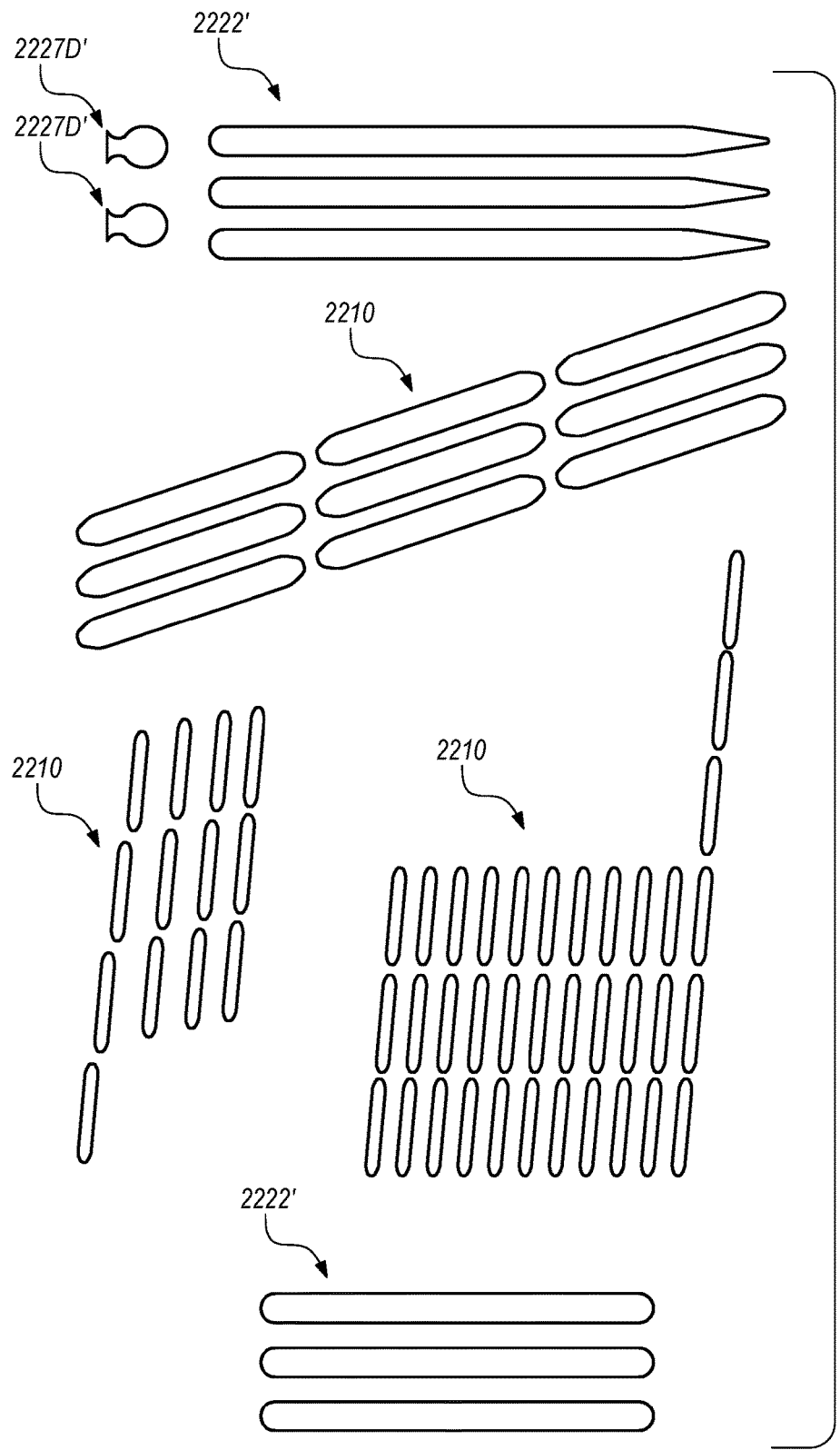

The anchoring mechanism 2227' and 2229 are formed by series of cuts 2222' (e.g., kerfs, slots, key-ways, recesses, or the like) along the length of the respective proximal 2204' and distal 2202 portions of the shunt 2200' (FIGS. 25F, 25K-L and 25M), forming the deformable elements 2227a' (FIGS. 25A-B, 25D-H) and 2229a (FIGS. 25A, 25C-F, 25K). The cuts 2222' terminate forming rounded ends 2222'a (FIGS. 25K-L) or may terminate in a vertex 2222'b (e.g., triangular shape, beveled/tapered, angular, or any suitable shape), as shown in FIG. 25L. The cuts 2222' and their patterns are preferably manufactured by laser cutting, etching or other suitable techniques. The cuts 2222' are radially spaced to form the deformable elements 2227a' and 2229a configured to extend radially outward when deployed assuming a malecot configuration (FIG. 25A-E). FIGS. 25F-M illustrate exemplary patterns and relative dimensions of the cuts 2210 and 2222' of the shunt 2200'. It should be appreciated that the relative dimensions depicted in FIGS. 25A-M are exemplary for the shunt 2200', which are not intended to limit the embodiment of the shunt 2200'.

Figure 32A:
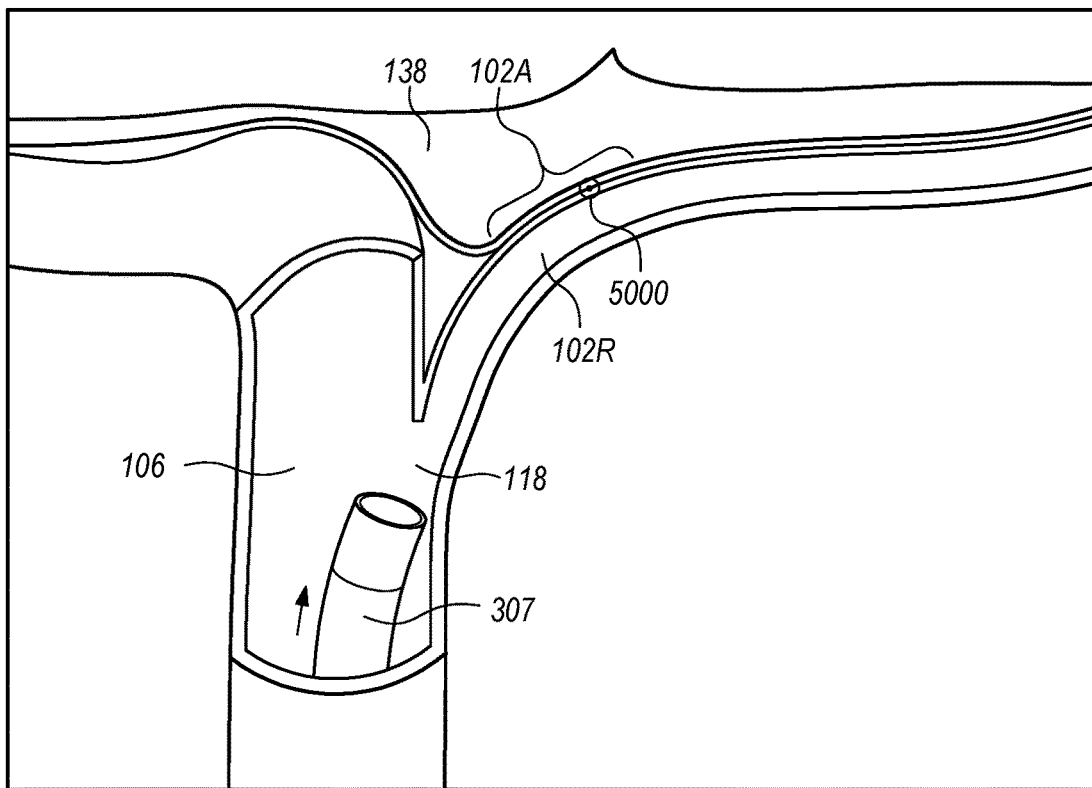
FIGS. 32A-O are perspective and cross-sectional views of exemplary methods for anchor delivery and shunt implantation procedures, according embodiments of the disclosed inventions.
Figure 32B:
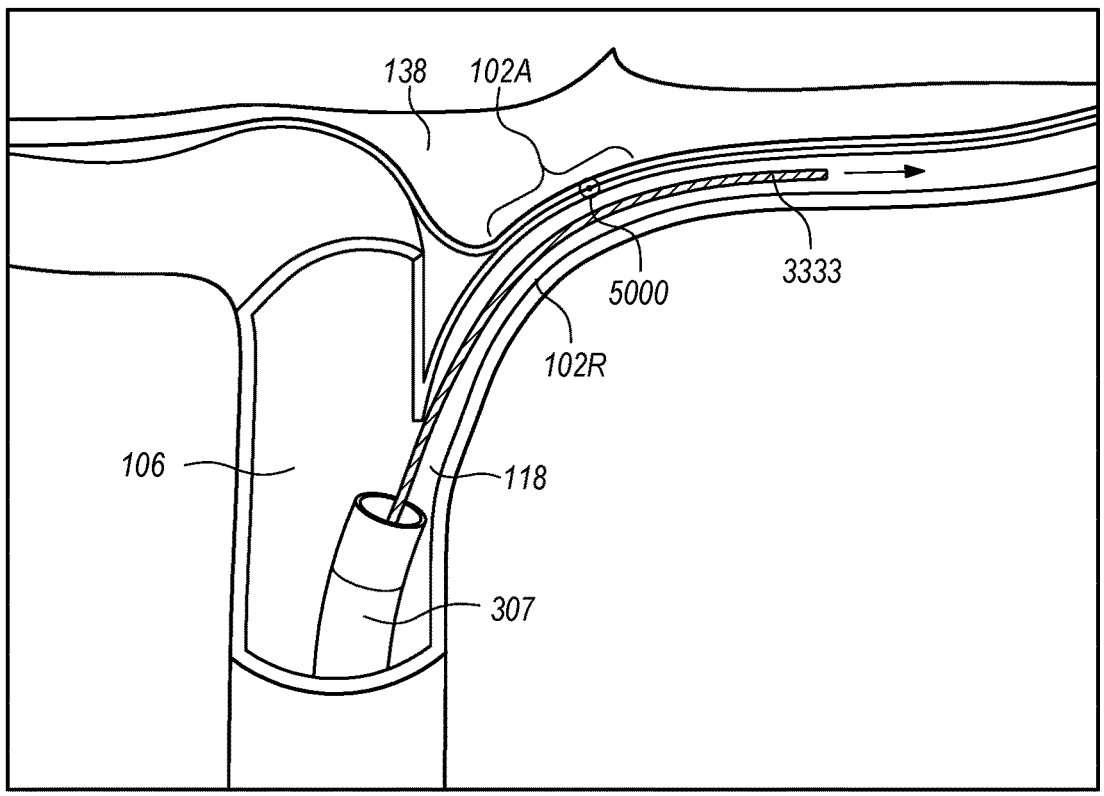
Figure 32C:
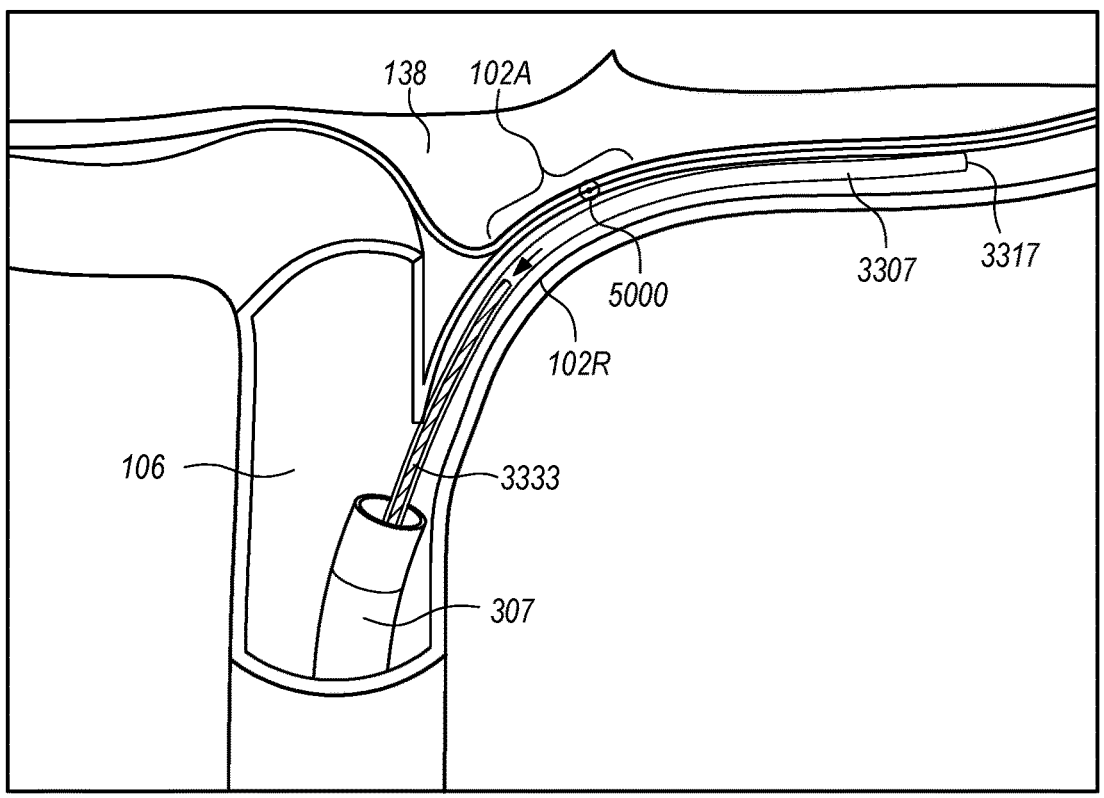
Figure 32D:
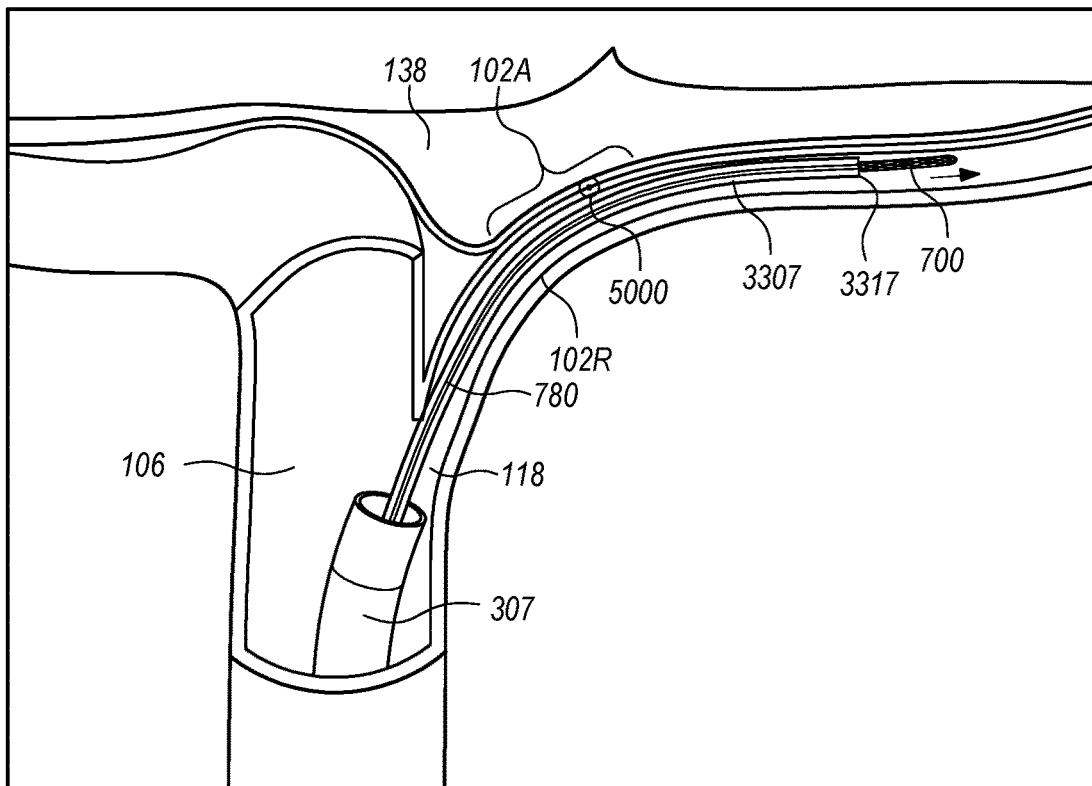
Figure 32E:
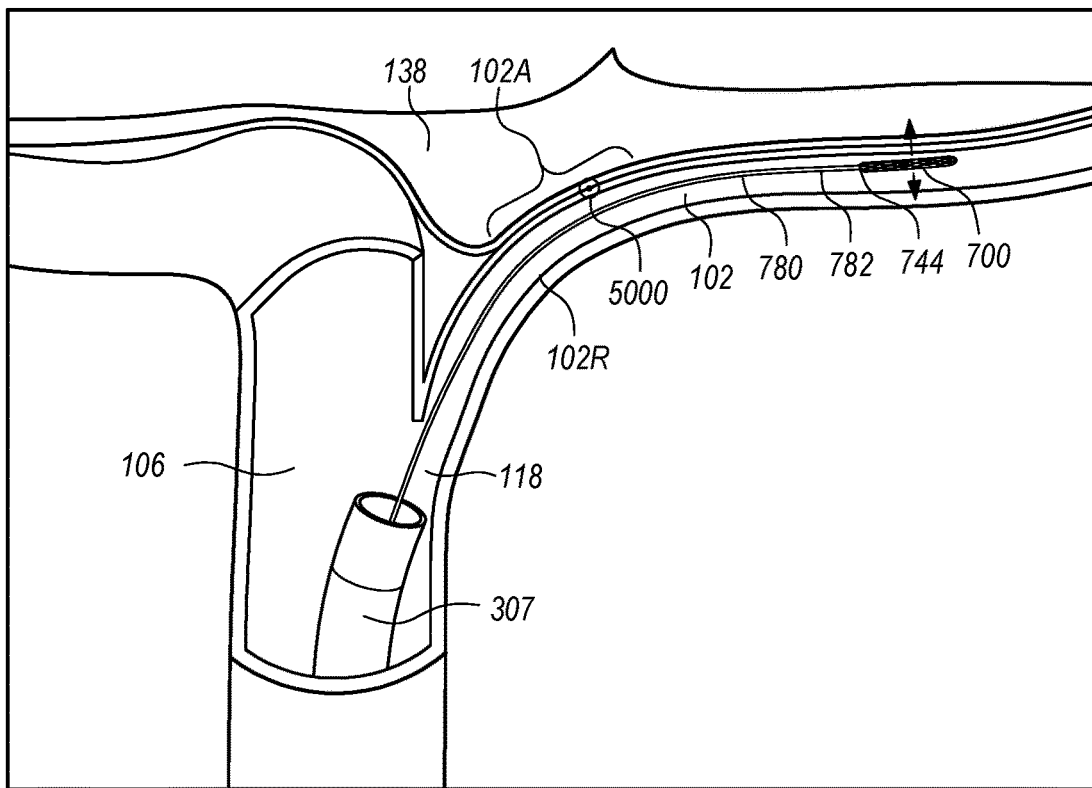
Figure 32F:
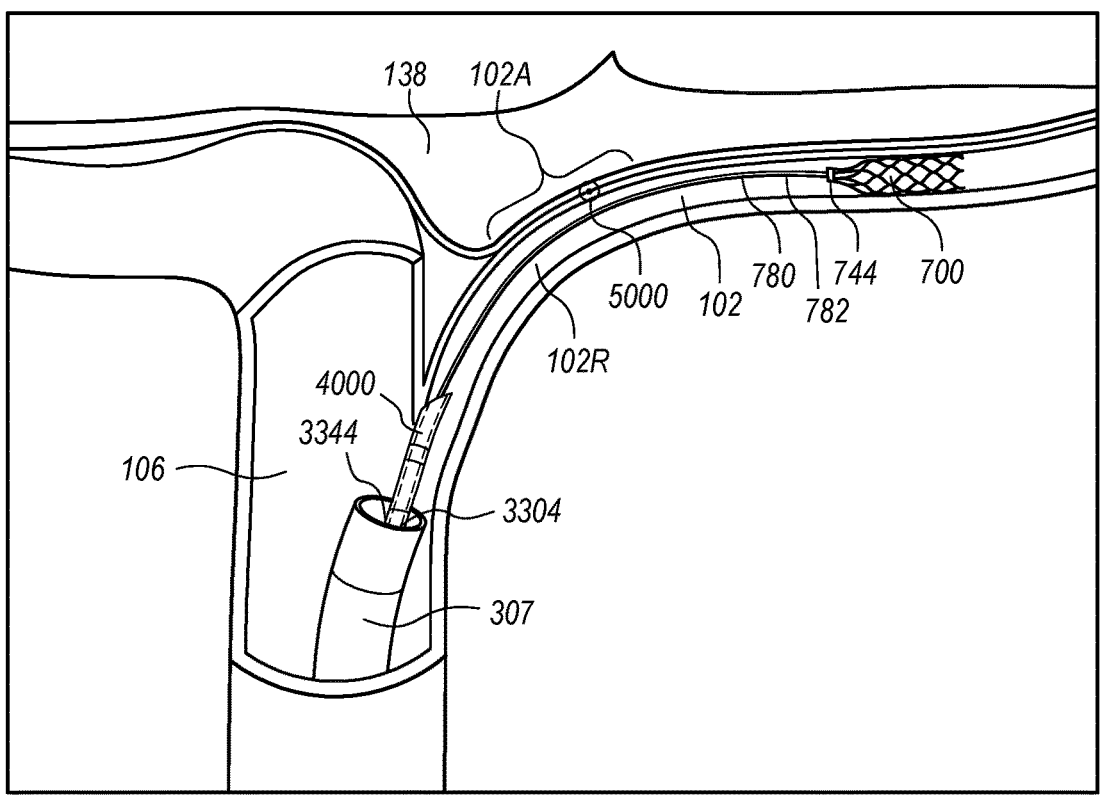
Figure 32G:
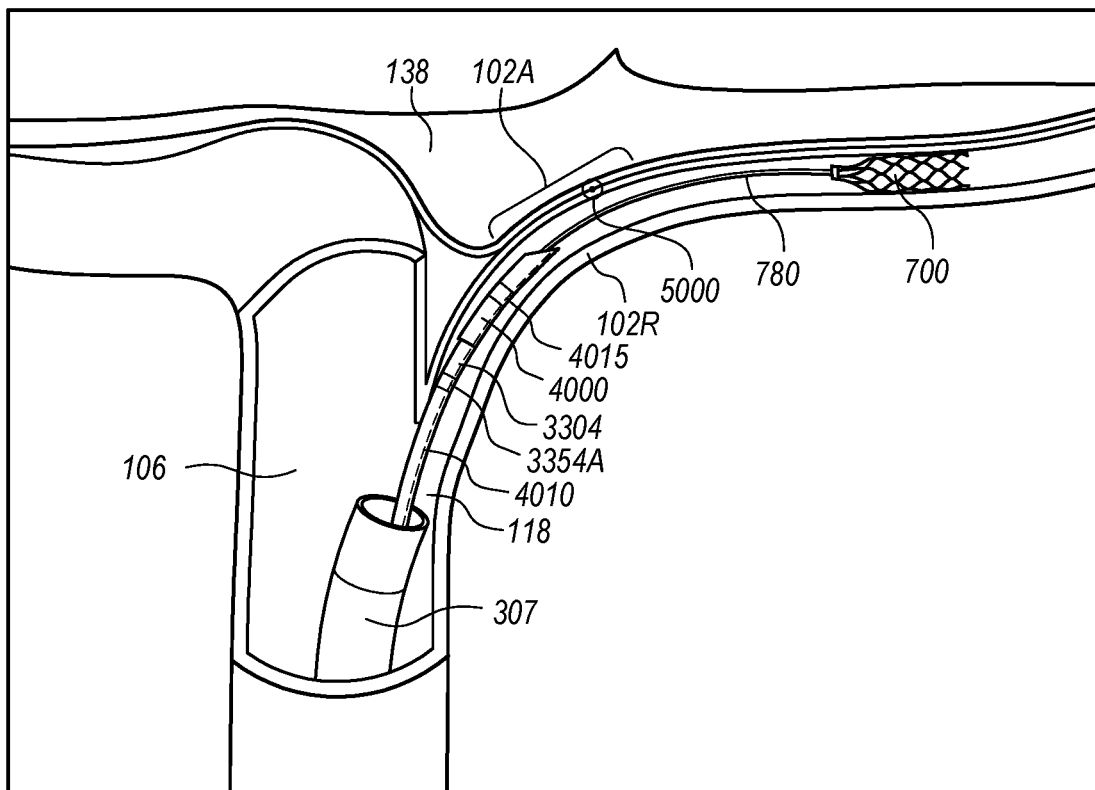
Figure 32H:
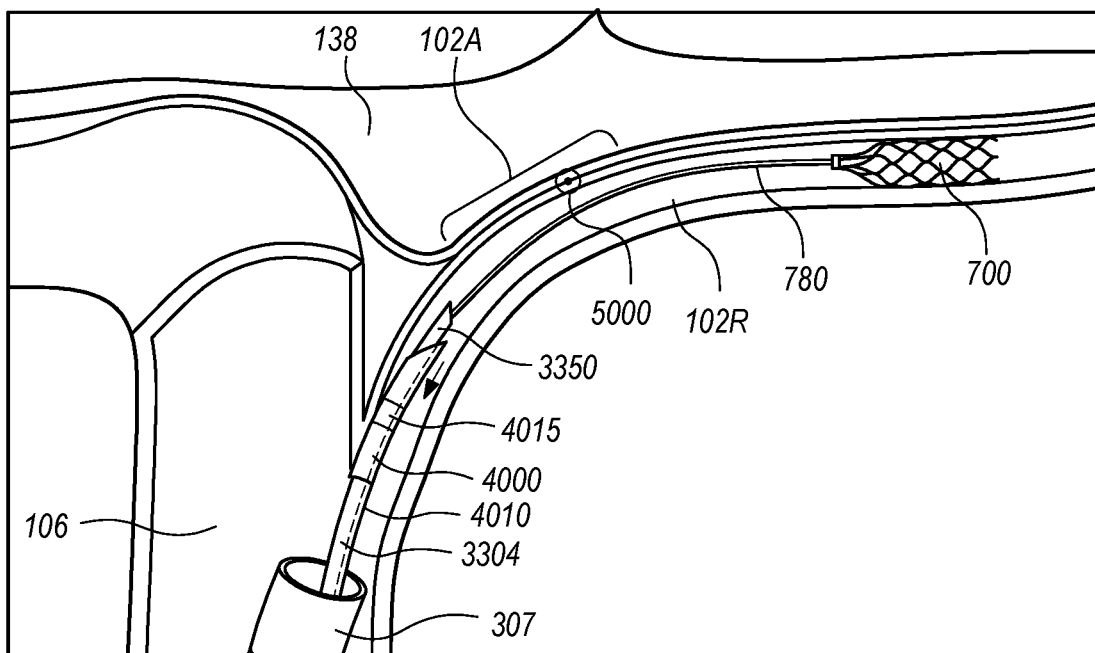
Figure 32I:
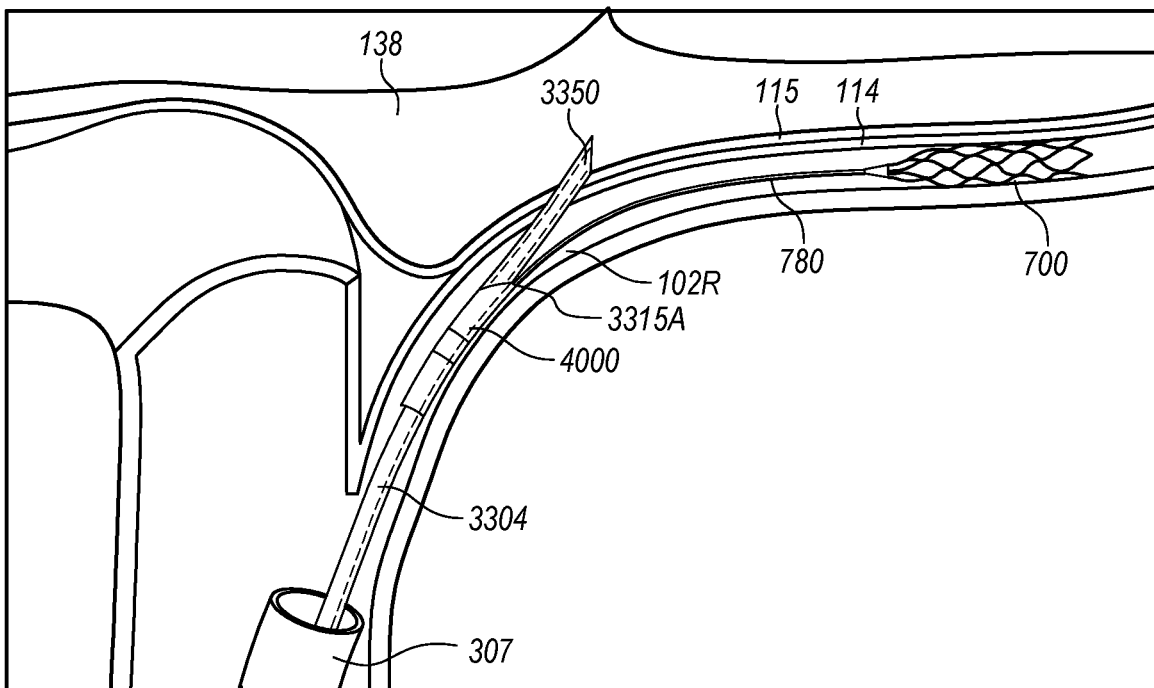
Figure 32J:
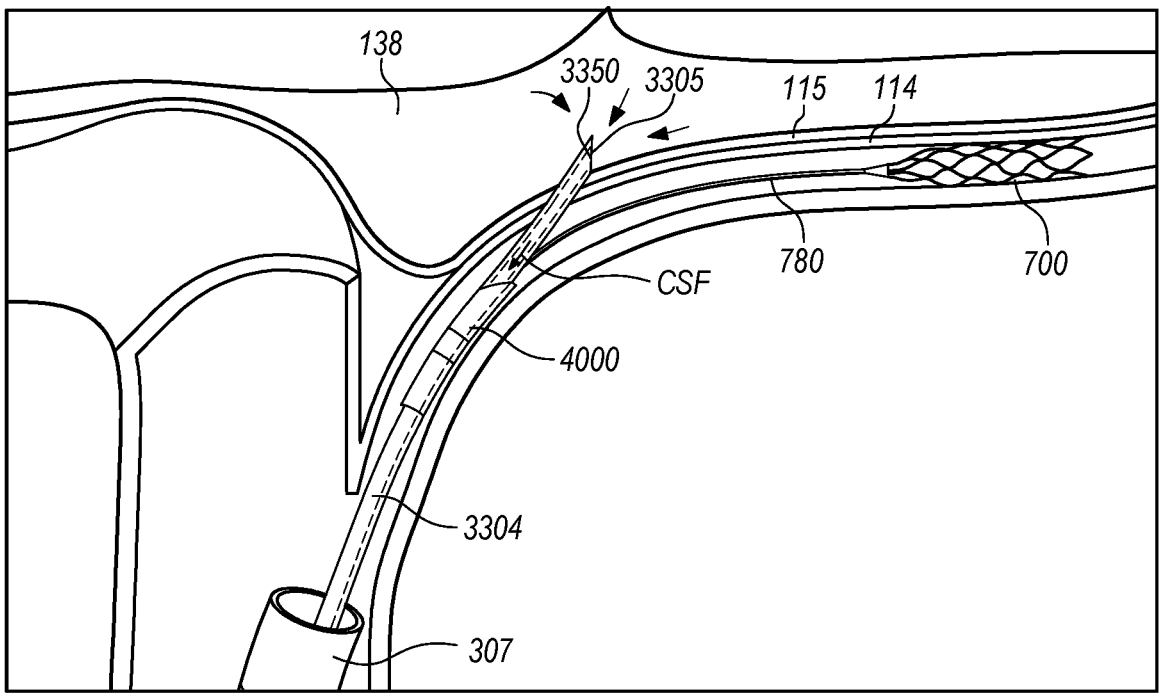
Figure 32K:
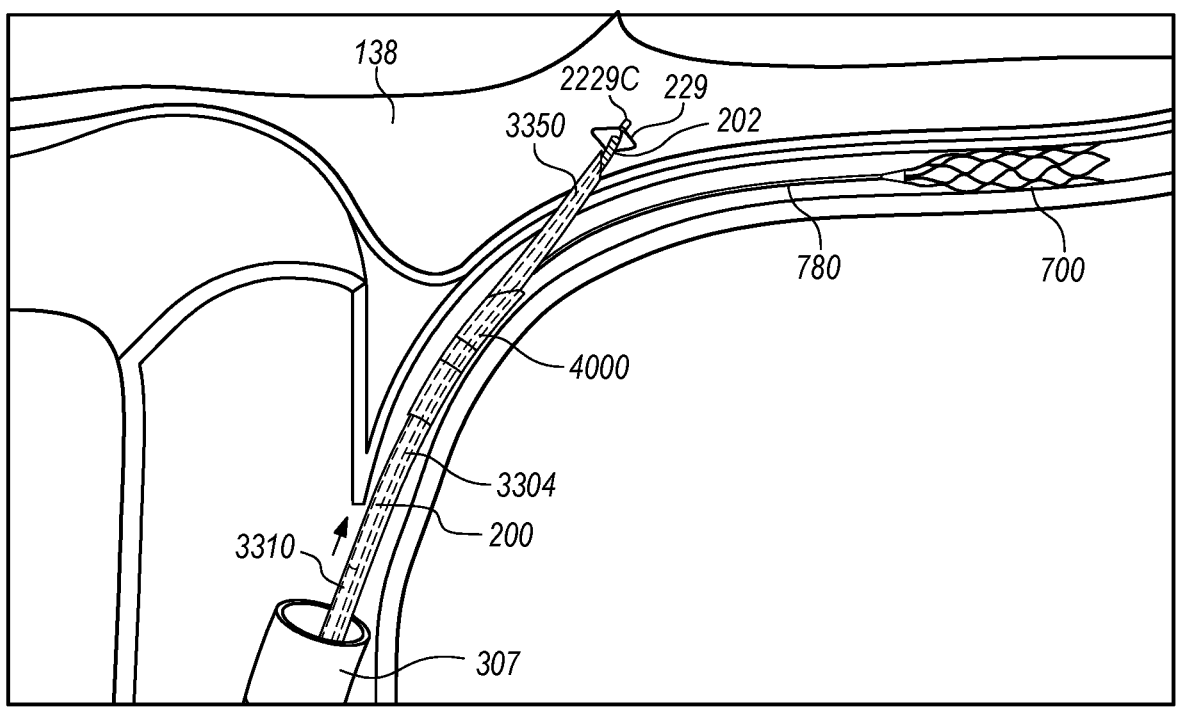
Figure 32L:
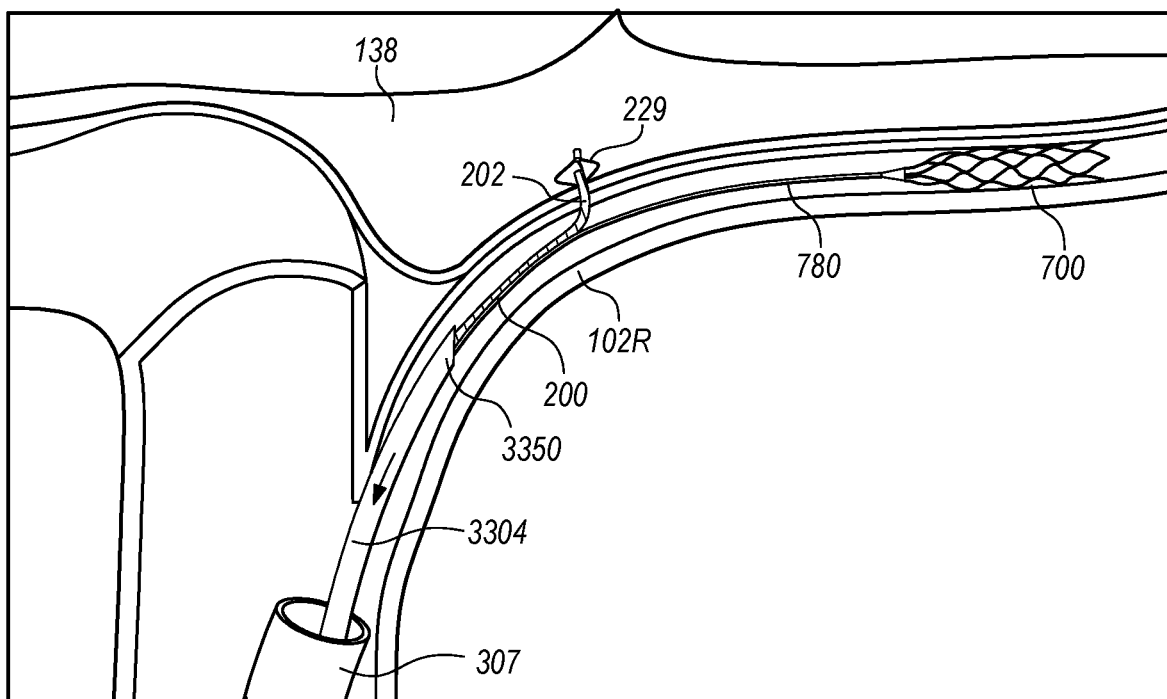
Figure 32M:
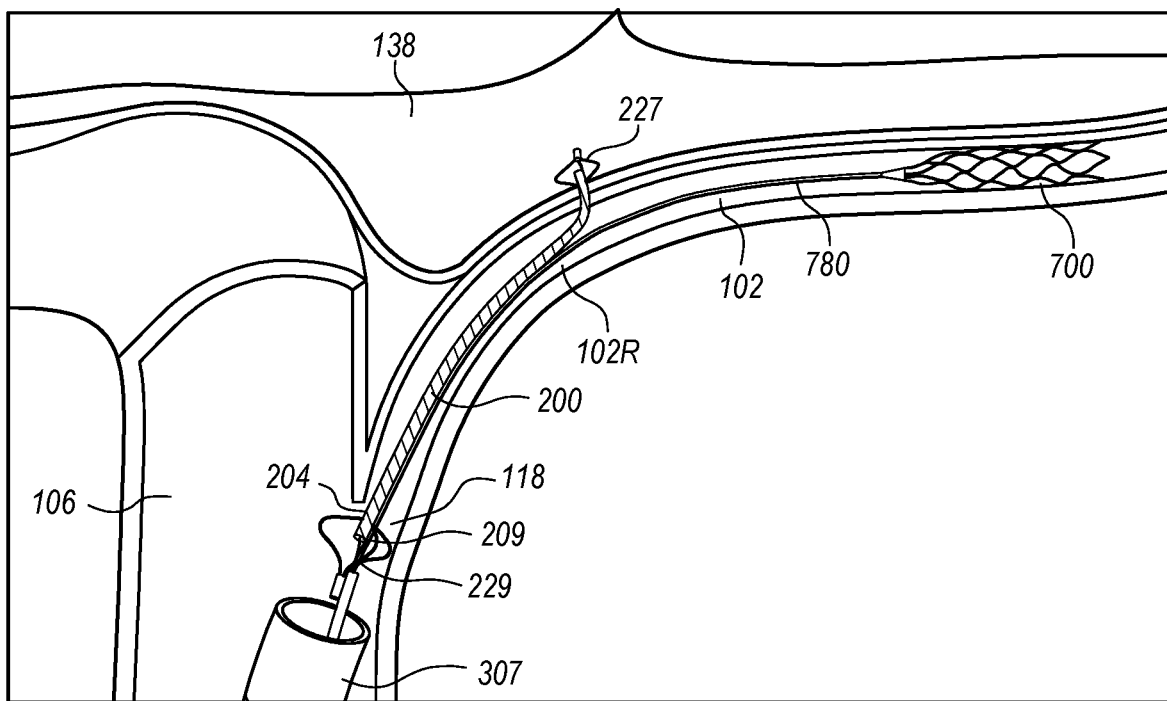
Figure 32N:
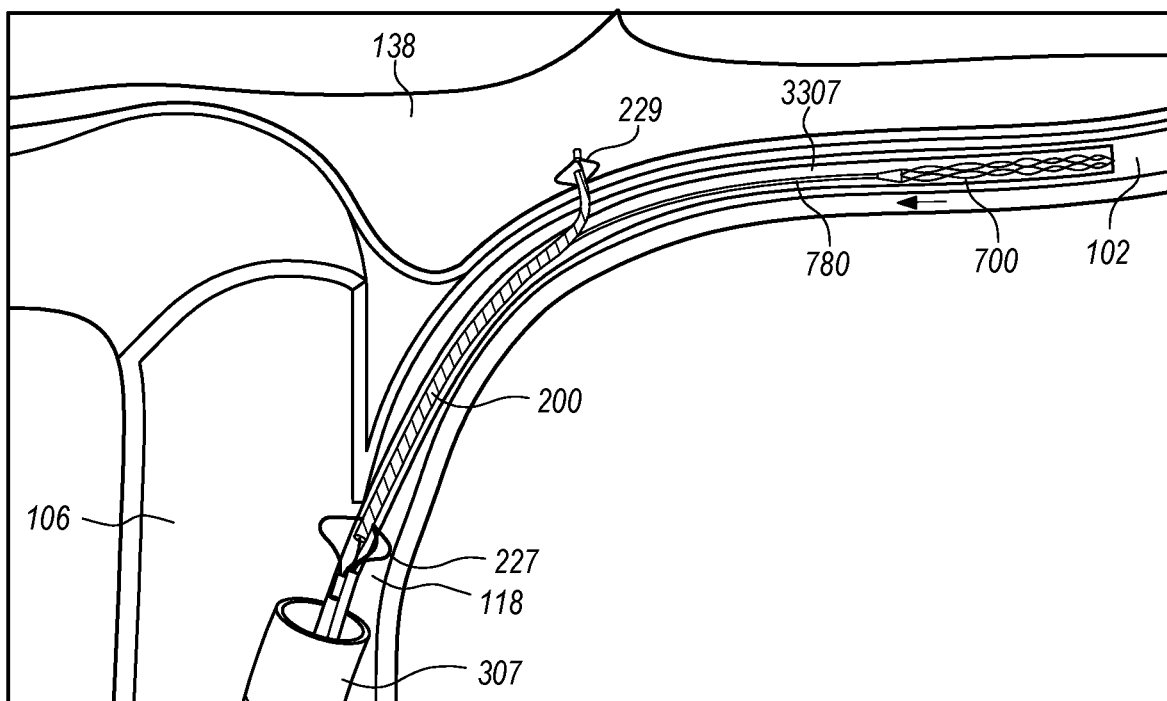
Figure 32O:
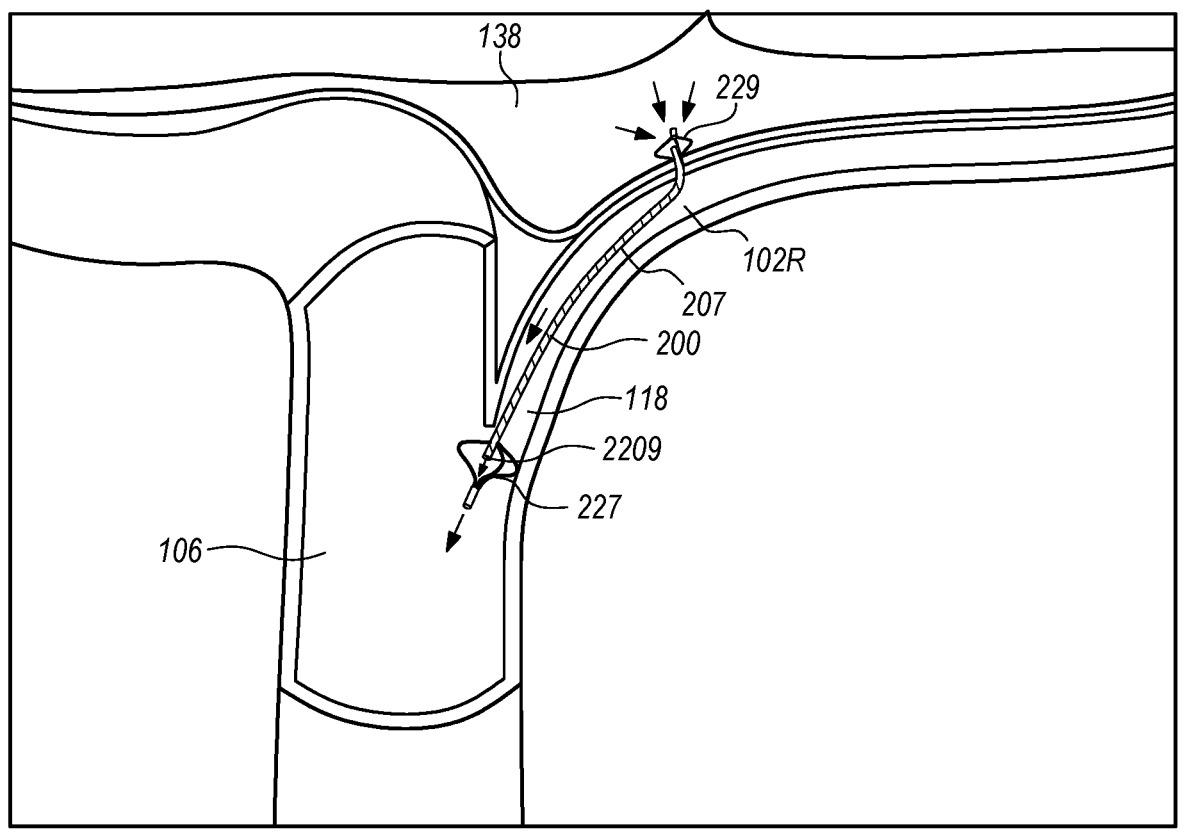

The deployed anchoring mechanism 2227' engages the jugular bulb 108, the jugular vein 106, the IPS wall 117, and/or another portion of the IPS 102, anchoring the proximal portion 2204' of the shunt 2200' within the jugular vein 106, so that the valve 2209 (not shown) is disposed within the jugular vein 106 or at least facing the blood flowing through the jugular vein (e.g., transversally disposed towards the vein), as shown, for example in FIG. 32O. Alternatively, the anchoring mechanism 2227' may engage the IPS walls 114 and 117 at the junction 118 (not-shown). The deployed anchoring mechanism 2229 secures the distal portion 2202 of the shunt 2200' within the CP angle cistern 138, so that CSF flows through the implanted shunt 2200' into the jugular vein 106 (e.g., FIG. 32O).

Figure 26E:
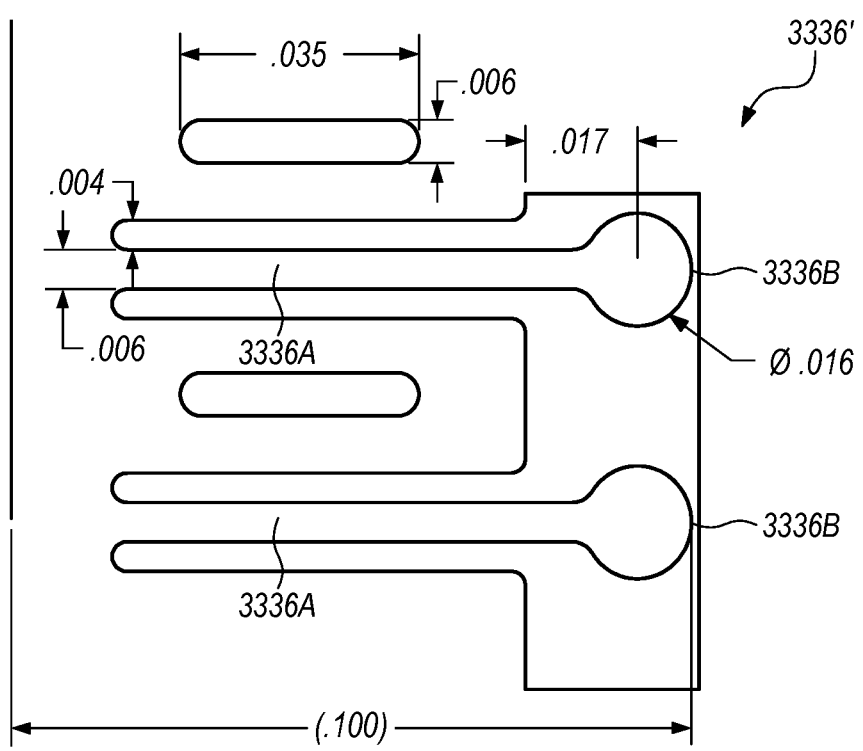

FIGS. 26A-F illustrate an alternative pusher member 3310', constructed according to embodiments of the disclosed inventions. For ease in illustration, the features, functions, and configurations of the pusher member 3310' that are the same or similar as in the pusher member of FIGS. 15C-1 and 15C-2 are given the same reference numerals and are incorporated herein. As described in FIGS. 15C-1 and 15C-2, the pusher member 3310 comprises a plurality of cuts 3311, a radiopaque marker 3314, and a distal interlocking element 3336. The pusher member 3310' may include a plurality of cuts (not shown in FIG. 26A) configured to increase flexibility of the pusher member 3310' during delivery of the shunt 2200'. The pusher member 3310' may further include a radiopaque marker disposed at the distal portion of the pusher member 3310' for imaging purposes. The pusher member 3310' includes a distal interlocking element 3336' configured to engage and disengage with the corresponding interlocking element 2227d' of the anchoring mechanism 2227' of the shunt 2200' of FIGS. 25A-B, 25D-H, as previously disclosed. In the embodiments of FIGS. 26A-F, the interlocking element 3336' includes at least two elongated elements 3336a, each elongated element 3336a terminating in a distal end 3336b. In the embodiments of FIGS. 26A-F, the distal ends 3336b include an arcuate and rounded configuration. The distal ends 3336b of the interlocking elements 3336a are sized and dimensioned (e.g., rounded ends, circular-arcuate cross-section, protrusion or the like) to meet, fit, interlock, engage and/or disengage with the proximal anchoring mechanism 2227' of the shunt 2200' of FIGS. 25A-B, 25D-H (e.g., eyelet, slot, recess, groove, or the like), which interface is better appreciated in FIGS. 27A-H. The interlocking elements 3336a have a preformed expanded or deployed configuration (e.g., outwardly expanded, flared out or the like) as shown in FIGS. 26A and 26D, and may be constructed from super-elastic materials such as Nitinol®. FIG. 26F is a cross-sectional view of the interlocking element 3336' of FIG. 26B. FIG. 26E illustrates an exemplary pattern used for laser cutting a tubular portion of super-elastic material to form the interlocking element 3336', including elements 3336a-b.

FIGS. 25A-26F discloses exemplary, relative dimensions, cut patters, angles, configurations and/or properties of the shunt 2200', pusher member 3310', radiopaque markers 2227c', and the interlocking elements 2227d' and 3336'. It should be appreciated that the disclosed dimensions, cut patterns, angles, configurations and/or properties are exemplary and not intended to limit the embodiments of FIGS. 25A-26F.

Figure 27A:
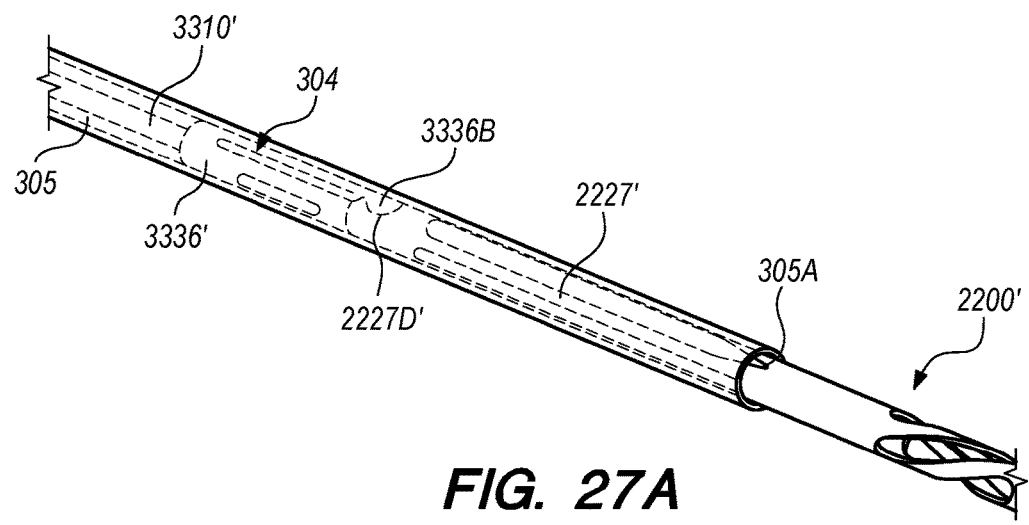
Figure 27B:
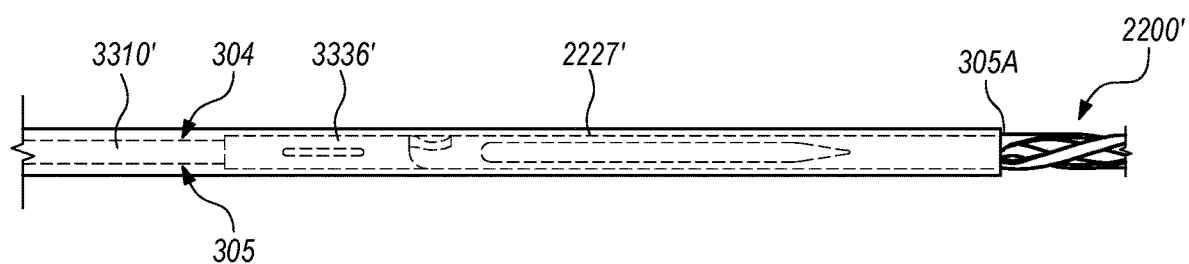

FIGS. 27A-H illustrate exemplary interfaces of the delivery catheter 304, pusher member 3310' and shunt 2200', according to embodiments of the disclosed inventions (e.g., FIGS. 6, 25A-26F). The delivery catheter 304 may further comprise a hypotube providing suitable column strength and flexibility, as previously described in FIGS. 12A-C. As shown in FIGS. 27A-B, the pusher member 3310' is disposed within the lumen 305 of the delivery catheter 304, having the interlocking member 3336', particularly the distal end 3336b, engaged with the interlocking member 2227d' of the shunt anchoring mechanism 2227'; the shunt 2200' is shown partially disposed within the delivery catheter lumen 305 (FIGS. 27A-B). The shunt 2200' may be deployed into the penetration site by advancing the shunt 2200' out of a distal end opening 305a of the delivery catheter 304, or by withdrawing the delivery catheter 304, or by a combination of advancing the shunt 2200' and withdrawing the catheter 304.

Figure 27C:
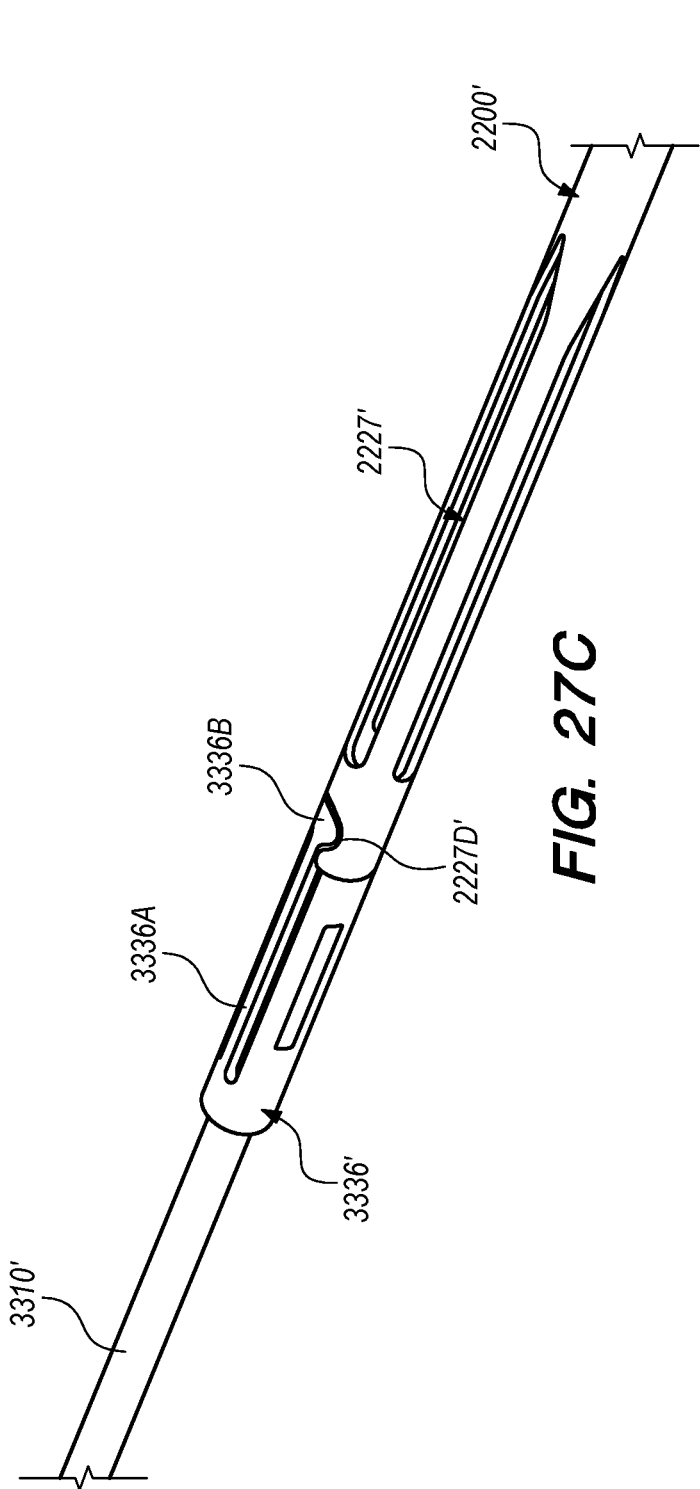
Figure 27D:
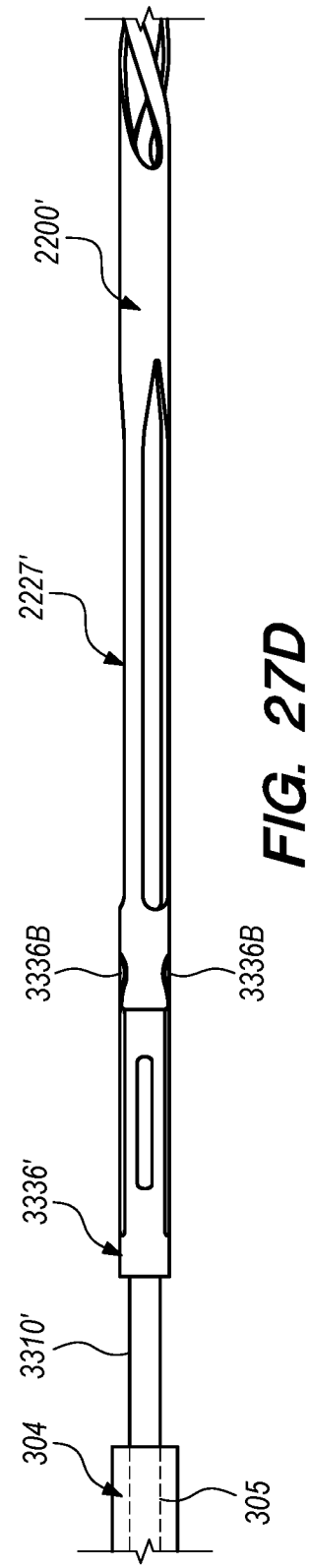

FIGS. 27C-D illustrate the pusher member 3310' and shunt 2200' interface having their respective interlocking members 3336'/3336b and 2227d' engaged, as they would be when disposed within the delivery catheter (not shown) (e.g., before the shunt 2200' is deployed into the penetration site, which will be described in further detail in FIGS. 32A-O). Although, the interlocking members 3336'/3336b and 2227d' of the respective pusher member 3310' and the shunt 2200' are engaged in FIGS. 27C-D, it should be appreciated that pusher member 3310' and shunt 2200' interface will disengage (e.g., pusher interlocking member 3336'/3336a-b outwardly expands or flares out) when the interface is no longer disposed within the delivery catheter lumen 305, as shown in FIGS. 27E-H.

FIGS. 27E-H illustrate the pusher member 3310' and shunt 2200' interface, having the interlocking members 3336'/3336a-b of the pusher member 3310' outwardly expanded (e.g., flared out) and the shunt 2200' (i.e., the anchoring mechanism interlocking member 2227d') disengaged from the pusher member 3310' (i.e., interlocking members 3336'/3336b). Further, the proximal anchoring mechanism 2227' of the shunt 2200' transitions from the delivery configuration (FIGS. 27A-D) to the deployed expanded configuration (FIGS. 27E-H). The plurality of deformable elements 2227a' (e.g., arms) of the proximal anchoring mechanism 2227' are disposed radially outward in the deployed configuration of the shunt 2200' (FIGS. 27E-H).

FIGS. 28A-G illustrate yet another exemplary elongate guide member 780 and anchor 700 interface for delivering or retracting the anchor from the IPS or CS, according to embodiments of the disclosed inventions. For ease in illustration, the features, functions, and configurations of the elongate guide member 780 and the anchor 700 of FIGS.

28A-G that are the same or similar as in the elongate guide member and the anchor of FIGS. 3A-J, 18A-F are given the same reference numerals and are incorporated herein. In the embodiments of FIGS. 28A-G, the elongate guide member 780 includes a proximal portion 784 and a distal portion 782 that is fixedly coupled to the anchor 700, via a radiopaque maker 744' (e.g., joint), as shown in FIGS. 28G-H). The radiopaque marker 744' includes a recess (e.g., aperture, socket, slot, groove, or the like) configured to receive the distal portion 782 of the elongate guide member 780 as shown by the cross-sectional view of FIG. 28H; the distal end of guide member 780 can then be welded (e.g., by laser welding) to the distal portion of marker 744'. As shown in FIGS. 28G-H, the anchor proximal portion 740 includes a recess 741 (e.g., aperture, socket, slot, groove, or the like) configured to receive the elongate guide member 780 and marker 744' assembly within recess 741. The longitudinal edges of marker 744' can then be welded to the interior edges of recess 741 in the proximal portion of anchor 700. FIG. 28D shows a view of the guide member 780, marker 744' and anchor 700 from the distal end of the anchor, with the anchor in a compressed or delivery configuration. This three-piece connection (i.e., recess 741 of anchor 700, marker 744', and distal portion 782 of guide member 780) advantageously couples the guide member to the anchor while also providing for visualization during the implant procedure (via marker 744') and strain relieving guide member 780 (by welding its distal portion to the marker). However, other suitable techniques for fixedly coupling the elongate guide member 780 to the anchor 700, with or without the radiopaque marker shown in FIGS. 28G-H (e.g., using a non-radiopaque material to create a joint 744' instead of marker 744', directly welding the distal portion 782 of the guide member to the proximal portion of the anchor without a joint or marker 744'), may be used (e.g., adhesive, bonding, or the like).

Additionally, as shown in FIG. 28H, the anchor 700 includes one or more radiopaque markers 722 disposed at the distal portion 720 of the anchor 700 to assist with the deployment, placement and/or withdrawal of the anchor 700 at the IPS 102 (e.g., FIGS. 7A-F, 32A-O). The markers 722 of the anchor 700 may include gold, or other suitable radiopaque materials coupled to the distal portion 720 of the anchor 700. The markers 722 may be embedded into distal portion 720 of the anchor 700 (e.g., press fit into the distal crowns of anchor 700 as shown in FIG. 28F), similarly to the markers 2227c of the anchoring mechanism 2227 of the shunt 2200, although, any other suitable technique for coupling the markers 722 to the anchor 700 may be used. It should be appreciated that the anchor 700 and the elongate guide member 780 may include any suitable markers for imaging purposes; for example, having arrow markers (e.g., FIGS. 30A-G) disposed in the joint 744'.

FIGS. 29A-G illustrate an alternative shunt delivery catheter 3304 for delivering the shunt into a target site of a patient, constructed in accordance with embodiments of the disclosed inventions. FIGS. 29C-E show cross section views at various points along the longitudinal axis of the shunt delivery catheter 3304, shown in a perspective longitudinal view in FIG. 29A; the FIGS. 29C, 29D and 29E cross section views correspond to the point identified by reference lines 29C, 29D and 29E along delivery catheter 3304 shown in FIG. 29A. FIG. 29B shows another perspective longitudinal cross-sectional view of the shunt delivery catheter 3304 of FIG. 29A. For ease in illustration, the features, functions, and configurations of the delivery catheter that are the same or similar as in the delivery catheter of FIGS. 10A-K, 21A-M are given the same reference numerals and are incorporated herein.

As shown in FIGS. 29D-E, the shunt delivery catheter 3304 includes three lumens 3315, 3305 and 3325. The first lumen 3315 is configured to accommodate the elongate guide member 780 (e.g., FIGS. 3A-4C, 18A-C, 28A-G), the second lumen 3305 is configured to receive, allow navigation and/or delivery of the shunt 200, 2200, 2200' (e.g., FIGS. 15A-Z, FIGS. 25A-M), and the third lumen 3025 is configured to accommodate the pull wire 4410 and guard 4000 (e.g., FIGS. 19A-20). As shown in FIGS. 29A-B, the lumen 3315 includes a rapid-exchange configuration, and the lumen 3305 may extend from the proximal portion 3342 to the distal portion 3344 of the shunt delivery catheter 3304. For example, the first lumen 3315 of the shunt delivery catheter 3304 extends distally from a first opening in a distal portion of the shunt delivery catheter 3304 to a second opening in the distal portion of the shunt delivery catheter 3304 that is distal to the first opening and proximal to the distal end opening. The lumen 3325 extends from the proximal portion 3342 to an area proximately to the distal portion 3344 of the catheter 3304 (FIGS. 29A-B). It should be appreciated that the diameter, length, size and dimensions of the lumens 3315, 3305 and 3325 of the delivery catheter 3304 are configured to allow passage of shunts, penetrating elements, needles, RF stylets, or any suitable surgical tool. Further, the lumens 3315, 3305 and 3325 of delivery catheter 3304 may include respective liners and/or can be coated with a hydrophilic agent to increase the lubricity of the lumens with respect to other delivery assembly components, as previously described and/or described in the related application incorporated by reference herewith.

The delivery catheter 3304 of FIGS. 29A-E includes the penetrating element 3350 on the distal portion 3344 of the catheter. The penetrating element 3350 may include a beveled-needle (e.g., FIG. 22, 24A-K) fixedly coupled to the distal portion 3444 of the delivery catheter 3304, as previously described. The penetrating element 3350 includes a penetrating element lumen 3555 in fluid communication with the lumen 3305 of the shunt delivery catheter 3304. Further, the delivery catheter 3304 of FIGS. 29A-E includes a radiopaque marker band 3354 proximately disposed to the penetrating element 3350. The radiopaque marker band 3354 may be disposed in an angle (not shown) with respect to the longitudinal axis of the catheter 3304 to indicate location and/or orientation of the distal portion 3344 of the catheter 3304 during use. The marker 3354 may include further directional features, such as arrow heads, or the like, as shown in FIGS. 30A-G. Additional markers 3354 may be disposed on any suitable sections of the delivery catheter 3304, such as proximately disposed to lumen openings (e.g., markers 3354a-b of FIGS. 21A-M). For example, a first radiopaque marker band that reinforces a circumferential portion of the shunt delivery catheter 3304 encompassing both the first and second shunt delivery catheter lumens proximate the first opening in the distal portion of the shunt delivery catheter, and a second radiopaque marker band that reinforces a circumferential portion of the shunt delivery catheter encompassing both the first and second shunt delivery catheter lumens proximate the first opening in the distal portion of the shunt delivery catheter 3304.

The shunt delivery catheter 3304 includes a reinforcing member 1345 (FIGS. 29A-B, FIGS. 29F-G) configured to reinforce the catheter 3304 while providing a suitable balance between column strength and flexibility (e.g., "pushability" and "torqueability"). The reinforcing member 1345 is composed of suitable biocompatible and/or elastomeric materials such as, stainless steel, Nitinol® or the like. The reinforcing member 1345 includes a plurality of cuts 1330 (e.g., kerfs, slots, key-ways, recesses, or the like) selectively disposed in sections of the reinforcing member 1345 along length L20 of the delivery catheter 3304, as shown in FIGS. 29A-B, and FIG. 29F. Alternatively, the cuts 1330 can be continuously disposed substantially along L20 (not shown). It should be appreciated that the cuts 1330 can have variable spiral cut patterns of kerf, pitch, cuts per rotation and cut balance along L20 or combinations thereof. Additionally, the reinforcing member 1345 of FIGS. 29A-G includes an inner liner 1360 and an outer jacket 1365 (FIG. 29B), as previously described and better appreciated in detail in FIG. 12C. The inner liner 1360 and outer jacket 1365 are configured to cover—substantially completely or partially—the cuts 1330 of the reinforcing member 1345, while maintaining the flexibility provided by the selective cuts 1330 and column strength afforded, in part, by the reinforcing member 1345.

The distal portion of the delivery catheter 3344, as shown in FIGS. 29A-B and FIG. 29F, further includes a stain-relief portion 3343 proximately disposed to the penetrating element 3350. The stain-relief portion 3343 is configured to avoid, minimize and/or resist kinking of the delivery catheter 3304 at the distal portion 3344 (e.g., transition area from the flexible distal portion 3344 of the catheter 3304 into the penetrating element 3350), during catheter use.

FIGS. 30A-G illustrates an alternative marker, constructed in accordance with embodiments of the disclosed inventions. The marker 3354 is composed of gold or any other suitable radiopaque materials and may be formed by cutting a tubular element in a suitable angle, as shown for example in angle A30 of FIG. 30A. FIGS. 30A-G are perspective, side and cross-sectional views of the angled marker 3354. FIGS. 30D-E are detailed views of respective edges 3354' and 3354" of FIG. 30C. Additionally, the marker 3354 may include any other relative size, geometry or configurations (e.g., arrow-head, different width of the band, asymmetric band, or the like) suitable to indicate position, direction and/or orientation of the element (e.g., member, component, instrument, penetrating element, or the like) where the marker is disposed. For example, an arrow-head marker disposed on the distal portion 3344 of shunt delivery catheter 3304 is configured to assist with the location, direction and/or rotational orientation of the penetrating element 3350 in the respective IPS or Cs.

Figure 31:
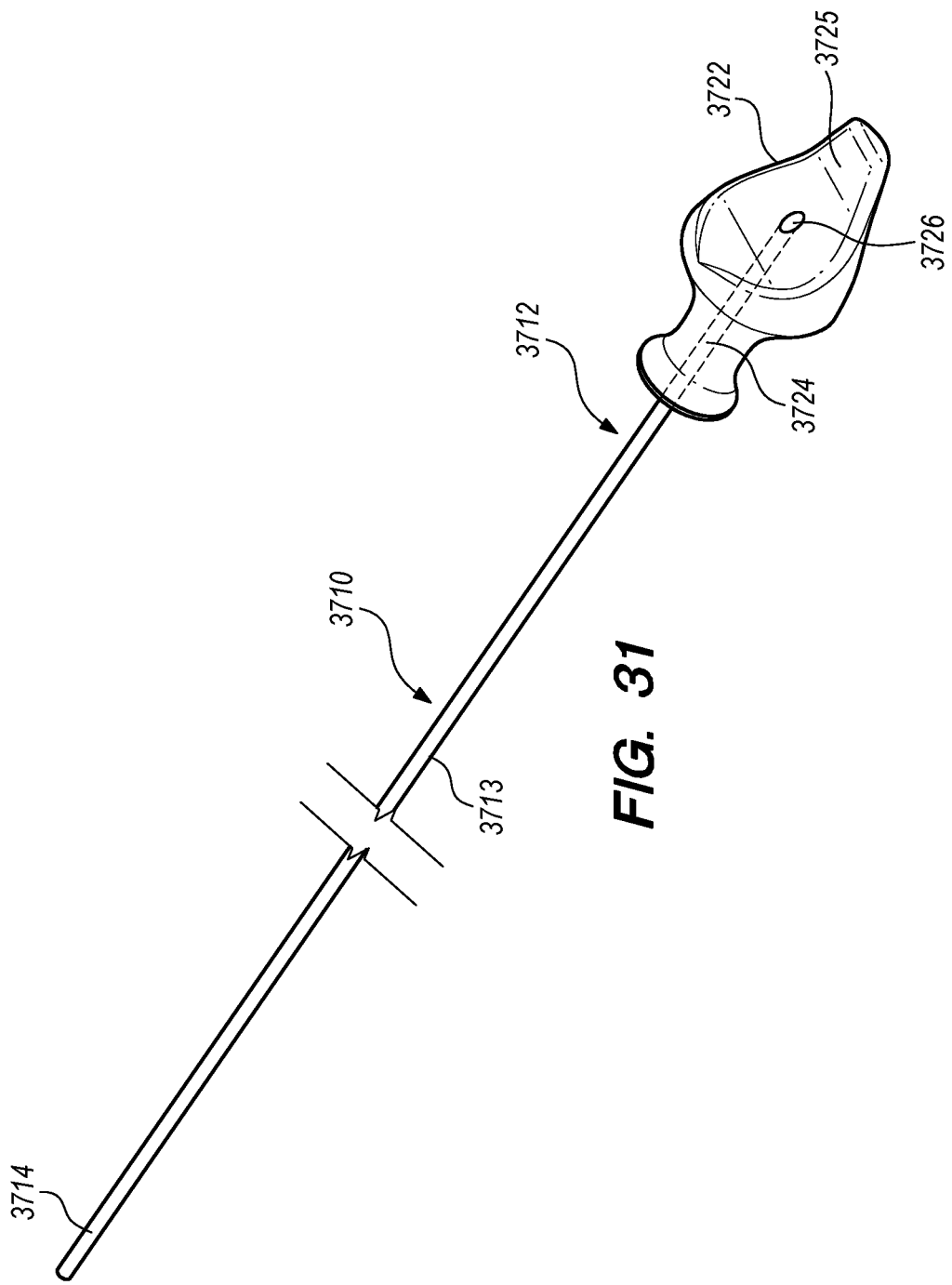
FIG. 31 is a perspective view of an anchor pusher tool constructed according to embodiments of the disclosed inventions.

FIG. 31 illustrates an anchor pusher tool 3710, constructed in accordance with embodiments of the disclosed inventions. The anchor pusher tool 3710 includes an elongated configuration, having a proximal portion 3712, a middle portion 3713 and a distal portion 3714, and a lumen 3724 extending therebetween (e.g., a hypotube or the like). The proximal portion 3712 of the pusher tool 3710 includes a handle 3722, the handle 3722 having a lumen opening 3726 in fluid communication with the lumen 3724, and an outer surface 3725. The anchor pusher tool 3710 is configured to translate (e.g., advance/retract) the anchor 700 (e.g., FIGS. 3A-5W, 18A-C and 28A-G) through the guide catheter 320, the anchor delivery catheter 304, or the like, into the IPS 102 (e.g., FIGS. 7A-D, 32A-O). The anchor pusher tool 3710 is further configured to receive the elongated guide member 780, and the handle 3722 is configured to grasp a portion of the guide member 780 extending proximally through the handle lumen 3724 for thereby pushing the guide member 780, and thus the anchor 700, distally through the anchor delivery catheter 3307.

During the shunt implantation procedure described in FIGS. 32A-O, the elongated guide member 780 may be disposed within the lumen 3724 of the anchor pusher tool 3710 for delivering the anchor into the IPS 102, while the proximal portion 784 of guide member 780 extends out the pusher tool 3710 (e.g., out through the lumen opening 3726 of handle 3722). An operator can pinch or hold the proximal portion 784 of guide member 780 extending through the handle 3722 against the handle outer surface 3725 and then advance the handle 3722 and guide member 780 into a micro catheter to advance the anchor 700 distally. The operator can then retract pusher tool 3710 proximally over the proximal portion 784 of guide member 780 (i.e., by releasing the proximal portion 784 of guide member 780 pinched or held against the handle outer surface 3725), and thereafter repeat the advancing and retracting acts until the anchor 700 reaches a desired location (e.g., distal end of micro catheter lumen). The use of the pusher tool 3710 facilitates the anchor 700 delivery and navigation by leveraging the column strength of guide member 780, as an alternative to having an anchor pusher member that extends at least the length of the micro catheter.

FIGS. 32A-O illustrate an exemplary shunt implantation procedure in a patient, in accordance with embodiments of the disclosed inventions. Prior and/or simultaneously to the shunt implantation procedure, the operator can obtain CT and/or MRI imaging (e.g., MRI, axial T2-weighted, axial CISS or FIESTA sequences, axial volumetric thin slice T1-weighted with gadolinium contrast) studies of the patient's intracranial anatomy to ascertain the sizing and relative proximity between the patient's right IPS 102R and left IPS 102L, CP angle cistern 138, arterial structures (e.g., basilar artery), and surrounding bony anatomy. The obtained imaging can also be used to assess the volume of unobstructed CSF space of CP angle cistern 138 surrounding the left and right IPS channels relative to a penetration site 5000 in an IPS 102 where an anastomosis will be made during the shunt implantation procedure. For ease in illustration, the penetration site 5000 is shown as a point or selected area in FIGS. 32A-O. However, a person skilled in the art should appreciate that the penetration site 5000 can be disposed at any points or areas in a selected dural venous sinus, such as any areas in the IPS 102, the first curved portion 102A or the second curved portion 102B of the IPS 102, as shown in FIG. 2C. Thus, the operator can use the imaging study to select one or more preferred shunt deployment locations along the first curved portion 102A and/or second curved portion 102B in the patient's right IPS 102R and/or left IPS 102L (e.g., FIG. 2C). To further illustrate the following exemplary procedure, the operator selects the patient's right IPS 102R and the penetration site 5000 along the first curve 102A of the IPS based on an imaging study, as shown in FIG. 32A.

The operator gains access to the patient's venous vasculature through the patient's right femoral vein using an introducer kit (e.g., Micropuncture Introducer Set from Cook Medical of Bloomington, Ind.) and the Seldinger technique. The operator then navigates a guide wire (e.g., guide-wires 302/308 of FIG. 6, 0.035" guide wire such as an 0.035" GLIDEWIRE from Terumo Interventional Systems of Somerset, N.J.) and a guide catheter 307 (e.g., guide catheter 320 of FIG. 6, 6 Fr catheter such as 6 Fr ENVOY Guiding Catheter from Codman Neuro of Raynham, Mass.) through the femoral vein access point, into the vena cava in the abdomen, through the chest past the heart and into the right jugular vein 106. The guide wire is coaxially disposed within and moves relative to the guide catheter 307. The operator can position the distal end of the guide catheter 307 about the JV-IPS junction 118 as shown in FIG. 32A, and in certain patient anatomies, the distal end of the guide catheter 307 can access the proximal portion of the IPS 102. Optionally, a sheath (e.g., 7 Fr Flexor Shuttle Guiding Sheath from Cook Medical of Bloomington, Ind.) may be advanced through the patient's venous vasculature, prior to advancing the guide catheter 307; the guide catheter 307 can then be advanced through the sheath lumen to the jugular vein or JV-IPS junction 118 (not shown). The sheath can provide additional support to the guide catheter, and other catheters, guide wires and/or components navigated to IPS 102 during the shunt implantation procedure.

The operator accesses the right IPS 102R and the cavernous sinus 104 with an anchor delivery catheter 3307 and micro wire 3333 coaxially disposed through the guide catheter 307 (FIGS. 32B and 32C). The anchor delivery catheter 3307 (e.g., catheter 304 of FIGS. 7A-D, 0.027" micro catheter such as a Phenom 27 Catheter from Cathera, Inc. of Mountain View, Calif., an Excelsior SL-10 Microcatheter from Stryker Neurovascular of Fremont, Calif., or a Marksman Micro Catheter from Medtronic of Irvine, Calif.) advances through the guide catheter 307, and rides over the micro wire (e.g., an 0.010", 0.014", or 0.018" guide wire such as a Synchro2 Guidewire from Stryker Neurovascular of Fremont, Calif.). The operator advances the micro wire 3333 and anchor delivery catheter 3307 through the JV-IPS junction 118 into the right IPS 102R. For example, the micro wire 3333 may be advanced distally and incrementally, followed by the anchor delivery catheter 3307, which may also advance distally and incrementally over the micro wire 3333. The operator may repeat the micro wire and catheter advancement acts in a serial fashion, such as, for example that the micro wire may be advanced to a distal location before with the anchor delivery catheter following thereafter in two separate advancements; or the micro wire and anchor delivery catheter can be advanced distally, simultaneously through the JV-IPS junction 118 and into the right IPS 102R. The operator can position the distal end of the anchor delivery catheter 3307 at a location distal to the penetration site 5000 in IPS wall 114 along first curve 102A of the right IPS 102R as shown in FIG. 32C. The operator withdraws the micro wire 3333 from the anchor delivery catheter 3307, leaving a distal opening 3317 of the anchor delivery catheter 3307 distally disposed to the penetration site 5000 in IPS wall 114 along first curve 102A of the right IPS 102R, as shown in FIG. 32C.

The operator can load the anchor 700 and elongate guide member 780 into the proximal opening (not show) of the anchor delivery catheter 3307. Using the anchor pusher tool of FIG. 31 and by loading the proximal portion 784 of guide member 780 through the pusher tool lumen 3724 as previously disclosed, the operator can advance the anchor 700 and guide member 780 through the anchor delivery catheter 3307 until the anchor 700 reaches the distal opening 3317 of the anchor delivery catheter, as shown in FIG. 32D. The operator then positions the distal portion of the anchor delivery catheter 3307 (i.e. with anchor 700 and guide member 780 disposed within the catheter 3307) at a desired location (e.g., in a dural venous sinus of a patient at a location distal to a curved portion of a wall of an IPS, FIGS. 1-2D, 32D-F) for anchor deployment, and withdraws the anchor delivery catheter 3307 while holding the anchor 700 in position using the guide member 780 and/or advances the anchor 700 via the guide member 780 through the distal opening 3317 of the anchor delivery catheter 3307 while holding the catheter 3307 in place until the anchor 700 advances out the distal opening 3317 and expands against the walls of the IPS 102. As depicted in FIG. 32E, the operator deploys/delivers the anchor 700 and guide member 780 via the anchor delivery catheter 3307 (i.e., out of the distal opening 3317) in the distal portion of the right IPS 102R. The delivered anchor 700 expands within the IPS 102, anchoring and/or securing its position within the IPS 102 (e.g., distally disposed to the penetration 5000 site along IPS wall 114 of the first curved portion 102A of the right IPS 102R). The distal portion 782 of guide member 780, such as the joint/marker 744 coupling the guide member 780 to the anchor 700, can be disposed in the IPS 102, as shown in FIGS. 32E-F. If the operator is satisfied with the deployment of the anchor 700 and/or the deployment location, the operator withdraws the anchor delivery catheter 3307 from the patient, leaving the deployed anchor 700 with the guide member 780 that extends proximally from the anchor 700 through the first curved portion 102A and junction 118, as shown in FIG. 32E. The deployed guide member 780 further extends through the patient's venous vasculature and out of the patient via the femoral vein access point (not shown). Alternatively, the operator can re-sheath and/or re-capture the deployed anchor 700 and guide member 780 into the anchor delivery catheter 3307, reposition the distal opening 3317 of the catheter 3307 to a desired location within the IPS 102 and redeploy the anchor 700 until the operator is satisfied with the deployment of the anchor 700 and/or deployment location.

Then, the operator advances a shunt delivery catheter 3304 (e.g., catheter 3304 of FIGS. 7E, 8A-10K, 16, 21A-M, 29A-F) into the patient's vasculature via the femoral vein access point and navigates the catheter 3304 through the JV-IPS junction 118 (as shown in FIG. 32F) to the penetration site 5000 along IPS wall 114 of the first curved portion 102A of the right IPS 102R. The operator can feed the proximal end of guide member 780 through the first lumen 3315 of shunt delivery catheter 3304, via the distal opening 3315a and proximal opening 3315b of the first lumen of the catheter 3304. The operator then advances the shunt delivery catheter 3304 over the guide member 780, through the femoral vein access point and tracks the shunt delivery catheter 3304 over the guide member 780 through the patient's venous vasculature, until the distal portion 3344 of the shunt delivery catheter 3304 is disposed proximately to the penetration site 5000 along the IPS wall 114 of the first curved portion 102A of the right IPS 102R, as shown in FIG. 32G. While tracking/advancing the shunt delivery catheter 3304, the operator can hold the guide member 780 stationary or pull proximally on the proximal portion 784 of the guide member 780 to facilitate advancement of the shunt delivery catheter 3304 through the patient's venous anatomy. Additionally, the operator can rotate the shunt delivery catheter 3304 while tracking/advancing over the guide member 780 to overcome any resistance (e.g., resistance/friction encountered while tracking the catheter through JV-IPS junction 118 and/or into right IPS 102R).

The operator can confirm the orientation of the shunt delivery catheter 3304 and the trajectory of penetrating element 3350 through IPS wall 114 into CP angle cistern 138 relative to the penetration site 5000 using one or more of the previously disclosed imaging techniques. The operator may use the distal 3354a and proximal 3354b markers located on the distal portion 3344 of the shunt delivery catheter 3304 to confirm the orientation and trajectory of the catheter 3304. The catheter markers will be visible under various imaging modalities used during the procedure (e.g., bi- or single-plane fluoroscopy). To the extent the operator has created a 3D reconstruction of the patient's anatomy of the penetration site 5000 (e.g., using 3D-rotational angiography or venography), the operator can confirm the orientation and/or trajectory of the penetrating element 3350 by combining the fluoroscopy and 3D reconstruction using a 3D road mapping technique.

The penetrating element 3350 disposed at the distal opening of the shunt delivery catheter 3304 is covered by a penetrating element guard 4000 (e.g., guard 4000 of FIGS. 19A-20) during the advancement of the catheter 3304 through the patient's vasculature. The operator withdraws (or alternatively, advances) the penetrating element guard 4000 to expose the penetrating element 3350 in the IPS 102 at the penetration site along IPS wall 114 of the first curved portion 102A of the right IPS 102R, as shown in FIG. 32H. The operator withdraws the guard 4000 by pulling the pull wire 4010 coupled to the guard 4000. While withdrawing the guard 4000 and using the previously disclosed imaging techniques, the operator will observe the guard marker 4015 transition proximally towards and/or until it abuts or overlaps with the catheter distal marker 3354a disposed on the distal portion 3344 of shunt delivery catheter 3304. Again, the operator can confirm the trajectory of penetrating element 3350 through the IPS wall 114 into CP angle cistern 138 using one or more of the previously disclosed imaging techniques before penetrating IPS wall 114. If the operator is unsatisfied with the trajectory of the penetrating element 3350 or penetration site 5000 on IPS wall 114, the operator can adjust the location of the distal portion 3344 of shunt delivery catheter 3304 until the operator is satisfied with the penetrating element 3350 location or that the element 3350 will penetrate the IPS wall 114 at the penetration site 5000 along the first curved portion 102A of the right IPS 102R. When adjusting the location of the distal portion 3344 of shunt delivery catheter 3304, the operator can re-sheath or cover the penetrating element 3350 by advancing the penetrating element guard 4000 via pull wire 4010, which can prevent inadvertent penetration, lesion or injury to the IPS walls that could occur if the penetrating element 3350 was uncovered or unprotected while the operator repositioned the shunt delivery catheter 3304 in the IPS 102.

With the penetrating element 3350 oriented along a desired trajectory at the penetration site in the IPS wall 114, the operator then advances the shunt delivery catheter 3304 so that penetrating element 3350 penetrates (e.g., pierces, passes through or the like, creating an anastomosis channel for the shunt) the dura of IPS wall 114, arachnoid layer 115, and into the CSF-filled subarachnoid space of CP angle cistern 138, as shown in FIG. 32I. The operator can pull proximally on the proximal portion of guide member 780 or hold the guide member 780 in place while advancing the shunt delivery catheter 3304 to cause the penetrating element 3350 to penetrate the IPS wall 114, which allows the portion of shunt delivery catheter 3304, distal of the lumen opening 3315a to track along the target trajectory and off-axis from the path of guide member 780 through the first curved portion 102A of the right IPS 102R. The operator ceases to advance the shunt delivery catheter 3304 when the penetrating element 3350 and the second lumen 3305 of the shunt delivery catheter 3304 have accessed the CP angle cistern 138. The operator can confirm access to the CP angle cistern 138 via one or more of the previously disclosed imaging techniques (e.g., by 3D road mapping). The operator may further confirm access to the CP angle cistern 138 via aspiration of CSF through the penetrating element 3350 and second lumen 3305 of shunt delivery catheter 3304 (e.g., aspirated CSF denoted by arrow-head lines in FIG. 32J). The operator can use a syringe (e.g., 1 cc syringe) coupled to the proximal portion of the shunt delivery catheter (not shown) to aspirate CSF through shunt delivery catheter 3304. The presence of clear CSF in the syringe can confirm a successful penetration through the IPS into the CP angle cistern 138. If the operator observes blood in the syringe, the penetrating element 3350 may be partially disposed in the IPS 102, IPS wall 114 or arachnoid layer 115. If the operator observes blood in the syringe, the operator may re-attempt to penetrate IPS wall 114 at the penetration site 5000, attempt to penetrate IPS wall 114 at another penetration site along the first curved portion 102A of right IPS 102R, attempt to penetrate IPS wall 114 along the second curved portion 102B of right IPS 102R as will be further described below, or abort the procedure.

After confirming that the penetrating element 3350 passed through the IPS wall 114 and arachnoid layer 115 to access CSF within CP angle cistern 138, the operator advances a pusher member 3310 (e.g., FIGS. 23A-D, pusher member 3310' of FIGS. 26A-27H) advancing a shunt 200 (e.g., shunt 2200 of FIGS. 15A-Z, shunt 2200' of FIGS. 25A-M) through the lumen 3305 of the shunt delivery catheter 3304 until the distal anchoring mechanism 229 of the shunt 200 deploys in the CP angle cistern 138, as shown in FIG. 32K. The operator can confirm that the distal anchoring mechanism 229 of the shunt 200 is deployed in the cistern by observing a radiopaque marker 2229c disposed on the distal portion 202 of the shunt 200, using any of the previously disclosed imaging techniques. By pulling the shunt pusher 3310 proximally (and, optionally, simultaneously pulling the shunt delivery catheter 3304 proximally), the distal anchoring mechanism 229 further expands, engages and/or anchors against the arachnoid layer 115 in CP angle cistern 138, as shown in FIG. 32L. The operator continues deploying the shunt 200 in the right IPS 102R as shown in FIG. 32L. By holding the shunt pusher member 3310 in place while withdrawing the shunt delivery catheter 3304, the shunt 200 continues to be deployed out of the shunt delivery catheter lumen 3305 into the IPS 102R. At this point in the procedure, the proximal portion 204 and the proximal anchoring mechanism 227 of the shunt 200 continues to be disposed within the lumen 3305 of the shunt delivery catheter 3304, while the distal portion 202 and the distal anchoring mechanism 209 of the shunt 200 are deployed in the CP angle cistern and right IPS 102R.

The operator completes deployment of the shunt 200 by deploying the proximal portion 204 and the proximal anchoring mechanism 227 of shunt 200 about the JV-IPS junction 118 or in jugular vein 106, as shown in FIG. 32M. By holding the shunt pusher member 3310 in place while withdrawing the shunt delivery catheter 3304, the shunt 200 continues deployment out of the shunt delivery catheter lumen 3305. As the engaged interface between the shunt proximal anchoring mechanism 227 and the pusher member interlocking elements 3336 emerge out of the shunt delivery catheter lumen 3305, the shunt/pusher member interface disengages, thereby releasing the shunt 200 from pusher member 3310, as shown in FIGS. 27A-H. Prior to disengagement of the shunt/pusher member interface, the operator may confirm a satisfactory or desired shunt deployment location in the patient.

After deployment of the shunt 200, the operator withdraws the shunt delivery catheter 3304 from the patient through the venous vasculature and out of the patient at the femoral vein access point. Optionally, the operator may hold the guide member 780 in place while withdrawing the shunt delivery catheter 3304 to avoid or minimize anchor 700 displacement or migration through IPS 102R. Then, the operator advances the anchor delivery catheter 3307 to re-sheath, recapture and/or withdraw the anchor 700 from the patient IPS 102, via the femoral vein access point. By feeding the proximal portion of the guide member 780 through the anchor delivery catheter 3307, the operator can advance the anchor delivery catheter 3307 over the guide member, and around the proximal anchoring mechanism 227 of the deployed shunt 200 in the jugular vein 106 or JV-IPS junction 118, until the distal opening 3317 of the anchor delivery catheter 3307 reaches the joint 744 between the guide member and anchor. The operator can then further advance the anchor delivery catheter 3307 and/or hold or pull the guide member 780 to re-sheath the anchor 700 into the catheter 3307 for withdrawal (e.g., the anchor 700 transitions from the expanded/deployed configuration into the compressed/delivery/withdrawal configuration), as shown in FIG. 32N. With the anchor 700 compressed within the anchor delivery catheter 3307, the operator withdraws the anchor delivery catheter 3307 and anchor 700 from the patient, through the venous vasculature and out of the femoral vein access point. Thereafter, the operator withdraws the guide catheter 307 from the patient.

The deployed shunt 200 (shown in FIG. 32O) including a valve 2209 (e.g., valve 209 of FIG. 7F, 2209 of FIGS. 15A-B, 25A) provide a one-way flow conduit to drain excess CSF from the patient's subarachnoid space into the jugular vein 106, thereby relieving the patient's elevated intracranial pressure. The arrows shown in FIG. 32O depict the direction of CSF flow from the CP angle cistern 138 into the shunt lumen 207, through valve 2209, and into the jugular vein 106. FIG. 32O shows the deployed shunt 200 when the procedure of implantation is completed.

A person skilled in the art should appreciate that in the event that the penetration of the IPS wall 114 at the penetration site 5000 of the first curved portion 102A is not possible or successful, the operator can continue the procedure by attempting to penetrate the IPS wall 114 along the second curved portion 102B of right IPS 102R (e.g., as shown in FIG. 2C) or at another location within IPS 102R. For example, in certain patient anatomies, an overhang of the petrous bone is present along the segment of the inferior petrosal sinus closest to the jugular bulb. This boney overhang then disappears from around the IPS as one progresses medially and superiorly in the skull along the course of the IPS. If the boney overhang is present on the IPS close to the jugular bulb, this can prevent the penetrating element 3350 from passing through the IPS wall 114 into CP angle cistern 138. The presence of this bony overhang can be confirmed during the shunt implant procedure by using one or more of the previously disclosed imaging techniques. If the operator suspects that the petrous bone overhang would prevent penetration into CP angle cistern 138, the operator can then continue the procedure by re-sheathing the penetrating element 3350 with the penetrating element guard 4000, and advancing the shunt delivery catheter 3304 over the guide member 780 until the distal opening of shunt delivery catheter 3304 is disposed at a target penetration site along the second curved portion 102B of right IPS 102R or another desired location distal to the petrous bone overhang. Optionally, the operator can rotate the shunt delivery catheter 3304 from about 45 to 180 degrees while tracking the catheter distally from the first curved portion 102A toward the second curved portion 102B in IPS 102R; by rotating the shunt delivery catheter 3304, the operator can orient the penetrating element 3350 such that further distal advancement of shunt delivery catheter 3304 will advance the penetrating element 3350 through IPS wall 114 at a target penetration along the second curved portion 102B of right IPS 102R. The operator can continue the procedure and deploy the shunt 200 through IPS wall 114 along the second curved portion 102B of right IPS 102R as previously described in the procedure of FIGS. 32A-O.

Further, a person skilled in the art should appreciate that if the operator inadvertently causes a tear in IPS wall 114, the operator may elect to abort the procedure. If using an embodiment of the anchor 700 that includes an outer polymeric layer that covers the cells of the anchor and a guide member 780 that can detach from anchor 700, the operator can, redeploy anchor 700 in the sinus lumen across the tear and leave the anchor 700 in the IPS 102 by detaching guide member 780; in this scenario, the anchor can prevent venous blood from leaking into the subarachnoid space and/or uncontrolled CSF leaking from the subarachnoid space into the venous system.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

The invention claimed is:

1. A system for endovascularly accessing a subarachnoid space (SAS) in a patient, the system comprising:
   an expandable anchor configured for being deployed in a dural venous sinus of a patient at a location distal to a curved portion of a wall of an inferior petrosal sinus (IPS) of the patient;
   an elongate guide member coupled to, and extending proximally from, the anchor;
   an SAS access catheter comprising a first lumen configured to receive the guide member, and a second lumen extending between respective proximal and distal openings in the SAS access catheter, a penetrating element coupled to a distal end of the SAS access catheter; and a guard at least partially disposed over, and movable relative to, the penetrating element, wherein the guard comprises a tubular guard body having a first guard body lumen or recess configured to receive the penetrating element, and a pull wire having a distal portion attached to the guard body, wherein the pull wire is configured to translate the guard body proximally or distally relative to the SAS access catheter so as to at least partially expose or cover, respectively, the penetrating element.

2. The endovascular SAS access system of claim 1, wherein the SAS access catheter further comprises a third lumen extending from the proximal opening to the distal portion of the SAS access catheter, wherein the third lumen is configured to receive the pull wire.

3. The endovascular SAS access system of claim 1, wherein a distal portion of the guard body is beveled or tapered.

4. The endovascular SAS access system of claim 1, wherein the guard body comprises a second guard body lumen configured to accommodate passage therethrough of the guide member.

5. The endovascular SAS access system of claim 1, further comprising a first radiopaque marker disposed in or on a wall of the guard body, wherein the guard body is movable relative to the penetrating element so that the first radiopaque marker may be positioned so as to at least partially overlie the penetrating element.

6. The endovascular SAS access system of claim 5, wherein the pull wire is coupled to the first radiopaque marker.

7. The endovascular SAS access system of claim 5, further comprising a second radiopaque marker disposed in or on the distal portion of the SAS access catheter, wherein the guard body is movable relative to the SAS access catheter so that the first radiopaque marker at least partially overlies the second radiopaque marker.

8. The endovascular SAS access system of claim 7, wherein the second radiopaque marker is disposed at an angle with respect to a longitudinal axis of the SAS access catheter and indicates an orientation of the penetrating element.

9. The endovascular SAS access system of claim 7, wherein the second radiopaque marker comprises a marker band that reinforces a circumferential portion of the SAS access catheter encompassing both the first and second SAS access catheter lumens.

10. The endovascular SAS access system of claim 1, further comprising an anchor pusher configured for translating the anchor through an anchor delivery catheter for deployment in the dural venous sinus.

11. The endovascular SAS access system of claim 10, wherein the anchor pusher comprises a handle having a lumen extending therethrough; and a hypo tube coupled to the handle, the hypo tube having a hypo tube lumen that is contiguous with or otherwise extends through the handle lumen, the respective handle and hypo tube lumens being configured to receive the guide member, wherein the handle is configured to grasp a portion of the guide member extending proximally through the handle lumen for thereby pushing the guide member, and thus the anchor, distally through the anchor deliver)/catheter.

12. A system for endovascularly accessing the subarachnoid space (SAS) in a patient, comprising:
an expandable anchor configured for being deployed in a dural venous sinus of a patient at a location distal to a curved portion of a sinus wall of the patient;
an elongate guide member coupled to, and extending proximally from, the anchor;
an SAS access catheter comprising a first lumen configured to receive the guide member, and a second lumen extending between respective proximal and distal openings in the SAS access catheter, a penetrating element coupled to a distal end of the SAS access catheter; and a guard at least partially disposed over, and movable relative to, the penetrating element, wherein the guard comprises a tubular guard body having a first guard body lumen or recess configured to receive the penetrating element, and a pull wire having a distal portion attached to the guard body, wherein the pull wire is configured to translate the guard body proximally or distally relative to the SAS access catheter so as to at least partially expose or cover, respectively, the penetrating element.

13. The endovascular SAS access system of claim 12, wherein the SAS access catheter further comprises a third lumen extending from the proximal opening to the distal portion of the SAS access catheter, wherein the third lumen is configured to receive the pull wire.

14. The endovascular SAS access system of claim 12, wherein a distal portion of the guard body is beveled or tapered.

15. The endovascular SAS access system of claim 12, wherein the guard body comprises a second guard body lumen configured to accommodate passage therethrough of the guide member.

16. The endovascular SAS access system of claim 12, further comprising a first radiopaque marker disposed in or on a wall of the guard body, wherein the guard body is movable relative to the penetrating element so that the first radiopaque marker may be positioned so as to at least partially overlie the penetrating element.

17. The endovascular SAS access system of claim 16, wherein the pull wire is coupled to the first radiopaque marker.

18. The endovascular SAS access system of claim 16, further comprising a second radiopaque marker disposed in or on the distal portion of the SAS access catheter, wherein the guard body is movable relative to the SAS access catheter so that the first radiopaque marker at least partially overlies the second radiopaque marker.

19. The endovascular SAS access system of claim 18, wherein the second radiopaque marker is disposed at an angle with respect to a longitudinal axis of the access catheter and indicates an orientation of the penetrating element.

20. The endovascular SAS access system of claim 18, wherein the second radiopaque marker comprises a marker band that reinforces a circumferential portion of the SAS access catheter encompassing both the first and second SAS access catheter lumens.

21. The endovascular SAS access system of claim 12, wherein the sinus wall comprises an inferior petrosal sinus of the patient.

22. The endovascular SAS access system of claim 12, wherein the dural venous sinus comprises an inferior petrosal sinus or cavernous sinus of the patient.

23. The endovascular SAS access implantation system claim 12, further comprising an anchor pusher configured for translating the anchor through an anchor delivery catheter for deployment in the dural venous sinus.

24. The endovascular SAS access system of claim 23, wherein the anchor pusher comprises a handle having a lumen extending therethrough; and a hypo tube coupled to the handle, the hypo tube having a hypo tube lumen that is contiguous with or otherwise extends through the handle lumen, the respective handle and hypo tube lumens being configured to receive the guide member, wherein the handle is configured to grasp a portion of the guide member extending proximally through the handle lumen for thereby pushing the guide member, and thus the anchor, distally through the anchor delivery catheter.

* * * * *